US007648708B2

(12) United States Patent
Gilbert et al.

(10) Patent No.: US 7,648,708 B2
(45) Date of Patent: Jan. 19, 2010

(54) *STREPTOCOCCUS PNEUMONIAE* PROTEINS AND NUCLEIC ACID MOLECULES

(75) Inventors: Christophe Francois Guy Gilbert, Villeurbanne cedex (FR); Philip Michael Hansbro, Newcastle (AU)

(73) Assignee: Sanofi Pastuer Limited, Toronto, Ontario (CA)

( * ) Notice: Subject to any disclaimer, the term of this patent is extended or adjusted under 35 U.S.C. 154(b) by 0 days.

(21) Appl. No.: 11/785,507

(22) Filed: Apr. 18, 2007

(65) Prior Publication Data

US 2008/0254070 A1 Oct. 16, 2008

Related U.S. Application Data

(60) Division of application No. 10/873,528, filed on Jun. 23, 2004, now abandoned, which is a division of application No. 09/769,787, filed on Jan. 26, 2001, now Pat. No. 6,936,252, which is a continuation of application No. PCT/GB99/02451, filed on Jul. 27, 1999.

(60) Provisional application No. 60/125,164, filed on Mar. 19, 1999.

(30) Foreign Application Priority Data

Jul. 27, 1998 (GB) ................................. 9816337.1

(51) Int. Cl.
*A61K 39/09* (2006.01)
*C12P 21/04* (2006.01)
*C07K 14/195* (2006.01)
*C07H 21/04* (2006.01)

(52) U.S. Cl. .............. 424/244.1; 424/184.1; 424/190.1; 435/69.1; 435/69.7; 435/252.3; 530/350; 536/23.1; 536/23.7

(58) Field of Classification Search ................... None
See application file for complete search history.

(56) References Cited

U.S. PATENT DOCUMENTS

| 6,420,135 | B1 | 7/2002 | Kunsch et al. |
| 6,573,082 | B1 | 6/2003 | Choi et al. |
| 6,699,703 | B1 | 3/2004 | Doucette-Stamm et al. |
| 6,800,744 | B1 | 10/2004 | Doucette-Stamm et al. |
| 6,936,252 | B2 | 8/2005 | Gilbert et al. |

FOREIGN PATENT DOCUMENTS

| EP | 0622081 | 11/1994 |
| WO | WO 95/06732 | 3/1995 |
| WO | WO 97/09994 | 3/1997 |
| WO | WO 97/37026 | 10/1997 |
| WO | WO 97/43303 | 11/1997 |
| WO | WO 98/18930 | 5/1998 |
| WO | WO 98/18931 | 5/1998 |
| WO | WO 98/26072 | 6/1998 |
| WO | WO 98/31786 | 7/1998 |
| WO | WO 99/15675 | 4/1999 |

OTHER PUBLICATIONS

Lederman et al (Molecular Immunology 28:1171-1181, 1991.*
Li et al (Proc. Natl. Acad. Sci. USA 77:3211-3214, 1980).*
Boslego et al, Chapter 17 in Vaccines and Immunotherapy 1991.*
Houghten et al. (Vaccines, 1986, Edited by Fred Brown: Cold Spring Harbor Laboratory).*
Anderson et al. (1996) "Immune Response in mice following immunization with DNA encoding fragment C of tetanus toxin." Infection and Immunity 64: 3168-3173.
Angel, et al. (1994) "Degradation of C3 by *Streptococcus pneumoniae*." Journal of Infectious Disease 170(3): 600-608.
Alonsodevelasco, et al. (Dec. 1995) "*Streptococcus pneumoniae*: Virulence Factors, Pathogenesis, and Vaccines." Microbiological Reviews 59(4): 591-603.
Breiman et al. (1990) Arch. Intern. Med. 150: 1401.
Breiman et al. (1994) J. Am. Med. Assoc. 271: 1831.
Bowie (1990) Science 257: 1306-1310.
Burgess, et al. (1990) The Journal of Cell Biology 111: 2129-2136.
Donnelly et al. (1997) Ann. Rev. Immunol. 15: 617-648.
Dougall et al. (Sep. 1994) Tibtech 12: 372-379.
Ellis (1988) Vaccines Chapter 29: 568-575.
Greenspan, et al. (1999) Nature Biotechnology 7: 936-937.
Herbert, et al. (1985) The Dictionary of Immunology (Academic Press) 3rd Ed. pp. 58-59.
Holmes, et al. (2001) Exp. Opin. Invest. Drugs 10(3): 511-519.
Jobling et al. (1991) Mol. Microbiol 5(7): 1755-67.
Kohler & Milstein (1975) Nature 256.
Kolkman et al. (1996) 178: 3736-3741.
Kovacevic et al. (1985) J. Bacteriol. 162: 521-528.
Kurar and Splitter (1997) Vaccine 15: 1851-57.
Lange et al. (Sep. 3, 1999) Gene 237(1): 223-234.
Lazar et al. (1988) Molecular and Cellular Biology 8(3): 1247-1252.
Le Loir et al. (1994) J. Bacteriol. 176: 5135-5139.
LeBlanc et al. (1978) PNAS USA 75: 3484-3487.
Li et al. (1997) PNAS 94: 13251-13256.
Liebl et al. (1992) J. Bacteriol. 174: 1854-1861.
Marck (1988) Nucleic Acids Research 16: 1829-1836.
Miller et al. (1987) J. Bacteriol. 169: 3508-3514.
Morrison et al. (1984) PNAS 81: 6851-6855.
Nanidwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).
Oultram and Klaenhammer (1985) FEMS Microbiological Letters 27: 129-134.

(Continued)

*Primary Examiner*—Robert B Mondesi
*Assistant Examiner*—Padma V Baskar
(74) *Attorney, Agent, or Firm*—Hunton & Williams LLP

(57) ABSTRACT

Protein antigens from *Streptococcus pneumoniae* are disclosed, together with nucleic acid sequences encoding them. Their use in vaccines and in screening methods is also described.

7 Claims, 2 Drawing Sheets

OTHER PUBLICATIONS

Pearson et al. (1988) "Improved tools for biological sequence comparison," Proc. Natl. Acad. Sci. USA, vol. 85, 2444-2448.
Poquet et al. (1998) J. Bacteriol. 180: 1904-1912.
Roitt, et al. (1993) Immunology p. 7.7-7.8.
Rudinger et al. (Jun. 1976) "Peptide Hormones" p. 6.
Schappert (1992) Vital and Health Statistics of the Centres for Disease Control/National Centre for Health Statistics 214: 1.
Shortle (1983) Gene 22: 181-189.
Siber (Sep. 1994) "Pneumococcal Disease: Prospects for a New Generation of Vaccines" Science vol. 265, pp. 1385-1387.
Simon and Chopin (1988) Biochimie 70: 559-567.
Stansfield (1987) "Acute respiratory infections in the developing world: strategies for prevention, treatment and control," Pediatric Infect Dis. Journal, vol. 6, 622-629.
Takeda et al. (1985) Nature 314: 452-454.
Taber's Cyclopedic Medical Dictionary (1985) 16$^{th}$ Ed. p. 1354.
van der Vossen, et al. (1985) Applied and Environmental Microbiology 50: 540-542.
Waterfield et al. (1995) Gene 165: 9-15.
Wells and Schoefield (1996) In Current advances in metabolism, genetics, and applications-NATO ASI Series H 98: 37-62.
Wells et al. (1993) J. Appl. Bacteriol. 74: 629-636.
Zhang et al. (1997) Infection and Immunity 176: 1035-1040.
Nandiwada, et al. (1996) "Genetic Analysis of a C3 degrading proteinase in *Steptococcus pneumoniae*." Abstracts of the General Meeting of the American Society for Microbiology vol. 96 p. 177 (Abstract B-134).

* cited by examiner

STREPTOCOCCUS PNEUMONIAE PROTEINS AND NUCLEIC ACID MOLECULES

This application is a divisional of U.S. patent application Ser. No. 10/873,528, filed Jun. 23, 2004, now abandoned, which is a divisional of U.S. patent application Ser. No. 09/769,787, filed Jan. 26, 2001, now U.S. Pat. No. 6,936,252, which is a continuation of PCT/GB99/02451, filed Jul. 27, 1999, which claims benefit of U.S. Provisional Application No. 60/125,164, filed Mar. 19, 1999, and which also claims benefit of United Kingdom 9816337.1, filed Jul. 27, 1998, the disclosures of which are all hereby incorporated by reference.

The present invention relates to proteins derived from *Streptococcus pneumoniae*, nucleic acid molecules encoding such proteins, the use of the nucleic acid and/or proteins as antigens/immunogens and in detection/diagnosis, as well as methods for screening the proteins/nucleic acid sequences as potential anti-microbial targets.

*Streptococcus pneumoniae*, commonly referred to as the pneumococcus, is an important pathogenic organism. The continuing significance of *Streptococcus pneumoniae* infections in relation to human disease in developing and developed countries has been authoritatively reviewed (Fiber, G. R., *Science*, 265:1385-1387 (1994)). That indicates that on a global scale this organism is believed to be the most common bacterial cause of acute respiratory infections, and is estimated to result in 1 million childhood deaths each year, mostly in developing countries (Stansfield, S. K., *Pediatr. Infect. Dis.*, 6:622 (1987)). In the USA it has been suggested (Breiman et al., *Arch. Intern. Med.*, 150:1401 (1990)) that the pneumococcus is still the most common cause of bacterial pneumoniae, and that disease rates are particularly high in young children, in the elderly, and in patients with predisposing conditions such as asplenia, heart, lung, and kidney disease, diabetes, alcoholism, or with immunosuppressive disorders, especially AIDS. These groups are at higher risk of pneumococcal septicaemia and hence meningitis and therefore have a greater risk of dying from pneumococcul infection. The pneumococcus is also the leading cause of otitis media and sinusitis, which remain prevalent infections in children in developed countries, and which incur substantial costs.

The need for effective preventative strategies against pneumococcal infection is highlighted by the recent emergence of penicillin-resistant pneumococci. It has been reported that 6.6% of pneumoccal isolates in 13 US hospitals in 12 states were found to be resistant to penicillin and some isolates were also resistant to other antibiotics including third generation cyclosporins (Schappert, S. M., *Vital and Health Statistics of the Centres for Disease Control/National Centre for Health Statistics*, 214:1 (1992)). The rates of penicillin resistance can be higher (up to 20%) in some hospitals (Breiman etal, J. Am. Med. Assoc., 271: 1831 (1994)). Since the development of penicillin resistance among pneumococci is both recent and sudden, coming after decades during which penicillin remained an effective treatment, these findings are regarded as alarming.

For the reasons given above, there are therefore compelling grounds for considering improvements in the means of preventing, controlling, diagnosing or treating pneumococcal diseases.

Various approaches have been taken in order to provide vaccines for the prevention of pneumococcal infections. Difficulties arise for instance in view of the variety of serotypes (at least 90) based on the structure of the polysaccharide capsule surrounding the organism. Vaccines against individual serotypes are not effective against other serotypes and this means that vaccines must include polysaccharide antigens from a whole range of serotypes in order to be effective in a majority of cases. An additional problem arises because it has been found that the capsular polysaccharides (each of which determines the serotype and is the major protective antigen) when purified and used as a vaccine do not reliably induce protective antibody responses in children under two years of age, the age group which suffers the highest incidence of invasive pneumococcal infection and meningitis.

A modification of the approach using capsule antigens relies on conjugating the polysaccharide to a protein in order to derive an enhanced immune response, particularly by giving the response T-cell dependent character. This approach has been used in the development of a vaccine against *Haemophilus influenzae*. There are issues of cost concerning both the multi-polysaccharide vaccines and those based on conjugates.

A third approach is to look for other antigenic components which offer the potential to be vaccine candidates.

BACKGROUND OF THE INVENTION

In the present application we provide a group of proteins antigens which are secreted/exported proteins.

BRIEF SUMMARY OF THE INVENTION

Thus, in a first aspect the present invention provides a *Streptococcus pneumoniae* protein or polypeptide having a sequence selected from those shown in Table 2 herein.

A protein or polypeptide of the present invention may be provided in substantially pure form. For example, it may be provided in a form which is substantially free of other proteins.

In a preferred embodiment, a protein or polypeptide having an amino acid sequence as shown in Table 3 is provided.

The invention encompasses any protein coded for by a nucleic acid sequence as shown in Table 1 herein.

DETAILED DESCRIPTION OF THE INVENTION

As discussed herein, the proteins and polypeptides of the invention are useful as antigenic material. Such material can be "antigenic" and/or "immunogenic". Generally, "antigenic" is taken to mean that the protein or polypeptide is capable of being used to raise antibodies or indeed is capable of inducing an antibody response in a subject. "Immunogenic" is taken to mean that the protein or polypeptide is capable of eliciting a protective immune response in a subject.

Thus, in the latter case, the protein or polypeptide may be capable of not only generating an antibody response and in addition non-antibody based immune responses.

The skilled person will appreciate that homologues or derivatives of the proteins or polypeptides of the invention will also find use in the context of the present invention, ie as antigenic/immunogenic material. Thus, for instance proteins or polypeptides which include one or more additions, deletions, substitutions or the like are encompassed by the present invention.

In addition, it may be possible to replace one amino acid with another of similar "type". For instance replacing one hydrophobic amino acid with another. One can use a program such as the CLUSTAL program to compare amino acid sequences. This program compares amino acid sequences and finds the optimal alignment by inserting spaces in either sequence as appropriate.

It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of analysis are contemplated in the present invention.

In the case of homologues and derivatives, the degree of identity with a protein or polypeptide as described herein is less important than that the homologue or derivative should retain its antigenicity or immunogenicity to *Streptoccocus pneumoniae*. However, suitably, homologues or derivatives having at least 60% similarity (as discussed above) with the proteins or polypeptides described herein are provided.

Preferably, homologues or derivatives having at least 70% similarity, more preferably at least 80% similarity are provided. Most preferably, homologues or derivatives having at least 90% or even 95% similarity are provided.

In an alternative approach, the homologues or derivatives could be fusion proteins, incorporating moieties which render purification easier, for example by effectively tagging the desired protein or polypeptide. It may be necessary to remove the "tag" or it may be the case that the fusion protein itself retains sufficient antigenicity to be useful.

In an additional aspect of the invention there are provided antigenic fragments of the proteins or polypeptides of the invention, or of homologues or derivatives thereof.

For fragments of the proteins or polypeptides described herein, or of homologues or derivatives thereof, the situation is slightly different. It is well known that is possible to screen an antigenic protein or polypeptide to identify epitopic regions, i.e., those regions which are responsible for the protein or polypeptide's antigenicity or immunogenicity. Methods for carrying out such screening are well known in the art. Thus, the fragments of the present invention should include one or more such epitopic regions or be sufficiently similar to such regions to retain their antigenic/immunogenic properties. Thus, for fragments according to the present invention the degree of identity is perhaps irrelevant, since they may be 100% identical to a particular part of a protein or polypeptide, homologue or derivative as described herein. The key issue, once again, is that the fragment retains the antigenic/immunogenic properties.

Thus, what is important for homologues, derivatives and fragments is that they possess at least a degree of the antigenicity/immunogenicity of the protein or polypeptide from which they are derived.

Gene cloning techniques may be used to provide a protein of the invention in substantially pure form, These techniques are disclosed, for example, in J. Sambrook et al *Molecular Cloning* 2nd Edition, Cold Spring Harbor Laboratory Press (1989). Thus, in a fourth aspect, the present invention provides a nucleic acid molecule comprising or consisting of a sequence which is:
(i) any of the DNA sequences set out in Table 1 or their RNA equivalents;
(ii) a sequence which is complementary to any of the sequences of (i);
(iii) a sequence which codes for the same protein or polypeptide, as those sequences of (i) or (ii);
(iv) a sequence which is has substantial identity with any of those of (i), (ii) and (iii);
(v) a sequence which codes for a homologue, derivative or fragment of a protein as defined in Table 1

In a fifth aspect the present invention provides a nucleic acid molecule comprising or consisting of a sequence which is:
(i) any of the DNA sequences set out in Table 4 or their RNA equivalents;
(ii) a sequence which is complementary to any of the sequences of (i);
(iii) a sequence which codes for the same protein or polypeptide, as those sequences of (i) or (ii);
(iv) a sequence which is has substantial identity with any of those of (i), (ii) and (iii);
(v) a sequence which codes for a homologue, derivative or fragment of a protein as defined in Table 4.

The nucleic acid molecules of the invention may include a plurality of such sequences, and/or fragments. The skilled person will appreciate that the present invention can include, novel variants of those particular novel nucleic acid molecules which are exemplified herein. Such variants are encompassed by the present invention. These may occur in nature, for example because of strain variation. For example, additions, substitutions and/or deletions are included. In addition, and particularly when utilising microbial expression systems, one may wish to engineer the nucleic acid sequence by making use of known preferred codon usage in the particular organism being used for expression. Thus, synthetic or non-naturally occurring variants are also included within the scope of the invention.

The term "RNA equivalent" when used above indicates that a given RNA molecule has a sequence which is complementary to that of a given DNA molecule (allowing for the fact that in RNA "U" replaces "T" in the genetic code).

When comparing nucleic acid sequences for the purposes of determining the degree of homology or identity one can use programs such as BESTFIT and GAP (both from the Wisconsin Genetics Computer Group (GCG) software package) BESTFIT, for example, compares two sequences and produces an optimal alignment of the most similar segments. GAP enables sequences to be aligned along their whole length and finds the optimal alignment by inserting spaces in either sequence as appropriate. Suitably, in the context of the present invention compare when discussing identity of nucleic acid sequences, the comparison is made by alignment of the sequences along their whole length.

Preferably, sequences which have substantial identity have at least 50% sequence identity, desirably at least 75% sequence identity and more desirably at least 90 or at least 95% sequence identity with said sequences. In some cases the sequence identity may be 99% or above.

Desirably, the term "substantial identity" indicates that said sequence has a greater degree of identity with any of the sequences described herein than with prior art nucleic acid sequences.

It should however be noted that where a nucleic acid sequence of the present invention codes for at least part of a novel gene product the present invention includes within its scope all possible sequence coding for the gene product or for a novel part thereof.

The nucleic acid molecule may be in isolated or recombinant form. It may be incorporated into a vector and the vector may be incorporated into a host. Such vectors and suitable hosts form yet further aspects of the present invention.

Therefore, for example, by using probes based upon the nucleic acid sequences provided herein, genes in *Streptococcus pneumoniae* can be identified. They can then be excised using restriction enzymes and cloned into a vector. The vector can be introduced into a suitable host for expression.

Nucleic acid molecules of the present invention may be obtained from *S._pneumoniae* by the use of appropriate probes complementary to part of the sequences of the nucleic acid molecules. Restriction enzymes or sonication techniques can be used to obtain appropriately sized fragments for probing.

Alternatively PCR techniques may be used to amplify a desired nucleic acid sequence. Thus the sequence data provided herein can be used to design two primers for use in PCR so that a desired sequence, including whole genes or fragments thereof, can be targeted and then amplified to a high degree. One primer will normally show a high degree of specificity for a first sequence located on one strand of a DNA molecule, and the other primer will normally show a high degree of specificity for a second sequence located on the complementary strand of the DNA sequence and being spaced from the complementary sequence to the first sequence.

Typically primers will be at least 15-25 nucleotides long.

As a further alternative chemical synthesis may be used. This may be automated. Relatively short sequences may be chemically synthesised and ligated together to provide a longer sequence.

In yet a further aspect the present invention provides an immunogenic/antigenic composition comprising one or more proteins or polypeptides selected from those whose sequences are shown in Tables 24, or homologues or derivatives thereof, and/or fragments of any of these. In preferred embodiments, the immunogenic/antigenic composition is a vaccine or is for use in a diagnostic assay.

In the case of vaccines suitable additional excipients, diluents, adjuvants or the like may be included. Numerous examples of these are well known in the art.

It is also possible to utilise the nucleic acid sequences shown in Table 1 in the preparation of so-called DNA vaccines. Thus, the invention also provides a vaccine composition comprising one or more nucleic acid sequences as defined herein. The use of such DNA vaccines is described in the art. See for instance, Donnelly et al, *Ann. Rev. Immunol.*, 15:617-648 (1997).

As already discussed herein the proteins or polypeptides described herein, their homologues or derivatives, and/or fragments of any of these, can be used in methods of detecting/diagnosing *S. pneumoniae*. Such methods can be based on the detection of antibodies against such proteins which may be present in a subject. Therefore the present invention provides a method for the detection/diagnosis of *S. pneumoniae* which comprises the step of bringing into contact a sample to be tested with at least one protein, or homologue, derivative or fragment thereof, as described herein. Suitably, the sample is a biological sample, such as a tissue sample or a sample of blood or saliva obtained from a subject to be tested.

In an alternative approach, the proteins described herein, or homologues, derivatives and/or fragments thereof, can be used to raise antibodies, which in turn can be used to detect the antigens, and hence *S. pneumoniae*. Such antibodies form another aspect of the invention. Antibodies within the scope of the present invention may be monoclonal or polyclonal.

Polyclonal antibodies can be raised by stimulating their production in a suitable animal host (e.g. a mouse, rat, guinea pig, rabbit, sheep, goat or monkey) when a protein as described herein, or a homologue, derivative or fragment thereof, is injected into the animal. If desired, an adjuvant may be administered together with the protein. Well-known adjuvants include Freund's adjuvant (complete and incomplete) and aluminium hydroxide. The antibodies can then be purified by virtue of their binding to a protein as described herein.

Monoclonal antibodies can be produced from hybridomas. These can be formed by fusing myeloma cells and spleen cells which produce the desired antibody in order to form an immortal cell line. Thus the well-known Kohler & Milstein technique (*Nature* 256 (1975)) or subsequent variations upon this technique can be used.

Techniques for producing monoclonal and polyclonal antibodies that bind to a particular polypeptide/protein are now well developed in the art. They are discussed in standard immunology textbooks, for example in Roitt et al, *Immunology* second edition (1989), Churchill Livingstone, London.

In addition to whole antibodies, the present invention includes derivatives thereof which are capable of binding to proteins etc as described herein. Thus the present invention includes antibody fragments and synthetic constructs. Examples of antibody fragments and synthetic constructs are given by Dougall et al in *Tibtech* 12 372-379 (September 1994).

Antibody fragments include, for example, Fab, F(ab')$_2$ and Fv fragments. Fab fragments (These are discussed in Roitt et al [supra]). Fv fragments can be modified to produce a synthetic construct known as a single chain Fv (scFv) molecule. This includes a peptide linker covalently joining $V_h$ and $V_l$ regions, which contributes to the stability of the molecule. Other synthetic constructs that can be used include CDR peptides. These are synthetic peptides comprising antigen-binding determinants. Peptide mimetics may also be used. These molecules are usually conformationally restricted organic rings that mimic the structure of a CDR loop and that include antigen-interactive side chains.

Synthetic constructs include chimaeric molecules. Thus, for example, humanised (or primatised) antibodies or derivatives thereof are within the scope of the present invention. An example of a humanised antibody is an antibody having human framework regions, but rodent hypervariable regions. Ways of producing chimaeric antibodies are discussed for example by Morrison et al in PNAS, 81, 6851-6855 (1984) and by Takeda et al in Nature. 314, 452454 (1985).

Synthetic constructs also include molecules comprising an additional moiety that provides the molecule with some desirable property in addition to antigen binding. For example the moiety may be a label (e.g., a fluorescent or radioactive label). Alternatively, it may be a pharmaceutically active agent.

Antibodies, or derivatives thereof, find use in detection/diagnosis of *S. pneumoniae*. Thus, in another aspect the present invention provides a method for the detection/diagnosis of *S. pneumoniae* which comprises the step of bringing into contact a sample to be tested and antibodies capable of binding to one or more proteins described herein, or to homologues, derivatives and/or fragments thereof.

In addition, so-called AFFIBODIES may be utilised. These are binding proteins selected from combinatorial libraries of an alpha-helical bacterial receptor domain (Nord et al,) Thus, Small protein domains, capable of specific binding to different target proteins can be selected using combinatorial approaches.

It will also be clear that the nucleic acid sequences described herein may be used to detect/diagnose *S. pneumoniae*. Thus, in yet a further aspect, the present invention provides a method for the detection/diagnosis of *S. pneumoniae* which comprises the step of bringing into contact a sample to be tested with at least one nucleic acid sequence as described herein. Suitably, the sample is a biological sample, such as a tissue sample or a sample of blood or saliva obtained from a subject to be tested. Such samples may be pre-treated before being used in the methods of the invention. Thus, for example, a sample may be treated to extract DNA. Then, DNA probes based on the nucleic acid sequences described herein (i.e., usually fragments of such sequences) may be used to detect nucleic acid from *S. pneumoniae*.

In additional aspects, the present invention provides:
(a) a method of vaccinating a subject against *S. pneumoniae* which comprises the step of administering to a subject a protein or polypeptide of the invention, or a derivative, homologue or fragment thereof, or an immunogenic composition of the invention;
(b) a method of vaccinating a subject against *S. pneumoniae* which comprises the step of administering to a subject a nucleic acid molecule as defined herein;
(c) a method for the prophylaxis or treatment of *S. pneumoniae* infection which comprises the step of administering to a subject a protein or polypeptide of the invention, or a derivative, homologue or fragment thereof, or an immunogenic composition of the invention;
(d) a method for the prophylaxis or treatment of *S. pneumoniae* infection which comprises the step of administering to a subject a nucleic acid molecule as defined herein;
(e) a kit for use in detecting/diagnosing *S. pneumoniae* infection comprising one or more proteins or polypeptides of the invention, or homologues, derivatives or fragments thereof, or an antigenic composition of the invention; and (f) a kit for use in detecting/diagnosing *S. pneumoniae* infection comprising one or more nucleic acid molecules as defined herein.

Given that we have identified a group of important proteins, such proteins are potential targets for anti-microbial therapy. It is necessary, however, to determine whether each individual protein is essential for the organism's viability. Thus, the present invention also provides a method of determining whether a protein or polypeptide as described herein represents a potential anti-microbial target which comprises inactivating said protein and determining whether *S. pneumoniae* is still viable, in vitro or in vivo.

A suitable method for inactivating the protein is to effect selected gene knockouts, ie prevent expression of the protein and determine whether this results in a lethal change. Suitable methods for carrying out such gene knockouts are described in Li et al, *P.N.A.S.*, 94:13251-13256 (1997).

In a final aspect the present invention provides the use of an agent capable of antagonising, inhibiting or otherwise interfering with the function or expression of a protein or polypeptide of the invention in the manufacture of a medicament for use in the treatment or prophylaxis of *S. pneumoniae* infection.

The invention will now be described with reference to the following examples, which should not be construed as in any way limiting the invention. The examples refer to the figures in which:

EXAMPLE 1

Figure 1:
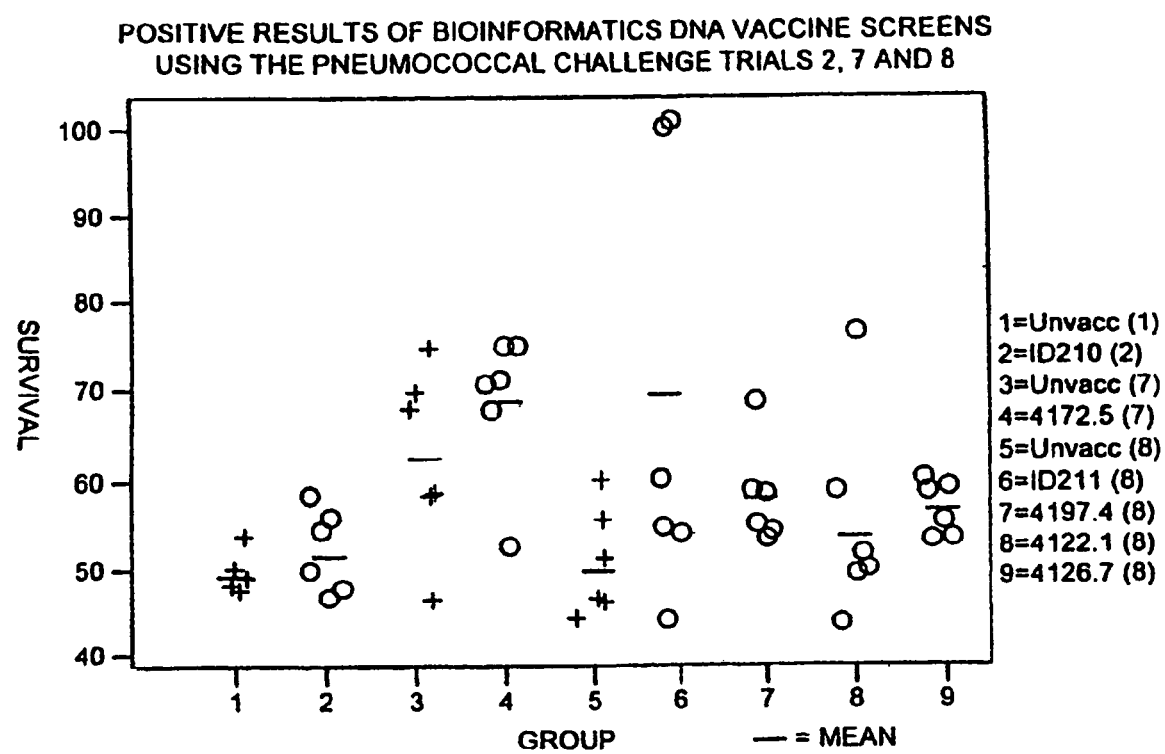
FIG. 1: shows the results of various DNA vaccine trials.

The Genome sequencing of *Streptococcus pneumoniae* type 4 is in progress at the Institute for Genomic Research (TIGR, Rockville, Md., USA). Up to now, the whole sequence has not been completed or published. On Nov. 21, 1997, the TIGR centre released some DNA sequences as contigs which are not accurate reflections of the finished sequence. These contigs can be downloaded from their website. We downloaded these contigs and created a local database using the application GCGToBLAST (Wisconsin Package Version 9.1, Genetics Computer Group (GCG), Madison, USA). This database can be searched with the FastA and TfastA procedures (using the method of Pearson and Lipman (*PNAS USA*, 85:2444-2448 (1988)).

Using FastA and TfastA procedures, the local pneumococcus database was searched for putative leader sequence or anchor sequence features. Relevant sequences were used to interrogate for comparative novel sequences. These were:

(i) already described leader sequences of *Streptococcus pneumoniae* (from proteins NanA, NanB, LytA, PapA, pcpA, PsaA and PspA);

(ii) the leader sequence of Usp45, a secreted protein from *Lactococcus lactis*;

(iii) new hypothetical leader sequences derived from the searches in (i) and (ii);

(iv) the anchor motif LPxTG (SEQ ID NO: 364), a feature common to many Gram-positive bacteria surface proteins which are anchored by a mechanism involving the Sortase complex proteins.

Provided below is an example of this approach, with reference to the sequences derived from the database (see table 1).

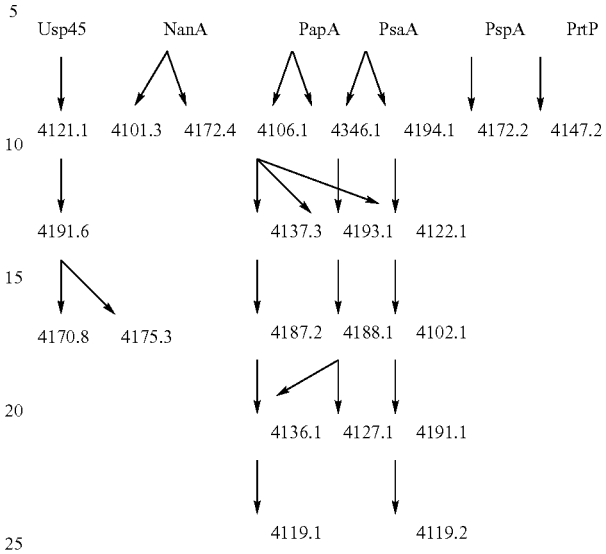

The protein leader sequences of different known exported proteins were used as a starting point for a search of the local pneumococcus database described above. The hypothetical proteins found with this search were then submitted to a Blast search in general databases such as EMBL, Swissprot etc. Proteins remaining unknown in the pneumococcus are kept and annotated. Then the search is performed again using the new potential protein leader sequence as a probe, using the TfastA procedure.

EXAMPLE 2

DNA Vaccine Trials

PcDNA3.1+ as a DNA Vaccine Vector

PcDNA3.1+

The vector chosen for use as a DNA vaccine vector was pcDNA3.1 (Invitrogen) (actually pcDNA3.1+, the forward orientation was used in all cases but may be referred to as pcDNA3.1 here on). This vector has been widely and successfully employed as a host vector to test vaccine candidate genes to give protection against pathogens in the literature (Zhang, et al., Kurar and Splitter, Anderson et al.). The vector was designed for high-level stable and non-replicative transient expression in mammalian cells. pcDNA3.1 contains the ColE1 origin of replication which allows convenient high-copy number replication and growth in *E. coli*. This in turn allows rapid and efficient cloning and testing of many genes. The pcDNA3.1 vector has a large number of cloning sites and also contains the gene encoding ampicillin resistance to aid in cloning selection and the human cytomegalovirus (CMV) immediate-early promoter/enhancer which permits efficient, high-level expression of the recombinant protein. The CMV promoter is a strong viral promoter in a wide range of cell types including both muscle and immune (antigen presenting) cells. This is important for optimal immune response as it remains unknown as to which cells types are most important in generating a protective response in vivo. A T7 promoter upstream of the multiple cloning site affords efficient expression of the modified insert of interest and which allows in vitro transcription of a cloned gene in the sense orientation.

Zhang, D., Yang, X., Berry, J. Shen, C., McClarty, G. and Brunham, R. C. (1997) "DNA vaccination with the major outer-membrane protein genes induces acquired immunity to *Chlamydia trachomatis* (mouse pneumonitis) infection". *Infection and Immunity*, 176, 1035-40.

Kurar, E. and Splitter, G. A. (1997) "Nucleic acid vaccination of *Brucella abortus* ribosomal L7/L12 gene elicits immune response". *Vaccine*, 15, 1851-57.

Anderson, R., Gao, X.-M., Papakonstantinopoulou, A., Roberts, M. and Dougan, G. (1996) "Immune response in mice following immunisation with DNA encoding fragment C of tetanus toxin". *Infection and Immunity*, 64, 3168-3173.

Preparation of DNA Vaccines

Oligonucleotide primers were designed for each individual gene of interest derived using the LEEP system. Each gene was examined thoroughly, and where possible, primers were designed such that they targeted that portion of the gene thought to encode only the mature portion of the gene protein. It was hoped that expressing those sequences that encode only the mature portion of a target gene protein, would facilitate its correct folding when expressed in mammalian cells. For example, in the majority of cases primers were designed such that putative N-terminal signal peptide sequences would not be included in the final amplification product to be cloned into the pcDNA3.1 expression vector. The signal peptide directs the polypeptide precursor to the cell membrane via the protein export pathway where it is normally cleaved off by signal peptidase I (or signal peptidase II if a lipoprotein). Hence the signal peptide does not make up any part of the mature protein whether it be displayed on the surface of the bacteria surface or secreted. Where a N-terminal leader peptide sequence was not immediately obvious, primers were designed to target the whole of the gene sequence for cloning and ultimately, expression in pcDNA3.1.

Having said that, however, other additional features of proteins may also affect the expression and presentation of a soluble protein. DNA sequences encoding such features in the genes encoding the proteins of interest were excluded during the design of oligonucleotides. These features included:

1. LPXTG (SEQ ID NO: 364) cell wall anchoring motifs.
2. LXXC ipoprotein attachment sites.
3. Hydrophobic C-terminal domain.
4. Where no N-terminal signal peptide or LXXC was present the start codon was excluded.
5. Where no hydrophobic C-terminal domain or LPXTG (SEQ ID NO: 364) motif was present the stop codon was removed.

Appropriate PCR primers were designed for each gene of interest and any and all of the regions encoding the above features was removed from the gene when designing these primers. The primers were designed with the appropriate enzyme restriction site followed by a conserved Kozak nucleotide sequence (in all cases) GCCACC was used. The Kozak sequence facilitates the recognition of initiator sequences by eukaryotic ribosomes) and an ATG start codon upstream of the insert of the gene of interest. For example the forward primer using a BamHI site the primer would begin GCGGGATCCGCCACCATG (SEQ ID NO: 365) followed by a small section of the 5' end of the gene of interest. The reverse primer was designed to be compatible with the forward primer and with a NotI restriction site at the 5' end in all cases (this site is T-GCGGCCGC) (SEQ ID NO:366).

PCR Primers

```
The following PCR primers were designed and used
to amplify the truncated genes of interest.
ID210
                                       (SEQ ID NO: 367)
Forward Primer
5' CGGATCCGCCACCATGTCTTCTAATGAATCTGCCGATG 3'

(SEQ ID NO: 368)
Reverse Primer
5' TTGCGGCCGCCTGTTTAGATTGGATATCTGTAAAGACTT 3'

4172.5
                                       (SEQ ID NO: 369)
Forward Primer
5' CGCGGATCCGCCACCATGGATTTTCCTTCAAATTTGGAGG 3'

(SEQ ID NO: 370)
Reverse Primer
5' TTGCGGCCGCACCGTACTGGCTGCTGACT 3'

ID211
                                       (SEQ ID NO: 371)
Forward Primer
5' CGGATCCGCCACCATGAGTGAGATCAAAATTATTAACGC 3'

(SEQ ID NO: 372)
Reverse Primer
5' TTGCGGCCGCCGTTCCATGGTTGACTCCT 3'

4197.4
                                       (SEQ ID NO: 373)
Forward Primer
5' CGCGGATCCGCCACCATGTGGGACATATTGGTGGAAAC 3'

(SEQ ID NO: 374)
Reverse Primer
5' TTGCGGCCGCTTCACTTGAGCAAACTGAATCC 3'

4122.1
                                       (SEQ ID NO: 375)
Forward Primer
5' CGCGGATCCGCCACCATGTCACAAGAAAAACAAAAATGAA 3'

(SEQ ID NO: 376)
Reverse Primer
5' TTGCGGCCGCATCGACGTAGTCTCCGCC 3'

4126.7
                                       (SEQ ID NO: 377)
Forward Primer
5' CGCGGATCCGCCACCATGCTGGTTGGAACTTTCTACTATCAAT 3'

(SEQ ID NO: 378)
Reverse Primer
5' TTGCGGCCGCAACTTTCGTCCCTTTTTGG 3'

4188.11
                                       (SEQ ID NO: 379)
Forward Primer
5' CGCGGATCCGCCACCATGGGCAATTCTGGCGGAA 3'

(SEQ ID NO: 380)
Reverse Primer
5' TTGCGGCCGCTTGTTTCATAGCTTTTTTGATTGTT 3'

ID209
                                       (SEQ ID NO: 381)
Forward Primer
5' CGCGGATCCGCCACCATGCTATTGATACGAAATGCAGGG 3'

(SEQ ID NO: 382)
Reverse Primer
5' TTGCGGCCGCAACATAATCTAGTAAATAAGCGTAGCC 3'

ID215
                                       (SEQ ID NO: 383)
Forward Primer
5' CGCGGATCCGCCACCATGACGGCGACGAATTTTC 3'
```

-continued (SEQ ID NO: 384)
Reverse Primer
5' TTGCGGCCGCTTAATTCGTTTTTGAACTAGTTGCT 3'

4170.4
(SEQ ID NO: 385)
Forward Primer
5' CGCGGATCCGCCACCATGGCTGTTTTTCTTCGCTATCATG 3'

(SEQ ID NO: 386)
Reverse Primer
5' TTGCGGCCGCTTTCTTCAACAAACCTTGTTCTTG 3'

4193.1
(SEQ ID NO: 387)
Forward Primer
5' CGCGGATCCGCCACCATGGGTAACCGCTCTTCTCGTAAC 3'

(SEQ ID NO: 388)
Reverse Primer
5' TTGCGGCCGCGCTTCCATCAAGGATTTTAGC 3'

Cloning

The insert along with the flanking features described above was amplified using PCR against a template of genomic DNA isolated from type 4 *S. pneumoniae* strain 11886 obtained from the National Collection of Type Cultures. The PCR product was cut with the appropriate restriction enzymes and cloned in to the multiple cloning site of pcDNA3.1 using conventional molecular biological techniques. Suitably mapped clones of the genes of interested were cultured and the plasmids isolated on a large scale (>1.5 mg) using Plasmid Mega Kits (Qiagen). Successful cloning and maintenance of genes was confirmed by restriction mapping and sequencing ~700 base pairs through the 5' cloning junction of each large scale preparation of each construct.

Strain Validation

A strain of type 4 was used in cloning and challenge methods which is the strain from which the *S. pneumoniae* genome was sequenced. A freeze dried ampoule of a homogeneous laboratory strain of type 4 *S. pneumoniae* strain NCTC 11886 was obtained from the National Collection of Type Strains. The ampoule was opened and the cultured re suspended with 0.5 ml of tryptic soy broth (0.5% glucose, 5% blood). The suspension was subcultured into 10 ml tryptic soy broth (0.5% glucose, 5% blood) and incubated statically overnight at 37° C. This culture was streaked on to 5% blood agar plates to check for contaminants and confirm viability and on to blood agar slopes and the rest of the culture was used to make 20% glycerol stocks. The slopes were sent to the Public Health Laboratory Service where the type 4 serotype was confirmed.

A glycerol stock of NCTC 11886 was streaked on a 5% blood agar plate and incubated overnight in a CO2 gas jar at 37° C. Fresh streaks were made and optochin sensitivity was confirmed.

Pneumococcal Challenge

A standard inoculum of type 4 *S. pneumoniae* was prepared and frozen down by passaging a culture of pneumococcus 1× through mice, harvesting from the blood of infected animals, and grown up to a predetermined viable count of around $10^9$ cfu/ml in broth before freezing down. The preparation is set out below as per the flow chart.

Streak pneumococcal culture and confirm identity
V

-continued

Grow over-night culture from 4-5 colonies on plate above
V
Animal passage pneumococcal culture
(i.p. injection of cardiac bleed to harvest)
V
Grow over-night from animal passaged pneumococcus
V
Grow day culture (to pre-determined optical density)
from over-night of animal passage and
freeze down at -70° C. - This is standard minimum
V
Thaw one aliquot of standard inoculum to viable count
V
Use standard inoculum
to determine effective dose
(called Virulence Testing)
V
All subsequent challenges- use standard inoculum to effective dose An aliquot of standard inoculum was diluted 500× in PBS and used to inoculate the mice.

Mice were lightly anaesthetised using halothane and then a dose of $1.4 \times 10^5$ cfu of pneumococcus was applied to the nose of each mouse. The uptake was facilitated by the normal breathing of the mouse, which was left to recover on its back.

*S. pneumoniae* Vaccine Trials

Vaccine trials in mice were carried out by the administration of DNA to 6 week old CBA/ca mice (Harlan, UK). Mice to be vaccinated were divided into groups of six and each group was immunised with recombinant pcDNA3.1+ plasmid DNA containing a specific target-gene sequence of interest. A total of 100 µg of DNA in Dulbecco's PES (Sigma) was injected intramuscularly into the tibialis anterior muscle of both legs (50 µl in each leg). A boost was carried using the same procedure 4 weeks later. For comparison, control groups were included in all vaccine trials. These control groups were either unvaccinated animals or those administered with non-recombinant pcDNA3.1+ DNA (sham vaccinated) only, using the same time course described above. 3 weeks after the second immunisation, all mice groups were challenged intra-nasally with a lethal dose of *S. pneumoniae* serotype 4 (strain NCTC 11886). The number of bacteria administered was monitored by plating serial dilutions of the inoculum on 5% blood agar plates. A problem with intranasal immunisations is that in some mice the inoculum bubbles out of the nostrils, this has been noted in results table and taken account of in calculations. A less obvious problem is that a certain amount of the inoculum for each mouse may be swallowed. It is assumed that this amount will be the same for each mouse and will average out over the course of innoculations. However, the sample sizes that have been used are small and this problem may have significant effects in some experiments. All mice remaining after the challenge were killed 3 or 4 days after infection. During the infection process, challenged mice were monitored for the development of symptoms associated with the onset of *S. pneumoniae* induced-disease. Typical symptoms in an appropriate order included piloerection, an increasingly hunched posture, discharge from eyes, increased lethargy and reluctance to move. The latter symptoms usually coincided with the development of a moribund state at which stage the mice were culled to prevent further suffering. These mice were deemed to be very close to death, and the time of culling was used to determine a survival time for statistical analysis. Where mice were found dead, the survival time was taken as the last time point when the mouse was monitored alive.

Interpretation of Results

A positive result was taken as any DNA sequence that was cloned and used in challenge experiments as described above which gave protection against that challenge. Protection was taken as those DNA sequences that gave statistically significant protection (to a 95% confidence level ($p<0.05$)) and also those which were marginal or close to significant using Mann-Whitney or which show some protective features for example there were one or more outlying mice or because the time to the first death was prolonged. It is acceptable to allow marginal or non-significant results to be considered as potential positives when it is considered that the clarity of some of the results may be clouded by the problems associated with the administration of intranasal infections.

Results for vaccine trials 2, 7 and 8 (see FIG. 1)

| Mouse number | Unvacc control (2) | ID210 (2) | Unvacc control (7) | 4172.5 (7) | Unvacc control (8) | ID211 (8) | 4197.4 (8) | 4122.1 (8) | 4126.7 (8) |
|---|---|---|---|---|---|---|---|---|---|
| | | | | | Mean survival times (hours) | | | | |
| 1 | 49.0 | 55.0 | 59.6 | 72.6 | 45.1 | 102.3T | 60.1 | 50.6 | 60.0 |
| 2 | 51.0 | 46.5 | 47.2 | 67.9 | 50.8 | 55.5 | 54.9 | 77.2 | 60.0 |
| 3 | 49.0 | 49.0 | 59.6 | 54.4 | 60.4 | 60.6* | 68.4 | 60.3 | 54.8 |
| 4 | 55.0 | 59.0 | 70.9 | 75.3 | 55.2 | 45.3 | 60.1 | 50.6 | 52.6 |
| 5 | 49.0 | 55.0 | 68.6* | 70.9 | 45.1 | 55.5 | 54.9 | 50.6* | 54.8 |
| 6 | 49.0 | 49.0 | 76.0 | 75.3 | 45.1 | 102.3T | 52.7 | 44.9 | 60 |
| Mean | 50.3 | 52.3 | 63.6 | 69.4 | 50.2 | 70.2 | 58.5 | 55.7 | 57.0 |
| sd | 2.4 | 4.8 | 10.3 | 7.9 | 6.4 | 25.3 | 5.7 | 11.6 | 3.4 |
| p value 1 | — | 0.3333 | — | 0.2104 | — | 0.0215 | 0.0621 | 0.4038 | 0.0833 |

*bubbled when dosed so may not have received full inoculum.
Tterminated at end of experiment having no symptoms of infection.
Numbers in brackets - survival times disregarded assuming incomplete dosing
p value 1 refers to significance tests compared to unvaccinated controls Statistical Analyses.

Trial 2—The group vaccinated with ID210 also had a longer mean survival time than the unvaccinated controls but the results are not statistically significant.

Trial 7—The group vaccinated with 4172.5 showed much greater survival times than unvaccinated controls although the differences were not statistically significant.

Trial 8—The group vaccinated with ID211 survived significantly longer than unvaccinated controls 4197.4, 4122.1 and 4126.7 vaccinated groups showed longer mean survival times than the unvaccinated group but the results were not statistically significant. The 4197.4 and 4126.7 groups also showed a prolonged time to the first death and the 4122.1 group showed 1 outlying result.

Figure 2:
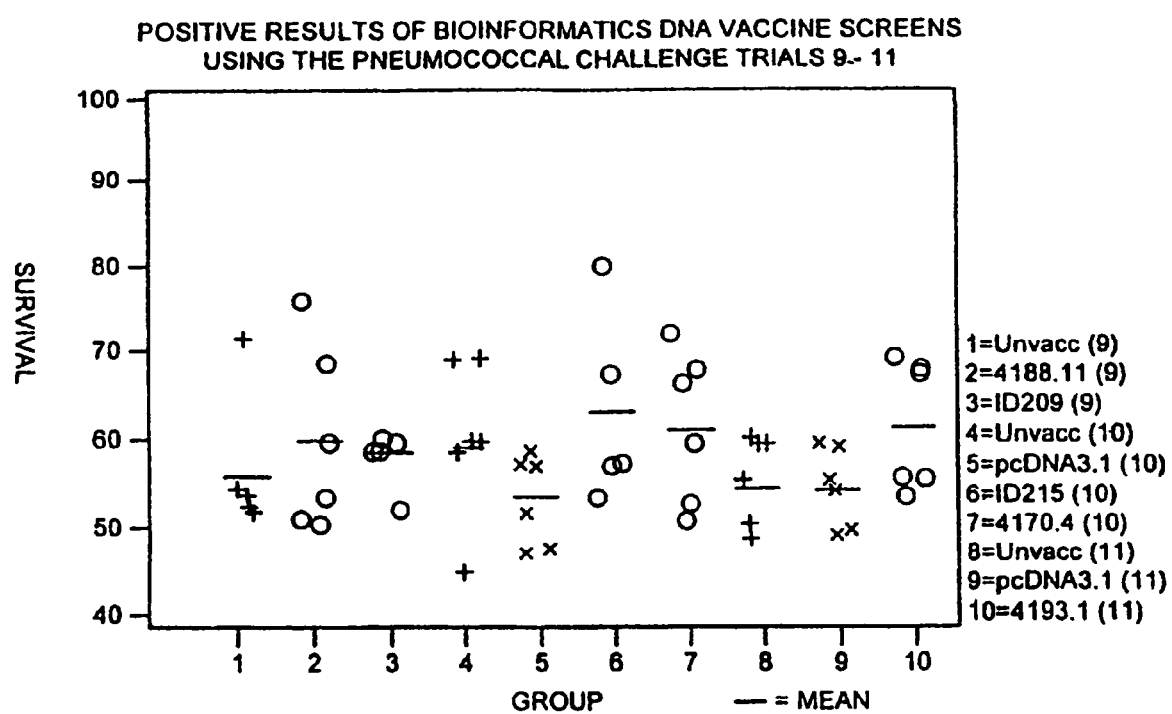
FIG. 2: shows the results of further DNA vaccine trials.

Results of pneumococcal challenge DNA vaccination trials 9-11 (see FIG. 2)

| Mouse number | Unvacc control (9) | 4188.11 (9) | ID209 (9) | Unvacc control (10) | pcDNA3.1+ (10) | ID215 (10) | 4170.4 (10) | Unvacc control (11) | pcDNA3.1+ (11) | 4193.1 (11) |
|---|---|---|---|---|---|---|---|---|---|---|
| | | | | | Mean survival times (hours) | | | | | |
| 1 | (98.5)T | 69.4 | 60.2 | 68.4 | 58.6 | 79.2 | 68.1 | 60.0 | 53.2 | 54.8 |
| 2 | 53.4 | 53.7 | 60.2 | 59.0 | 58.6 | 54.2 | 58.6 | 50.0 | 50.4 | 54.8 |
| 3 | 53.4 | 51.2 | 60.2 | 59.0 | 50.8 | (103.2)*T | 50.9 | 60.0 | 55.4 | 68.7* |
| 4 | 53.4 | 75.0 | (98.0)*T | 45.1* | 58.6 | 58.8 | 72.1 | 55.0 | 60.6 | 54.8 |
| 5 | 70.8 | 51.2 | 60.2 | 68.4 | 46.5 | 68.3 | 68.1 | 60.0 | 50.4 | 68.7 |
| 6 | 53.4 | 61.2 | 52.9 | 59.0 | 48.9 | 58.8 | 54.0 | 50.0 | 60.6 | 68.7* |
| Mean | 56.9 | 60.3 | 58.8 | 59.8 | 53.6 | 63.9 | 62.0 | 55.8 | 55.1 | 61.7 |
| Sd | 7.8 | 10.0 | 3.3 | 8.5 | 5.6 | 10.0 | 8.7 | 5.0 | 4.6 | 7.6 |
| p value 1 | — | 0.3894 | 0.2519 | — | 0.0307 | <30.0 | <39.0 | — | — | 0.1837 |
| p value 2 | — | — | — | — | — | 0.0168 | 0.0316 | — | — | 0.0829 |

*bubbled when dosed so may not have received full inoculum.
Tterminated at end of experiment having no symptoms of infection.
Numbers in brackets - survival times disregarded assuming incomplete dosing
p value 1 refers to significance tests compared to unvaccinated controls
p value 2 refers to significance tests compared to pcDNA3.1+ vaccinated controls Statistical Analyses.

Trial 9—Although not statistically significant the groups vaccinated with 4188.11 and ID209 did have noticeably higher mean survival times than unvaccinated controls.

Trial 10—The unvaccinated control group survived for a significantly longer period than the pcDNA3.1+ vaccinated group. The groups vaccinated with ID215 and 4170.4 showed statistically significant longer survival times compared to the sham vaccinated group (p=0.0168 and 0.0316) but not compared to the unvaccinated group.

Trial 11—The group vaccinated with 4193.1 was the most promising and survived an average of 6.5 hours longer than the pcDNA3.1+ vaccinated group and 6 hours longer than the unvaccinated group although the results were not statistically significant.

TABLE 1

4101.1 (SEQ. ID. NO. 208)

ATGGAAGAGTTAGTGACCTTAGATTGTTTGTTTATTGACAGAACTAAGATTGAAGCC
AATGCCAACAAGTATAGTTTTGTGTGGAAGAAAACGACAGAGAAATTCTCCGCCAA
ACTTCAAGAACAGATACAGGTCTATTTTCAAGAAGAAATCACTCCCCTTCTGATTAA
ATATGCCATGTTTGATAAGAAACAAAAGAGAGGGTATAAAGAGTCAGCTAAAAACT
TAGCGAATTGGCACTATAATGACAAGGAGGATAGCTACACACATCCTGATGGCTGG
TATTATCGTTTTCACCATACCAAATATCAGAAAACACAGACAGACTTTCAACAAGAA
ATCAAGGTTTACTACGCCGACGAACCTGAATCAGCCCCTCAAAAGGGACTGTATATG
AACGAACGCTATCAAAACTTGAAAGCTAAAGAATGTCAGGCGCTTTTATCTCCCCAA
GGTAGACAGATTTTCGCTCAACGCAAGATTGATGTGGAACCTGTCTTTGGGCAGATA
AAGGCTTCTTTGGGTACAAGAGATGTAATCTGAGAGGGAAGCGTCAAGTGAGAAT
TGACATGGGATTGGTACTTATGGCCAATAACCTCCTAAAATATAGTAAAATGAAATA
A 4101.3 (SEQ. ID. NO. 209)

ATGGGGAAAGGCCATTGGAATCGGAAAAGAGTTTATAGCATTCGTAAGTTTGCTGT
GGGAGCTITGCTCAGTAATGATTGGGACTTGTGCAGTTTTATTAGGAGGAAATATAGC
TGGAGAATCTGTAGTTTATGCGGATGAAACACTTATTACTCATACTGCTGAGAAACC
TAAAGAGGAAAAAATGATAGTAGAAGAAAAGGCTGATAAAGCTTTGGAAACTAAA
AATATAGTTGAAAGGACAGAACAAAGTGAACCTAGTTCAACTGAGGCTATTGCATC
TGAGAAGAAAGAAGATGAAGCCGTAACTCCAAAAGAGGAAAAAGTGTCTGCTAAA
CCGGAAGAAAAAGCTCCAAGGATAGAATCACAAGCTTCAAATCAAGAAAAACCGCT
CAAGGAAGATGCTAAAGCTGTAACAAATGAAGAAGTGAATCAAATGATTGAAGACA
GGAAAGTGGATTTTAATCAAAATTGGTACTTTAAACTCAATGCAAATTCTAAGGAAG
CCATTAAACCTGATGCAGACGTATCTACGTGGAAAAAATTAGATTTACCGTATGACT
GGAGTATCTTTAACGATTTCGATCATGAATCTCCTGCACAAAATGAAGGTGGACAGC
TCAACGGTGGGGAAGCTTGGTATCGCAAGACTTTCAAACTAGATGAAAAAGACCTC
AAGAAAAATGTTCGCCTTACTTTTGATGGCGTCTACATGGATTCTCAAGTTTATGTCA
ATGGTCAGTTAGTGGGGCATTATCCAAATGGTTATAACCAGTTCTCATATGATATCA
CCAAATACCTTCAAAAAGATGGTCGTGAGAATGTGATTGCTGTCCATGCAGTCAACA
AACAGCCAAGTAGCCGTTGGTATTCAGGAAGTGGTATCTATCGTGATGTGACTTTAC
AAGTGACAGATAAGGTGCATGTTGAGAAAAATGGGACAACTATTTTAACACCAAAA
CTTGAAGAACAACAACATGGCAAGGTTGAAACTCATGTGACCAGCAAAATCGTCAA
TACGGACGACAAAGACCATGAACTTGTAGCCGAATATCAAATCGTTGAACGAGGTG
GTCATGCTGTAACAGGCTTAGTTCGTACAGCGAGTCGTACCTTAAAAGCACATGAAT
CAACAAGCCTAGATGCGATTTTAGAAGTTGAAAGACCAAAACTCTGGACTGTTTAA
ATGACAAACCTGCCTTGTACGAATTGATTACGCGTGTTTACCGTGACGGTCAATTGG
TTCATGCTAAGAAGGATTTGTTTGGTTACCGTTACTATCACTGGACTCCAAATGAAG
GTTTCTCTTTGAATGGTGAACGTATTAAATTCCATGGAGTATCCTGCACCACGACC
ATGGGGCGCTTGGAGCAGAAGAAAACTATAAAGCAGAATATCGCCGTCTCAAACAA
ATGAAGGAGATGGGAGTTAACTCCATCCGTACAACCCACAACCCTGCTAGTGAGCA
AACCTTGCAAATCGCAGCAGAACTAGGTTTACTCGTTCAGGAAGAGGCCTTTGATAC
GTGGTATGGTGGCAAGAAACCTTATGACTATGGACGTTTCTTTGAAAAAGATGCCAC
TCACCCAGAAGCTCGAAAAGGTGAAAAATGGTCTGATTTTGACCTACGTACCATGGT
CGAAAGAGGCAAAAACAACCCTGCTATCTTCATGTGGTCAATTGGTAATGAAATAG
GTGAAGCTAATGGTGATGCCCACTCTTTAGCAACTGTTAAACGTTTGGTTAAGGTTA
TCAAGGATGTTGATAAGACTCGCTATGTTACCATGGGAGCAGATAAATCCGTTTCG
GTAATGGTAGCGGAGGGCATGAGAAAATTGCTGATGAACTCGATGCTGTTGGATTT
AACTATTCTGAAGATAATTACAAAGCCCTTAGAGCTAAGCATCCAAAATGGTTGATT
TATGGATCAGAAACATCTTCAGCTACCCGTACACGTGGAAGTTACTATCGCCCTGAA
CGTGAATTGAAACATAGCAATGGACCTGAGCGTAATTATGAACAGTCAGATTATGG
AAATGATCGTGTGGGTTGGGGGAAAACAGCAACCGCTTCATGGACTTTTGACCGTG
ACAACGCTGGCTATGCTGGACAGTTTATCTGGACAGGTACGGACTATATTGGTGAAC
CTACACCATGGCACAACCAAAATCAAACTCCTGTTAAGAGCTCTTACTTTGGTATCG
TAGATACAGCCGGCATTCCAAAACATGACTTCTATCTCTACCAAAGCCAATGGGTTT
CTGTTAAGAAGAAACCGATGGTACACCTTCTTCCTCACTGGAACTGGGAAAACAAA
GAATTAGCATCCAAAGTAGCTGACTCAGAAGGTAAGATTCCAGTTCGTGCTTATTCG
AATGCTTCAGTGTAGAATTGTTCTTGAATGGAAAATCTCTTGGTCTTAAGACTTTCA
ATAAAAAACAAACCAGCGATGGGCGGACTTACCAAGAAGGTGCAAATGCTAATGAA
CTTTATCTTGAATGGAAAGTTGCCTATCAACCAGGTACCTTGGAAGCAATTGCTCGT
GATGAATCTGGCAAGGAAATTGCTCGAGATAAGATTACGACTGCTGGTAAGCCAGC
GGCAGTTCGTCTTATTAAGGAAGACCATGCGATTGCAGCAGATGGAAAAGACTTGA
CTTACATCTACTATGAAATTGTTGACAGCCAGGGGAATGTGGTTCCAACTGCTAATA
ATCTGGTTCGCTTCCAATTGCATGGCCAAGGTCAACTGGTCGGTGTAGATAACGGAG
AACAAGCCAGCCGTGAACGCTATAAGGCGCAAGCAGATGGTTCTTGGATTCGTAAA
GCATTTAATGGTAAAGGTGTGCCATTGTCAAATCAACTGAACAAGCAGGGAAATTC

TABLE 1-continued

```
ACCCTGACTGCCCACTCTGATCTCTTGAAATCGAACCAAGTCACTGTCTTTACTGGTA
AGAAAGAAGGACAAGAGAAGACTGTTTTGGGGACAGAAGTGCCAAAAGTACAGAC
CATTATTGGAGAGGCACCTGAAATGCCTACCACTGTTCCGTTTGTATACAGTGATGG
TAGCCGTGCAGAACGTCCTGTAACCTGGTCTTCAGTAGATGTGAGCAAGCCTGGTAT
TGTAACGGTGAAAGGTATGGCTGACGGACGAGAAGTAGAAGCTCGTGTAGAAGTGA
TTGCTCTTAAATCAGAGCTACCAGTTGTGAAACGTATTGCTCCAAATACTGACTTGA
ATTCTGTAGACAAATCTGTTTCCTATGTTTGATTGATGGAAGTGTTGAAGAGTATG
AAGTGGACAAGTGGGAGATTGCCGAAGAAGATAAAGCTAAGTTAGCAATTCCAGGT
TCTCGTATTCAAGCGACCGGTTATTTAGAAGGTCAACCAATTCATGCAACCCTTGTG
GTAGAAGAAGGCAATCCTGCGGCACCTGCAGTACCAACTGTAACGGTTGGTGGTGA
GGCAGTAACAGGTCTTACTAGTCAAAAACCAATGCAATACCGCACTCTTGCTTATGG
AGCTAAGTTGCCAGAAGTCACAGCAAGTGCTAAAAATGCAGCTGTTACAGTTCTTCA
AGCAAGCGCAGCAAACGGCATGCGTGCGAGCATCTTTATTCAGCCTAAAGATGGTG
GCCCTCTTCAAACCTATGCAATTCAATTCCTTGAAGAAGCGCCAAAAATTGCTCACT
TGAGCTTGCAAGTGGAAAAAGCTGACAGTCTCAAAGAAGACCAAACTGTCAAATTG
TCGGTTCGAGCTCACTATCAAGATGGAACGCAAGCTGTATTACCAGCTGATAAAGTA
ACCTTCTCTACAAGTGGTGAAGGGAAGTCGCAATTCGTAAAGGAATGCTTGAGTTG
CATAAGCCAGGAGCAGTCACTCTGAACGCTGAATATGAGGGAGCTAAAGACCAAGT
TGAACTCACTATCCAAGCCAATACTGAGAAGAAGATTGCGCAATCCATCCGTCCTGT
AAATGTAGTGACAGATTTGCATCAGGAACCAAGTCTTCCAGCAACAGTAACAGTTG
AGTATGACAAAGGTTTCCCTAAAACTCATAAAGTCACTTGGCAAGCTATTCCGAAAG
AAAAACTAGACTCCTATCAAACATTTGAAGTACTAGGTAAAGTTGAAGGAATTGAC
CTTGAAGCGCGTGCAAAAGTCTCTGTAGAAGGTATCGTTTCAGTTGAAGAAGTCAGT
GTGACAACTCCAATCGCAGAAGCACCACAATTACCAGAAAGTGTTCGGACATATGA
TTCAAATGGTCACGTTTCATCAGCTAAGGTTGCATGGGATGCGATTCGTCCAGAGCA
ATACGCTAAGGAAGGTGTCTTTACAGTTAATGGTCGCTTAGAAGGTACGCAATTAAC
AACTAAACTTCATGTTCGCGTATCTGCTCAAACTGAGCAAGGTGCAAACATTTCTGA
CCAATGGACCGGTTCAGAATTGCCACTTGCCTTTGCTTCAGACTCAAATCCAAGCGA
CCCAGTTTCAAATGTTAATGACAAGCTCATTTCCTACAATAACCAACCAGCCAATCG
TTGGACAAACTGGAATCGTACTAATCCAGAAGCTTCAGTCGGTGTTCTGTTTGGAGA
TTCAGGTATCTTGAGCAAACGCTCCGTTGATAATCTAAGTGTCGGATTCCATGAAGA
CCATGGAGTTGGTGTACCGAAGTCTTATGTGATTGAGTATTATGTTGGTAAGACTGT
CCCAACAGCTCCTAAAAACCCTAGTTTTGTTGGTAATGAGGACCATGTCTTTAATGA
TTCTGCCAACTGGAAACCAGTTACTAATCTAAAAGCCCCTGCTCAACTCAAGGCTGG
AGAAATGAACCACTTTAGCTTTGATAAAGTTGAAACCTATGCTGTTCGTATTCGCAT
GGTTAAAGCAGATAACAAGCGTGGAACGTCTATCACAGAGGTACAAATCTTTGCGA
AACAAGTTGCGGCAGCCAAGCAAGGACAAACAAGAATCCAAGTTGACGGCAAAGA
CTTAGCAAACTTCAACCCTGATTTGACAGACTACTACCTTGAGTCTGTAGATGGAAA
AGTTCCGGCAGTCACAGCAAGTGTTAGCAACAATGGTCTCGCTACCGTCGTTCCAAG
CGTTCGTGAAGGTGAGCCAGTTCGTGTCATCGCGAAAGCTGAAAATGGCGACATCTT
AGGAGAATACCGTCTGCACTTCACTAAGGATAAGAGCTTACTTTCTCATAAACCAGT
TGCTGCGGTTAAACAAGCTCGCTTGCTACAAGTAGGTCAAGCACTTGAATTGCCGAC
TAAGGTTCCAGTTTACTTCACAGGTAAAGACGGCTACGAAACAAAAGACCTGACAG
TTGAATGGGAAGAAGTTCCAGCGGAAAATCTGACAAAAGCAGGTCAATTTACTGTT
CGAGGCCGTGTCCTTGGTAGTAACCTTGTTGCTGAGATCACTGTACGAGTGACAGAC
AAACTTGGTGAGACTCTTTCAGATAACCCTAACTATGATGAAAACAGTAACCAGGCC
TTTGCTTCAGCAACCAATGATATTGACAAAAACTCTCATGACCGCGTTGACTATCTC
AATGACGGAGATCATTCAGAAAATCGTCGTTGGACAAACTGGTCACCAACACCATC
TTCTAATCCAGAAGTATCAGCGGGTGTGATTTTCCGTGAAAATGGTAAGATTGTAGA
ACGGACTGTTACACAAGGAAAAGTTCAGTTCTTTGCAGATAGTGGTACGGATGCACC
ATCTAAACTCGTTTTAGAACGCTATGTCGGTCCAGAGTTTGAAGTGCCAACCTACTA
TTCAAACTACCAAGCCTACGACGCAGACCATCCATTCAACAATCCAGAAAATTGGG
AAGCTGTTCCTTATCGTGCGGATAAAGACATTGCAGCTGGTGATGAAATCAACGTAA
CATTTAAAGCTATCAAAGCCAAAGCTATGAGATGGCGTATGGAGCGTAAAGCAGAT
AAGAGCGGTGTTGCGATGATTGAGATGACCTTCCTTGCACCAAGTGAATTGCCTCAA
GAAAGCACTCAATCAAAGATTCTTGTAGATGGAAAAGAACTTGCTGATTTCGCTGAA
AATCGTCAAGACTATCAAATTACCTATAAAGGTCAACGGCCAAAAGTCTCAGTTGA
AGAAAACAATCAAGTAGCTTCAACTGTGGTAGATAGTGGAGAAGATAGCTTTCCAG
TACTTGTTCGCCTCGTTTCAGAAAGTGGAAAACAAGTCAAGGAATACCGTATCCACT
TGACTAAGGAAAAACCAGTTTCTGAGAAGACAGTTGCTGCTGTACAAGAAGATCTT
CCAAAAATCGAATTTGTTGAAAAAGATTTGGCATACAAGACAGTTGAGAAAAAGA
TTCAACACTGTATCTAGGTGAAACTCGTGTAGAACAAGAAGGAAAAGTTGGAAAAG
AACGTATCTTTACAGCGATTAATCCTGATGGAAGTAAGGAAGAAAAACTCCGTGAA
GTGGTAGAAGTTCCGACAGACCGCATCGTCTTGGTTGGAACCAAACCAGTAGCTCA
AGAAGCTAAAAAACCACAAGTGTCAGAAAAGCAGATACAAAACCAATTGATTCAA
GTGAAGCTAGTCAAACTAATAAAGCCCAGTTACCAAGTACAGGTAGTGCGGCAAGC
CAAGCAGCAGTAGCAGCAGGTTTAACTCTTCTAGGTTTGAGTGCAGGATTAGTAGTT
ACTAAAGGTAAAAAAGAAGACTAG
```

4101.5 (SEQ. ID. NO. 210)

```
ATGGATGCAATCTTTGACCTAATCGGAAAGGTTTTCAATCCCATCTTAGAAATGGGT
GGACCTGTCATCATGTTAATCATTTTGACAGTATTGGCTTTACTTTTTGGAGTGAAAT
TCTCCAAAGCGCTTGAAGGTGGTATCAAACTTGCCATCGCTCTTACAGGTATCGGTG
CTATCATCGGTATGCTAAACACTGCTTTCTCAGCATCACTAGCAAAATTCGTTGAAA
ACACTGGTATCCAATTGAGTATTACCGACGTTGGTTGGGCACCACTTGCTACAATCA
CTTGGGGTTCTGCTTGGACACTATACTCTTGCTCATCATGTTGATTGTCAACATAGT
GATGCTAGCTATGAAGAAAACAGATACACTTGATGTCGATATCTTTGATATCTGGCA
CTTGTCTATCACAGGTCTCTTGATTAAATGGTATGCTGATAACAATGGTGTGAGTCA
```

TABLE 1-continued

```
AGGGGTTTCACTCTTTATTGCTACAGCAGCTATCGTCCTTGTCGGTGTGTTGAAAATT
ATCAACTCTGACTTGATGAAACCTACATTTGATGACCTTCTTAACGCCCCAAGTTCAT
CACCAATGACATCAACTCACATGAACTACATGATGAACCCAGTTATCATGGTTTTGG
ATAAGATTTTTGAAAAATTCTTCCCAGGCCTTGATAAATATGACTTTGATGCTGCTA
AATTGAACAAGAAAATCGGTTTCTGGGGATCTAAATTCTTCATCGGTTTCATCCTTG
GTATCGTTATCGGTATTATGGGAACTCCACATCCAATTGCAGGTGTTGCAGATGCAG
ATAAATGGCGTCTTGTTATCAAAGGATGGTTGTCTCTTGGTTTGACTGCCGGTGTATC
TTTGGAACTCTTCTCACTTATCGGTTCATGGTTCATCGCAGCCGTAGAACCACTATCA
CAAGGTATTACAAACGTTGCTACTAAACGTCTTCAAGGACGTAAATTCAATATCGGT
CTTGACTGGCCATTCATCGCTGGTCGTGCTGAAATCTGGGCTTGTGCCAACGTACTT
GCACCAATCATGTTGATTGAAGCAGTGCTCTTTCAAAAGTTGGAAATGGTATCTTG
CCACTTGCAGGTATCATCGCTATGGGTGTTACTCCAGCTCTCTTGGTTGTAACTCGTG
GTAAATTGCTCCGTATGATTATCTTCGGAACACTCTTGTTGCCACTCTTCCTTCTTTC
AGGTACACTTATTGCACCATTTGCAACAGAACTTGCTAAAGGTGTAGGTGCCTTCCC
AGAAGGTGTGAGCCAAACTCAATTGATTACTCACTCTACTCTTGAAGGACCAATCGA
AAAACTTCTTGGTTGGACAATTGGTAACACTACAACTGGTGATATCAAAGCAATCCT
TGGTGCAGTAGTCTTCCTTGTATTCTATATCGGTATCTTTGGTTGGTACAGAAAACAA
ATGATCAAACGTAACGAAGAGTACGCAGCAAAAGCAAAATAA 4102.1 (SEQ. ID. NO. 211)

ATGAAGATTATGAAAAAAAAATATTGGACTTTAGCGATATTATTCTTTTGTTTGTTCA
ATAATTCTGTTACTGCTCAAGAAATACCTAAAAATCTTGATGGCAATATAACTCACA
CTCAGACTAGCGAAAGTTTTTCTGAATCTGATGAAAAACAGGTTGACTATTCTAATA
AAAATCAAGAAGAAGTAGACCAAAATAAATTTCGTATTCAAATCGATAAGACAGAA
TTATTTGTAACAACAGATAAACATTTAGAAAAAAACTGTTGTAAATTGGAACTTGAA
CCACAAATAAATAACGATATTGTTAACTCTGAAAGTAATAATTTACTAGGCGAAGAT
AATTTAGATAATAAAATTAAGGAAAATGTTTCTCATCTAGATAATAGAGGAGGAAA
TATAGAGCATGACAAAGATAACTTAGAATCGTCGATTGTAAGAAAATATGAATGGG
ATATAGATAAAGTTACTGGTGAGGCGAAAGTTATAAATTATATTCTAAAAGTAAT
CTAAAGTTTCAATTGCTATTTTAGATTCAGGAGTCGATTTACAAAATACTGGATTACT
GAAAAATCTTTCAAATCACTCAAAAAACTATGTCCCCAATAAAGGATATTTAGGAA
AAGAGGAGGGAGGAAGGAATAATATCAGATATTCAAGATAGATTAGGTCATGGT
ACGGCTGTTGTAGCTCAAATTGTAGGGGATGACAATATTAATGGAGTAAATCCTCAC
GTTAATATTAACGTCTATAGAATATTTGGTAAGTCGTCAGCTAGTCCAGATTGGATT
GTAAAAGCAATTTTTGATGCTGTAGATGATGGCAATGATATTATCAATCTTAGTACT
GGACAATATTTAATGATTGATGGAGAATATGAGGACGGAACAAATGATTTGAAAC
ATTTTGAAGTATAAAAAGGCTATTGATTACGCGAATCAAAAAGGAGTAATTATAGT
AGCTGCATTAGGGAATGACTCCCTAAATGTATCAAATCAGTCAGATTTATTGAAACT
TATTAGTTCACGCAAAAAAGTAAGAAAACCAGGATTAGTAGTTGATGTTCCAAGTTA
TTTCTCATCTACAATTTCGGTCGGAGGCATAGATCGCTTAGGTAATTTATCAGATTTT
AGCAATAAAGGGGATTCTGATGCAATATATGCGCCTGCAGGCTCAACATTATCTCTT
TCAGAATTAGGACTTAATAACTTTATTAATGCAGAAAATATAAAGAAGATTGGATT
TTTTCGGCAACACTAGGAGGATATACGTATCTTTATGGAAACTCATTTGCTGCTCCTA
AAGTTTCTGGTGCGATTGCAATGATTATTGATAAATACAAATTAAAAGATCAGCCCT
ATAATTATATGTTTGTAAAAAAATTCTGGAAGAAACATTACCAGTAA 4106.1 (SEQ. ID. NO. 212)

ATGAAGAAAACATGGAAAGTGTTTTTAACGCTTGTAACAGCTCTTGTAGCTGTTGTG
CTTGTGGCCTGTGGTCAAGGAACTGCTTCTAAAGACAACAAAGAGGCAGAACTTAA
GAAGGTTGACTTTATCCTAGACTGGACACCAAATACCAACCACACAGGGCTTTATGT
TGCCAAGGAAAAAGGTTATTTCAAAGAAGCTGGAGTGGATGTTGATTGAAATTGC
CACCAGAAGAAAGTTCTTCTGACTTGGTTATCAACGGAAAGGCACCATTTGCAGTGT
ATTTCCAAGACTACATGGCTAAGAAATTGGAAAAAGGAGCAGGAATCACTGCCGTT
GCAGCTATTGTTAACACAATACATCAGGAATCATCTCTCGTAAATCTGATAATGTA
AGCAGTCCAAAAGACTTGGTTGGTAAGAAATATGGGACATGGAATGACCCAACTGA
ACTTGCTATGTTGAAAACCTTGGTAGAATCTCAAGGTGGAGACTTTGAAAGGTTGA
AAAAGTACCAAATAACGACTCAAACTCAATCACACCGATTGCCAATGGCGTCTTTGA
TACTGCTTGGATTTACTACGGTTGGGATGGTATCCTTGCTAAATCTCAAGGTGAGAT
GCTAACTTCATGTACTTGAAAGACTATGTCAAGGAGTTTGACTACTATTCACCAGTT
ATCATCGCAAACAACGACTATCTGAAAGATAACAAAGAAGAAGCTCGCAAAGTCAT
CCAAGCCATCAAAAAAGGCTACCAATATGCCATGGAACATCCAGAAGAAGCTGCAG
ATATTCTCATCAAGAATGCACCTGAACTCAAGGAAAAACGTGACTTTGTCATCGAAT
CTCAAAAATACTTGTCAAAAGAATACGCAAGCGACAAGGAAAATGGGGTCAATTT
GACGCAGCTCGCTGGAATGCTTTCTACAAATGGGATAAAGAAAATGGTATCCTTAA
AGAAGACTTGACAGACAAAGGCTTCACCAACGAATTTGTGAAATAA 4106.4 (SEQ. ID. NO. 213)

ATGATAAAAAATCCTAAATTATTAACCAAGTCTTTTTTAAGAAGTTTTGCAATTCTA
GGTGGTGTTGGTCTAGTCATTCATATAGCTATTTATTTGACCTTTCCTTTTTATTATAT
TCAACTGGAGGGGAAAAGTTTAATGAGAGCGCAAGAGTGTTTACGGAGTATTTAA
AGACTAAGACATCTGATGAAATTCCAAGCTTACTCCAGTCTTATTCAAAGTCCTTGA
CCATATCTGCTCACCTTAAAAGAGATATTGTAGATAAGCGGCTCCCTCTTGTGCATG
ACTTGGATATTAAAGATGGAAAGCTATCAATTTATATCGTGATGTTAGATATGTCTG
TTAGTACAGCAGATGGTAAACAGGTAACCGTGCAATTTGTTCACGGGGTGGATGTCT
ACAAAGAAGCAAAGAATATTTTGCTTTTGTATCTCCCATATACATTTTTGGTTACAAT
TGCTTTTTCCTTTGTTTTTCTTATTTTTATACTAAACGCTTGCTCAATCCTCTTTTTTA
```

TABLE 1-continued

CATTTCAGAAGTGACTAGTAAAATGCAAGATTTGGATGACAATATTCGTTTTCATCA
AACTAGGAAAGATGAAGTTGGTGAAGTTGGAAAACAGATTAATGGTATGTATGAGC
ACTTGTTGAAGGTTATTTATGAGTTGGAAAGTCTGTAATGAGCAAATTGTAAATTG
CAAAATCAAAAGGTTTCCTTTGTCCGCGGAGCATCACATGAGTTGAAAACCCCTTTA
GCCAGTCTTAGAATTATCCTAGAGAATATGCAGCATAATATTGGAGATTACAAAGAT
CATCCAAATATATTGCAAAGAGTATAAATAAGATTGACCAGATGAGCCACTTATTA
GAAGAAGTACTGGAGTCTTCTAAATTCCAAGAGTGGACAGAGTGTCGTGAGACCTT
GACTGTTAAGCCAGTTTTAGTAGATATTTTATCACGTTATCAAGAATTAGCTCATTCA
ATAGGTGTTACAATTGAAAATCAATTGACAGATGCTACCAGGGTCGTCATGAGTCTT
AGGGCATTGGATAAGGTTTTGACAAACCTGATTAGTAATGCAATTAAATATTCAGAT
AAAAATGGGCGTGTAATCATATCCGAGCAAGATGGCTATCTCTCTATCAAAAATACA
TGTGCGCCTCTAAGTGACCAAGAACTAGAACATTTATTTGATATATTCTATCATTCTC
AAATCGTGACAGATAAGGATGAAAGTTCCGGTTTGGGTCTTTACATTGTGAATAATA
TTTTAGAAAGCTATCAATGGATTATAGTTTTCTCCCTTATGAACACGGTATGGAATT
TAAGATTAGCTTGTAG 4106.6 (SEQ. ID. NO. 214)

ATGTATTTAGGAGATTTGATGGAGAAAGCCGAGTGTGGTCAATTTTCAATACTTTCC
TTTCTATTACAAGAGTCTCAGACGACCGTCAAGGCTGTAATGGAAGAAACAGGATTT
TCAAAAGCAACCCTAACCAAATATGTCACCCTGCTCAATGACAAGGCTTTGGATAGT
GGCTTAGAGCTGGCTATTCACTCAGAAGATGAAAATCTGCGTCTGTCTATCGGTGCA
GCTACCAAGGGGAGAGATATTCGGAGCTTGTTTTTGGAGAGTGCTGTTAAATACCAG
ATTTTGGTTTATCTTCTACCACCAACAGTTTTTAGCCCATCAGCTGGCTCAAGAAT
TGGTGATTAGCGAGGCTACGCTTGTCGTCACTTGGCTGGTTTAAATCAGATTTTGTC
AGAATTGATTTATCCATCCAAAATGGCCGTTGGCGAGGTCCAGAGCATCAGATTCA
CTATTTCTATTTCTGTCTTTTCCGAAAGGTCTGGTCGAGTCAGGAATGGGAAGGTCA
CATGCAGAAACCAGAGAGAAAACAGGAGATTGCCAATTTAGAGGAAATCTGCGGTG
CAAGTTTGTCTGCGGGGCAGAAATTGGACTTGGTTCTCTGGGCTCACATCAGTCAAC
AACGTCTTCGGGTCAATGCTTGTCAGTTTCAAGTCATAGAAGAGAAAATGCGAGGGT
ATTTTGACAATATCTTTTATCTTCGTTTGCTGAGAAAGGTTCCGTCCTTTTTGCTGG
GCAACATATTCCACTAGGAGTTGAGGATGGTGAGATGATGATATTCTTCTCTTTTCTC
CTATCTCATCGCATCTTCCTCTTCATACTATGGAGTATATTCTGGTTTTGGAGGGC
AGTTGGCAGATTTACTGACGCAATTGATTCAAGAAATGAAGAAGGAGGAACTATTG
GGGGATTATACAGAGGACCATGTCACCTATGAACTCAGTCAGCTTTGTGCTCAAGTC
TATCTCTATAAGGGCTATATTTTACAGGATCGCTACAAGTACCAGTTAGAGAATCGT
CATCCATATTTACTGATGGAACATGATTTTAAAGAGACAGCAGAGGAGATTTTCAT
GCTCTACCTGCTTTTCAACAGGGGACAGATTTAGATAAGAAGATTCTCTGGGAATGG
CTCCAGTTAATCGAATATATGGCTGAAAACGGTGGCCAGCATATGCGGATTGGTCTG
GATTTGACATCTGGTTTTCTTGTCTTTTCAAGGATGGCAGCCATTTTGAAACGGTATT
TGGAATACAATCGTTTTATTACCATTGAAGCTTATGACCCTAGTCGGCATTATGATTT
GCTGGTTACCAATAACCCGATTCATAAGAAGGAACAGACACCAGTCTATTATTTAAA
AAATGACTTGGATATGGAGGATTTGGTAGCGATTCGCCAGTTATATTCACTTAA 4106.7 (SEQ. ID. NO. 215)

ATGGAATTTTCAAAAGAAAACACGTGAATTGTCAATTAAAAAAATGCAGGAACGTA
CCCTGGACCTCTTGATTATCGGTGGAGGAATCACAGGAGCTGGTGTAGCCTTGCAGG
CGGCAGCTAGCGGTCTTGAGACTGGTTTGATGAAATGCAAGACTTTGCAGAAGGA
ACATCTAGTCGTTCAACAAAATTGGTTCACGGAGGACTTCGTTACCTCAAACAATTT
GACGTAGAAGTGGTCTCAGATACGGTTTCTGAACGTGCAGTGGTTCAACAAATCGCT
CCACACATTCCAAAATCAGATCCAATGCTCTTACCAGTTTACGATGAAGATGGAGCA
ACCTTTAGCCTCTTCCGTCTTAAAGTAGCCATGGACTTGTACGACCTCTTGGCAGGTG
TTAGCAACACACCAGCTGCGAACAAGGTTTTGAGCAAGGATCAAGTCTTGGAACGC
CAGCCAAACTTGAAGAAGGAAGGCTTGGTAGGAGGTGGAGTGTATCTTGACTTCCG
TAACAACGATGCGCGTCTCGTGATTGAAAACATCAAACGTGCCAACCAAGACGGTG
CCCTCATTGCCAACCACGTGAAGGCAGAAGGCTTCCTCTTTGACGAAAGTGGCAAG
ATTACAGGTGTTGTAGCTCGTGATCTCTTGACAGACCAAGTGTTTGAAATCAAGGCC
CGTCTGGTTATTAATCAACAGGTCCTTGGAGTGATAAAGTACGTAATTTGTCTAAT
AAGGGAACGCAATTCTCACAAATGCGCCCAACTAAGGGAGTTCACTTGGTAGTAGA
TTCAAGCAAAATCAAGGTTTCACAGCCAGTTTACTTCGACACAGGTTTGGGTGACGG
TCGTATGGTCTTTGTTCTCCCACGTGAAAACAAGACTTACTTTGGTACAACTGATAC
AGACTACACAGGTGATTTGGAGCATCCAAAAGTAACTCAAGAAGATGTAGATTATC
TACTTGGCATTGTCAACAACCGCTTCCCAGAATCCAACATCACCATTGATGATATCG
AAAGCAGCTGGGCAGGTCTTCGTCCATTGATTGCAGGGAACAGTGCCTCTGACTATA
ATGGTGAAATAACGGTACCATCAGTGATGAAAGCTTTGACAACTTGATTGCGACTG
TTGAATCTTATCTCTCCAAAGAAAAAACACGTGAAGATGTTGAGTCTGCTGTCAGCA
AGCTTGAAAGTAGCACATCTGAGAACATTTGGATCCATCTGCAGTTTCTCGTGGGT
CTAGCTTGGACCGTGATGACAATGGTCTCTTGACTCTTGCTGGTGGTAAAATCACAG
ACTACCGTAAGATGGCTGAAGGAGCTATGAGCGCGTGGTTGACATCCTCAAAGCA
GAATTTGACCGTAGCTTTAAATTGATCAATTCTAAAACTTACCCTGTTTCAGGTGGA
GAATTGAACCCAGCAAATGTGGATTCAGAAATCGAAGCCTTTGCGCAACTTGGAGT
ATCACGTGGTTTGGATAGCAAGGAAGCTCACTATCTGGCAAATCTTTACGGTTCAAA
TGCACCGAAAGTCTTTGCACTGCTCACAGCTTGGAACAAGCGCCAGGACTCAGCTT
GGCAGATACTTTGTCCCTTCACTATGCAATGCGCAATGAGTTGACTCTTAGCCCAGT
TGACTTCCTTCTTCGTCGTACCAATCACATGCTCTTTATGCGTGATAGCTTGGATAGT
ATCGTTGAGCCAATTTTGGATGAAATGGGACGATTCTATGACTGGACAGAAGAAGA
AAAAGCAACTTACCGTGCTGATGTCGAAGCAGCTCTCGCTAACAACGATTTAGCAG
AATTAAAAAATTAA

TABLE 1-continued 4106.8 (SEQ. ID. NO. 216)

ATGATGAATGAATTATTTGGAGAATTTCTAGGGACTTTAATCCTGATTCTTCTAGGA
AATGGTGTTGTTGCAGGTGTGGTTCTTCCTAAAACCAAGAGCAATAGCTCAGGTTGG
ATTGTGATTACTATGGGTTGGGGGATTGCAGTTGCGGTTGCAGTCTTTGTATCTGGC
AAGCTCAGTCCAGCTTATTTAAACCCAGCTGTGACCATCGGTGTGGCCTTAAAAGGT
GGTTTGCCTTGGGCTTCCGTTTTGCCTTATATCTTAGCCCAGTTCGCAGGGGCCATGC
TGGGTCAGATTTTGGTTTGGTTGCAATTCAAACCTCACTATGAGGCAGAAGAAAATG
CAGGCAATATCCTGGCAACCTTCAGTACTGGACCAGCCATCAAGGATACTGTATCAA
ACTTGATTAGCGAAATCCTTGGAACTTTTGTTTTGGTGTTGACAATCTTTGCTTTGGG
TCTTTACGACTTTCAGGCAGGTATCGGAACCTTTGCAGTGGGAACTTTGATTGTCGG
TATCGGTCTATCACTAGGTGGGACAACAGGTTATGCCTTGAACCCAGCTCGTGACCT
TGGACCTCGTATCATGCACAGCATCTTGCCAATTCCAAACAAGGGAGACGGAGACT
GGTCTTACGCTTGGATTCCTGTTGTAGGCCCTGTTATCGGAGCAGCCTTGGCAGTGCT
TGTATTCTCACTTTTCTAG 4106.10 (SEQ. ID. NO. 217)

ATGAAAAGGACCTGGAGGAACTCATTCGTGACAAATCTTAATACACCTTTTATGATT
GGCAATATTGAGATTCCCAATCGTACCGTTTTAGCGCCTATGGCTGGCGTGACCAAC
TCAGCCTTTCGTACTATCGCAAAGGAGCTCGGAGCTGGACTCGTTGTAATGGAAATG
GTCTCTGACAAGGGAATCCAATACAACAACGAAAAAACCCTGCACATGCTTCATAT
CGATGAGGGCGAAAACCCTGTCTCTATCCAACTTTTTGGTAGCGATGAAGACAGCCT
AGCACGCGCAGCAGAATTCATCCAAGAAAACACCAAGACCGATATCGTCGATATCA
ACATGGGCTGCCCTGTCAACAAAATCGTGAAGAACGAAGCTGGTGCTATGTGGCTC
AAGGATCCAGACAAGATTTACTCCATCATCAACAAGGTCCAGTCTGTCCTTGATATC
CCACTTACTGTCAAAATGCGTACCGGCTGGGCGGACCCATCTCTTGCAGTAGAAAAT
GCTCTCGCTGCTGAAGCTGCAGGTGTTTCTGCCCTCGCCATGCATGGCCGTACCCGT
GAACAAATGTATACTGGCCACGCAGACCTTGAGACCCTTTACAAGGTTGCCCAAGCT
CTAACCAAGATTCCATTCATCGCCAACGGTGATATCCGTACTGTCCAAGAAGCCAAG
CAACGCATCGAAGAAGTTGGTGCTGACGCAGTCATGATTGGCCGAGCTGCCATGGG
AAATCCTTACCTCTTCAACCAAATCAACCATTACTTTGAAACAGGAGAAATCCTACC
TGATTTGACCTTTGAAGACAAGATGAAGATCGCCTAGGAACACTTGAAACGATTGAT
TAACCTCAAAGGAGAAAACGTCGCAGTTCGTGAATCCGCGGTCTCGCTCCTCACTA
TCTCCGTGGAACATCTGGCGCTGCCAAACTCCGTGGAGCCATTTCGCAAGCCAGCAC
CCTGGCAGAGATTGAAACCCTCTTGCAATTGGAGAAGGCTTAA 4107.1 (SEQ. ID. NO. 218)

ATGACAAAGAAGAAAATTGAGCGTATTTCTGTAATACACCGAGAAAAGATTTTATG
GCTCAAGTGGTATTTCATGCGAGATAAAGAACAACCTAAGTATAGTGTCCTTGAGCG
TAAAATGTTTGATGCTGCTAAAAATCAAGATATGCTAGCTTATCAAAATACGCAAC
TATCAAGCAGATAACAGATATTAGGGTACAAACAAGTGAGGCTGACATTTTAGAGG
CTGTAAAAGAGGTTTATGTGTACAATCACATGAATGTTATCGGAGCTTGTCAGCGGA
TATTATTTATCAGTCAATCACCAGCTTATGATAAGTTAAATAAGTGGTTTAATATCTA
TTCTGATTTGTATTTTAGCGTTGTACCCTTGCCCAAAATGGGGGTATATCATGAGATG
GTAGGTATCTAG 4107.2 (SEQ. ID. NO. 219)

ATGAAAAAATTCCAACGAGGCTGAGATGAAATTACTTTATACTGATATTCGGACTTCT
TTGACAGAAATTCTAACAAGAGAGGCAGAAGAGCTAGTTGCAGCTGGCAAGCGGGT
CTTCTACATTGCCCCCAACTCTCTTTCTTTTGAAAAGGAACGCGCCGTGCTGGAATAC
TTGTCCCAGCAGGCTTCTTTTCGATTACCGTCACGCGCTTTGCTCAAATGGCTCGCT
ATCTGGTCTTGAATGATTTACCAGCTAAAACTACTCTTGATGATATCGGTCTTGGGTT
GGCCTTTTACAAATGCCTTGCCGAACTCGATCCCAAGGACTTGCGTGTTTATGGCGC
TATTAAGCAGGATCCTCAATTGATCCAGCAGTTAATTGAGCTTTACCATGAGATGAC
CAAATCTCAGATGAGTTTTTTGGACTTGGAGAATTTAACAGATGAGGATAAGAGGG
CGGATTTACTCTTGATTTTTGAGAAAGTAACAGCCTATCTTAATCAAGGTCAGTTAG
CCCAGGAAAGTCAGTTGTCCCATTTGATTGAGGCTATTGAGAATGACAAGGTAAGTA
GTGATTTTAATCAAATCGCCTTGGTCATTGACGGCTTTACTCGTTTTTCTGCTGAGGA
AGAGCGGGTTGTGGACTTACTTCACGGCAAAGGTGTTGAGATTGTTATCGGGGCTTA
TGCTAGTAAGAAAGCCTATACCAGTCCTTTTAGCGAGGGCAATCTCTACCAAGCCAG
CGTAAAATTTCTCCATCATCTGGCTTCTAAATACCAAACGCCTGCTCAGGACTGTTCT
CAAACTCATGAGAAGATGGATAGTTTTGACAAGGCCTCTCGTTTGTTGGAGTCTTCT
TATGACTTTTCAGAACTCGCTTTGGATGTCGATGAGAAAGACCGTGAAAATTTACAA
ATCTGGTCTTGTTTGACGCAAAAGGAGGAGTTGGAGCTAGTAGCCCGTAGTATTCGT
CAGAAATTACATGAGAACTCAGACCTGAGCTACAAGCATTTTCGTATTCTCTTGGGG
GATGTAGCTTCTTACCAGTTATCTCTCAAAACCATTTTTGACCAGTATCAGATTCCTT
TTTATCTTGGTAGAAGCGAAGCCATGGCTCATCATCCCTTGACTCAGTTTGTCGAGTC
TATTTTAGCTTTAAAACGTTACCGTTTTCGTCAGGAGGATTTGATTAATCTTCTTAGA
ACTGATTTGTATACTGACCTCAGTCAGTCTGATATTGATGCTTTTGAGCAATATATCC
GCTATCTTGGTATCAATGGCTTGCCAGCCTTTCAGCAAACCTTCACCAAATCCCACC
ATGGAAAATTTAATCTTGAGCGTTTGAATGTCCTCCGCCTGAGAATTTTAGCACCTCT
TGAAACCCTCTTTGCCAGCCGAAAACAAAAGGCTGAAAAACTCCTACAAAAATGGA
GTGTCTTTCAAAAGAAGGAGCTGTGACCAAGCAGTTACAAGATTTGACAACCACTT
TGGAAGCTGTAGAACAGGAAAGACAAGCCGAAGTTTGGAAGGCTTTCTGCCATGTT
TTAGAACAATTTGCGACTGTTTTTGCTGGTTCACAGGTTAGTCTGGAAGACTTCCTAG

TABLE 1-continued

```
CCTGCTCCATTCTGGAATGAGTTTGTCCCAATACCGTACCATTCCAGCAACAGTGGA
CACTGTTCTGGTGCAGCGTTACGATTTGATTGCACCATTGACTGCTGACTTTGTCTAT
GCTATTGGACTAACTCAGGACCATTTACCAAAAATTTCTCAAAACACCAGTCTTCTG
ACAGATGAAGAAAGGCAAAACCTAAACCAAGCGACCGAAGAAGGCGTTCAATTACT
GATTGCCAGCAGTGAAAATCTCAAGAAAAATCGCTACACTATGCTTTCCTTGGTCAA
TTCTGCTCGTAAGCAGTTGTTCTTGTCGGCTCCAAGCCTTTTTAACGAAAGTGAAAGT
AAGGAATCTGCCTATCTTCAAGAGTTGATCCATTTTGGATTTAGGCGGAGAGAGAAG
AGGATGAATCACAAAGGACTGTCTAAGGAGGATATGGGGTCCTATCACAGTCTTTTG
TCTAGTCTGGTTGCCTATCACCAGCAGGGTGAGATGAGCGATACTGAGCAAGATTTG
ACTTTTGTCAAGGTTCTGTCGCGTGTCATAGGTAAAAAACTAGATCAGCAAGGTCTG
GAAAATCCAGCTATCCCAACCAGTCCAAGCAGCAAGACCTTAGCCAAGGACACCTT
GCAAGCTCTCTATCCTGCCAAACAGGAGTTTTACCTGTCTACGTCGGGTTTGACAGA
GTTTTATCGCAATGAATACAGTTATTTCCTACGCTACGTTTTAGGCTTGCAGGAGGA
ATTACGTTTGCATCCTGATGCCCGTAGTCACGGGAATTTCTTGCATCGTATCTTTGAA
CGCGCCTTACAGTTGCCTAATGAAGATTCCTTTGACCAACGTCTAGAACAAGCTATT
CAAGAAACCAGTCAAGAACGCGAATTTGAAGCTATTTATCAAGAAACTTTGGAAGC
CCAGTTTACCAAGGAAGTTTTGCTTGATGTTGCACGGACAACTGGACATATTCTCCG
ACACAATCCAGCCATCGAAACCATCAAAGAAGAAGCAAATTTTGGTGGAAAAGACC
AAGCCTTTATTCAATTAGACAATGGACGCAGTGTCTTTGTACGAGGCAAGGTGGACC
GGATTGACCGTTTGAAAGCTAATGGAGCGATAGGAGTAGTAGACTACAAATCCAGT
CTGACTCAGTTCCAGTTTCCTCATTTCTTTAATGGGCTCAATTCTCAGTTACCAACCT
ATCTTGCTGCCCTAAAAAGAGAAGGGGAGCAGAACTTTTTCGGCGCCATGTACTTGG
AAATGGCTGAACCTGTCCAATCTCTGATGGCGGTAAAAAGTCTGGCAGGAGCAGTG
GTAGAAGCCAGCAAATCTATGAAATACCAAGGGCTCTTCTTGGAAAAAGAAAGCAG
TTATTTAGGCGAATTTTATAACAAAAACAAGGCTAATCAACTGACAGATGAGGAATT
TCAGCTCCTACTGGACTACAATGCCTATCTTTACAAGAAAGCTGCTGAGAAGATTTT
AGCAGGCCGGTTCGCCATCAATCCTTATACTGAAAATGGCAGAAGCATTGCCCCATA
CGTCCAGCAACATCAGGCTATTACAGGCTTTGAAGCCAATTACCATCTGGGCCAAGC
CCGTTTCCTAGAAAAGTTGGACCTAGCTGATGGCAAGCGTCTGGTCGGAGAAAAAC
TCAAGCAAGCTTGGCTTGAAAAAAATAAGAGAGGAGTTGAATCGATGA
```

4107.3 (SEQ. ID. NO. 220)

```
ATGAAGCTTATTCCCTTTTTAAGTGAGGAGGAGATTCAAAAACTGCAAGAAGCAGA
AGCAAATTCGAGCAAGGAACAGAAGAAAACTGCCGAGCAAATCGAAGCTATCTACA
CTTCTGCCCAGAATATCCTGGTCTCAGCATCGGCTGGTTCTGGAAAGACCTTTGTCAT
GGCAGAGCGCATTCTGGACCAATTGGCGCGTGGTGTCGAAATTTCTCAACTCTTTAT
CTCAACCTTTACCGTCAAGGCTGCAACTGAACTTAAAGAACGTTTAGAGAAAAAAA
TCAGCAAGAAAATCCAAGAAACAGATGATGTCGACCTCAAACAACACTTGGGTCGC
CAGTTGGCAGACCTACCCAACGCTGCCATTGGAACCATGGATTCTTTCACACAAAAA
TTCCTTGGCAAACATGGTTATCTGCTTGATATTGCACCTAATTTCCGTATTTTACAAA
ACCAAAGCGAGCAACTTATTCTCGAAAACGAAGTCTTTCATGAGGTCTTTGAAGCGC
ATTACCAAGGTAAACAGAAAGAGACCTTTAGTCATTTGCTGAAAAACTTTGCTGGGC
GTGGCAAGGACGAACGGGGTCTGCGCCAGCAGGTCTATAAAATCTATGACTTCCTCC
AATCCACCAGTAATCCTCAAAAGTGGCTGAGTGAATCTTTCCTCAAAGGATTTGAGA
AAGCTGATTTTACCAGTGAAAAAGAAAAACTGACCGAGCAAATCAAACAAGCCCTT
TGGGATTTGGAAAGCTTTTTCCGTTACCATCTGGATAACGATGCCAAGGAGTTTGCA
AAGGCTGCCTATTTAGAAAATGTTCAGTAATTCTGGATGAAATTGGCTCCCTAAAT
CAGGAGTCCGATAGTCAGGCTTATCAGGCAGTGCTTGCGCGTGTTGTCGCCATCTCT
AAGGAGAAAAACGGTCGAGCTCTGACTAATGCCAGCCGTAAGGCTGATTTGAAGCC
CCTGGCTGATGCCTACAACGAAGAGAAAGACCCAGTTTGCTAAACTAGGACAAT
TATCAGACCAGATAGCGATTCTCGACTATCAAGAACGTTATCATGGAGACACTTGGA
AACTAGCTAAAACCTTCCAATCTTTCATGAGCGATTTTGTAGAGGCTTATCGTCAGA
GAAAACGACAGGAAAATGCCTTCGAATTCGCTGATATCAGCCATTACACCATTGAG
ATTTTAGAGAATTTCCCACAAGTTCGTGAGTCTTATCAGGAGCGCTTCCATGAAGTC
ATGGTCGATGAGTATCAGGATACCAACCATATTCAAGAACGGATGCTGGAATTGTTG
TCTAATGGCCACAATCGCTTTATGGTGGGAGATATCAAGCAATCCATCTATCGTTTC
CGTCAGGCAGACCCGCAGATTTTCAATGAGAAATTCCAACGCTATGCGCAAAATCC
CCAAGAAGGCAGGCTCATTATCCTCAAGGAAAATTTCCGTAGTAGTTCAGAAGTGCT
GTCAGCAACCATGATGTCTTTGAACGTCTCATGGACCAAGAGGTCGGCGAAATCA
ACTATGATAACAAGCACCAGCTTGTTTTTGCCAATACCAAACTGACTCCCAATCCAG
ACAACAAGGCAGCATTTCTCCTCTACGACAAGGACGATACAGGTGAGGAAGAAGAG
AGTCAAACAGAAACGAAACTAACAGGCGAAATGCGCTTAGTTATCAAGGAGATTCT
GAAACTTCATCAAGAAAAGGTGTTGCCTTTAAGGAAATTGCCCTTCTGACCTCCAG
CCGCAGTCGTAATGACCAGATTCTCCTCGCCCTGTCTGAGTACGGAATTCCTGTCAA
AACTGACGGAGAGCAAAACAATTATCTCCAATCCCTAGAAGTGCAAGTCATGCTAG
ACACTCTTCGTGTCATTCACAATCCCTGCAAGACTACGCCTTGGTTGCCCTTATGAA
GTCTCCAATGTTTGGTTTTGATGAGGATGAGCTAGCACGTTTGTCCCCTTCAGAAAGC
AGAGGATAAAGTCCACGAAAATCTCTATGAGAAACTGGTCAATGCACAAAAAATGG
CAAGTAGTCAAAAAGGCTTGATTCACACAGCTCTAGCTGAAAAACTAAAGCAATTC
ATGGATATCCTAGCTTCTTGGCGCTTGTATGCCAAAACCCACTCTCTCTATGACTTGA
TTTGGAAGATTTACAACGACCGTTTTTATTATGACTATGTTGGGGCTTTGCCGAATGG
TCCTGCTAGGCAGGCCAATCTCTATGCCCTAGCACTGCGTGCTGATCAATTTGAAAA
GAGCAATTTCAAAGGTTTGTCGCGTTTTATTCGTATGATTGACCAAGTCTTAGAAGC
CCAGCACGATTTGGCAAGCGTGGCCGTCGCACCGCCAAAAGATGCAGTAGAGCTCA
TGACCATCCACAAGAGTAAAGGGCTGGAGTTTCCTTACGTCTTTATCCTCAATATGG
ATCAAGATTTCAACAAGCAAGACTCTATGTCAGAAGTCATTCTCAGTCGTCAGAATG
GTCTTGGTGTCAAATATATTGCCAAGATGGAGACAGGGGCAGTAGAAGACCACTAT
CCTAAAACCATCAAACTCTCCATTCCTAGTCTGACCTATAGGCAGAACGAAGAGGA
```

TABLE 1-continued

```
ATTACAGCTAGCAAGCTATTCTGAGCAGATGCGTTTGCTGTATGTTGCTATGACGCG
GGCTGAGAAAAAGCTCTATCTTGTCGGCAAGGGTTCTCGTGAAAAGCTGGAATCCA
AGGAATACCCAGCAGCCAAAAATGGGAAACTAAATAGCAATACTAGACTGCAAGCA
CGGAATTTCCAAGATGGCTTTGGGCTATCAGTAAAGTGTTTACTAAGGACAAGCTC
AACTTTAGTTATCGTTTTATTGGCGAAGATCAGTTGACCAGAGAAGCTATCGGAGAG
TTGGAAACCAAGAGTCCTCTCCAAGATAGCTCCCAAGCAGACAATCGTCAGTCAGA
TACCATCAAAGAAGCTCTGGAAATGCTGAAGGAGGTGGAAGTTTATAATACTCTTCA
CCGCGCAGCTATTGAACTTCCTAGTGTTCAAACCCCAAGTCAAATCAAGAAATTCTA
CGAACCAGTTATGGATATGGAAGGTGTCGAGATTGCTGGTCAAGGTCAGTCAGTAG
GCAAGAAAATCAGCTTCGATTTGCCAGATTTTTCAACCAAAGAAAAGGTAACTGGA
GCTGAGATTGGTAGTGCTACTCACGAACTCATGCAGAGAATTGACCTCAGCCAGCA
ACTAACCCTTGCTAGCCTAACAGAAACACTCAAACAAGTTCAAACTAGCCAAGCTG
TCAGAGACAAGATCAATCTTGATAAAATTCTTGCTTTCTTTGACACAGTACTCGGTC
AGGAAATTCTTGCTAATACCGACCATCTTTATCGCGAGCAACCTTTCTCCATGCTCA
AACGAGACCAAAAGAGTCAGGAAGACTTTGTTGTCCGTGGTATCCTTGATGGCTATC
TGCTTTACGAAAACAAAATTGTTCTGTTCGACTACAAGACAGACCGCTATGATGAAC
CAAGTCAACTCGTAGACCGCTATCGTGGTCAGTTAGCTCTATACGAAGAGGCTTTAT
CACGAGCCTATTCGATTGAAAATATTGAAAAATACTTGATTTTACTCGGTAAAGACG
AGGTTCAAGTTGTAAAAGTATAA
```

4109.1 (SEQ. ID. NO. 221)

```
ATGGAACTTGCTCGCCATGCTGAAACGTTGGGAGTAGATGCTATTGCAACGATTCCA
CCAATTTATTTCCGCTTGCCAGAATACTCAGTTGCCAAATACTGGAACGATATCAGT
TCTGCAGCTCCAAACACAGACTACGTGATTTACAACATTCCTCAATTGGCAGGGGTT
GCTTTGACTCCAAGCCTTTACACAGAAATGTTGAAAAATCCTCGTGTTATCGGTGTG
AAGAACTCTTCTATGCCAGTTCAAGATATCCAAACCTTTGTCAGCCTTGGTGGAGAA
GACCATATCGTCTTTAATGGTCCTGATGAGCAGTTCCTAGGAGGACGCCTCATGGGG
GCTAGGGCTGGTATCGGTGGTACTTATGGTGCTATGCCAGAACTCTTCTTGAAACTC
AATCAGTTGATTGCGGATAAGGACCTAGAAACAGCGCGTGAATTGCAGTATGCTAT
CAACGCAATCATTGGTAAACTCACTTCTGCTCATGGAAATATGTACGGTGTCATCAA
AGAAGTCTTGAAAATCAATGAAGGCTTGAATATTGGATCTGTTCGTTCACCATTGAC
ACCAGTGACTGAAGAAGATCGTCCAGTTGTAGAAGCGGCTGCTGCCTTGATTCGTGA
AACCAAGGAGCGCTTCCTCTAA
```

4110.2 (SEQ. ID. NO. 222)

```
ATGTATAAGACAAAGTGTTTACGAGAGAAGTTAGTATTATTTTTAAAAATTTTCTTC
CCAATCCTGATCTACCAATTTGCCAATTATTCTGCCTCTTTTGTTGATACTGCAATGA
CAGGTCAATACAACACTATGGACTTGGCTGGTGTATCTATGGCAACCAGTATCTGGA
ATCCTTTCTTTACATTTCTAACAGGGATTGTGTCAGCCTTGGTGCCTATCATTGGTCA
CCATCTTGGTCGAGGCAAAAAGGAAGAAGTTGCGTCTGATTTTTACCAATTTATTTA
TTTGGCCTTGGGCCTATCTGTGGTCTTGCTGGGGATGGTACTTTTCTTGGCACCAATA
ATCTTGAATCATATTGGGTTAGAAGCAGCAGTAGCGGCAGTAGCGGTTCGCTATCTT
TGGTTTTTATCTATCGGGATTATCCCCTTGTTGCTCTTTAGCGTCATTCGTTCCTTGCT
GGATTCGCTGGGCTTGACCAAACTGTCCATGTACCTCATGCTTTTCTTACTCCCTCTC
AATAGCGGATTTAACTATCTCTTGATTTACGGTGCCTTTGGTGTTCCACAACTGGGA
GGGGCTGGTGCTGGTTTAGGAACATCCTTGGCCTACTGGGTCTTGCTTGGGATTCT
GTTCTGGTTTTATTTAAACAGGAGAAGCTCAAAGCCTTACACCTTGAGAACGAATT
CCACTTAATATGGATAAAATTAAGGAAGGAGTTCGTTTAGGTCTGCCTATTGGGGGA
ACTGTCTTCGCGGAAGTGGCTATCTTTTCAGTGGTTGGCTTGATTATGGCTAAGTTTT
CGCCCTTGATTATAGCTAGTCACCAGTCAGCTATGAACTTTTCAAGTCTTATGTACGC
CTTTTCCTATGAGTATCTCATCGGCTATGGCTATTGTCGTTTCCTATGAAGTGGGAGCC
AAGCGATTTGATGATGCGAAAACCTATATTGGTCTAGGAAGATGGACTGCCCTCATT
TTTGCGGCCTTCACCTTAACCTTCCTTTACATTTTTAGGGGAAATGTGGCCAGTCTTT
ATGGTAACGACCCAAAATTTATCGATTTGACAGTGCGTTTTTTAACTTATAGTCTTTT
CTTCCAGTTAGCAGATACCTTTGCGGCGCCGCTTCAGGGAATTTTGCGGGGGTATAA
GGATACAGTTATTCCTTTTTACCTTGGTTTGCTTGGTTATTGGGGCGTAGCAATCCCT
GTGTACGCTATTTGA
```

4112.2 (SEQ. ID. NO. 223)

```
ATGAGTACTTTAGCAAAAATAGAAGCGCTCTTGTTTGTAGCGGGTGAAGATGGGATT
CGGGTCCGCCAGTTAGCTGAACTCCTCTCTCTGCCACCGACAGGCATCCAGCAAAGT
TTAGGAAAATTAGCCCAGAAGTATGAAAAGGACCCAGATTCCAGTTTGGCTTTGATT
GAGACAAGTGGTGCTTATAGATTGGTGACCAAGCCTCAATTTGCAGAGATTTTGAAG
GAATACTCTAAGGCGCCTATCAACCAGAGCTTGTCTCGGGCTGCCCTTGAGACCTTG
TCCATTATTGCCTACAAACAGCCGATTACGCGGATAGAAATTGATGCCATCCGTGGA
GTTAACTCGAGTGGAGCCTTGGCAAAGTTGCAGGCTTTTGACCTGATAAAGGAAGA
CGGGAAAAAGGAAGTATTGGGGCGCCCCAACCTCTATGTGACTACGGATTATTTCCT
AGATTCATGGGGATAAACCATTTAGAAGAATTACCAGTGATTGATGAGCTTGAGA
TTCAAGCCCAAGAAAGCCAATTATTTGGTGAAAGGATAGAAGAAGATGAGAATCAA
TAA
```

4113.1 (SEQ. ID. NO. 224)

```
ATGGATACGATGATTAGTAGATTTTTTCGCCATTTTATTTGAAGCCTTAAAAAGTTTGA
AACGAAATGGTTGGATGACAGTAGCTGCTGTCAGTTCAGTCATGATTACTTTGACCT
TGGTGGCAATATTTGCATCTGTTATTTTCAATACAGCGAAACTAGCTACAGATATTG
```

TABLE 1-continued

AAAATAATGTCCGTGTAGTAGTTTATATCCGAAAGGATGTGGAAGATAATAGTCAG
ACAATTGAAAAGAAGGTCAAACTGTTACAAATAATGACTACCACAAGGTATATGA
TTCTTTGAAGAACATGTCTACGGTTAAAAGTGTTACCTTTTCAAGTAAAGAAGAACA
ATATGAAAAATTAACCGAGATAATGGGAGATAACTGGAAAATCTTTGAAGGAGATG
CCAATCCTCTCTATGATGCCTATATTGTAGAGGCAAACACTCCAAATGATGTAAAAA
CTATAGCCGAAGATGCTAAAAAAATTGAAGGTGTCTCTGAGGTTCAAGATGGCGGT
GCCAATACAGAAAGACTCTTCAAGTTAGCTTCATTTATCCGTGTTTGGGGACTAGGG
ATTGCTGCTTTGTTAATTTTTATCGCAGTTTTCTTGATTTCAAATACCATTCGTATTAC
CATTATTTCCCGCAGTCGCGAAATTCAAATCATGCGCTTGGTCGGAGCTAAAAACAG
TTATATCCGTGGACCGTTCTTGTTAGAAGGAGCCTTTATCGGTTTATTGGGAGCTATC
GCACCATCTGTTTTGGTCTTTATTGTTTATCAAATTGTTTACCAATCTGTCAACAAAT
CGTTGGTAGGGCAAAATCTATCCATGATTAGTCCAGATTTATTTAGTCCGTTGATGA
TTGCCCTACTATTTGTGATTGGGGTTTTCATTGGTTCATTGGGATCAGGAATATCCAT
GCGCCGATTCTTGAAGATTTAG 4117.1 (SEQ. ID. NO. 225)

ATGAAGAAAGTAAGATTTATTTTTTTAGCTCTGCTATTTTTCTTAGCTAGTCCAGAGG
GTGCAATGGCTAGTGATGGTACTTGGCAAGGAAAACAGTATCTGAAAGAAGATGGC
AGTCAAGCAGCAAATGAGTGGGTTTTTGATACTCATTATCAATCTTGGTTCTATATA
AAAGCAGATGCTAACTATGCTGAAAATGAATGGCTAAAGCAAGGTGACGACTATTT
TTACCTCAAATCTGGTGGCTATATGGCCAAATCAGAATGGGTAGAAGACAAGGGAG
CCTTTTATTATCTTGACCAAGATGGAAAGATGAAAAGAAATGCTTGGGTAGGAACTT
CCTATGTTGGTGCAACAGGTGCCAAAGTAATAGAAGACTGGGTCTATGATTCTCAAT
ACGATGCTTGGTTTTATATCAAAGCAGATGGACAGCACGCAGAGAAAGAATGGCTC
CAAATTAAAGGGAAGGACTATTATTTCAAATCCGGTGGTTATCTACTGACAAGTCAG
TGGATTAATCAAGCTTATGTGAATGCTAGTGGTGCCAAAGTACAGCAAGGTTGGCTT
TTTGACAAACAATACCAATCTTGGTTTTACATCAAAGAAAATGGAAACTATGCTGAT
AAAGAATGGATTTTCGAGAATGGTCACTATTATTATCTAAAATCCGGTGGCTACATG
GCAGCCAATGAATGGATTTGGGATAAGGAATCTTGGTTTTATCTCAAATTTGATGGG
AAAATGGCTGAAAAGAATGGGTCTACGATTCTCATAGTCAAGCTTGGTACTACTTC
AAATCCGGTGGTTACATGACAGCCAATGAATGGATTTGGGATAAGGAATCTTGGTTT
TATCTCAAATCTGATGGGAAAATAGCTGAAAAGAATGGGTCTACGATTCTCATAGT
CAAGCTTGGTACTACTTCAAATCCGGTGGTTACATGACAGCCAATGAATGGATTTGG
GATAAGGAATCTTGGTTTTACCTCAAATCTGATGGGAAAATAGCTGAAAAGAATG
GGTCTACGATTCTCATAGTCAAGCTTGGTACTACTTCAAATCTGGTGGCTACATGGC
GAAAAATGAGACAGTAGATGGTTATCAGCTTGGAAGCGATGGTAAATGGCTTGGAG
GAAAAACTACAAATGAAAATGCTGCTTACTATCAAGTAGTGCCTGTTACAGCCAATG
TTTATGATTCAGATGGTGAAAAGCTTTCCTATATATCGCAAGGTAGTGTCGTATGGC
TAGATAAGGATAGAAAAAGTGATGACAAGCGCTTGGCTATTACTATTTCTGGTTTGT
CAGGCTATATGAAAACAGAAGATTTACAAGCGCTAGATGCTAGTAAGGACTTTATC
CCTTATTATGAGAGTGATGGCCACCGTTTTTATCACTATGTGGCTCAGAATGCTAGT
ATCCCAGTAGCTTCTCATCTTTCTGATATGGAAGTAGGCAAGAAATATTATTCGGCA
GATGGCCTGCATTTTGATGGTTTTAAGCTTGAGAATCCCTTCCTTTTCAAAGATTTAA
CAGAGGCTACAAACTACAGTGCTGAAGAATTGGATAAGGTATTTAGTTTGCTAAAC
ATTAACAATAGCCTTTTGGAGAACAAGGGCGCTACTTTTAAGGAAGCCGAAGAACA
TTACCATATCAATGCTCTTTATCTCCTTGCCCATAGTGCCCTAGAAAGTAACTGGGG
AAGAAGTAAAATTGCCAAAGATAAGAATAATTTCTTTGGCATTACAGCCTATGATAC
GACCCCTTACCTTTCTGCTAAGACATTTGATGATGTGGATAAGGGAATTTTAGGTGC
AACCAAGTGGATTAAGGAAAATTATATCGATAGGGGAAGAACTTTCCTTGGAAACA
AGGCTTCTGGTATGAATGTGGAATATGCTTCAGACCCTTATTGGGCGAAAAAATTG
CTAGTGTGATGATGAAAATCAATGAGAAGCTAGGTGGCAAAGATTAG 4119.2 (SEQ. ID. NO. 226)

ATGAAAAAAGTATTACAAAAATATTGGGCATGGGCTTTTGTGGTCATCCCCCTCTTG
TTACAAGCAATTTTCTTCTATGTGCCGATGTTTCAAGGAGCCTTTTACAGTTTTACCA
ACTGGACAGGATTGACTTATAACTACAAATTTGTTGGCTTAAACAACTTTAAGCTCC
TCTTCATGGATCCAAAATTCATGAATGCGATTGGCTTTACCGCAATCATTGCGATTG
CCATGGTGGTTGTGAGATTGCACTCGGGATCTTCATTGCGCGTGTCTTGAATTCTA
AAAATCAAAGGCCAAACCTTCTTCCGTGCTTGGTTCTTCTTCCCAGCTGTTTTATCTGG
TTTGACAGTGGCTTTGATCTTCAAGCAAGTCTTCAACTACGGTCTTCCAGCGATTGG
AAATGCCCTTCATATTGAATTTTTCCAAACCAGTCTTTTAGGGACTAAGTGGGGAGC
AATCTTTGCGGCTGTCTTTGTCCTTCTTTGGCAAGGGGTTGGCTATGCCCATCATCATC
TTCCTAGCTGGTTTGCAATCTATTCCAACTGAGATTACAGAGGCAGCAAGGATTGAT
GGTGCGACTAGCAAGCAAGTTTTCTGGAACATTGAATTGCCTTACTTGCTACCAAGT
GTCTCTATGGTCTTTATCCTAGCCTAAAAGGTGGGCTGACTGCCTTTGACCAAGTCTT
TGCCATGACCGGTGGTGGTCCAAACAATGCCACAACCTCACTTGGGCTCTTGGTTTA
TAACTATGCCTTTAAAAACAACCAATTCGGTTATGCCAATGCCATTGCCGTAATCTT
GTTCTTCTTAATTGTAGTGATTTCGATCATCCAATTGAGAGTATCTAAGAAATTTGAA
ATTTAA 4119.3 (SEQ. ID. NO. 227)

ATGATGAAACAAGATGAAAGAAAAGCCCTGATTGGCAAATACATTCTATTGATTCT
AGGATCGGTTCTGATTTTAGTGCCGCTCCTTGCTACCCTCTTTAGTTCCTTCAAACCC
ACTAAGGATATTGTAGATAATTTCTTTGGCTTTCCAACCAACTTCACATGGGACAAC
TTTAGCCGTCTCTTAGCTGATGGGATTGGAGGCTATTATTGGAACTCTGTCGTCATCA
CTGTCTTGTCTTTACTTGCAGTAATGATCTTTATCCCTATGGCAGCGTACTCCATCGC

TABLE 1-continued

TCGCAATATGAGTAAAAGAAAAGCCTTTACCATCATGTATACCCTCTTAATCCTCGG
AATCTTCGTACCTTTCCAAGTCATCATGATTCCGATTACGGTTATGATGAGTAAACTC
GGTTTGGCTAATACCTTTGGTTTGATCTTGCTCTACTTGACCTATGCGATTCCACAGA
CCCTCTTTCTCTATGTTGGCTATATCAAAATCTCGATTCCAGAAAGTCTGGATGAAGC
AGCAGAGATCGATGGGGCTAATCAATTTACAACCTATTTCCGCATCATCTTCCCAAT
GATGAAACCGATGCATGCGACAACCATGATCATCAATGCCCTTTGGTTCTGGAATGA
CTTCATGTTGCCACTCCTTGTCTTGAACCGGGATTCCAAAATGTGGACTCTGCCTTTG
TTCCAATACAACTACGCAGGCCAATATTTCAACGACTACGGACCAAGCTTTGCCTCT
TACGTGGTCGGCATTATCAGTATCACCATTGTCTATCTCTTCTTCCAACGCCATATCA
TTTCAGGAATGAGCAACGGGGCAGTGAAGTAA 4119.4 (SEQ. ID. NO. 228)

ATGAAAAGTATTCTTCAGAAAATGGGGGAGCATCCGATGCTGCTTCTTTTTCTTAGC
TATAGTACTGTTATATCCATTCTTGCACAAAATTGGATGGGTCTTGTGGCTTCAGTAG
GAATGTTTCTATTTACTATTTTCTTTTTGCACTATCAGTCGATTTTATCCCATAAATTC
TTTCGATTGATTTTGCAGTTTGTCTTGTTTGGTAGTGTCTTGTCAGCTGCTTTTGCCAG
TTTAGAACATTTCCAAATTGTGAAGAAATTTAACTATGCTTTTCTTTCACCCAATATG
CAGGTGTGGCATCAGAACCGGGCAGAAGTGACCTTCTTTAATCCTAATTATTATGGA
ATTATTTGTTGTTTCTGTATTATGATTGCTTTCTATCTGTTTACAACGACCAAGTTGA
ATTGGTTGAAAGTATTCTGTGTGATTGCAGGCTTTGTTAATCTCTTTGGTTTGAACTT
TACTCAAAATCGAACTGCCTTTCCTGCTATTATCGCTGGAGCAATTATCTATCTCTTT
ACGACTATTAAAAACTGGAAGGCCTTTTGGCTTAGTATTGGGGTCTTCGCGATTGGT
TTGAGTTTCCTCTTTTCTAGTGATTTGGGAGTTCGAATGGGTACTTTAGACTCTTCTA
TGGAAGAACGCATTTCTATCTGGGATGCTGGGATGGCCTTGTTTAAGCAAAATCCTT
TTTGGGGTGAAGGGCCATTGACCTATATGAACTCTTATCCTCGGATACATGCTCCTT
ATCATGAACATGCCCACAGTCTTTATATTGATACGATTCTGAGTTACGGAATTGTGG
GGACTATTTTATTAGTTTTGTCTTCTGTTGCTCCTGTTCGCTTGATGATGGATATGAG
TCAGGAGTCGGGGAAACGTCCGATTATCGGCCTTTATCTATCTTTCCTTACAGTGGTT
GCTGTGCACGGAATTTTTGACTTGGCTCTCTTCTGGATTCAGTCAGGCTTTATTTTCT
TGCTAGTTATGTGCAGTATTCCATTGGAGCATCGAATGTTGGTATCGGACATGACGG
ATTAA 4120.1 (SEQ. ID. NO. 229)

ATGTCAAAGATGGATGTTCAGAAAATCATTGCACCGATGATGAAGTTTGTGAATATG
CGTGGCATTATAGCTCTAAAAGATGGGATGTTAGCAATTTTGCCATTGACAGTAGTT
GGTAGTTTGTTCTTGATTATGGGACAATTGCCGTTCGAAGGATTAAATAAGAGCATT
GCTAGTGTTTTTGGAGCTAATTGGACAGAGCCGTTTATGCAAGTATATTCAGGAACT
TTTGCTATTATGGGTCTAATTTCTTGTTTTTCAATTGCCTATTCTTATGCTAAGAATAG
CGGCGTAGAGGCTTTACCAGCTGGACTTCTATCTGTATCTGCATTCTTTATTTTGCTA
AGATCATCTTATATCCCTAAACAAGGTGAGGCGATTGGGGACGCTATTAGTAAAGTT
TGGTTTGGAGGCCAAGGAATTATCGGTGCTATCATTATAGGTTTGGTAGTAGGAAGT
ATTTATACCTTCTTTATAAAGAGAAAAATTGTTATTAAGATGCCAGAACAAGTTCCA
CAAGCTATTGCCAAACAGTTTGAAGCAATGATTCCAGCATTTGTAATTTTCTTATCTT
CTATGATTGTATATATTTTAGCGAAGTCATTGACTAATGGCGGAACATTCATAGAAA
TGATTTATTCTGCTATTCAAGTTCCGTTGCAAGGTTTAACTGGATCTTTGTATGGTGC
TATTGGAATTGCATTCTTTATATCATTTTTGTGGTGGTTTGGTGTTCATGGGCAATCG
GTAGTAAATGGAGTAGTGACAGCTCTGCTTTTATCTAATCTTGATGCTAATAAAGCT
ATGTTAGCCTCTGCTAATCTATCATTAGAAAATGGTGCACATATTGTTACTCAACAA
TTTTTAGATTCATTTTTAATTCTATCAGGTTCAGGGATTACGTTTGGTCTTGTAGTTGC
CATGCTTTTTGCAGCAAATCAAACAATACCAAGCCTTAGGAAAAGTTGCAGCTTTT
TCCAGCAATATTTAACGTAAATGAGCCAGTTGTATTTGGATTTCCGATTGTCATGAA
TCCAGTTATGTTTGTACCTTTCATTCTTGTTCCTGTACTTGCAGCTGTGATAGTATATG
GAGCTATTGCAACAGGTTTCATGCAGCCATTCTCAGGGGTAACATTGCCTTGGAGTA
CACCAGCTATTTTATCAGGATTTTTGGTGGGTGGATGGCAAGGAGTTATTACTCAGC
TGGTGATATTAGCGATGTCTACATTGGTTTATTTTCCATTCTTTAAAGTACAGGATCG
TTTAGCTTACCAAAATGAAATCAAACAATCTTAG 4121.2 (SEQ. ID. NO. 230)

ATGAAGAAAAAGGACTTAGTAGACCAACTAGTCTCAGAGATCGAGACGGGGAAAGT
CAGGACACTGGGAATATACGGTCATGGAGCTTCAGGTAAATCAACCTTTGCACAGG
AATTGTACCAAGCTTTAGATTCTACTACAGTAAATTTGCTAGAGACAGATCCTTATA
TCACCTCAGGACGCCATCTGGTACTACCCAAGGACGCGCCGAATCAAAAGGTGACA
GCCAGTCTGCCAGTGGCGCATGAACTGGAGAGTTTGCAGAGAGATATCCTTgCTTGC
AGGCGGGTATGGATGTCTTGA 4122.1 (SEQ. ID. NO. 231)

ATGAAGAAAAGATACCTAGTCTTGACAGCTTTGCTAGCCTTGAGTCTAGCAGCTTGT
TCACAAGAAAAAACAAAAAATGAAGATGGAGAAACTAAGACAGAACAGACAGCCA
AAGCTGATGGAACAGTCGGTAGTAAGTCTCAAGGAGCTGCCCAGAAGAAAGCAGAA
GTGGTCAATAAAGGTGATTACTACAGCATTCAAGGGAAATACGATGAAATCATCGT
AGCCAACAAACACTATCCATTGTCTAAAGACTATAATCCAGGGGAAAATCCAACAG
CCAAGGCAGAGTTGGTCAAACTCATCAAAGCGATGCAAGAGGCAGGTTTCCCTATT
AGTGATCATTACAGTGGTTTTAGAAGTTATGAAAACTCAGACCAAGCTCTATCAAGA
TTATGTCAACCAAGATGGAAAGGCAGCAGCTGACCGTTACTCTGCCCGTCCTGGCTA
TAGCGAACACCAGACAGGCTTGGCCTTTGATGTGATTGGGACTGATGGTGATTTGGT

TABLE 1-continued

GACAGAAGAAAAAGCAGCCCAATGGCTCTTGGATCATGCAGCTGATTATGGCTTTGT
TGTCCGTTATCTCAAAGGCAAGGAAAAGGAAACAGGCTATATGGCTGAAGAATGGC
ACCTGCGTTATGTAGGAAAAGAAGCTAAAGAAATTGCTGCAAGTGGTCTCAGTTTG
GAAGAATACTATGGCTTTGAAGGCGGAGACTACGTCGATTAA 4125.6 (SEQ. ID. NO. 232)

ATGCGTAAATTCTTAATTATTTTGTTGCTACCAAGTTTTTTGACCATTTCAAAAGTCG
TTAGCACAGAAAAAGAAGTCGTCTATACTTCGAAAGAAATTTATTACCTTTCACAAT
CTGACTTGGTATTTATTTTAGAGAAAAATTAAGTTCTCCCATGGTTTATGGAGAGGT
TCCTGTTTATGCGAATGAAGATTTAGTAGTGGAATCTGGGAAATTGACTCCCAAAC
AAGTTTTCAAATAACCGAGTGGCGCTTAAATAAACAAGGAATTCCAGTATTTAAGCT
ATCAAATCATCAATTTATAGCTGCGGACAAACGATTTTTATATGATCAATCAGAGGT
AACTCCAACAATAAAAAAGTATGGTTAGAATCTGACTTTAAACTGTACAATAGTCC
TTATGATTTAAAAGAAGTGAAATCATCCTTATCAGCTTATTCGCAAGTATCAATCGA
CAAGACCATGTTTGTAGAAGGAAGAGAATTTCTACATATTGATCAGGCTGGATGGGT
AGCTAAAGAATCAACTTCTGAAGAAGATAATCGGATGAGTAAAGTTCAAGAAATGT
TATCTGAAAAATATCAGAAAGATTCTTTCTCTATTTATGTTAAGCAACTGACTACTG
GAAAAGAAGCTGGTATCAATCAAGATGAAAAGATGTATGCAGCCAGCGTTTTGAAA
CTCTCTTATCTCTATTATACGCAAGAAAAAATAAATGAGGGTCTTTATCAGTTAGAT
ACGACTGTAAAATACGTATCTGCAGTCAATGATTTTCCAGGTTCTTATAAACCAGAG
GGAAGTGGTAGTCTTCCTAAAAAGAAGATAATAAAGAATATTCTTTAAAGGATTT
AATTACGAAAGTATCAAAAGAATCTGATAATGTAGCTCATAATCTATTGGGATATTA
CATTTCAAACCAATCTGATGCCACATTCAAATCCAAGATGTCTGCCATTATGGGAGA
TGATTGGGATCCAAAAGAAAAATTGATTTCTTCTAAGATGGCCGGGAAGTTTATGGA
AGCTATTTATAATCAAAATGGATTTGTGCTAGAGTCTTTGACTAAAACAGATTTTGA
TAGTCAGCGAATTGCCAAAGGTGTTTCTGTTAAAGTAGCTCATAAAATTGGAGATGC
GGATGAATTTAAGCATGATACGGGTGTTGTCTATGCAGATTCTCCATTTATTCTTTCT
ATTTTCACTAAGAATTCTGATTATGATACGATTTCTAAGATAGCCAAGGATGTTTAT
GAGGTTCTAAAATGA 4125.7 (SEQ. ID. NO. 233)

ATGAAAAAACAAAATAATGGTTTAATTAAAAATCCTTTTCTATGGTTATTATTTATCT
TTTTCCTTGTGACAGGATTCCAGTATTTCTATTCTGGGAATAACTCAGGAGGAAGTC
AGCAAATCAACTATACTGAGTTGGTACAAGAAATTACCGATGGTAATGTAAAAGAA
TTAACTTACCAACCAAATGGTAGTGTTATCGAAGTTTCTGGTGTCTATAAAAATCCT
AAAACAAGTAAAGAAGAAACAGGTATTCAGTTTTTCACGCCATCTGTTACTAAGGTA
GAGAAATTTACCAGCACTATTCTTCCTGCAGATACTACCGTATCAGAATTGCAAAAA
CTTGCTACTGACCATAAAGCAGAAGTAACTGTTAAGCATGAAAGTTCAAGTGGTATA
TGGATTAATCTACTCGTATCCATTGTGCCATTTGGAATTCTATTCTTCTCCTATTCTC
TATGATGGGAAATATGGGAGGAGGCAATGGCCGTAATCCAATGAGTTTTGGACGTA
GTAAGGCTAAAGCAGCAAATAAAGAAGATATTAAAGTAAGATTTTCAGATGTTGCT
GGAGCTGAGGAAGAAAAACAAGAACTAGTTGAAGTTGTTGAGTTCTTAAAAGATCC
AAAACGATTCACAAAACTTGGAGCCCGTATTCCAGCAGGTGTTCTTTTTGGAGGGACC
TCCGGGGACAGGTAAAACTTTGCTTGCTAAGGCAGTCGCTGGAGAAGCAGGTGTTC
CATTCTTTAGTATCTCAGGTTCTGACTTTGTAGAAATGTTTGTCGGAGTTGGAGCTAG
TCGTGTTCGCTCTCTTTTTGAGGATGCCAAAAAAGCAGCACCAGCTATCATCTTTATC
GATGAAATTGATGCTGTTGGACGTCAACGTGGAGTCGGTCTCGGCGGAGGTAATGA
CGAACGTGAACAAACCTTGAACCAACTTTTGATGAGATGGATGGTTTTGAGGGAA
ATGAAGGGATTATCGTCATCGCTGCGACAAACCGTTCAGATGTACTTGACCCTGCCC
TTTTTGCGTCCAGGACGTTTTGATAGAAAAGTATTGGTTGGTCGTCCTGATGTTAAAG
GTCGTGAAGCAATCTTGAAAGTTCACGCTAAGAATAAGCCTTTAGCAGAAGATGTTG
ATTTGAAATTAGTGGCTCAACAAACTCCAGGCTTTGTTGGTGCTGATTTAGAGAATG
TCTTGAATGAAGCAGCTTTAGTTGCTGCTCGTCGCAATAAATCGATAATTGATGCTT
CAGATATTGATGAAGCAGAAGATAGAGTTATTGCTGGACCTTCTAAGAAAGATAAG
ACAGTTTCACAAAAAGAACGAGAATTGGTTGCTTACCATGAGGCAGGACATACCAT
TGTTGGTCTAGTCTTGTCGAATGCTCGCGTTGTCCATAAGGTTACAATTGTACCACGC
GGCCGTGCAGGCGGATACATGATTGCACTTCCTAAAGAGGATCAAATGCTTCTATCT
AAAGAAGATATGAAAGAGCAATTGGCTGGCTTAATGGGTGGACGTGTAGCTGAAGA
AATTATCTTTAATGTCCAAACCACAGGAGCTTCAAACGACTTTGAACAAGCGACACA
AATGGCACGTGCAATGGTTACAGAGTACGGTATGAGTGAAAAACTTGGCCCAGTAC
AATATGAAGGAAACCATGCTATGCTTGGTGCACAGAGTCCTCAAAAATCAATTTCAG
AACAAACAGCTTATGAAATTGATGAAGAGGTTCGTTCATTATTAAATGAGGCACGA
AATAAAGCTGCTGAAATTATTCAGTCAAATCGTGAAACTCACAAGTTAATTGCAGAA
GCATTATTGAAATACGAAACATTGGATAGTACACAAATTAAAGCTCTTTACGAAACA
GGAAAGATGCCTGAAGCAGTAGAAGAGGAATCTCATGCACTATCCTATGATGAAGT
AAAGTCAAAAATGAATGACGAAAAATAA 4125.10 (SEQ. ID. NO. 234)

ATGAGGGAACCAGATTTTTTAAATCATTTTCTCAAGAAGGGATATTTCAAAAAGCAT
GCTAAGGCGGTTCTAGCTCTTTCTGGTGGATTAGATTCCATGTTTCTATTTAAGGTAT
TGTCTACTTATCAAAAAGAGTTAGAGATTGAATTGATTCTAGCTCATGTGAATCATA
AGCAGAGAATTGAATCAGATTGGGAAGAAAAGGAATTAAGGAAGTTGGCTGCTGAA
GCAGAGCTTCCTATTTATATCAGCAATTTTTCAGGAGAATTTTCAGAAGCGCGTGCA
CGAAATTTTCGTTATGATTTTTTCAAGAGGTCATGAAAAAGACAGGTGCGACAGCT
TTAGTCACTGCCCACCATGCTGATGATCAGGTGGAAACGATTTTTATGCGCTTGATT
CGAGGAACTCGCTTGCGCTATCTATCAGGAATTAAGGAGAAGCAAGTAGTCGGAGA

TABLE 1-continued

GATAGAAATCATTCGTCCCTTCTTGCATTTTCAGAAAAAAGACTTTCCATCAATTTTT
CACTTTGAAGATACATCAAATCAGGAGAATCATTATTTTCGAAATCGTATTCGAAAT
TCTTACTTACCAGAATTGGAAAAAGAAAATCCTCGATTTAGGGATGCAATCTTAGGC
ATTGGCAATGAAATTTTAGATTATGATTTGGCAATAGCTGAATTATCTAACAATATT
AATGTGGAAGATTTACAGCAGTTATTTTCTTACTCTGAGTCTACACAAAGAGTTTTA
CTTCAAACTTATCTGAATCGTTTTCCAGATTTGAATCTTACAAAAGCTCAGTTTGCTG
AAGTTCAGCAGATTTTAAAATCTAAAAGCCAGTATCGTCATCCGATTAAAAATGGCT
ATGAATTGATAAAAGAGTACCAACAGTTTCAGATTTGTAAAATCAGTCCGCAGGCTG
ATGAAAAGGAAGATGAACTTGTGTTACACTATCAAAATCAGGTAGCTTATCAAGGA
TATTTATTTTCTTTTGGACTTCCATTAGAAGGTGAATTAATTCAACAAATACCTGTTT
CACGTGAAACATCCATACACATTCGTCATCGAAAAACAGGAGATGTTTTGATTAAAA
ATGGGCATAGAAAAAAACTCAGACGTTTATTTATTGATTTGAAAATCCCTATGGAA
AGAGAAACTCTGCTCTTATTATTGAGCAATTTGGTGAAATTGTCTCAATTTTGGGAA
TTGCGACCAATAATTTGAGTAAAAAAACGAAAAATGATATAATGAACACTGTACTTT
ATATAGAAAAAATAGATAGGTAA 4126.1 (SEQ. ID. NO. 235)

ATGAAGCGTTCTTCTCTTTTAGTTAGAATGGTTATTTCCATCTTTCTGGTCTTTCTCAT
TCTCCTAGCTCTGGTTGGAACTTTCTACTATCAATCAAGTTCTTCAGCCATTGAGGCC
ACCATTGAGGGCAACAGCCAAACGACCATCAGCCAGACTAGCCACTTTATTCAGTCT
TATATCAAAAAACTAGAAACCACCTCGACTGGTTTGACCCAGCAGACGGATGTTCTG
GCCTATGCTGAGAATCCCAGTCAAGACAAGGTCGAGGGAATCCGAGATTGTTTTTG
ACCATCTTGAAGTCAGATAAGGACTTGAAAACTGTTGTGCTGGTGACCAAATCTGGT
CAGGTCATTTCTACAGATGACAGTGTGCAGATGAAAACTTCCTCTGATATGATGGCT
GAGGATTGGTACCAAAAGGCCATTCATCAGGGAGCTATGCCTGTTTTGACTCCAGCT
CGTAAATCAGATAGTCAGTGGGTCATTTCTGTCACTCAAGAACTTGTTGATGCAAAG
GGAGCCAATCTTGGTGTGCTTCGTTTGGATATTTCTTATGAAACTCTGGAAGCCTATC
TCAATCAACTCCAGTTGGGGCAGCAGGGCTTTGCCTTCATTATCAATGAAAACCATG
AATTTGTCTACCATCCTCAACACACAGTTTATAGTTCGTCTAGCAAAATGGAGGCTA
TGAAACCCTACATCGATACAGGTCAGGTTATACTCCTGGTCACAAATCCTACGTCA
GTCAAGAGAAGATTGCAGGAACTGATTGGACGGTGCTTGGCGTGTCATCATTGGAA
AAGTTAGACCAGGTTCGGAGTCAGCTCTTGTGGACCTTGCTTGGGGCCAGTGTCACA
TCTCTTCTTGTCTGTCTCTGCTTAGTGTGGTTCAGTCTTAAACGCTGGATTGCTCCTTT
GAAGGATTTGAGAGAAACCATGTTGGAAATTGCTTCTGGTGCTCAAAATCTTCGTGC
CAAGGAAGTTGGTGCCTATGAACTGAGAGAAGTAACTCGCCAATTTAATGCTATGTT
GGATCAGATTGATCAGTTGATGGTAGCTATTCGTAGCCAGGAAGAAACGACCCGTC
AGTACCAACTTCAAGCCCTTTCGAGCCAGATTAATCCACATTTCCTCTATAACACTTT
GGACACCATCATCTGGATGCTGAATTTCATGATAGTCAGCGAGTGGTGCAGGTGAC
CAAGTCCTTGGCAACCTATTTCCGCTTGGCGCTCAATCAAGGCAAGGACTTGATTTG
TCTCTCTGACGAAATCAATCATGTCCGCCAGTATCTCTTTATCCAGAAACAACGCTA
TGGAGATAAGCTTGGAATACGAAATTAATGAAAATGTTGCCTTTGATAATTTAGTCT
TACCCAAGCTGGTCCTACAACCCCTTGTAGAAAATGCTCTTTACCATGGCATTAAGG
AAAAGGAAGGTCAGGGCCATATTAAACTTTCTGTCCAGAAACAGGATTCGGGATTG
GTCATCCGTATTGAGGATGATGGCGTTGGCTTCCAAGATGCTGGTGATAGTAGTCAA
AGTCAACTCAAACGTGGGGGAGTTGGTCTTCAAAATGCGATCAACGGCTCAAACTTC
ATTTTGGAGCCAATTACCATATGAAGATTGATTCTAGACCCCAAAAAGGGACGAAA
GTTGAAATATATATAAATAGAATAGAAACTAGCTAA 4126.7 (SEQ. ID. NO. 236)

ATGAAGCGTTCTTCTCTTTTAGTTAGAATGGTTATTTCCATCTTTCTGGTCTTTCTCAT
TCTCCTAGCTCTGGTTGGAACTTTCTACTATCAATCAAGTTCTTCAGCCATTGAGGCC
ACCATTGAGGGCAACAGCCAAACGACCATCAGCCAGACTAGCCACTTTATTCAGTCT
TATATCAAAAAACTAGAAACCACCTCGACTGGTTTGACCCAGCAGACGGATGTTCTG
GCCTATGCTGAGAATCCCAGTCAAGACAAGGTCGAGGGAATCCGAGATTGTTTTTG
ACCATCTTGAAGTCAGATAAGGACTGAAAACTGTTGTGCTGGTGACCAAATCTGGT
CAGGTCATTTCTACAGATGACAGTGTGCAGATGAAAACTTCCTCTGATATGATGGCT
GAGGATTGGTACCAAAAGGCCATTCATCAGGGAGCTATGCCTGTTTTGACTCCAGCT
CGTAAATCAGATAGTCAGTGGGTCATTTCTGTCACTCAAGAACTTGTTGATGCAAAG
GGAGCCAATCTTGGTGTGCTTCGTTTGGATATTTCTTATGAAACTCTGGAAGCCTATC
TCAATCAACTCCAGTTGGGGCAGCAGGGCTTTGCCTTCATTATCAATGAAAACCATG
AATTTGTCTACCATCCTCAACACACAGTTTATAGTTCGTCTAGCAAAATGGAGGCTA
TGAAACCCTACATCGATACAGGTCAGGTTATACTCCTGGTCACAAATCCTACGTCA
GTCAAGAGAAGATTGCAGGAACTGATTGGACGGTGCTTGGCGTGTCATCATTGGAA
AAGTTAGACCAGGTTCGGAGTCAGCTCTTGTGGACCTTGCTTGGGGCCAGTGTCACA
TCTCTTCTTGTCTGTCTCTGCTTAGTGTGGTTCAGTCTTAAACGCTGGATTGCTCCTTT
GAAGGATTTGAGAGAAACCATGTTGGAAATTGCTTCTGGTGCTCAAAATCTTCGTGC
CAAGGAAGTTGGTGCCTATGAACTGAGAGAAGTAACTCGCCAATTTAATGCTATGTT
GGATCAGATTGATCAGTTGATGGTAGCTATTCGTAGCCAGGAAGAAACGACCCGTC
AGTACCAACTTCAAGCCCTTTCGAGCCAGATTAATCCACATTTCCTCTATAACACTTT
GGACACCATCATCTGGATGCTGAATTTCATGATAGTCAGCGAGTGGTGCAGGTGAC
CAAGTCCTTGGCAACCTATTTCCGCTTGGCGCTCAATCAAGGCAAGGACTTGATTTG
TCTCTCTGACGAAATCAATCATGTCCGCCAGTATCTCTTTATCCAGAAACAACGCT
ATGGAGATAAGCTGGAATACGAAATTAATGAAAATGTTGCCTTTGATAATTTAGTCT
TACCCAAGCTGGTCCTACAACCCCTTGTAGAAAATGCTCTTTACCATGGCATTAAGG
AAAAGGAAGGTCAGGGCCATATTAAACTTTCTGTCCAGAAACAGGATTCGGGATTG
GTCATCCGTATTGAGGATGATGGCGTTGGCTTCCAAGATGCTGGTGATAGTAGTCAA
AGTCAACTCAAACGTGGGGGAGTTGGTCTTCAAAATGCGATCAACGGCTCAAACTT

TABLE 1-continued

CATTTTGGAGCCAATTACCATATGAAGATTGATTCTAGACCCCAAAAAGGGACGAA
AGTTGAAATATATATAAATAGAATAGAAACTAGCTAA 4127.4 (SEQ. ID. NO. 237)

ATGTTTTTTAAATTATTAAGAGAAGCTCTTAAAGTCAAGCAGGTTCGATCAAAAATT
TTATTTACAATTTTTATCGTTTTGGTCTTTCGTATCGGAACTAGCATTACAGTTCCTG
GTGTGAATGCCAATAGCTTGAATGCTTTAAGTGGATTATCCTTCTTAAACATGTTGA
GCTTGGTGTCGGGGAATGCCCTAAAAAACTTTTCGATTTTTGCCCTAGGAGTTAGTC
CCTATATCACCGCTTCTATTGTTGTCCAACTCTTGCAAATGGATATTTTACCCAAGTT
TGTAGAGTGGGGTAAACAAGGGGAAGTAGGTCGAAGAAAATTGAATCAAGCTACTC
GTTATATTGCTCTAGTTCTCGCTTTTGTGCAATCTATCGGGATTACAGCTGGTTTTAA
TACCTTGGCTGGAGCTCAATTGATTAAAACTGCTTTAACTCCACAAGTTTTTCTGACG
ATTGGTATCATCTTAACAGCTGGTAGTATGATTGTCACTTGGTTGGGTGAGCAAATT
ACAGATAAGGGATACGGAAACGGTGTTTCCATGATTATCTTTGCCGGGATTGTTTCC
TCAATTCCAGAGATGATTCAGGGCATCTATGTGGACTACTTTGTGAACGTCCCAAGT
AGCCGTATCACTTCATCTATCATTTTCGTAATCATTTTGATTATTACTGTATTGTTGAT
TATTTACTTTACAACTTATGTTCAACAAGCAGAATACAAAATTCCAATCCAATATAC
TAAGGTTGCACAAGGTGCTCCATCTAGCTCTTACCTTCCGTTAAAAGTAAACCCTGC
TGGAGTTATCCCTGTTATCTTTGCCAGTTCGATTACTGCAGCGCCTGCGGCTATTCTT
CAGTTTTTGAGTGCCACAGGTCATGATTGGGCTTGGGTAAGGGTAGCACAAGAGAT
GTTGGCAACTACTTCTCCAACTGGTATTGCCATGTATGCTTTGTTGATTATTCTCTTT
ACATTCTTCTATACGTTTGTACAGATTAATCCTGAAAAAGCAGCAGAGACCTACAAA
AGAGTGGTGCCTATATCCATGGAGTTCGTCCTGGTAAAGGTACAGAAGAATATATGT
CTAAACTTCTTCGTCGTCTTGCAACTGTTGGTTCCCTCTTCCTTGGTGTGA 4127.5 (SEQ. ID. NO. 238)

ATGGATATTAGACAAGTTACTGAAACCATCGCCATGATTGAGGAGCAAAACTTCGA
TATTAGAACCATTACCATGGGGATTTCTCTTTTGGACTGTATCGATCCAGATATCAAT
CGTGCTGCGGAGAAAATCTATCAAAAAATTACGACAAAGGCGGCTAATTTAGTAGC
TGTTGGTGATGAAATTGCGGCTGAGTTGGGAATTCCTATCGTTAATAAGCGTGTATC
GGTGACACCTATTTCTCTGATTGGGGCAGCGACAGATGCGACGGACTACGTGGTTCT
GGCAAAAGCGCTTGATAAGGCTGCGAAAGAGATTGGTGTGGACTTTATTGGTGGTTT
TTCTGCCTTAGTACAAAAAGGTTATCAAAAGGGAGATGAGATTCTCATCAATTCCAT
TCCTCGCGCTTTGGCTGAGACGGATAAGGTCTGCTCGTCAGTCAATATCGGCTCAAC
CAAGTCTGGTATTAATATGACGGCTGTGGCAGATATGGGACGAATTATCAAGGAAA
CAGCAAATCTTTCAGATATGGGAGTGGCCAAGTTGGTTGTATTCGCTAATGCTGTTG
AGGACAATCCATTTATGGCGGGTGCCTTTCATGGTGTTGGGGAAGCAGATGTTATCA
TCAATGTCGGAGTTTCTGGTCCTGGTGTTGTGAAACGTGCTTTGGAAAAAGTTCGTG
GACAGAGCTTTGATCTAGTAGCCGAAACAGTTAAGAAAACTGCCTTTAAAATCACTC
GTATCGGTCAATTGGTTGGTCAAATGGCCAGTGAGAGACTGGGTGTGGAGTTTGGTA
TTGTGGACTTGAGTTTGGCACCAACCCCTGCGGTTGGAGACTCTGTGGCACGTGTCC
TTGAGGAAATGGGGCTAGAAACAGTTGGCACGCATGGAACGACGGCTGCCTTGGCC
CTCTTGAACGACCAAGTTAAAAAGGGTGGAGTGATGGCCTGCAACCAAGTCGGTGG
TTTATCTGGTGCCTTTATCCCTGTTTCTGAGGATGAAGGAATGATTGCTGCAGTGCAA
AATGGCTCTCTTAATTTAGAAAAACTAGAAGCTATGACGGCTATCTGTTCTGTGGA
TTGGATATGATTGCCATCCCAGAAGATACGCCTGCTGAAACTATGCGGCTATGATT
GCGGATGAAGCAGCAATCGGTGTTATCAACATGAAAACAACAGCTGTTCGTATCATT
CCCAAAGGAAAAGAAGGCGATATGATTGAGTTTGGTGGTCTATTAGGAACTGCACC
CGTTATGAAGGTTAATGGGGCTTCGTCTGTCGACTTCATCTCTCGCGGTGGACAAAT
CCCAGCACCAATTCATAGTTTTAAAAATTAA 4128.1 (SEQ. ID. NO. 239)

ATGACACAGATTATTGATGGGAAAGCTTTAGCGGCCAAATTGCAGGGGCAGTTGGC
TGAAAAGACTGCAAAATTAAAGGAAGAAACAGGTCTAGTGCCTGGTTTGGTAGTGA
TTTTGGTTGGGGACAATCCAGCCAGCCAAGTCTACGTTCGCAACAAGGAGAGGTCA
GCCCTTGCGGCTGGTTTCCGTAGCGAAGTAGTACGGGTTCCAGAGACCATTACTCAA
GAGGAATTCTTAGACCTGATTGCTAAATACAATCAGGATCCAGCTTGGCATGGGATT
TTGGTTCAGTTGCCATTACCAAAACACATTGATGAAGAGGCGGTTCTATTGGCTATT
GACCCAGCAAAAGGATGTGGATGGTTTCCATCCTCTAAACATGGGGCGTCTTTGGTC
TGGTCATCCAGTCATGATTCCTTCGACACCGGCAGGAATTATGGAAATGTTCCATGA
ATATGGGATTGACT6TGGAAGGTAAAAATGCAGTCGTCATCGGTCGATCCAATATTG
TCGGAAAACCTATGGCCCAGCTTCTTTTGGCAAAGAATGCAACAGTAACCTTGACTC
ACTCACGTACTCATAATCTTTCCAAGGTGGCTGCAAAAGCAGATATTCTGGTTGTTG
CAATCGGTCGTGCCAAGTTTGTGACTGCTGACTTTGTCAAACCAGGTGCGGTAGTCA
TTGACGTTGGGATGAACCGCGATGAAAATGGTAAGCTCTGTGGGGATGTTGATTATG
AGGCGGTTGCCCCACYTTGCTAGCCACATTACGCCAGTCCCTGGAGGTGTCGGTCCTA
TGACCATTTACTATGCTGATGGAGCAAACCTATCAGGCAGCACTTAGGACATTGGATA
GAAAATAA 4128.2 (SEQ. ID. NO. 240)

ATGTCTAAATTTAATCGTATTCATTTGGTGGTACTGGATTCTGTAGGAATCGGTGCA
GCACCAGATGCTAATAACTTTGTCAATGCAGGGGTTCCAGATGGAGCTTCTGACACA
CTGGGACACATTTCAAAAACAGTTGGTTTGAATGTCCCAAACATGGCTAAAATAGGT
CTTGGAAATATTCCTCGTGAAACTCCTCTTAAGACTGTAGCAGCTGAAAGCAATCCA
ACTGGATATGCAACAAAATTAGAGGAAGTATCTCTTGGTAAGGATACTATGACTGG

TABLE 1-continued

ACACTGGGAAATCATGGGACTCAACATTACTGAGCCTTTCGATACTTTCTGGAACGG
ATTCCCAGAAGAAATCCTGACAAAAATCGAAGAATTCTCAGGACGCAAGGTTATTC
GTGAAGCCAACAAACCTTATTCAGGAACGGCTGTTATCTATGATTTTGGACCACGTC
AGATGGAAACTGGAGAGTTGATTATCTATACTTCAGCTGACCCTGTTTTGCAGATTG
CTGCCCACGAAGACATTATCCTTTGGATGAATTGTACCGTATCTGTGAATACGCTC
GTTCGATTACCCTTGAGCGTCCTGCCCTTCTTGGTCGCATCATTGCTCGCCCTTATGT
AGGTGAACCAGGTAACTTCACTCGTACGGCAAACCGTCGTGACTTGGCTGTATCTCC
ATTTTTCCCAACTGTTTTGGATAAATTGAATGAGGCTGGTATCGATACTTATGCTGTG
GGTAAAATCAACGATATCTTTAACGGTGCTGGTATCAACCATGACATGGGTCACAAC
AAGTCAAATAGTCATGAATTGATACACTATTGAAGACTATGGGACTTGCTGAGTTT
GAAAAAGGATTCTCATTCACAAACCTAGTTGACTTTGATGCCCTTTACGGCCATCGT
CGTAATGCTCACGGTTACCGTGATTGCTTGCATGAGThTGATGAACGCTTACCTGAA
ATTATCGCAGCTATGAGAGAGAATGACCTTCTCTTGATTACTGCGGACCATGGAAAT
GACCCAACGTATGCAGGAACGGATCACACTCGGGAATATATTCCATTGTTGGCCTAT
AGCCCTGCCTTTAAAGGAAATGGTCTCATTCCAGTAGGACATTTTGCAGATATTTCA
GCGACTGTTGCCGATAACTTTGGTGTGGAAACTGCTATGATTGGGGAAAGTTTCTTA
GATAAATTGGTATAA 4129.2 (SEQ. ID. NO. 241)

ATGTTTATTTCCATCAGTGCTGGAATTGTGACATTTTTACTAACTTTAGTAGAAATTC
CGGCCTTTATCCAATTTTATAGAAAGGCGCAAATTACAGGCCAGCAGATGCATGAG
GATGTCAAACAGCATCAGGCAAAAGCTGGGACTCCTACAATGGGAGGTTTGGTTTTC
TTGATTACTTCTGTTTTGGTTGCTTTCTTTTTCGCCCTATTTAGTAGCCAATTCAGCAA
TAATGTGGGAATGATTTTGTTCATCTTGGTCTTGTATGGCTTGGTCGGATTTTTAGAT
GACTTTCTCAAGGTCTTTCGTAAAATCAATGAGGGGCTTAATCCTAAGCAAAAATTA
GCTCTTCAGCTTCTAGGTGGAGTTATCTTCTATCTTTTCTATGAGCGCGGTGGCGATA
TCCTGTCTGTCTTTGGTTATCCAGTTCATTTGGGATTTTTCTATATTTTCTTCGCTCTTT
TCTGGCTAGTCGGTTTTTCAAACGCAGTAAACTTGACAGACGGTGTTGACGGTTTAG
CTAGTATTTCCGTTGTGATTAGTTTGTCTGCCTATGGAGTTATTGCCTATGTGCCAGG
TCAGATGGATATTCTTCTAGTAATTCTTGCCATGATTGGTGGTTTGCTCGGTTTCTTC
ATCTTTAACCATAAGCCTGCCAAGGTCTTTATGGGTGATGTGGGAAGTTTGGCCCTA
GGTGGGATGCTGGCAGCTATCTCTATGGCTCTCCACCAAGAATGGACTCTCTTGATT
ATCGGAATTGTGTATGTTTTTGAAACAACTTCTGTTATGATGCAAGTCAGTTATTTCA
AACTGACAGGTGGTAAACGTATTTTCCGTATGACGCCTGTACATCACCATTTTGAGC
TTGGGGGATTGTCTGGTAAAGGAAATCCTTGGAGCGAGTGGAAGGTTGACTTCTTC
TTTTGGGGAGTGGGACTTCTAGCAAGTCTCCTGACCCTAGCAATTTTATATTTGATGT
AA 4133.1 (SEQ. ID. NO. 242)

TTGTTTAAGAAAAATAAAGACATTCTTAATATTGCATTGCCAGCTATGGGTGAAAAC
TTTTTGCAGATGCTAATGGGAATGGTGGACAGTTATTTGGTTGCTCATTTAGGATTG
ATAGCTATTTCAGGGGTTTCAGTAGCTGGTAATATTATCACCATTTATCAGGCGATTT
TCATCGCTCTGGGAGCTGCTATTTCCAGTGTTATTTCAAAAAGCATAGGGCAGAAAG
ACCAGTCGAAGTTGGCCTATCATGTGACTGAGGCGTTGAAGATTACCTTACTATTAA
GTTTCCTTTTAGGATTTTTGTCCATCTTCGCTGGGAAAGAGATGATAGGACTTTTGGG
GACGGAGAGGGATGTAGCTGAGAGTGGTGGACTGTATCTATCTTTGGTAGGCGGAT
CGATTGTTCTCTTAGGTTTAATGACTAGTCTAGGAGCCTTGATTCGTCGCAACGCATA
ATCCACGTCTGCCTCTCTATGTTAGTTTTTTATCCAATGCCTTGAATATTCTTTTTTCA
AGTCTAGCTATTTTTGTTCTGGATATGGGGATAGCTGGTGTTGCTTGGGGGACAATT
GTGTCTCGTTTGGTTGGTCTTGTGATTTTGTGGTCACAATTAAAACTGCCTTATGGGA
AGCCAACTTTTGGTTTAGATAAGGAACTGTTGACCTTGGCTTTACCAGCAGCTGGAG
AGCGACTTATGATGAGGGCTGGAGATGTAGTGATCATTGCCTTGGCTGTTTCTTTTG
GGACGGAGGCAGTTGCTGGGAATGCAATCGGAGAAGTCTTGACCCAGTTTAACTAT
ATGCCTGCCTTTGGCGTCGCTACGGCAACGGTCATGCTGTTGCCCGAGCAGTTGGA
GAGGATGATTGGAAAAGAGTGCTAGTTTGAGTAAACAAACCTTTTGGCTTTCTCTG
TTCCTCATGTTGCCCCTGTCCTTTAGTATATATGTCTTGGGTGTACCATTAACTCATCT
CTATACGACTGATTCTCTAGCGGTGGAGGCTAGTGTTCTAGTGACACTGTTTTCACTA
CTTGGGACCCCTATGACGACAGGAACAGTCATCTATACGGCAGTCTGGCAGGGATT
AGGAAATGCACGCCTCCCTTTTTATGCGACAAGTATAGGAATGTGGTGTATCCGCAT
TGGGACAGGATATCTGATGGGATTGTGCTTGGTTGGGGCTTGCCTGGTATTTGGGC
AGGGTCTCTCTTGGATAATGGTTTTCGCTGGTTATTTCTACGCTATCGTTACCAGCGC
TATATGAGCTTGAAAGGATAG 4135.2 (SEQ. ID. NO. 243)

ATGCAAACCAAGAAAAACACTCGCAAGCAGCCGTTCTTGGCTTGCAGCACTTACTA
GCCATGTACTCAGGATCTATCCTGGTTCCCATCATGATTGCGACAGCCCTTGGCTATT
CAGCTGAGCAGTTGACCTACCTGATTTCTACAGATATCTTCATGTGTGGGGTGGCAA
CCTTCCTCCAACTCCAACTCAACAAATACTTTGGGATTGGACTCCCAGTCGTTCTTGG
AGTTGCATTCCAGTCGGTCGCTCCCTTGATTATGATTGGGCAAAGCCATGGTAGTGG
CGCTATGTTTGGTGCCCTTATCGCATCTGGGATTTACGTGGTTCTTGTTTCAGGCATC
TTCTCAAAAGTAGCCAATCTCTTCCCATCTATCGTAACAGGATCTGTTATTACCACGA
TTGGTTTAACCTTGATCCCTGTCGCTATTGGAAATATGGGAAATAACGTTCCAGAGC
CAACTGGTCAAAGTCTCTTGCTTGCAGCTATTACTGTTCTGATTATCCTCTTGATCAA
CATCTTTACCAAAGGATTTATCAAGTCTATCTCTATTTTGATTGGTCTGGTTGTTGGA
ACTGCCATTGCTGCTACTATGGGCTTGGTGGACTTCTCTCCTGTTGCGGTAGCTCCAC
TTGTCCATGTCCCAACTCCACTCTACTTTGGGATGCCAACCTTTGAAATCTCATCTAT

TABLE 1-continued

```
TGTCATGATGTGTATCATCGCAACGGTGTCTATGGTTGAGTCAACTGGTGTTTATCTG
GCCTTGTCTGATATCACAAAGGAATCCAATCGACAGCACGCGCCTTCGCAACGGAT
ACCGCGCAGAAGGTTTGGCCGTACTTCTCGGAGGAATCTTTAACACCTTCCCTTACA
CCGGATTTTCACAAAACGTTGGTTTGGTTAAATTGTCAGGCATCAAAAAACGCCTGC
CAATCTACTACGCAGCTGGTTTCCTGGTTCTCCTTGGACTGCTTCCTAAGTTTGGCGC
CCTTGCCCAAATCATTCCAAGCTCCGTCCTCGGTGGTGCCATGCTGGTAATGTTTGGT
TTTGTATCAATTCAAGGGATGCAAATCCTCGCCCGTGTTGACTTTGCTAACAATGAA
CACAACTTCCTTATCGCAGCTGTTTCAATCGCTGCAGGTGTCGGTCTCAACAACAGT
AATCTCTTTGTCAGCATGCCGACAGCCTTCCAAATGTTCTTCTCAAACGGAATCGTC
GTAGCCAGCCTACTCGCTATTGTCCTCAATGCCGTATTAAATCATAAAAAGAAATAA
```

4136.2 (SEQ. ID. NO. 244)

```
ATGAAAGATAGAATAAAAGAATATTTACAAGACAAGGGAAAGGTGACTGTTAATGA
TTTGGCTCAGGCTTGGGAAAAGACAGTTCCAAGGATTTTCGTGAGTTGATTAAAACC
TTGTCCTTAATGGAAAGAAAGCACCAAATTCGTTTTGAAGAAGATGGTAGTCTGACA
TTAGAAATTAAGAAAAAACATGAGATTACCCTCAAGGGGATTTTTCATGCCCATAAA
AATGGCTTTGGCTTTGTTAGTCTGGAAGGCGAGGAGGACGACCTTTTTGTAGGGAAA
AATGATGTCAACTATGCTATTGATGGTGATACCGTCGAGGTAGTGATTAAGAAAGTC
GCTGACCGCAATAAGGGAACAGCAGCAGAAGCCAAAATTATTGATATCCTAGAACA
CAGTTTGACAACAGTTGTCGGCAAATCGTTCTGGATCAGGAAAAACCTAAGTATGC
TGGCTATATTCGTTCAAAAAATCAGAAAATCAGTCAACCGATTTATGTTAAGAAACC
AGCCCTAAAATTAGAAGGAACAGAAGTTCTCAAAGTCTTTATCGATAAATACCCAA
GCAAGAAACATGATTTCTTTGTCGCGAGTGTTCTCGATGTAGTGGGACACTCAACGG
ATGTCGGAATTGATGTTCTTGAGGTCTTGGAATCAATGGACATTGTATCCGAGTTTC
CAGAAGCTGTTGTTAAGGAAGCAGAAAGTGTGCCTGATGCTCCGTCTCAAAAGGAT
ATGGAAGGTCGTCTGGATCTAAGAGATGAATTACCTTTACCATTGACGGTGCGGAT
GCCAAGGACTTGGACGATGCAGTGCATATCAAGGCTCTGAAAAATGGCAATCTGGA
GTTTGGGGTTCACATCGCAGATGTTTCTTATTATGTGACCGAGGGGTCTGCCCTTGAC
AAGGAAGCCCTTAACCGTGCGACTTCTGTTTACGTGACAGACCGAGTGGTGCCAATG
CTTCCAGAACGACTATCAAATGGCATCTGCTCTCAATCCCCAAGTTGACCGCCTG
ACCCAGTCTGCTATTATGGAGATTGATAAACATGGTCGTGTGGTCAACTATACCATT
ACACAAACAGTTATCAAGACCAGTTTTCGTATGACCTATAGCGATGTCAATGATATC
CTAGCTGGCGATGAAGAAAAGAGAAAAGAATATCATAAAATTGTATCAAGTATCGA
ACTCATGGCCAAGCTTCATGAAACTTTAGAAAACATGCGTGTGAAACGTGGAGCTCT
CAATTTTGATACCAATGAAGCGAAGATTTTAGTGGATAAACAAGGTAAGCCTGTTGA
TATCGTTCTTCGGCAGCGTGGTATTGCCGAGCGGATGATGAGTCTTTTATGTTGATG
GCTAATGAAACAGTTGCCGAACATTTCAGCAAGTTGGATTTGCCTTTTATCTATCGA
ATTCACGAGGAGCCTAAGGCTGAAAAGGTTCAGAAGTTTATTGATTATGCTTCGAGT
TTTGGCTTGCGCATTTATGGAACTGCCAGTGAGATTAGTCAGGAGGCACTTCAAGAC
ATCATGCGTGCTGTTGAGGGAGAACCTTATGCAGATGTATTGTCCATGATGCTTCTT
CGCTCTATGCAGCAGGCTCGTTATTCGGAGCACAATCACGGCCACTATGGACTAGCT
GCTGACTATTATACTCACTTTACCAGTCCAATTCGTCGTTATCCAGACCTTCTTGTTC
ACCGTATGATTCGGGATTACGGCCGTTCTAAGGAAATAGCAGAGCATTTTGAACAA
GTGATTCCAGAGATTGCGACCCAGTCTTCCAACCGTGAACGTCGTGCCATAGAAGCT
GAGCGTGAAGTCGAAGCCATGAAAAAGGCTGAGTATATGGAAGAATACGTGGGTGA
AGAGTATGATGCAGTTGTATCAAGTATTGTCAAATTCGGTCTCTTTGTCGAATTGCC
AAACACAGTTGAAGGCTTGATTCACATCACTAATCTGCCTGAATTTTATCATTTCAAT
GAGCGTGATTTGACTCTTCGTGGAGAAAAATCAGGTATCACTTTCCGAGTGGGTCAG
CAGATCCGTATCCGTGTTGAAAGAGCGGATAAAATGACTGGAGAGATTGATTTTTCA
TTCGTACCTAGTGAGTTTGATGTGATTGAAAAAGGCTTGAAACAGTCTAGTCGTAGT
GGCAGAGGGCGTGATTCAAATCGTCGTTCGGATAAGAAGGAAGACAAGAGAAAATC
AGGACGCTCAAATGATAAGCGTAAGCATTCACAAAAAGACAAGAAGAAAAAAGGA
AAGAAACCTTTTCACCGGAAGTAGCTAAGAAAGGAGCCAAGCATGGCAAAGGGCG
AGGGAAAGGTCGTCGCACAAAATAA
```

4137.2 (SEQ. ID. NO. 245)

```
ATGGGCACAACAGGATTTACAATAATTGACTTAATATCTTGATTGTTTATTTACTTG
CGGTGTTGGTTGCAGGTATCTATTTCTCTAAAAAAGAGATGAAAGGAAAGAGTTCT
TTAAAGGAGATGGTTCGGTTCCTTGGTATGTTACTTCGGTATCCATTTTTGCCACAAT
GCTCAGTCCGATTTCCTTCTTGGGACTCGCTGGTAGCTCTTATGCAGGTAGCTGGATT
TTATGGTTTGCTCAATTAGGGATGGTAGTAGCTATTCCACTGACAATTCGTTTTATCT
TACCTATCTTTGCACGGATAGACATCGATACGGCATATGATTACTTGGATAAACGTT
TTAATTCTAAAAGCACTTCGTATATTTTCAGCACTCTTGTTATTATTTATCAATTGG
GACGTATGTCTATCATTATGTACCTCCCATCAGCTGGTTTATCAGTATTGACAGGAAT
TGACATCAATATTTTGATTATTTTGATGGGTGTAGTTGCAATTGTTTATTCTTATACT
GGTGGTCTAAAATCCGTATTATGGACAGACTTTATTCAAGGTGTGATTCTGATTAGT
GGTGTCGTTTTAGCTTTATTTGTACTGATTGCTAATATTAAAGGTGGCTTTGGTGCAG
TAGCAGAAACATTAGCAAACGGGAAATTCCTTGCTGCAAATGAAAAACTTTTCGATC
CTAACTTGCTTTCAAACTCCATCTTTTTAATTGTGATGGGTTCAGGCTTTACAATCTT
GTCTTCCTATGCTTCATCTCAAGATTTGGTTCAACGTTTTACTACAACACAAATATT
AAGAAACTTAATAAGATGTTGTTCACAAACGGTGTTTTGTCACTTGCAACTGCAACA
GTCTTTTACTTGATTGGTACAGGCTTGTACGTATTCTATCAAGTACAAAATGCAGAT
AGTGCAGCTAGCAATATCCCTCAAGACCAAATCTTTATGTACTTTATTGCATACCAG
TTACCAGTAGGTATCACAGGTTTGATCTTGGCAGCGATTTATGCAGCATCTCAATCA
ACTATTTCAACAGGTTTGAACTCTGTTGCAACTTCATGGACATTGGATATTCAAGAT
GTCATTTCTAAAAATATGTCAGACAATCGTCGTACGAAAATTGCACAATTCGTATCT
CTAGCAGTAGGTTTATTCTCAATTGGTGTTTCCATTGTCATGGCTCACTCAGATATTA
```

TABLE 1-continued

AATCTGCATACGAATGGTTCAATAGTTTCATGGGACTTGTACTTGGTCTACTTGGTG
GTGTATTTATTCTTGGATTTGTTTCTAAAAAAGCAAATAAACAAGGTGCTTATGCAG
CGCTGATTGTATCAACCATCGTCATGGTATTTATTAAATACTTCCTTCCTCCAACAGC
TGTTAGCTACTGGGCATATTCATTGATTTCAATCTCTGTATCAGTAGTTTCAGGTTAT
ATTGTATCTGTTCTTACTGGAAATAAAGTATCTGCACCTAAATATACAACGATTCAT
GATATTACAGAAATTAAAGCGGATTCAAGTTGGGAAGTTCGTCACTAA 4138.1 (SEQ. ID. NO. 246)

ATGAAATTTAGTAAAAAATATATAGCAGCTGGATCAGCTGTTATCGTATCCTTGAGT
CTATGTGCCTATGCACTAAACCAGCATCGTTCGCAGGAAAATAAGGACAATAATCGT
GTCTCTTATGTGGATGGCAGCCAGTCAAGTCAGAAAAGTGAAAACTTGACACCAGA
CCAGGTTAGCCAGAAAGAAGGAATTCAGGCTGAGCAAATTGTAATCAAAATTACAG
ATCAGGGCTATGTAACGTCACACGGTGACCACTATCATTACTATAATGGGAAGTTC
CTTATGATGCCCTCTTTAGTGAAGAACTCTTGATGAAGGATCCAAACTATCAACTTA
AAGACGCTGATATTGTCAATGAAGTCAAGGGTGGTTATATCATCAAGGTCGATGGA
AAATATTATGTCTACCTGAAAGATGCAGCTCATGCTGATAATGTTCGAACTAAAGAT
GAAATCAATCGTCAAAAACAAGAACATGTCAAAGATAATGAGAAGGTTAACTCTAA
TGTTGCTGTAGCAAGGTCTCAGGGACGATATACGACAAATGATGGTTATGTCTTTAA
TCCAGCTGATATTATCGAAGATACGGGTAATGCTTATATCGTTCCTCATGGAGGTCA
CTATCACTACATTCCCAAAAGCGATTTATCTGCTAGTGAATTAGCAGCAGCTAAAGC
ACATCTGGCTGGAAAAAATATGCAACCGAGTCAGTTAAGCTATTCTTCAACAGCTAG
TGACAATAACACGCAATCTGTAGCAAAAGGATCAACTAGCAAGCCAGCAAATAAAT
CTGAAAATCTCCAGAGTCTTTTGAAGGAACTCTATGATTCACCTAGCGCCCAACGTT
ACAGTGAATCAGATGGCCTGGTCTTTGACCCTGCTAAGATTATCAGTCGTACACCAA
ATGGAGTTGCGATTCCGCATGGCGACCATTACCACTTTATTCCTACAGCAAGCTTTC
TGCCTTAGAAGAAAAGATTGCCAGAATGGTGCCTATCAGTGGAACTGGTTCTACAGT
TTCTACAAATGCAAAACCTAATGAAGTAGTGTCTAGTCTAGGCAGTCTTTCAAGCAA
TCCTTCTTCTTTAACGACAAGTAAGGAGCTCTCTTCAGCATCTGATGGTTATATTTT
AATCCAAAAGATATCGTTGAAGAAACGGCTACAGCTTATATTGTAAGACATGGTGA
TCATTTCCATTACATTCCAAAATCAAATCAAATTGGGCAACCGACTCTTCCAAACAA
TAGTCTAGCAACACCTTCTCCATCTCTTCCAATCAATCCAGGAACTTCACATGAGAA
ACATGAAGAAGATGGATACGGATTTGATGCTAATCGTATTATCGCTGAAGATGAATC
AGGTTTTGTCATGAGTCACGGAGACCACAATCATTATTTCTTCAAGAAGGACTTGAC
AGAAGAGCAAATTAAGGTGCGCAAAAACATTTAG 4139.1 (SEQ. ID. NO. 247)

ATGAAAAAAAGAGCAATAGTGGCAGTCATTGTACTGCTTTTGATTGGGCTGGATCAG
TTGGTCAAATCCTATATCGTCCAGCAGATTCCACTGGGTGAAGTGCGCTCCTGGATC
CCCAATTTCGTTAGCTTGACCTACCTGCAAAATCGAGGTGCAGCCTTTTCTATCTTAC
AAGATCAGCAGCTGTTATTCGCTGTCATTACTCTGGTTGTCGTGATAGGTGCCATTTG
GTATTTACATAAAACACATGGAGGACTCATTCTGGATGGTCTTGGGTTTGACTCTAA
TAATCGCGGTGGTCTTGGAAACTTTATTGACAGGGTCAGTCAGGGCTTTGTTGTGG
ATATGTTCCACCTTGACTTTATCAACTTTGCAATTTTCAATGTGGCAGATAGCTATCT
GACGGTTGGAGTGATTATTTTATTGATTGCAATGCTAAAAGAGGGAAATAAATGGAA
ATTAA 4139.5 (SEQ. ID. NO. 248)

ATGAATACAAATCTTGCAAGTTTTATCGTTGGACTGATCATCGATGAAAACGACCGT
TTTTACTTTGTGCAAAAGGATGGTCAAACCTATGCTCTTGCTAAGGAAGAAGGCCAA
CATACAGTAGGGGATACGGTCAAAGGTTTTGCATACACGGATATGAAGCAAAAACT
CCGCCTGACAACCTTAGAAGTGACTGCCACTCAGGACCAATTTGGTTGGGGACGTGT
CACAGAGGTTCGTAAGGACTTGGGTGTCTTTGTGGATACAGGCCTTCCTGACAAGGA
AATCGTTGTCACTCGATATTCTCCCTGAGCTCAAGGAACTCTGGCCTAAGAAGGG
CGACCAACTCTACATCCGTCTTGAAGTGGATAAGAAAGACCGTATCTGGGGCCTCTT
GGCTTATCAAGAAGACTTCCAACGTCTTGCTCGTCCTGCCTACAACAACATGCAGAA
CCAAAACTGGCCAGCCATTGTTTACCGTCTCAAGCTGTCAGGAACTTTTGTTTACCTA
CCAGAAAATAATATGCTTGGTTTTATTCATCCTAGCGAGCGTTACGCAGAGCCACGT
TTGGGGCAAGTATTAGATGCGCGCGTTATTGGTTTCCGTAAGTGGACCGCACTCTGA
ACCTCTCCCTCAAACCACGCTCCTTTGAAATGTTGGAAAACGATGCTCAGATGATTT
TGACTTATTTGGAAAGCAATGGCGGTTTCATGACCTTAAATGACAAGTCATCTCCAG
ACGACATCAAGGCAACCTTTGGCATTTCTAAAGGTCAGTTCAAGAAAGCTTTAGGTG
GTCTTATGAAGGCTGGTAAAATCAAGCAGGACCAGTTTGGGACAGAGTTGATTTAG 4139.8 (SEQ. ID. NO. 249)

ATGAAAGATGTTAGTCTATTTTTATTGAAAAAAGTTTTCAAAAGCCGCTTAAACTGG
ATTGTCTTAGCTTTATTTGTATCTGTACTCGGTGTTACCTTTTATTTAAATAGTCAGAC
TGCAAACTCACACAGCTTGGAGAGCAGGTTGGAAAGTCGCATTGCAGCCAACGAGA
GGGCTATCAATGAAAATGAAGAGAAACTCTCCCAAATGTCTGATACCAGCTCGGAG
GAATACCAGTTTGCTAAAAATAATTTAGACGTGCAAAAAAATCTTTTGACGCGAAA
GACAGAAATTCTGACTTTATTAAAAGAAGGGCGCTGGAAAGAAGCCTACTATTTGC
AGTGGCAAGATGAAGAGAAGAATTATGAATTTGTATCAAATGACCCGACTGCTAGC
CCTGGCTTAAAAATGGGGGTTGACCGCGAACGGAAGATTTACCAAGCCCTGTATCCC
TTGAACATAAAAGCACATACTTTGGAGTTTCCGACCCACGGGATTGATCAGATTGTC
TGGATTTTAGAGGTTATCATCCCAAGTTTGTTTGTGGTTGCTATTATTTTTATGCTAA
CACAACTATTTGCAGAAAGATATCAAAATCATCTGGACACAGCTCACTTATATCCTG

TABLE 1-continued

```
TTTCAAAAGTGACATTTGCAATATCCTCTCTTGGAGTGGAGTGGGATATGTAACTG
TGCTGTTTATCGGAATCTGTGGCTTTTCTTTTCTAGTGGGAAGTCTGATAAGTGGTTT
TGGACAGTTAGATTATCCCTACCCAATTTATAGCTTAGTGAATCAAGAAGTAACTAT
TGGGAAAATACAAGATGTATTATTTCCTGGCTTGCTCTTAGCTTTCTTAGCCTTTATC
GTCATTGTGGAAGTGTGTACTTGATTGCTTACTTTTTCAAGCAAAAAATGCCTGTCC
TCTTTCTTTCACTCATTGGGATTGTTGGCTTATTGTTTGGTATCCAAACCATTCAGCCT
CTTCAAAGGATTGCACATCTGATTCCCTTTACTTACTTGCGTTAGTGGAGATTTTAT
CTGGAAGATTACCTAAGCAGATTGATAATGTCGATCTAAATTGGAGCATGGGAATG
GTCTTACTTCCTTGCCTGATTATCTTTTTGCTATTGGGAATTCTATTTATTGAAAGATG
GGGAAGTTCACAGAAAAAAGAATTTTTTAATAGATTCTAG
```

4141.1 (SEQ. ID. NO. 250)

```
ATGATGAAGTTCATATTGGATATTGTTAGTACACCAGCTATTTTAGTAGCTTTAATTG
CAATCTTAGGATTAGTTCTTCAGAAGAAGAAATTACCTGATATTATTAAAGGTGGAA
TTAAGACCTTTGTTGGTTTCTTAGTTGTATCTGGTGGTGCAGGAATTGTACAAAATTC
TTTAAATCCATTTGGTACCATGTTTGAGCATGCTTTTCATTTATCTGGCGTTGTGCCG
AATAATGAAGCAATTGTAGCTGTAGCTTTAACAACATATGGCTCAGCTACTGCAATG
ATTATGTTTGCAGGCATGGTGTTCAATATCTTAATCGCTCGTTTTACTCGATTTAAAT
ATATTTTTTTAACAGGGCACCACACTCTATATATGGCATGTATGATTGCGGTCATTTT
ATCAGTTGCTGGCTTTACTAGCTTGCCTCTCATCTTACTAGGAGGATTAGCACTCGGT
ATTATTATGAGTATTTCCCCAGCATTTGTGCAAAAATATATGGTTCAATTAACTGGA
AATGACAAGGTAGCTTTAGGTCATTTCAGTTCTTTGGGATATTGGTTGAGTGGTTTTA
CTGGTAGCCTTATCGGTGACAAATCAAAATCAACAGAGGACATTAAATTTCCAAAG
AGTTTAGCTTTTTTACGTGATAGTACTGTTAGTATTACTTTATCCATGGCAGTTATTT
ACATTATTGTAGCTATCTTTGCAGGGTCAGAATATATAGAAAAAGAAATCAGTAGTG
GTACAAGTGGTCTAGTTTATGCTTTACAATTAGCAGGTCAATTTGCAGCAGGGGTAT
TTGTTATTTTAGCAGGTGTTCGCCTTATTTTGGGCGAAATTGTTCCAGCCTTTAAAGG
TATTTCAGAGCGTCTTGTACCTAATTCAAAACCTGCTTTGGATTGTCCGATTGTTTAT
ACTTATGCACCCAATGCAGTTCTAATTGGATTTATCTCTAGTTTGTTGGTGGTTTAG
TAAGTATGGTAATTATGATTGCTTCAGGAACGGTTGTTATCTTACCAGGTGTTGTGCC
TCATTTCTTCTGTGGAGCGACTGCAGGTGTCATTGGGAATGCATCTGGTGGTGTTCGT
GGAGCCACTATTGGAGCATTTTTACAAGGTATTTTAATCAGTTTTCTTCCAGTCTTTT
TAATGCCAGTTTTGGGAGGACTTGGTTTCCAAGGATCAACTTTCTCAGATGCAGATT
TTGGTCTATCAGGAATTATTTTAGGAATGTTAAATCAATTTGGCTCACAAGCAGGCA
TTGTGATTGGTCTTGTTCTTATTCTAGCAGTTATGTTTGGAGTATCCTTTATTAAAAA
GCCATCTGCAACGGAGGAATAA
```

4142.3 (SEQ. ID. NO. 251)

```
ATGATTAAAACATTTCTCTCTGCCCTTTCGGTCATTCTCTTTTCTATCCCTATCATAAC
TTATTCTTTTTTCCCATCTTCTAATCTTAACATTTGGCTATCTACCCAACCTATCTTGG
CACAGATTTATGCCTTCCCCTTAGCTACTGCAACTATGGCTGCTATTTTAAGTTTCTT
ATTTTTTTTCCTATCTTTTTACAAGAAAAATAAACAAATACGGTTTTACTCTGGCATT
TTGCTCTTACTATCGCTCATATTACTATTATTCGGAACAGATAAAACCCTTTCTTCTG
CATCAAATAAGACTAAAAACTTAAAATTAGTAACTTGGAACGTCGCTAATCAAATA
GAAGCACAACATATTGAGCGAATTTTTAGCCATTTTGACGCCGATATGGCTATATTC
CCTGAACTAGCTACCAATATCAGAGGTGAGCAAGAAAACCAGAGAATCAAACTATT
GTTTCATCAAGTTGGACTTTCTATGGCCAACTATGATATTTTCACTTCTCCACCTACC
AATAGTGGAATAGCTCCTGTGACTGTGATTGTCAAGAAAAGTTATGGTTTCTATACA
GAAGCTAAAACTTTTCATACAACACGGTTCGGGACAATTGTATTACATTCGAGAAAA
CAAAATATACCAGATATCATTGCCTTGCATACTGCGCCTCCTCTGCCAGGTTTAATG
GAAATCTGGAAGCAAGACTTAAACATCATTCATAATCAATTGGCTTCAAAATATCCA
AAGGCTATTATTGCAGGTGATTTTAATGCAACTATGCGTCATGGAGCACTTGCAAAA
ATAAGCTCTCATAGGGACGCATTAAATGCACTGCCACCTTTTGAAAGAGGAACTTGG
AATAGCCAAAGTCCAAAACTTTTTAATGCAACAATAGATCATATTTTATGCCTAAA
AACCACTACTATGTTAAAGATTTAGACATTGTAAGTTTTCAAAACTCTGATCATAGA
TGTATTTTTACAGAAATCACATTTTAA
```

4142.4 (SEQ. ID. NO. 252)

```
ATGAATCCAATCCAAAGATCTTGGGCTTATGTCAGCAGAAAGCGACTGAGAAGTTTT
ATTTTATTTCTGATTTATTGGTCTTATTGGCCGGAATTTCAGCCTGTTTGACTCTGAT
GAAGTCCAACAAAACAGTAGAAAGCAATCTTTATAAATCACTCAATACATCTTTTTC
TATTAAGAAGATAGAGAATGGTCAGACATTCAAGTTGTCAGACCTAGCATCTGTAA
GCAAGATTAAGGGCTGGAAAATGTCTCTCCTGAACTTGAAGGGTCGCAAAACTA
AAAGACAAGGAAGCAGTGACTGGCGAGCAGAGCGTGGAGCGTGATGATTTATCAGC
TGCAGACAATAACTTGGTTAGCTTAACGGCTCTTGAGGATTCATCCAAGGATGTAAC
CTTTACCAGTTCGGCTTTCAATCTAAAAGAAGGGCGACACCTTCAAAAAGGGGATTC
CAAGAAAATCCTTATCCACGAAGAATTGGCTAAGAAGAACGGTCTTTCGCTTCATGA
CAAGATTGGCTTGGATGCTGGTCAGTCTGAATCTGGAAAAGGACAAACAGTAGAGT
TTGAGATTATCGGCATCTTTTCTGGTAAAAAACAAGAGAAATTCACAGGCTGTCTT
CTGACTTCAGTGAAAATCAAGTCTTTACAGACTATGAAAGTAGCCAAACCCTTTTGG
GCAATAGTGAAGCTCAAGTCAGTGCAGCACGCTTCTATGTAGAAAATCCTAAGGAA
ATGGACGGACTCATGAAGCAGGTAGAAAACTTGGCCTTGGAAAATCAAGGCTACCA
AGTCGAAAGGAAACAAGGCTTTTGAACAAATCAAAGACTCAGTTGCAACTTTCC
AAACCTTCCTGACCATCTTCCTTTATGGGATGTTGATAGCAGGAGCTGGAGCCTTAA
TTCTGGTTTTGTCTCTCTGGTTGAGAGAACGGGTCTATGAAGTGGGGATTTTACTTGC
ACTTGGAAAAGGCAAGAGCTCGATCTTCCTACAATTCTGTTTAGAGGTAGTTTTGGT
```

TABLE 1-continued

ATCTCTTGGAGCTTTGCTTCCAGCATTTGTTGCAGGAAACGCAATCACAACTTACCT
ACTCCAAACTCTACTAGCAAGTGGAGATCAGGCAAGCTTACAAGATACACTAGCCA
AAGCAAGCAGTTTATCAACTAGCATCTTATCTTTTGCAGAATCCTATGTTTTCTAGT
TCTGCTTAGTTGCTTATCTGTAGCCCTTTGTTTCCTATTCTTATTTAGAAAATCACCGA
AAGAAATTTTATCATCTATTAGTTAA 4142.5 (SEQ. ID. NO. 253)

ATGTTACACAACGCATTTGCCTATGTTACAAGGAAGTTTTTCAAATCGATTGTCATCT
TCCTGATTATTCTCCTCATGGCGAGCTTGAGTTTGGTCGGCTTGTCAATCAAGGGAG
CTACTGCCAAGGCTTCTCAGGAGACCTTTAAAAATATCACCAATAGCTTCTCCATGC
AAATCAATCGTCGCGTCAACCAAGGAACGCCTCGTGGTGCTGGGAATATCAAGGGT
GAAGACATCAAAAAAATCACCGAAAACAAGGCCATTGAGTCTTATGTCAAACGTAT
CAACGCTATCGGAGATTTGACTGGATATGACCTGATTGAAACGCCAGAAACCAAGA
AGAATCTCACTGCTGATCGTGCCAAGCGTTTTGGAAGTAGCTTGATGATTACAGGTG
TCAATGACTCCTCTAAAGAAGACAAGTTTGTCTCTGGTTCTTATAAACTAGTCGAAG
GAGAGCACTTAACCAACGACGACAAGGATAAAATCCTCTTGCACAAGGACTTGGCA
GCCAAACACGGCTGGAAAGTAGGGGACAAGGTTAAACTGGACTCTAATATCTACGA
TGCAGATAATGAAAAGGAGCCAAGGAAACAGTTGAAGTGACAATCAAGGGACTCT
TTGATGGTCATAATAAGTCAGCAGTAACCTACTCACAAGAACTTTACGAAAACACA
GCTATTACAGACATTCACACTGCTGCAAAACTTTATGGATACACAGAAGACACAGCC
ATTTATGGGACGCAACCTTCTTTGTAACAGCAGACAAGAACTTGGATGATGTTATG
AAAGAGTTGAATGGCATCAGTGGTATCAACTGGAAGAGCTACACACTCGTCAAGAG
CTCCTCTAACTACCCAGCTCTTGAGCAATCTATCTCTGGTATGTACAAGATGGCCAA
CCTCCTCTTCTGGGGTAGCTTGAGCTTCTCAGTTCTCCTCCTTGCCCTCTTGCTCAGC
CTTTGGATCAACGCCCGTCGCAAGGAAGTGGGAATTCTCCTCTCTATCGGCCTCAAG
CAGGCAAGTATCTTGGGTCAATTCATCACCGAATCTATCTTGATTGCTATCCCTGCTC
TAGTTTCTGCTTACTTCCTAGCTAATTACACTGCCCGTGCAATTGGAAACACTGTCCT
TGCCAATGTGACTTCAGGTGTTGCCAAACAGGCTAGTAAGGCGGCTCAAGCCTCTAA
CCTTGGTGGTGGTGCAGAAGTAGATGGCTTTAGCAAGACCTTGTCGAGCCTAGACAT
TTCCATTCAGACATCAGACTTTATCATCATTTTTGTCCTTGCCTGGTTCTAGTGGTTC
TCGTTATGGCGCTTGCTTCAAGCAATCTCCTTAGAAAACAACCAAAAGAGCTCTTGC
TGGATGGTGAATAA 4144.1 (SEQ. ID. NO. 254)

ATGTCACAGGATAAACAAATGAAAGCTGTTTCTCCCCTTCTGCAGCGAGTTATCAAT
ATCTCATCGATTGTCGGTGGGGTTGGGAGTTTGATTTTCTGTATTTGGGCTTATCAGG
CTGGGATTTTACAATCCAAGGAAACCCTCTCTGCCTTTATCCAGCAGGCAGGCATCT
GGGGTCCACCTCTCTTTATCTTTTTACAGATTTTACAGACTGTCGTCCCTATCATTCC
AGGGGCCTTGACCTCGGTGGCTGGGGTCTTTATCTACGGGCACATCATCGGGACTAT
CTACAACTATATCGGCATCGTGATTGGCTGTGCCATTATCTTTTATCTAGTGCGCCTA
TACGGAGCTGCCTTTGTCCAGTCTGTCGTCAGCAAGCGCACCTACGACAAGTACATC
GACTGGCTAGATAAGGGCAATCGTTTTGACCGCTTCTTTATTTTTATGATGATTTGGC
CCATTAGCCCAGCTGACTTTCTCTGTATGCTGGCTGCCCTGACCAAGATGAGCTTCA
AGCGCTACATGACCATCATCATTCTGACCAAACCCTTTACCCTCGTGGTTTATACCTA
CGGTCTGACCTATATTATTGACTTTTTCTGGCAAATGCTTTGA 4144.2 (SEQ. ID. NO. 255)

ATGAGAAATATGTGGGTTGTAATCAAGGAAACCTATCTTCGACATGTCGAGTCATGG
AGTTTCTTCTTTATGGTGATTTCGCCGTTCCTCTTTTTAGGAATCTCTGTAGGAATTG
GGCATCTCCAAGGTTCTTCTATGGCTAAAAATAATAAAGTGGCAGTAGTGACAACA
GTGCCATCTGTAGCAGAAGGACTGAAGAATGTAAATGGTGTTAACTTCGACTATAA
AGACGAAGCAAGTGCCAAAGAAGCAATTAAAGAAGAAAATTAAAAGGTTATTTG
ACCATTGATCAAGAAGATAGTGTTCTAAAGGCAGTTTATCATGGCGAAACATCGCTT
GAAAATGGAATTAAATTTGAGGTTACAGGTACACTCAATGAACTGCAAAATCAGCT
TAATCGTTCAACTGCTTCCTTGTCTCAAGAGCAGGAAAAACGCTTAGCGCAGACAAT
TCAATTCACAGAAAAGATTGATGAAGCCAAGGAAAATAAAAAGTTTATTCAAACAA
TTGCAGCAGGTGCCTTAGGATTCTTTCTTTATATGATTCTGATTACCTATGCGGGTGT
AACAGCTCAGGAAGTTGCCAGTGAAAAAGGCACCAAAATTATGGAAGTCGTTTTTT
CTAGCATAAGGGCAAGTCACTATTTCTATGCGCGGATGATGGCTCTGTTTCTAGTGA
TTTTAACGCATATTGGGATCTATGTTGTAGGTGGTCTGGCTGCCGTTTTGCTCTTTAA
AGATTTGCCATTCTTGGCTCAGTCTGGTATTTTGATCACTTGGGAGATGCTATCTCA
CTGAATACCTTGCTCTTTATTTTGATCAGTCTTTTCATGTACGTAGTCTTGGCAGCCTT
CCTAGGATCTATGGTTTCTCGTCCTGAGGACTCAGGGAAAGCCTTGTCGCCTTTGAT
GATTTTGATTATGGGTGGTTTTTTGGAGTGACAGCTCTAGGTGCAGCTGGTGACAA
TCTCCTCTTGAAGATTGGTTCTTATATTCCCTTTATTTCGACCTTCTTTATGCCGTTTC
GAACGATTAATGACTATGCGGGGGAGCAGAAGCATGGATTTCACTTGCTATTACA
GTGATTTTTGCGGTGGTAGCAACAGGATTTATCGGACGCATGTATGCTAGTCTCGTT
CTTCAAACGGATGATTTAGGGATTTGGAAAACCTTTAAACGTGCCTTATCTTATAAA
TAG 4144.3 (SEQ. ID. NO. 256)

ATGACAGAAACCATTAAATTGATGAAGGCTCATACTTCAGTGCGCAGGTTTAAAGA
GCAAGAAATTCCCCAAGTAGACTTAAATGAGATTTTGACAGCAGCCCAGATGGCAT
CATCTTGGAAGAATTTCCAATCCTACTCTGTGATTGTGGTACGAAGTCAAGAGAAGA
AAGATGCCTTGTATGAATTGGTACCTCAAGAAGCCATTCGCCAGTCTGCTGTTTTCCT

TABLE 1-continued

```
TCTCTTTGTCGGAGATTTGAACCGAGCAGAAAAGGGAGCCCGACTTCATACCGACAC
CTTCCAACCCCAAGGTGTGGAAGGTCTCTTGATTAGTTCGGTCGATGCAGCTCTTGC
TGGACAAAACGCCTTGTTGGCAGCTGAAAGCTTGGGCTATGGTGGTGTGATTATCGG
TTTGGTTCGATACAAGTCTGAAGAAGTGGCAGAGCTCTTTAACCTACCTGACTACAC
CTATTCTGTCTTTGGGATGGCACTGGGTGTGCCAAATCAACATCATGATATGAAACC
GAGACTGCCACTAGAGAATGTTGTCTTTGAGGAAGAATACCAAGAACAGTCAACTG
AGGCAATCCAAGCTTATGACCGTGTTCAGGCTGACTATGCTGGGGCGCGTGCGACCA
CAAGCTGGAGTCAGCGCCTAGCAGAACAGTTTGGTCAAGCTGAACCAAGCTCAACT
AGAAAAAATCTTGAACAGAAGAAATTATTGTAG
```

4146.1 (SEQ. ID. NO. 257)

```
ATGTTAAAACTTATTGCTATTGTTGGAACAAATTCAAAACGTTCTACAAACCGTCAA
TTGCTTCAATACATGCAAAAACACTTTACTGACAAAGCTGAAATTGAACTTGTTGAA
ATCAAGGCCATTCCTGTCTTCAACAAACCAGCTGACAAGCAAGTACCTGCTGAAATA
TTGGAAATTGCTGCTAAAATCGAAGAGGCAGATGGCGTTATTATCGGTACTCCTGAG
TATGATCACTCTATTCCAGCTGTTTTGATGAGCGCTCTTGCTTGGTTGTCTTATGGTA
TTTACCCACTTTTGAACAAACCAATCATGATTACAGGTGCTTCTTACGGTACGCTTGG
TTCATCTCGTGCCCAATTGCAACTTCGTCAAATCTTGAATGCTCCTGAAATCAAGGC
AAATGTTCTTCCAGATGAATTCTTGCTCTCACACTCTCTTCAAGCATTTAACCCAAGT
GGCGACTTGGTTGACCTTGATGTTATCAAGAAATTGGATGCCATCTTTGATGCTTC
CGTATCTTTGTAAAAATCACAGAAAAATTACGTAATGCACAAGAATTACTTCGCAAA
GATGCTGAAGACTTTGACTGGGAAAATTTGTAA
```

4146.2 (SEQ. ID. NO. 258)

```
ATGAATACCTATCAATTAAATAATGGAGTAGAAATTCCAGTATTGGGATTTGGAACT
TTTAAGGCTAAGGATGGAGAAGAAGCCTATCGTGCAGTGTTAGAAGCCTTGAAGGC
TGGTTATCGTCATATTGATACGGCGGCGATTTATCAGAATGAAGAAAGTGTTGGTCA
AGCAATCAAAGATAGCGGAGTTCCACGTGAAGAAATGTTCGTAACTACCAAGCTTT
GGAATAGTCAGCAAACCTATGAGCAAACTCGTCAAGCTTTGGAAAAATCTATAGAA
AAACTGGGCTTGGATTATTTGGATTTGTATTTGATTCATTGGCCGAACCCAAAACCG
CTCAGAGAAAATGACGCATGGAAAACTCGCAATGCGGAAGTTTGGAGAGCGATGGA
AGACCTCTATCAAGAAGGGAAAATCCGTGCTATCGGCGTTAGCAATTTTCTTCCCCA
TCATTTGGATGCCTTGCTTGAAACTGCAACTATCGTTCCTGCGGTCAATCAAGTTCGC
TTGGCGCCAGGTGTGTATCAAGATCAAGTCGTAGCTTACTGTCGTGAAAAGGGAATT
TTATTGGAAGCTTGGGGGCCTTTTGGACAAGGAGAACTGTTTGATAGCAAGCAAGTC
CAAGAAATAGCAGCAAATCACGGAAAATCGGTTGCTCAGATAGCCTTGGCCTGGAG
CTTGGCAGAAGGATTTTTACCACTTCCAAAATCTGTCACAACCTCTCGTATTCAAGCT
AATCTTGATTGCTTTGGAATTGAACTGAGTCATGAGGAGAGAGAAACCTTAAAAAC
GATTGCTGTTCAATCGGGTGCTCCACGAGTTGATGATGTGGATTTCTAG
```

4147.1 (SEQ. ID. NO. 259)

```
ATGAGGTGCAAAATGCTTGATCCAATTGCTATTCAACTAGGACCCCTAGCCATTCGT
TGGTATGCCTTATGTTTGTGACAGGCTTGATTCTTGCGGTTTATTTGACCATGAAAG
AAGCACCTAGAAAGAAGATCATACCAGACGATATTTTAGATTTTATCTTAGTAGCCT
TTCCCTTGGCTATTTTAGGAGCTCGTCTCTACTATGTTATTTTCCGATTTGATTACTAT
AGTCAGAATTTAGGAGAGATTTTTGCCATTTGGAATGGTGGTTTGGCCATTTACGGT
GGTTTGATAACTGGGGCTCTTGTGCTCTATATCTTTGCTGACCGTAAACTCATCAATA
CTTGGGATTTTCTAGATATTGCGGCGCCTAGCGTTATGATTGCTCAAAGTTTGGGGC
GTTGGGGTAATTTCTTTAACCAAGAAGCTTATGGTGCAACAGTGGATAATCTGGATT
ATCTACCTGGCTTTATCCGTGACCAGATGTATATTGAGGGGAGCTACCGTCAACCGA
CTTTCCTTTATGAGTCTCTATGGAATCTGCTGGCTTTGCCTTGATTCTGATTTTTAGA
CGGAAATGGAAGAGTCTCAGACGAGGTCATATCACGGCCTTTTACTTGATTTGCTAT
GGTTTCGGTCGTATGGTTATCGAAGGTATGCGAACAGATAGTCTCATGTTCTTCGGC
TTTCGAGTGTCCCAATGGCTGTCAGTTGTCCTTATCGGTCTCGGTATAATGATCGTA
TTTATCAAAATCGAAAGAAGGCCCCTTACTATATTACAGAGGAGGAAAACTAA
```

4147.2 (SEQ. ID. NO. 260)

```
ATGGGTAAATTATCCTCAATCCTTTTAGGAACCGTTTCAGGTGCAGCTCTTGCCTTGT
TTTTAACAAGTGATAAGGGCAAACAAGTTTGCAGTCAGGCTCAAGATTTTCTAGATG
ATTTGAGAGAAGATCCGGAGTATGCCAAGGAGCAAGTCTGTGAAAAACTGACAGAA
GTTAAGGAGCAGGCTACAGATTTTGTTCTGAAAACAAAAGAACAGGTTGAGTCAGG
TGAAATCACTGTGGACAGTATACTTGCTCAAACTAAATCCTATGCTTTTCAAGCGAC
AGAAGCATCAAAAAATCAATTAAATAATCTCAAGGAGCAATGGCAAGAAAAAGCC
GAAGCTCTTGATGACTCAGAAGAGATTGTGATTGATATAACAGAAGAATAA
```

4147.3 (SEQ. ID. NO. 261)

```
ATGAAAACTAAATTGATCTTTTGGGGCTCTATGCTCTTTCTCCTCTCCCTCTCCATCC
TTCTGACCATTTATCTGGCTTGATTTTCTATCCTATGGAGATTCAGTGGCTAAACTTA
ACGAATCGAGTCTATCTAAAACCAGAAACCATTCAATACAATTTTCATATCTTGATG
AATTATCTGACCAATCCTTTTAGTCAGGTCTTACAGATGCCTGATTTTCGTTCGTCAG
CAGCTGGTCTGCACCATTTCGCAGTGGTCAAGAATCTCTTTCATTGGTTCAGCTAGT
AGCTCTAGTGACACTGCCAAGTTTCTATGTCTTTGTCAATAGGATTGTGAAAAAGGA
CTTTTTGTCTCTTTATCGAAAAGTCTCCTGGCTCTAGTAGTCTTACCTGTGATGATT
GGACTTGGGGGAGTTTTCATTGGTTTTGACCAATTCTTTACTCTTTTCCATCAAATTC
```

TABLE 1-continued

TCTTTGTGGGAGATGATACCTGGCTTTTTGATCCAGCCAAGGATCCTGTTATTATGAT
TTTGCCAGAGACCTTCTTTCTTCATGCCTTCCTCCTCTTTTTTGCCCTCTATGAAAACT
TCTTTGGCTATCTGTATCTGAAAAGTCGTAGGAAGTGA 4149.1 (SEQ. ID. NO. 262)

ATGACTTATCATTTTACTGAAGAATACGATATTATTGTAATTGGTGCGGGACACGCT
GGGGTTGAGGCTTCCTTGGCCGCTAGCCGTATGGGCGTAAGGTCCTGCTTGCGACC
ATCAATATTGAAATGCTGGCTTTCATGCCTTGTAATCCCTCTATCGGTGGTTCTGCCA
AGGGGATTGTCGTGCGTGAAGTCGATGCCCTCGGTGGCGAGATGGCCAAAACCATT
GACAAGACTTACATCCAGATGAAGATGCTAAACACAGGGAAGGGGCCAGCTGTCCG
TGCCCTTCGTGCGCAGGCTGACAAGGAACTTTACTCTAAGGAGATGCGCAAGACGG
TTGAAAACCAAGAAAATCTGACCCTTCGTCAAACCATGATTGATGAGATTTTGGTGG
AAGATGGCAAGGTTGTCGGTGTGCGTACAGCCACCCATCAAGAATATGCTGCTAAG
GCTGTTATTGTGACGACAGGGACTGCTCTCCGTGGGGAAATTATCATCGGAGACCTC
AAGTACTCATCAGGTCCTAACCACAGCTTGGCTTCTATTAACCTAGCTGACAATCTC
AAGGAACTGGGTCTCGAAATCGGTCGTTTCAAGACAGGACCCCTCCACGTGTCAAG
GCTTCTTCTATCAATTACGATGTGACAGAAATTCAGCCAGGAGACGAAGTGCCTAAT
CATTTCTCATACACTTCACGTGATGAGGATTATGTCAAGGACCAAGTACCATGCTGG
TTGACCTATACCAATGGTACCAGTCATGAGATTATCCAAAACAACCTCCACCGTGCG
CCTATGTTTACAGGTGTGGTCAAGGGAGTGGGGCCTCGTTACTGTCCGTCGATTGAA
GACAAGATTGTGCGCTTTGCGGACAAGGAACGTCACCAACTCTTCCTTGAGCCAGAA
GGGCGCATTACTGAGGAAGTCTATGTGCAAGGACTTTCAACCAGTCTGCCTGAGGAT
GTCCAGCGTGACTTGGTGCATTCCATCAAAGGTTTGGAAAATGCAGAGATGATGCG
GACAGGTTATGCTATTGAGTATGATATGGTCTTGCCTCATCAGTTGCGTGCGACTTTG
GAAACCAAGAAAATCTCAGGTCTCTTCACTGCTGGTCAGACAAATGGAACATCAGG
TTACGAAGAGGCAGCAGGCCAAGGGATTATCGCGGGTATCAATGCGGCTCTGAAAA
TCCAAGGCAAGCCTGAATTGATTTTGAAGCGCAGTGATGGTTATATCGGGGTGATGA
TCGACGACTTGGTGACCAAGGGAACCATTGAACCCTACCGTCTCTTGACCAGTCGTG
CTGAATACCGTCTCATTCTTCGTCATGACAATGCTGATATGCGCTTGACTGAGATGG
GACGCGAGATTGGCCTTGTGGACGATGAACGCTGGGCTCGTTTTGAAATCAAGAAA
AATCAATTTGATAATGAGATGAAGCGCCTAGACAGTATCAAACTCAAGCCAGTCAA
GGAAACCAATGCCAAGGTTGAGGAGATGGGCTTCAAACCCTTGACCGATGCAGTGA
CAGCCAAGGAATTCCTTCGCCGTCCAGAAGTTTCTTACCAAGATGTGGTGGCCTTCA
TCGGACCAGCTGCAGAAGACTTGGATGACAAGATTATCGAATTGATTGAAACAGAA
ATCAAGTATGAAGGCTATATTTCCAAAGCCATGGACCAGGTTGCCAAGATGAAACG
CATGGAAGAAAAACGCATTCCGGCCAATATCGACTGGGATGACATTGATTCTATCGC
AACCGAAGCCCGTCAGAAGTTCAAACTCATCAATCCAGAAACCATCGGCCAAGCCA
GCCGTATTTCGGGAGTAAACCCAGCAGATATTTCTATTTTGATGGTGTATCTGGAAG
GTAAAAATCGTAGTATTTCTAAAACTCTTCAAAAATCAAAATGA 4149.2 (SEQ. ID. NO. 263)

ATGAAAGTATTAGCTTTTGATACGTCCAGCAAGGCTCTTTCTCTGGCTATTTTAGAGG
ATAAGCAGGTTCTTGCCGAGACGACGATTAATATTAAGAAAAATCACAGTATTACTC
TTATGCCTGCCATCGATTTTTTGATGGCAAGTTTGGATTGGACACCCAAGGATTGG
ACCGAATCGTGGTAGCTGAAGGGCCGGGTAGCTATACAGGCTTGCGAATTGCGGTA
GCAACTGCTAAGACCTTAGCTCACACCCTGAACATCGAGTTGGTTGGTATGTCGAGT
CTCTTGGCTCTGGTGCCCCATCAACAAGAAGGTTTGTTTGTCCCCTTGATGGATGCGC
GTCGCAATAATGTTTATGCAGGATTTTATGAAAATGCCAAACCTGTCATGGCAGAAG
CGCACCTATCTTTTGAAGAGGTGCTAGAAAAAGTCAAGGGTACTAGTCAGGTAACCT
TTGTCGGAGAAGTTGGCCCCTTTGTTGAGCAGATTCAAAAACACTTGCCAAGGACTG
ATTACAAAGAAACATTGCCCAATGCAGCTAATCTAGCTCTTTTGGCCTGGGACAAGG
AAGCAGACTCCTTGCATGATTTTGTGCCGAATTACCTCAAACGAGTCGAGGCTGAGG
AAAACTGGCTCAAGAACCATACCGAGTCTGGCGAGTCTTACATTAAACGCCTATGA 4149.3 (SEQ. ID. NO. 264)

ATGATAGAAATCAAGCGAATTCAACAACAGCCTGACCTAGCTCAAGCCATCTACGC
TGTTATGGCAGCTGTTTACCTAGTCAGTCCTTGGACTCTGGAGCAAATCCAAGCAGA
TCTGTCCCAAGACCAGACTTGGTATGCATTGGCTTATGATGGGGCAGAAGTGATTGG
ATTTCTAGCTGTGCAGGAGAATCTTTTTGAAGCAGAAGTCCTGCAAATCGTGTCAA
AGGAGCTTATCAGGGTCAGGGGATTGCGTCagCCTTGTTTGCTCAATTGCCGACAGAC
AAGGAAATTTTCCTCGAAGTCAGACAGTCAAATCAACGAGCGCAAGCAATTTTACAA
GAAAGAAAAGATGACAGTTATCGCTGAGCGAAAGGCCTACTACCATGACCCAGTCG
AGGACGCCATTATCATGAAGAGAGAAATAGATGAAGGATAG 4152.2 (SEQ. ID. NO. 265)

ATGACAAAACAAGTCTTATTAGTGGATGATGAAGAACACATTCTGAAATTGCTTGAC
TACCATTTAAGTAAGGAAGGCTTTTCTACTCAATTGGTGACAAATGGACGGAAGGCC
TTAGCTTTGGCAGAAACAGAACCCTTTGATTTTATCTTGCTTGATATCATGTTACCAC
AATTAGATGGCATGGAAGTTTGTAAGCGGCTGAGAGCCAAAGGCGTCAAAACTCCA
ATTATGATGGTTTCTGCGAAAGTGATGAATTTGATAAGGTTTTGGCCTTGGAATTA
GGGGCTGATGACTACCTGACCAAGCCTTTTAGCCCTAGAGAATTGCTGGCGGCGTGC
AAGGCTGTCCTCAGGCGAACTAAAGGAGAACAAGAAGGGATGATTCAGATAATAT
CGCTGACGATTCTTGGCTATTTGGGACCTTGAAAGTATACCCTGAGCGTCATGAAGT
CTACAAGGCGAATAAGTTACTGAGTTTGACCCCAAAAGAATTTGAAAGCGATAAAA
ATCCGTTTTTTGAAGTTTTCAAAGTTTCGAAAGTAACCGCCCAATAA

TABLE 1-continued 4154.1 (SEQ. ID. NO. 266)

ATGACTACTTTTAAAGATGGATTTTTATGGGGTGGTGCTGTTGCTGCTCATCAACTTG
AAGGTGGATGGCAAGAAGGTGGCAAGGGAATTAGTGTTGCTGATGTTATGACTGCT
GGTCGTCATGGAGTAGCTCGTGAAATACTTTGGGAGTTTTAGAGGGTAAATATTATC
CAAATCATGAGGCGATAGATTTTTATCACCGTTATAAAGAAGATATAGCACTTTTTG
CTGAAATGGGATTCAAGTGCTTCCGTACCTCTATTGCATGGACACGTATCTTTCCAA
AAGGTGATGAGTTAGAGCCGAATGAAGAAGGATTACAGTTTTATGATAATCTTTTTG
ATGAATGCTTAAAGAATGGTATTGAACCTGTCATCACTCTATCTCATTTTGAAATGC
CTTATCACTTAGTGACCGAATATGGTGGTTGGAAAAATAGGAAATTGATTGATTTCT
TTGCTCGTTTTGCAGAAGTCGTATTTAAACGTTACAAAGATAAGGTTAAATATTGGA
TGACTTTCAATGAAATCAATAATCAAGCGAATTATCAGGAAGATTTTGCACCATTTA
CTAACTCAGGTATTGTATATGAGGAAGGTGATAATAGAGAAGCAATTATGTATCAA
GCAGCACATTACGAATTAGTTGCTTCTGCACGAGCTGTAAAAATTGGTCATGAGATT
AATCCAGATTTTCAAATAGGTTGTATGATTGCGATGTGTCCAATTTATCCAGTTACTT
GCAATCCTAAGGATATCTTAATGGCAATGAAAGCTATGCAGAAGCGTTATTATTTTG
CTGATGTGCATGTTTTAGGTAAATATCCTGAGCATATTTTCAAGTATTGGGAACGAA
AAGGTATTTCAGTTGATTTTACTGCCCAGGATAAAGAAGATTTACTTGGTGGGACTG
TAGATTACATTGGTTTCAGTTACTATATGTCCTTTGCTATCGACTCTCATCGTGAAAA
TAATCCTTATTTTGATTATCTTGAAACAGAAGATTTAGTGAAAAATAATTATGTTAA
GGCTTCTGAATGGGAGTGGCAAATTGATCCAGAAGGTTTGCGTTATGCGTTAAATTG
GTTTACAGACCACTATCACTTACCACTCTTTATTGTTGAAAATGGTTTTGGAGCTATA
GATCAAGTTGCAGCAGATGGTATGGTACATGATGATTATAGAATTGAATATCTAGGT
GCCCATATTCGTGAAATGAAAAAGGCTGTAGTTGAAGATGGTGTTGATTTAATGGGT
TATACTCCATGGGGATGTATTGATTTGGTTCAGCTGGTACCGGTGAAATGCGGAAA
CGTTATGGCTTTATTTATGTAGATAAAGATGATAATGGGAAGGGAAGTTATAATCGT
TCCCCGAAAAAATCTTTTGGCTGGTATAAGGAAGTTATTTCATCTAACGGTGAATCA
GTAGAATAG 4154.2 (SEQ. ID. NO. 267)

ATGGATCAACAAAACGGGTTGTTTGGTTTTCTTGAAAACCATGTTATGGGACCAATG
GGCAAACTTGCTCAGTTTAAAGTAGTACGTGCTATCACGGCTGCAGGTATGGCTGCT
GTACCATTTACTATTGTAGGATCAATGTTTTTGGTATTCAGTATTTTGCCACAAGCTT
TCTCATTTTGGCCAATTGTGGCAGATATTTTCTCTGCTTCATTTGATAAATTCACATC
ACTTTACATGGTTGCAAACTATGCGACTATGGGTTCTCTATCTCTTTATTTCGTTCTA
TCACTTGCATATGAATTGACAAAAATTTATGCAGAGGAAGAAGAACTCAATATGAA
TCCTCTTAATGGTGCCTTGCTTGCCTTGATGGCTTTTGTCATGACAGTACCGCAAATC
ATTTTTGATGGTGGAATGATGAAGACTGTGACAAGTCTAAAAGAAGGTGCAGTAAT
TGCAGATGGATGGGCAATGGGAAATGTCGTCGCACGTTTTGGGACAACAGGGATTT
TTACCGCAATCATTATGGCAATTGTGACTGTCTTATTTATCGTATGTGTTAAACA
TAATTGGGTTATTAAAATGCCTGAAGCTGTTCCAGAAGGAGTTTCTCGTGGATTTAC
CGCTTTGGTTCCGGGATTTGTTGTTGCATTTGTTGTTATCTTTATCAACGGTCTTCTTG
TAGCAATGGGAACAGATATTTTTAAAGTCATTGCAATTCCATTTGGTTTTGTATCCAA
TCTGACTAATTCGTGGATTGGTTTAATGATTATTTATCTATTGACTCAACTACTTTGG
ATTGTAGGTATCCACGGTGCGAACATTGTTTTTGCATTTGTTAGTCCAATTGCTCTTG
CTAACATGGCTGAAAATGCTGCTGGCGGGCACTTCGCTGTTGCAGGTGAATTTTCTA
ATATGTTTGTAATTGCAGGTGGTTCTGGTGCAACTTTAGGACTATGTTTATATATTGC
TTTTGCCTCTAAATCTGAACAGCTTAAAGCAATAGGACGAGCATCTGTAGTTCCAGC
CTTATTTAATATTAATGAACCATTAATTTTTGGATTACCTATTATCTATAATCCAGCC
TTGGCTATACCATTTATTTTAGCACCAATGGTTACTGCTACTATTTATTACGTAGCGA
ATTCTCTAAACTTTATTAAGCCAATTATCGCACAGGTTCCATGGCCAACTCCAGTAG
GGATTGGAGCTTTCTTAGGGACAGCAGATCTTCGAGCTGTATTAGTTGCTCTAGTAT
GTGCATTTGCAGCATTCCTAGTCTATCTTCCATTCATCCGTGTATATGATCAAAAATT
GGTGAAAGAAGAGCAAGGTATCTAA 4155.1 (SEQ. ID. NO. 268)

ATGAAAAAATTTTATGTAAGTCCAATTTTTCCTATTCTAGTAGGATTGATTGCGTTTG
GAGTCTTATCCACTTTCATTATTTTTGTTAATAATAATCTGTTGACGGTTTTAATTTTG
TTTCTTTTTGTAGGAGGCTATGTTTTTTTATTTAAGAAACTGAGAGTGCATTATACAA
GGAGTGATGTAGAACAGATACAGTATGTAAACCACCAAGCGGAAGAAAGTTTGACA
GCTCTATTGAACAGATGCCTGTAGGTGTTATGAAATTGAATTTATCTTCTGGAGAG
GTTGAGTGGTTTAATCCCTATGCTGAATTGATTTTGACCAAGGAAGATGGTGATTTT
GATTTAGAAGCTGTTCAAACGATTATCAAGGCTTCAGTAGGAAATCCGTCTACTTAT
GCCAAGCTTGGTGAGAAGCGTTATGCTGTTCATATGGATGCTTCTTCCGGTGTTTTGT
ATTTTGTAGATGTATCCAGGGAACAAGCCATAACAGATGAATTGGTAACAAGTAGA
CCAGTGATTGGGATTGTCTCTGTGGATAATTATGATGATTTGGAGGATGAAACTTCT
GAGTCAGATATTAGTCAAATCAATAGTTTTGTAGCTAATTTTATATCAGAGTTTTCAG
AAAAAACACATGATGTTTTCTCGTCGGGTAAGTATGGATCGATTTTATCTATTTACTGA
CTACACGGTGCTGAGGGCTTGATGAATGATAAATTTTCTGTTATTGATGCTTTCAGA
GAAGAGTCGAAACAGAGACAGTTGCCCTTGACCTTAAGTATGGGATTCTTATGGC
GATGGAAATCATGATGAGATAGGGAAAGTTGCTTTGCTCAATTTGAACTTGGCTGAA
GTACGTGGTGGCGACCAGGTGGTTGTTAAGGAAAACGACGAAACGAAAAATCCAGT
TTATTTTGGTGGTGGGTCTGCTGCTTCAATCAAGCGTACACGGACTCGTACGCGCGC
TATGATGACAGCTATTTCAGATAAGATTCGGAGTGTAGATCAGGTTTTTGTAGTCGG
TCACAAAAATTTAGACATGGATGCTTTGGGCTCTGCTGTAGGTATGCAGTTGTTCGC
CAGCAATGTGATTGAAAATAGCTATGCTCTTTATGATGAAGAACAAATGTCTCCAGA

TABLE 1-continued

```
TATTGAACGAGCTGTTTCATTCATAGAAAAAGAAGGAGTTACGAAGTTGTTGTCTGT
TAAGGATGCAATGGGGATGGTGACCAATCGTTCTTTGTTGATTCTTGTAGACCATTC
AAAGACAGCCTTAACATTATCAAAAGAATTTTATGATTTATTTACCCAAACCATTGT
TATTGACCACCATAGAAGGGATCAGGATTTTCCAGATAATGCGGTTATTACTTATAT
CGAAAGTGGTGCAAGTAGTGCCAGTGAGTTGGTAACGGAATTGATTCAGTTCCAGA
ATTCTAAGAAAAATCGTTTGAGTCGTATGCAAGCAAGTGTCTTGATGGCTGGTATGA
TGTTGGATACTAAAAATTTCACCTCGCGAGTAACTAGTCGGACATTTGATGTTGCTA
GCTATCTCAGAACGCGCGGAAGTGATAGTATTGCTATCCAGGAAATCGCTGCGACA
GATTTTGAAGAATATCGTGAGGTCAATGAACTTATTTTACAGGGGCGTAAATTAGGT
TCAGATGTACTAATAGCAGAGGCTAAGGACATGAAATGCTATGATACAGTTGTTATT
AGTAAGGCAGCAGATGCCATGTTAGCCATGTCAGGTATTGAAGCGAGTTTTGTTCTT
GCGAAGAATACACAAGGATTTATCTCTATCTCAGCTCGAAGTCGTAGTAAACTGAAT
GTACAACGGATTATGGAAGAGTTAGGCGGTGGAGGCCACTTTAATTTGGCAGCAGC
TCAAATTAAAGATGTAACCTTGTCAGAAGCAGGTGAAAAACTGACAGAAATTGTAT
TAAATGAAATGAAGGAAAAGGAGAAAGAAGAATGA
```

4156.1 (SEQ. ID. NO. 269)

```
ATGAAAGAGAAAAATATGTGGAAAGAATTGTTGAATCGTGCAGGCTGGATTTTGGT
CTTTTTACTTGCCGTCCTTTTATATCAGGTTCCCCTAGTGGTTACCTCTATTTTGACTT
TAAAAGAAGTAGCCCTGCTACAGTCAGGGCTGATAGTTGCTGGCCTTTCAATTGTGG
TTCTGGCTCTATTTATTATGGGAGCTCGTAAAACCAAGTTAGCTAGTTTTAATTTTTC
TTTTTTTAGAGCTAAAGATTTGGCACGTTTGGGCTTGAGTTATCTAGTTATTGTCGGG
TCAAATATACTTGGTTTCCATTTTATTGCAACTGTCAAATGAGACGACAACAGCTAAC
CAGTCTCAGATTAATGATATGGTTCAAAATAGTTCGTTGATTTCCAGTTTCTTCTTGC
TAGCCTTGCTTGCTCCGATTTGTGAGGAAATCTTGTGTCGTGGGATTGTTCCTAAAAA
GATTTTCCGAGGCAAGGAGAACTTGGGATTGTAGTCGGTACGATTGTGTTTGCTTTT
ATTGCATCAACCAAGTAATTTACCTTCTTTATTGATTTATGGAGGTATGTCGACAGTT
CTATCTTGGACAGCCTACAAGACCCAACGTTTGGAAATGTCGATCTTGCTTCACATG
ATTGTTAATGGGATTGCTTTCTGTTTGTTGGCTCTTGTGGTGATTATGAGTCGGACAT
TAGGAATTTCTGTTTAAATGAAAGAGAAAAATATGTGGAAAGAATTGTTGAATCGT
GCAGGCTGGATTTTGGTCTTTTTACTTGCCGTCCTTTTATATCAGGTTCCCCTAGTGG
TTACCTCTATTTTGACTTTAAAAGAAGTAGCCCTGCTACAGTCAGGGCTGATAGTTG
CTGGCCTTTCAATTGTGGTTCTGGCTCTATTTATTATGGGAGCTCGTAAAACCAAGTT
AGCTAGTTTTAATTTTTCTTTTTTTAGAGCTAAAGATTTGGCACGTTTGGGCTTGAGT
TATCTAGTTATTGTCGGGTCAAATATACTTGGTTCCATTTTATTGCAACTGTCAAATG
AGACGACAACAGCTAACCAGTCTCAGATTAATGATATGGTTCAAAATAGTTCGTTGA
TTTCCAGTTTCTTCTTGCTAGCCTTGCTTGCTCCGATTTGTGAGGAAATCTTGTGTCGT
GGGATTGTTCCTAAAAAGATTTTCCGAGGCAAGGAGAACTTGGGATTGTAGTCGGT
ACGATTGTGTTTGCTTTATTGCATCAACCAAGTAATTTACCTTCTTTATTGATTTATG
GAGGTATGTCGACAGTTCTATCTTGGACAGCCTACAAGACCCAACGTTTGGAAATGT
CGATCTTGCTTCACATGATTGTTAATGGGATTGCTTTCTGTTTGTTGGCTCTTGTGGT
GATTATGAGTCGGACATTAGGAATTTCTGTTTAA
```

4156.4 (SEQ. ID. NO. 270)

```
ATGGATACACAAAAGATTGAAGCGGCTGTAAAAATGATTATCGAGGCTGTAGGAGA
GGACGCTAATCGCGAGGGCTTGCAGGAAACACCTGCTCGTGTAGCCCGTATGTATCA
AGAGATTTTTTCAGGTCTTGGTCAAACAGCAGAGGAACATTTGTCAAAATCCTTTGA
AATTATTGACGATAATATGGTGGTAGAAAAGGATATCTTTTTCCATACCATGTGTGA
ACACCACTTCTTGCCATTTTATGGTAGAGCGCACATTGCCTACATTCCAGATGGTCGT
GTGGCAGGCTTGTCTAAGCTAGCCCGTACGGTTGAAGTTTATTCGAAAAAACCACAA
ATTCAAGAACGTTTGAATATCGAAGTGGCCGATGCCTTGATGGACTATCTAGGTGCT
AAAGGAGCCTTTGTTGTCATTGAGGCGGAACATATGTGTATGAGTATGCGTGGTGTTT
AGAAAAACCAGGCACTGCAACCTTGACGACAGTAGCTCGTGGTCTATTTGAAACAGA
TAAGGATCTCCGTGACCAAGCTTATCGTTTAATGGGGCTATAA
```

4157.2 (SEQ. ID. NO. 271)

```
ATGAAAGACTTGTTTTTAAAGAGAAAGCAGGCCTTTCGTAAGGAGTGTCTTGGTTAT
CTGCGCTATGTGCTCAATGACCACTTTGTCTTGTTCCTGCTTGTCCTGTTGGGCTTTCT
AGCCTACCAGTACAGTCAACTCTTACAACATTTTCCTGAAAATCATTGGCCTATCTT
TTGTTTGTAGGAATTACGTCTGTTTTACTTTTACTTTGGGGAGGAACTGCCACCTATA
TGGAGGCTCCAGACAAGCTCTTTCTCTTAGTTGGAGAAGAGGAAATTAAGCTCCATC
TCAAGCGTCAAACTGGCATTTCCCTAGTCTTTTGGCTCTTTGTACAGACCCTTTTCTT
GCTGTTATTTGCGCCTTTATTTTTAGCAATGGGTTATGGCTTGCCAGTTTTCTGCTCT
ATGTGCTTTTATTGGGGGTAGGAAAATATTTCCACTTTTGTCAAAAGGCCAGCAAAT
TTTTCACTGAAACTGGACTGGACTGGGACTATGTTATTTCTCAAGAAAGCAAGCGTA
AGCAAGTCTTGCTTCGTTTCTTTGCCCTCTTTACGCAGGTCAAGGGAATTTCAAACAG
CGTTAAGCGTCGTGCCTATCTGGACTTTATTTTAAAGGCTGTTCAGAAGGTGCCTGG
GAAGATTTGGCAAAATCTCTATCTGCGTTCTTATCTGCGAAATGGCGACCTCTTTGCT
CTCAGTCTTCGTCTTCTCTTGCTTTGCCTTGCTGGCGCAGGTTTTTATCGAGCAAGCT
TGGATTGCGACAGCAGTGGTAGTTCTCTTTAACTACCTCTTGCTCTTCCAGTTGCTGG
CCCTCTATCATGCCTTTGACTACCAGTATTTGACCCAACTCTTTCCGCTGGACAAGGG
GCAAAAGGAAAAAGGCTTACAGGAGGTAGTTCGAGGATTGACCAGTTTTGTTTTACT
TGTGGAATTAGTTGTTGGGTTGATTACCTTCCAAGAAAAACTAGCCCTTCTAGCCTT
ACTAGGAGCTGGTTTGGTTTTACTAGTCTTGTATTTGCCTTATCAGGTAAAACGTCAG
ATGCAGGACTAA
```

TABLE 1-continued 4258.2 (SEQ. ID. NO. 272)

ATGAGAAAATCAATAGTATTAGCGGCAGATAATGCCTATCTTATTCCTTTAGAGACG
ACTATAAAGTCTGTATTGTATCACAATAGAGATGTTGATTTTTATATTCTCAACAGTG
ATATAGCTCCTGAATGGTTTAAATTATTGGGGAGAAAAATGGAAGTTGTGAATTCTA
CAATTCGCAGTGTACACATTGATAAAGAACTTTTTGAAAGCTATAAAACAGGACCTC
ATATAAATTATGCTTCTTACTTTAGATTTTTTGCGACAGAAGTGGTTGAATCTGATAG
GGTATTGTATCTGGATTCCGATATCATTGTAACTGGGGAACTAGCTACTTTGTTTGAG
ATAGATCTCAAAGGATATTCAATTGGTGCTGTTGATGATGTCTATGCCTATGAAGGA
CGAAAATCTGGATTTAATACTGGTATGTTACTAATGGATGTTGCAAAGTGGAAAGAA
CATTCTATTGTCAATAGTTTATTGGAATTAGCGGCCGAGCAGAATCAAGTTGTTCAT
CTTGGGGATCAGAGTATTTTAAATATTTATTTTGAGGATAATTGGCTAGCCTTAGAT
AAAACATATAATTATATGGTGGGTATTGATATTTATCACCTTGCTCAAGAATGTGAA
CGTCTAGATGACAATCCACCTACAATTGTTCACTATGCTAGTCATGATAAACCTTGG
AATACATATAGTATATCTAGACTACGTGAATTATGGTGGGTTTATAGAGATTTGGAT
TGGTCAGAGATTGCTTTTCAACGTTCCGATTTAAATTATTTTGAAAGAAGCAATCAG
TCTAAAAAACAAGTGATGCTTGTGACATGGAGTGCAGATATAAAACATTTAGAGTA
TTTAGTACAACGGTTACCTGATTGGCATTTTCATTTGGCTGCACCGTGTGATTGTTCT
GAGGAGCTGACCTCTCTATCACAGTATACGAATGTAACAGTATATCAAAATGTATTA
CATAGTAGAATTGATTGGCTATTGGACGATTCTATAGTTTATTTAGATATTAATACA
GGTGGAGAGGTTTTTAATGTAGTTACAAGGGCACAAGAAAGTGGCAAGAAAATCTT
CGCTTTTGATATCACACGTAAAAGTATGGATGATGGACTCTATGACGGTATTTTTTCT
GTGGAGAGACCAGATGATTTAGTGGATAGAATGAAGAATATAGAGATAGAGTAA 4158.2 (SEQ. ID. NO. 273)

ATGACTAAGATTTATTCGTCAATAGCAGTAAAAAAAGGACTATTTACCTCATTTCTA
CTGTTTATCTATGTATTGGGAAGTCGTATTATTCTCCCTTTTGTTGACCTAAATACTA
AAGATTTTTAGGAGGTTCAACAGCCTATCTAGCCTTCTCAGCCGCCCTAACAGGTG
GGAATCTAAGAAGTTTATCAATTTTTTCTGTTGGATTATCCCCTTGGATGTCCGCCAT
GATTTTATGGCAGATGTTTCTTTTTCTAAACGGTTGGGTTTAACATCTACGTCTATA
GAAATACAAGATCGCCGTAAAATGTACCTGACCTTGCTAATTGCTGTGATTCAATCC
TTGGCAGTTAGCTTGAGACTGCCAGTACAATCCTCCTATTCTGCAATATTGGTTGTTC
TAATGAATACAATATTGCTGATAGCAGGAACATTTTTTCTTGTTTGGTTGTCAGATTT
AAATGCGAGTATGGGGATTGGAGGTTCTATTGTAATCCTCCTATCCAGTATGGTTTT
AAATATTCCTCAGGATGTTTTGGAAACATTTCAGACAGTACACATTCCAACAGGGAT
TATTGTGTTACTTGCTTTATTAACCCTTGTCTTTTCTTATTTACTTGCCCTTATGTATC
GAGCTCGCTATTTGGTTCCTGTTAATAAAATTGGCTTACACAATCGATTTAAACGCT
ATTCTTATCTCGAAATCATGTTGAATCCTGCAGGTGGGATGCCTTATATGTATGTGAT
GAGTTTTCTTAGTGTACCAGCTTATTTGTTCATCTTGTTGGGATTTATTTTCCCTAATC
ATTCAGGGTTAGCGGCTTTATCAAAGGAATTTATGGTTGGAAAGCCTTTGTGGGTCT
ATGTTTATATTTCGGTCTTATTTTTATTTAGTATCATTTTTGCTTTTGTTACGATGAAT
GGGAGAAGAGATTGCAGACCGTATGAAAAATCTGGAGAATACATTTATGGTATTTA
TCCAGGTGCGGATACTAGTCGATTTATTAATCGATTGGTCCTTCGTTTCTCAGTCATA
GGTGGTCTCTTTAATGTGATTATGGCAGGTGGTCCCATGCTTTTTGTTTTGTTTGATG
AAAAGTTATTACGATTGGCAATGATTCCAGGCTTATTTATGATGTTCGGGGGGCATGA
TTTTTACGATTAGAGACGAGGTCAAGGCTTTAAGGCTAAATGAGACCTATAGACCTT
TGATTTAG 4158.3 (SEQ. ID. NO. 274)

ATGTCCTCTCTTTCGGATCAAGAATTAGTAGCTAAAACAGTAGAGTTTCGTCAGCGT
CTTTCCGAGGGAGAAAGTCTAGACGATATTTTGGTTGAAGCTTTTGCTGTGGTGCGT
GAAGCAGATAAGCGGATTTTAGGGATGTTTCCTTATGATGTTCAAGTCATGGGAGCT
ATTGTCATGCACTATGAAATGTTGCTGAGATGAATACGGGGGAAGGTAAGACCTT
GACAGCTACCATGCCTGTCTATTTGAACGCTTTTCAGGAGAAGGAGTGATGGTTGT
GACTCCTAATGAGTATTTATCAAAGCGTGATGCCGAGGAAATGGGTCAAGTTTATCG
TTTTCTAGGATTGACCATTGGTGTACCATTTACGGAAGATCCAAAGAAGGAGATGAA
AGCTGAAGAAAAGAAGCTTATCTATGCTTCGGATATCATCTACACAACCAATAGTAA
TTTAGGTTTTGATTATCTAAATGATAACCTAGCCTCGAATGAAGAAGGTAAGTTTTT
ACGACCGTTTAACTATGTGATTATTGATGAAATTGATGATATCTTGCTTGATAGTGC
ACAAACTCCTCTGATTATTGCGGGTTCTCCTCGTGTTCAGTCTAATTACTATGCGATC
ATTGATACACTTGTAACAACCTTGGTCGAAGGAGAGGATTATATCTTTAAAGAGGAG
AAAGAGGAGGTTTGGCTCACTACTAAGGGGGCCAAGTCTGCTGAGAATTTCCTAGG
GATTGATAATTTATACAAGGAAGAGCATGCGTCTTTTGCTCGTCATTTGGTTTATGCG
ATTCGAGCTCATAAGCTCTTTACTAAAGATAAGGACTATATCATTCGTGGAAATGAG
ATGGTACTGGTTGATAAGGGAACAGGGCGTCTAATGGAAATGACTAAACTTCAAGG
AGGTCTCCATCAGGCTATTGAAGCCAAGGAACATGTCAAATTATCTCCTGAGACGCG
GGCTATGGCCTCGATCACCTATCAGAGTCTTTTTAAGATGTTTAATAAGATATCTGGT
ATGACAGGGACAGGTAAGGTCGCGGAAAAAGAGTTTATTGAAACTTACAATATGTC
TGTAGTACGCATTCCAACCAATCGTCCGAGACAACGGATTGACTATCCAGATAATCT
ATATATCACTTTACCTGAAAAAGTGTATGCATCCTTGGAGTACATCAAGCAATACCA
TGCTAAGGGAAATCCTTTACTCGTTTTTGTAGGCTCAGTTGAAATGTCTCAACTCTAT
TCGTCTCTCTTGTTTCGTGAAGGGATTGCCCATAATGTCCTAAATGCTAATAATGCGG
CGCGTGAGGCTCAGATTATCTCCGAGTCAGGTCAGATGGGGGCTGTGACAGTGGCT
ACCTCTATGGCAGGACGTGGTACGGATATCAAGCTTGGTAAAGGAGTCGCAGAGCT
TGGGGGCTTGATTGTTATTGGGACTGAGCGGATGGAAAGTCAGCGGATCGACCTAC
AAATTCGTGGCCGTTCTGGTCGTCAGGGAGATCCTGGTATGAGTAAATTTTTTGTAT
CCTTAGAGGATGATGTTATCAAGAAATTTGGTCCATCTTGGGTGCATAAAAAGTACA

TABLE 1-continued

AAGACTATCAGGTTCAAGATATGACTCAACCGGAAGTATTGAAAGGTCGTAAATAC
CGGAAACTAGTCGAAAAGGCTCAGCATGCCAGTGATAGTGCTGGACGTTCAGCACG
TCGTCAGACTCTGGAGTATGCTGAAAGTATGAATATACAACGGGATATAGTCTATAA
AGAGAGAAATCGTCTAATAGATGGTTCTCGTGACTTAGAGGATGTTGTTGTGGATAT
CATTGAGAGATATACAGAAGAGGTAGCGGCTGATCACTATGCTAGTCGTGAATTATT
GTTTCACTTTATTGTGACCAATATTAGTTTTCATGTTAAAGAGGTTCCAGATATATA
GATGTAACTGACAAAACTGCAGTTCGTAGCTTTATGAAGCAGGTGATTGATAAAGA
ACTTTCTGAAAAGAAAGAATTACGTTAATCAACATGACTTATATGAACAGTTTTTAC
GACTTTCACTGCTTAAAGCCATTGATGACAACTGGGTAGAGCAGGTAGACTATCTAC
AACAGCTATCCATGGCTATCGGTGGTCAATCTGCTAGTCAGAAAAATCCAATCGTAG
AGTACTATCAAGAAGCCTACGCGGGCTTTGAAGCTATGAAAGAACAGATTCATGCG
GATATGGTGCGTAATCTCCTGATGGGGCTGGTTGAGGTCACTCCAAAAGGTGAAATC
GTGACTCATTTTCCATAA 4158.4 (SEQ. ID. NO. 275)

ATGATAGGGACTTTCGCCGCTGCTCTTGTAGCTGTACTAGCAAATTTCATCGTCCCTA
TTGAAATTACCCCAAATAGTGCCAATACTGAAATTGCACCACCAGATGGGATTGGGC
AGGTTCTCAGCAACCTCTTGCTCAAACTGGTTGACAACCCAGTCAACGCCCTGCTTA
CTGCTAACTATATTAGAATCTTATCTTGGGCAGTCATTTTTGGAATCGCTATGAGAG
AAGCCAGTAAAAATAGTCAAGAATTGCTAAAAACTATCGCTGACGTGACTTCTAAA
ATTGTCGAATGGATCATCAATCTGGCTCCATTTGGAATCCTTGGTCTTGTTTTTAAAA
CCATTTCTGACAAGGGAGTCGGAAGCCTTGCCAACTACGGTATTTTATTGGTTCTATT
AGTAACGACTATGCTTTTTGTTGCCCCTGTGGTCAACCCTTTGATTGCCTTCTTCTTTA
TGAGACGCAATCCTTACCCTCTAGTTTGGAACTGCCTCCGTGTCAGCGGTGTGACAG
CCTTTTTCACTCGTAGTTCTGCGACTAACATTCCTGTCAACATGAAACTCTGCCATGA
CCTTGGACTCAACCCAGATACCTATTCTGTTTCTATCCCACTCGGTTCTACTATCAAT
ATGGCTGGAGTAGCGATTACCATTAACCTTTTGACCCTTGCTGCAGTTAACACTCTTG
GAATTCCTGTTGACTTTGCCACAGCCTTTGTCCTCAGTGTGGTAGCAGCTATCTCATC
CTGTGATGCTTCAGGTATTGCCGGAGGTTCCCTCCTTCTTATCCCAGTTGCTTGTAGC
CTTTTCGGTATTTCTAACGATATTGCCATACAAATTGTTGGGGTTGGTTTTGTGATTG
GTGTCATCCAAGACTCATGTGAAACAGCCCTTAACTCTTCTACAGATGTCCTCTTTAC
CGCCGTTGCCGAATACGCAGCAACCCGTAAAAAATAA 4158.5 (SEQ. ID. NO. 276)

ATGTCTATTAGCCAACGTACGACCAAGCTCATCTTAGCTACCTGTCTTGCCTGCCTGC
TTGCTTATTTTCTCAATCTTTCGTCAGCAGTTTCGGCTGGAATTATCGCTCTCTTGAG
CCTATCTGATACGCGTAGAAGTACTTTAAAACTGGCTCGCAATCGTCTTTTTTCTATG
CTTCTAGCTCTGGCTATCGGTGTTCTAGCTTTTCACTTGAGCGGATTTCATATCTGGA
GTCTCGGCCTCTATCTGGCCTTCTACGTTCCTTTAGCCTACAAGATGGGCTGGGAAAT
TGGCATCACACCAAGCACTGTTTTGGTTAGCCATCTCTTGGTTCAAGAGTCAACCTCT
CCAGACCTTCTAGTCAATGAATTCCTTCTCTTTGCTATTGGTACAGGATTTGCCTTGC
TTGTTAATCTCTATATGCCTTCACGAGAAGAGGAAATCCAGCACTACCACACGCTGG
TGGAAGAAAAGTTAAAAGATATCCTCCAGCGCTTCAAATACTATTTATCCAGAGGA
GACGGACGCAACCGAGCACAGCTGGTAGCAGAATTAGACACGCTTTTGAAAGAAGC
CCTCAGACTGGTCTATTTGGATCACTCTGACCACCTCTTTCACCAGACAGACTACCA
TATCCACTACTTTGAGATGAGACAGCGACAAAGTCGTATCCTGAGAAACATGGCCC
AACAGATTAACACTTGTCACCTTGCCGCCAGTGAAAGCCTGATCTTAGCGCAACTCT
TTTCAAAAATTGCAGGTCAACTGAGCCAGACCAATCCTGCTTCTGATTTGCTAGATG
AAATTGAACGTTATCTGGAAGTCTTCCGGAACCGCAGTCTGCCCAAGACAAGAGAA
GAATTTGAAACCCGCGCCACCCTTCTTCAACTCCTACGTGAAGCCAAAACCTTCATC
CAAGTAAAAGTTGATTTTTACCAAAAATATAGACAGTAA 4158.6 (SEQ. ID. NO. 277)

ATGGAAATCATGTCGCTTGCGATTGCTGTTTTTGCCGTCATCATTGGTTTAGTCATTG
GATATGTCAGCATCTCAGCTAAGATGAAATCATCTCAGGAAGCTGCAGAGTTGATGC
TTTTAAATGCTGAACAAGAAGCAACTAATTTACGTGGACAAGCTGAGCGTGAAGCG
GATTTACTTGTTAATGAAGCCAAACGTGAAAGCAAGTCTCTTAAAAAAGAAGCACT
ATTGGAGGCAAAGAAGAAGCCAGAAAATACCGTGAAGAAGTGGACGCTGAATTC
AAATCAGAACGTCAAGAACTCAAACAAATCGAAAGTCGTTTGACAGAGAGACTAC
TAGCCTTGACCGTAAGGACGACAATTTGACGAGTAAAGAACAAACACTTGAACAAA
AAGAACAAAGTATTTCTGATAGAGCGAAAAACCTTGATGCGCGTGAAGAGCAATTA
GAGGAAGTCGAAAGACAAAAAGAAGCAGAACTAGAGCGTATTGGTGCGCTGTCTCA
GGCAGAAGCACGAGATATTATCTTGGCTCAGACAGAGGAAAACTTGACCAGGGAGA
TTGCCAGTCGCATTCGCGAAGCTGAGCAAGAGGTCAAGGAACGTTCTGACAAAATG
GCCAAGGACATCTTGGTTCAAGCTATGCAACGTATCGCTGGTGAATATGTAGCGGAG
TCAACAAACTCAACAGTTCATCTGCCAGACGATACTATGAAGGGACGCATTATTGGT
CGTGAAGGTCGTAACATTCGTACCTTTGAAAGTTTGACAGGGGTCGATGTGATTATC
GACGATACACCAGAAGTGGTGACCTTGTCAGGATTTGATCTCGATTCGTCGTGAGATT
GCCCGTATGACTATGGAAATGTTGCTCAAAGATGGTCGTATACATCCAGCTCGTATC
GAAGAGTTGGTTGAGAAAAACCGTCAAGAGATTGACAATAAGATTCGTGAATACGG
TGAGGCTGCTGCCTATGAAATTGGTGCGCCAAACCTTCATCCAGACTTGATGAAGAT
TATGGGACGTTTCAGTCCGTACTTCATATGGACAAAATGTTTTGCGCCATTCGATT
GAGGTTGCTAAGTTGGCTGGTATCATGGCGAGCGAACTTGGTGAAAATGCGGCTCTT
GCCCGTCGTGCTGGATTCCTTCACGATATCGGGAAAGCCATTGACCATGAGGTTGAA
GGTAGCCACGTTGAAATCGGTATGGAATTGGCCCGTAAGTACAAGGAACCCCCAGT
TGTGGTGAATACGATTGCTAGTCACCACGGAGATGTTGAAGCTGAGAGCGTGATAG

TABLE 1-continued

CAGTTATCGTCGCTGCAGCAGATGCCTTGAGCGCAGCCCGTCCAGGTGCTCGTAGTG
AGTCTCTTGAAAGCTACATCAAGCGTCTCCATGATTTGGAAGAAATTGCTAACGGCT
TTGAAGGAGTGCAAACTAGCTTTGCCCTTCAAGCAGGACGTGAAATTCGTATCATGG
TCAATCCAGGAAAAATCAAGGACGACAAAGTCACAATCTTGGCTCACAAAGTTCGT
AAGAAAATTGAAAACAATCTCGATTATCCAGGAAATATCAAGGTAACCGTGATTCG
CGAGCTTCGTGCAGTAGATTATGCTAAATAA 4158.7 (SEQ. ID. NO. 278)

ATGATGTTAAAACCCTCTATTGATACCTTGCTCGACAAGGTTCCTTCAAAATATTGAG
TCGTAATCTTGGAAGCAAAACGTGCCCACGAATTGGAAGCAGGTGCCCCAGCAACT
CAAGGTTTCAAGTCTGAAAAATCAACTCTTCGCGCTTTAGAAGAAATCGAATCAGGA
AACGTTACAATTCACCCAGATCCAGAAGGAAAACGTGAAGCAGTGCGTCGCCGTAT
CGAAGAAGAAAACGCCGCAAAGAAGAAGAAGAAAAGAAAATCAAAGAGCAAATTG
CTAAAGAAAAAGAAGATGGTGAAAAAATTTAA 4161.1 (SEQ. ID. NO. 279)

ATGTCAGCATATCAATTACCGACCGTATGGCAGGATGAAGCTAGTAATCAAGGAGC
TTTTACGGGGCTAAACAGACCAACAGCAGGTGCCCGTTTCGAACAAAACTTGCCAA
AAGGAGAACAAGCTTTTCAGCTTTATTCACTGGGAACACCAAATGGTGTGAAGGTTA
CTATCTTATTGGAAGAATACTAGAAGCTGGTTTTAAGGAAGCGGCTTACGACTTGT
ATAAGATTGCTATCATGGATGGGGATCAATTCGGATCAGACTTTGTGAAGCTCAATC
CAAATTCCAAGATTCCAGCCTTATTGGACCAGTCAGGTACTGAAAACGTAAGAGTCT
TTGAGTCTGCTCATATTCTTCTTTACCTTGCTGAGAAATTTGGAGCCTTTTTACCAAG
TAATCCTGTGGAAAAGGTAGAAGTTTTGAATTGGCTATTCTGGCAAGCAGGTGCAGC
ACCTTTTCTAGGTGGGGGATTTGGACATTTCTTCAATTATGCTCCTGAAAAATTGGA
ATATCCTATTAACCGTTTTACGATGGAAGTGAAACGCCAGTTGGATTTATTGGATAA
GGAATTGGCTCAGAAACCTTATATTGCAGGCAATGACTATACGATTGCAGATATTGC
TATCTGGTCTTGGTATGGACAGTTAGTTCAAGGAAATCTTTACCAAGGTTCTGCAAA
ATTCTTGGATGCCTCAAGTTATCAAAATCTAGTAAAATGGGCAGAAAAAATTGCCAA
TCGTCCAGCTGTTAAGCGTGGCTTGGAAGTAACTTATACAGAAATTAAATAG 4161.2 (SEQ. ID. NO. 280)

TTGGCAAGCTTGATCACTTCTATCATCATGTTCTATGTCGGTTTCGATGTTCTAAGAG
ATACCATTCAAAAGATTCTCAGTCGGGAAGAAACGGTCATTGATCCTCTTGGTGCAA
CTCTAGGAATCATTTCTGCAGCGATTATGTTTGTGGTCTATCTCTACAATACTCGCCT
CAGTAAGAAATCCAACTCCAATGCGCTGAAGGCAGCTGCTAAGGACAATCTTTCTG
ACGCTGTTACCTCACTTGGAACCGCCATTGCCATCCTAGCTAGTAGTTTCAATTATCC
GATTGTGGATAAACTGGTTGCTATCATCATCACTTTCTTTATCTTGAAGACTGCCTAT
GATATCTTCATCGAGTCTTCCTTTAGTCTTTCAGATGGCTTTGACGACCGCCTGCTCG
AGGACTACCAAAAGGCTATCATGGAAATTCCCAAAATCAGCAAGGTCAAATCGCAA
AGAGGTCGCACCTACGGTAGCAACATCTACCTGGATATTACACTAGAGATGAATCCT
GACTTGTCTGTTTTTGAAAGCCATGAAATCGCGGATCAGGTCGAGTCTATGCTGGAG
GAGCGTTTTGGCGTCTTTGATACCGATGTCCATATCGAACCAGCACCTATCCCTGAG
GATGAAATTTTAGACAATGTCTATAAAAAATTGCTTATGCGTGAACAATTGATTGAC
CAAGGAAACCAACTAGAAGAACTCTTGACTGATGATTTTGTCTATATTCGCCAAGAT
GGGAGAGCAGATGGATAAAGAGGCTTATAAGACCAAAAAAGAGTTAAATTCTGCTAT
CAAGGACATTCAAATTACTTCCATCAGTCAAAAAACCAAACTCATCTGCTATGAGTT
AGATGGTATCATCCATACCAGTATCTGGCGTCGCCACGAAACCTGGCAAAATATCTT
TCATCAAGAAACCAAAAAAGAATAG 4162.1 (SEQ. ID. NO. 281)

ATGACAATTAAACTAGTAGCAACGGATATGGACGGAACCTTCCTAGATGGGAATGG
ACGCTTTGATATGGATCGTCTCAAGTCTCTCTTGGTTTCCTACAAGGAAAAAGGGAT
TTACTTTGCGGTAGCTTCGGGTCGGGATTTCTGTCTCTAGAAAAATTATTTGCTGGT
GTTCGTGATGACATTATTTTCATCGCGGAAAATGGCAGTTTGGTAGAGTATCAAGGT
CAGGACTTGTATGAAGCGACTATGTCTCGTGACTTTTTATCTGGCAACTTTTGAAAAG
CTGAAAACTTCACCTTATGTAGATATCAATAAACTGCTCTTGACGGGTAAGAAGGGT
TCATATGTTCTAGATACGGTTGATGAGACCTATTTGAAAGTGAGTCAGCACTATAAT
GAAAATATCCAAAAAGTAGCGAGTTTGGAAGATATCACAGATGACATTTTCAAATTT
ACAACCAACTTCACAGAAGAAACGCTGGAAGATGGGGAGGCTTGGGTAAACGAAA
ACGTTCCTGGTGTTAAGGCCATGACAACTGGCTTTGAATCCATTGATATTGTTCTGG
ACTATGTCGATAAGGGAGTGGCCATTGTTGAATTAGTTAAAAAACTTGGTATCACAA
TGGATCAGGTCATGGCTTTTGGAGACAATCTTAATGACTTACATATGATGCAGGTTG
TGGGACATCCTGTAGCTCCTGAAAATGCACGACCTGAATTTAGAATTAGCAAAGA
CTGTGATTGGTCACCATAAGGAACGGTCGGTTATAGCTTATATGGAGGGCTTATAA 4162.2 (SEQ. TD. NO. 282)

ATGGCAGATATAAAATTGATTGCATTGGACTTGGACGGGACCTTGCTGACTACTGAT
AAAAGGCTGACGGATCGTACCAAGGAAACCTTGCAAGCTGCGCGTGATCGTGGTAT
CAAGGTCGTATTGACAACTGGTCGTCCCTTAAAAGCCATGGATTTCTTTCTCCATGA
GTTAGGGACTGACGGTCAGGAAGATGAGTATACCATTACTTTTAATGGTGGATTAGT
TCAGAAAATACAGGAGAAATCCTTGATAAAACAGTCTTTTCATATGATGATGTGGC
ACGTTTGTATGAAGAAACAGAGAAATTATCACTGCCTCTTGATGCCATCTCAGAAGG
AACAGTTTATCAAATCCAATCGGACCAAGAAAGTCTTTATGCCAAATTCAATCCAGC

TABLE 1-continued

TTTGACCTTTGTTCCAGTGGACTTTGAAGACTTATCTAGTCAAATGACCTACAACAA
ATGCGTGACTGCCTTTGCTCAAGAACCCTTGGATGCAGCCATTCAGAAGATTTCTCC
AGAATTGTTTGACCAATATGAAATCTTTAAATCACGTGAAATGTTGCTAGAATGGTC
ACCAAAGAATGTTCATAAAGCAACAGGTTTGGCAAAACTAATCAGCCATCTTGGAA
TCGACCAAAGTCAAGTGATGGCTTGTGGTGACGAGGCCAATGACCTCTCTATGATTG
AATGGGCAGGTCTTGGTGTTGCTATGCAAAACGCTGTTCCTGAAGTAAAGGCAGCCG
CAAATGTAGTGACGCCGATGACCAACGATGAGGAAGCTGTCGCCTGGGCTATCGAA
GAATATGTGCTAAAGGAGAACTAA 4164.2 (SEQ. ID. NO. 283)

ATGGAAAGTTTACTTATTCTATTATTAATTGCCAATCTAGCTGGTCTCTTTCTGATTT
GGCAAAGGCAGGATAGGCAGGAGAAACACTTAAGTAAGAGCTTGGAGGATCAGGC
AGATCATTTGTCAGACCAGTGGATTACCGCTTTGACCAAGCCAGACAAGCCAGCCA
GTTAGACCAAAAAGATTTGGAAGTGGTTGTCAGCGACCGTTTGCAAGAAGTGCGGA
TTGAATTGCACCAAGGTCTGACCCAAGTCCGTCAAGAAATGACAGATAATCTCCTCC
AAACTAGAGACAAGACAGACCAACGTCTCCAAGCCTTGCAGGAATCAAATGAGCAA
CGTTTGGAACAAATGCGCCAGACGGTCGAGGAAAAACTAGAAAAGACCTTGCAGAC
ACGCTTACAGGCTTCCTTTGAGACAGTTTCTAAACAACTGGAGTCTGTCAATCGTGG
CCTTGGGAGAAATGCAGACAGTTGCCCGTGATGTCGGAGCTCTTAACAAGGTTCTCTC
TGGAACCAAGACGCGAGGGATTCTGGGAGAATTGCAACTGGGGCAAATTATTGAAG
ACATCATGACACCTGCCCAGTACGAACGAGAATACGCAACGGTTGAAAACTCTAGT
GAACGAGTGGAGTATGCCATCAAGTTACCCGGACAAGGCGACCAAGAATACGTCTA
TCTGCCAATTGACTCTAAGTTTCCACTGGCAGATTATTTACCGCTTGGAAGAAGCCTA
TGAGACAGGTGACAAGGATGAGATTGAACGCTGTCGTAAGTCACTCCTAGCAAGCG
TCAAGCGCTTTGCTAGGGATATTAGGAACAAGTACATAGCACCACCTCGGACGACC
AATTTTGGAGTTTTGTTTGTTCCGACAGAAGGTCTCTACTCAGAAATCGTCCGCAATC
CGGTCTTCTTTGATGATTTGAGACGGGAAGAACAGATTATTGTTGCAGGACCAAGTA
CCCTATCAGCCCTTCTTAACTCCCTATCAGTTGGTTTCAAGACCCCTTAATATCCAAA
GAGTGCCGACCCATATCAGCAAGACTCTTGCCAGTGTCAAGACCGAGTTTGGCAAGTT
TGGTGGTATTCTGGTCAAGGCACAAAAACATCTCCAACATGCCTCTGGCAATATTGA
TGAATTATTAAACCGTCGTACCATAGCTATCGAGCGGACGATCCGTCACATTGAGTT
GTCAGAAGGTGAGCCTGCGCTTGATCTACTCCATTTTCAAGAAAATGAGGAAGAAT
ATGAAGATTAG 4164.3 (SEQ. ID. NO. 284)

ATGAAGATTAGTCACATGAAAAAAGATGAGTTATTTGAAGGCTTTTACCTAATCAAA
TCAGCTGACCTGAGGCAAACTCGAGCTGGGAAAAACTACCTAGCCTTTACCTTCCAA
GATGATAGTGGCGAGATTGATGGGAAGCTCTGGGATGCCCAACCTCATAACATTGA
GGCCTTTACCGCAGGTAAGGTTGTCCACATGAAAGGACGCCGAGAAGTTTATAACA
ATACCCCTCAAGTCAATCAAATTACTCTCCGCCTGCCTCAAGCTGGTGAACCCAATG
ACCCAGCTGATTTCAAGGTCAAGTCACCAGTTGATGTCAAGGAAATTCGTGACTACA
TGTCGCAAATGATTTCAAAATTGAAAATCCTGTCTGGCAACGGATTGTCCGAAATC
TCTACACCAAGTATGATAAGGAATTCTACTCCTATCCAGCTGCCAAGACCAACCACC
ATGCCTTTGAAACGGGCTTGGCCTATCATACGGCGACCATGGTGCGTTTGGCAGACG
CTATTAGCGAAGTTTATCCTCAGCTCAATAAGAGCCTGCTCTATGCGGGGATTATGT
TGCATGACTTAGCTAAGGTCATCGAGTTGACGGGGCCAGACCAGACAGAGTACACA
GTGCGAGGTAATCTTCTTGGACATATCGCTCTCATTGATAGCGAAATTACCAAGACA
GTTATGGAACTCGGCATCGATGATACCAAGGAAGAAGTCGTTTTGCTTCGTCATGTC
ATCCTCAGTCACCACGGCTTGCTTGAGTATGGAAGCCCAGTCCGTCACGCATTATG
GAAGCAGAGATTATCCATATGATTGACAATCTGGATGCAAGCATGATGATGATGTC
AACAGCTCTTGCTTTGGTGGATAAAGGAGAGATGACCAATAAAATCTTCGCTATGGA
TAATCGTTCCTTCTATAAACCAGATTTAGATTAA 4166.2 (SEQ. ID. NO. 285)

ATGAGTGAAAAAGCTAAAAAAGGGTTTAAGATGCCTTCATCTTACACCGTATTATTG
ATAATCATTGCTATTATGGCAGTGCTAACTTGGTTTATCCCTGCGGGGGCCTTTATAG
AAGGTATTTACGAGACTCAGCCTCAAAATCCACAAGGGATTTGGGATGTCCTGATGG
CACCGATTCGGGCTATGCTAGGTACTCATCCAGAGGAAGGTTCGCTCATTAAAGAAA
CGAGCGCAGCGATTGATGTAGCCTTCTTCATCCTTATGGTTGGTGGTTTCCTTGGCAT
TGTCAACAAAACTGGTGCTCTTGACGTAGGGATTGCCTCTATCGTGAAGAAGTATAA
GGGCCGCGAAAAAATGTTAATTTTGGTACTGATGCCTTTGTTTGCCCTCGGTGGTAC
AACTTATGGTATGGGTGAAGAAACAATGGCCTTCATCCACTCCTTGTGCCAGTTAT
GATGGCCGTTGGTTTTGATAGCCTGACTGGTGTTGCAATTATTTTGCCTCGGTTCTCAA
ATCGGCTGTTTGGCATCTACTCTGAATCCATTTGCGACAGGTATTGCTTCAGCGACTG
CGGGAGTTGGTACAGGGGACGGTATCGTACTTCGTCGATCTTCGGGTTACCTTGA
CTGCTCTTAGTACTTGGTTTGTTTACCGTTATGCGGATAAGATTCAAAAAGATCCGA
CTAAGTCACTGGTTTATAGTACTCGCAAAGAAGATTTGAAACACTTTAACGTAGAAG
AATCTTCATCTGTAGAATCTACACTTAGCAGCAAACAAAAATCAGTTCTCTTCTTATT
TGTGTTGACATTCATCTTGATGGTATTGAGCTTCATTCCATGGACAGACCTTGGCGTT
ACCATTTTTGATGACTTTAATACTTGGTTGACTGGTCTTCCAGTTATTGGTAATATTG
TCGGTTCATCTACTTCTGCACTAGGTACTTGGTACTTCCCAGAAGGCGCAATGCTCTT
TGCCTTTATGGGTATCCTGATTGGTGTTATTTATGGTCTTAAAGAAGATAAGATTATC
TCTTCCTTCATGAATGGTGCTGCTGACTTGCTCAGTGTTGCCTTGATCGTAGCGATTG
CTCGTGGTATTCAAGTTATCATGAACGACGGTATGATTACCGATACAATCCTCAACT
GGGGTAAAGAAGGCTTGAGCGGTCTATCTTCACAAGTCTTTATCGTTGTAACTTATA
TCTTCTATCTACCTATGTCATTCTTGATCCCATCTTCATCTGGTCTTGCCAGCGCAACT

TABLE 1-continued

ATGGGTATCATGGCTCCACTTGGAGAATTTGTAAATGTCCGTCCTAGCTTGATTATC
ACTGCTTACCAATCTGCTTCAGGTGTCTTGAACTTGATTGCACCAACATCTGGTATTG
TGATGGGAGCTCTTGCACTTGGACGTATCAACATTGGTACTTGGTGGAAATTCATGG
GCAAACTCGTAGTCGCTATTATTGTAGTGACCATCGCCCTTCTTCTCCTGGAACCTT
CCTTCCATTCCTATAA 4166.3 (SEQ. ID. NO. 286)

ATGAAAATAGATATAACAAATCAAGTTAAAGATGAATTTCTTATATCATTAAAAACC
TTGATTTCCTATCCTTCAGTACTCAATGAAGGAGAAAATGGAACACCTTTTGGACAA
GCAATCCAAGATGTCCTAGAAAAAACTTTAGAGATTTGTCGAGACATAGGTTTCACT
ACCTATCTTGACCCTAAAGGTTATTACGGATATGCAGAAATCGGTCAGGGAGCAGA
GCTTCTGGCCATTCTCTGTCATTTGGATGTTGTTCCATCAGGTGATGAAGCAGATTGG
CAGACACCGCCATTTGAAGCAACTATCAAAGACGGCTGGGTATTCGGACGTGGTGT
CCAAGATGATAAAGGCCCTTCGCTCGCAGCTCTCTATGCAGTAAAAAGCTTGCTGGA
CCAAGGTATTCAGTTCAAAAAGCGCGTACGCTTTATCTTTGGTACCGATGAGGAAAC
CCTCTGGCGCTGCATGGCACGCTACAATACCATCGAAGAACAGGCCAGTATGGGCT
TTGCACCTGACTCATCTTTCCTCTGACCTATGCTGAAAAAGGGCTTCTACAGGTCAA
ACTTCATGGCCCTGGATCGGATCAACTAGAGCTTGAAGTAGGAGGCGCCTTTAACGT
TGTACCAGACAAGGCCAACTACCAAGGTCTCCTCTATGAACAGGTTTGTAACGGTCT
CAAAGAAGCTGGTTATGATTACCAAACCACTGAACAAACCGTAACGGTTCTCGGAG
TGCCAAAGCATGCTAAGGATGCTAGTCAAGGTATCAATGCTGTCATCCGACTAGCTA
CCATTCTTGCTCCTCTCCAAGAACACCCTGCTCTCAGTTTTCTTGCAACACAAGCAGG
TCAAGACGGCACAGGAAGACAAATCTTTGGTGATATAGCAGATGAACCTTCTGGTC
ACCTATCCTTTAATGTCGCAGGTCTCATGATCAATCATGAACGTTCTGAAATCCGTAT
TGACATTCGGACTCCTGTCTTAGCTGACAAGGAAGAACTAGTAGAGTTGCTTACAAG
ATGTGCACAAAACTACCAACTCCGCTACGAAGAGTTTGACTATCTAGCGCCTCTATA
CGTCGCAGAAGACAGTAAACTCGTTAGCACACTGATGCAAATCTACCAAGAAAAGA
CTGGCGATAACAGTCCTGCTATTTCATCCGGTGGTGCCACTTTTGCTCGCACCATGCC
AAATTGTGTAGCCTTCGGCGCCTTATTCCCAGGAGCGAAGCAGACAGAACATCAGG
CAAATGAATGTGCCGTTCTAGAAGATTTGTACCGTGCTATGGATATTTATGCCGAAG
CCGTCTATCGACTTGCAACTTAA 4169.1 (SEQ. ID. NO. 287)

ATGTCTAATCATTTGTCAAGTTGTTAGTCTCTCAATTATTTGCAAATTTAGCAGATA
TTTTCTTTAGAGTAACAATCATTGCTAACATATACATTATTTCAAAATCAGTAATTGC
CACATCACTAGTTCCTATCTTAATAGGAATATCCTCTTTTGTTGCGAGTCTTTTAGTT
CCGTTGGTTACTAAAAGGTTAGCGCTAAATAGGGTTTTATCTTTATCTCAATTTGGAA
AGACTATATTATTGGCGATACTGGTAGGAATGTTTACCGTAATGCAATCCGTAGCGC
CTTTGGTGACCTATCTATTTGTTGTTGCAATTTCCATACTAGATGGTTTTGCAGCACC
CGTTTCCTATGCTATTGTGCCACGCTATGCGACCGATTTGGGTAAGGCTAATTCAGC
CTTATCAATGACTGGTGAAGCTGTTCAATTGATAGGTTGGGGATTAGGTGGACTCTT
GTTTGCAACAATTGGTCTGTTACCTACCACGTGTATCAATTTAGTCTTGTATATCATT
TCTAGCTTTCTGATGTTATTTCTTCCTAACGCTGAAGTGGAGGTGTTAGAGTCAGAA
ACTAATCTTGAAATTTTGCTCAAAGGTTGGAAGTTAGTTGCTAGAAATCCTAGATTA
AGACTTTTTGTATCAGCAAATTTATTGGAAATTTTTTCAAATACGATTTGGGTTTCTT
CCATTATACTTGTTTTTGTAACGGAGTTATTAAATAAAACGGAAAGTTACTGGGGAT
ATTCTAATACAGCATACTCTATTGGTATTATAATTAGTGGCTTAATTGCTTTAGGCT
ATCTGAAAAGTTCCTTGCTGCTAAATGGGAAGGGGAATTATTCACCCCAAATCTAAA
AACCATCCAGAATCCTTGCCTTAGCTTAGATCCTGGATGGTTTCTTTTTTCACCCAAT
GGGTGTTTTTTACTAGACAAAAAGAGTTTCCCCTTTATGGTATAAGTGTAGAAAAA
AACACAAAAAGAAAGGAAACTCACATGAACAGTTTACCAAATCATCACTTCCAAAA
CAAGTCTTTTTACCAACTATCTTTCGATGGAGGTCATTTAACCCAGTATGGTGGTCTT
ATCTTTTTTCAGGAACTTTTTTCCCAGTTGAAACTAAAAGACGGATTTCTAAGTATT
TAGTAACGAATGACCAACGCCGCTACTGTCGTTATTCGGATTCAGATATCCTTGTCC
AGTTCCTCTTTCAACTGTTAACAGGTTATGGAACGGACTATGCTTGTAAAGAATTGT
CAGCTGATGCCTACTTTCCAAAATTGTTGGAAGGAGGGCAGCTTGCTTCACAGCCAA
CCTTATCCCGTTTTCTTTCCAGAACTGACGAGGAAACAGTCCATAGTTTGCGATGCCT
CAACCTTGAATTGGTCGAATTCTTTTTACAGTTTCACCAGCTAAACCAACTCATTGTA
GATATCGATTCTACCCATTTCACAACTTATGGCAAGCAAGAAGGTGTTGCTTATAAC
GCCCACTATCGTGCTCATGGCTATCATCCTCTTTATGCTTTCGAGGGGAAGACAGGT
TATTGTTTCAATGCCCAGCTTCGTCCTGGTAATCGTTATTGTTCTGAAGAGGCAGACA
GCTTTATCACACCTGTTTTAGAACGGTTTAATCAACTTCTCTTTCGAATGGATAGTGG
CTTTGCGACCCCAAAATTATACGATTTAATTGAAAAAACAGGGCAATACTACCTCAT
AAAACTCAAGAAAAATACTGTTCTGAGCCGTCTTGGAGACCTTTCCCTCCCTTGCCC
ACAGGATGAGGACTTAACCATCTTGCCCCACTCCGCCTACTCAGAAACTCTCTATCA
AGCAGGATCTTGGTCGCACAAGCGTCGTGTCTGCCAGTTCTCTGAACGAAAAGAAG
GAAACTTGTTCTACGATGTTATTTCTCTCGTTACAAATATGACGAGTGGAACAAGCC
AAGACCAGTTTCAGCTTTATCGTGACGTGGTCAAGCCGAGAATTTCATCAAGGAGA
TGAAGGAGGGATTTTTTGGCGATAAAACGGATAGTTCAACCTTAATCAAAAACGAA
GTTCGTATGATGATGAGCTGTATCGCCTACAATCTCTATCTTTTTCTCAAACATCTAG
CTGGAGGTGACTTCCAAACTTTAACAATCAAACGCTTCCGCCATCTTTTTCTTCACGT
GGTGGGAAAATGTGTTCGAACAGGACGCAAGCAGCTCCTCAAATTGTCTAGTCTCTA
TGCCTATTCCGAATTGTTTTCAGCACTTTATTCTAGGATTAGAAAAGTCAACCTGAAT
CTTCCTGTTCCTTATGAACCACCTAGAAGAAAAGCGTCGTTAATGATGCATTAA

TABLE 1-continued 4169.3 (SEQ. ID. NO. 288)

ATGATGGAGTTTTTTCAACAGCTTCCTCATTTAGAGCCATATGGCAATCCTCAGTATT
TTGTTTATGTGATTGCTGCAACCTTGCCCATCTTTATAGGTCTCTTTTTCAAGAAACG
CTTTGCCTGGTATGAAGTGTTGGTAAGTCTCTTCTTTATTGTCACCATGTTGGTGGGT
GGAAAGACCAATCAACTAGCTGCCTTGGGTATTTACCTTTGCTGGGAAATATTGCTC
CTGCTTTTCTACAAGCATTATCGAAAAAGCAAGGATGGCAAGTGGGTCTTCTACTTA
GTTAGTTTTCTGTCCCTACTTCCGATTATCTTTGTCAAGGTGCAACCAGCTATCAATG
GAACGCAGTCTTTGCTTGGGTTCTTGGGAATTTCTTACCTGACCTTTCGTTCGGTTGG
AATTGTCATCGAGCTGAGAGATGGAGTGATTAAGGATTTTACCCTCTGGGAATTCCT
CCGTTTCCTTCTCTTCATGCCAACTTTCTCGAGTGGTCCAATCGATCGCTTTAAGCGA
TTTAATGAAAATTATCAGGCTATTCCTGAGCGAGATGAGTTGATGGATATGCTGGAT
GAATCTGTCCGCTATATCATGTGGGGCTTTTTGTATAAGTTTATCCTAGCTCATGTTT
TAGGAGAGACCTTACTACCTCCTCTGAAGAATTTAGCCTTGCAGTCAGGTGGCTTCT
TTAATCTCTATGCCTTGGCAGTTATGTATACTTTTGGTCTGGAACTCTTCTTTGACTTT
GCAGGTTATTCTATGTTTGCTTTGGCCATCTCAAACTTGATGGGAATCCGTAGCCCTA
TCAACTTTAACAAGCCCTTTTTATCAAGGGATTTAAAGGAGTTTTGGAATCGCTGGC
ATATGAGTCTGTCCTTCTGGTTCCGTGACTTTGTCTTTATGCGAATGGTGATGGTGTT
AACCAGAAAGAAAGTCTTTAAAAATCGTAATGTAACCTCAAGCATGGCCTACATTGT
AAATATGCTGATTATGGGATTTTGGCATGGTGTGACCTGGTACTATATCGCCTATGG
ACTCTTTCATGGACTAGGCTTGGTCATCAATGATGCCTGGGTTCGCAAGAAAAAAC
GCTCAATAAGGAACGGAAAAAAGCAGGGAAGGCTGCCCTACCTGAGAATCGCTGGA
TTCAGTTGCTTGGCATGGTTGTCACTTTCCATGTTGTCATGTTGTCATTCTTAATCTTT
TCTGGATTCTTGAATAATCTATGGTTTAAAAAATAA 4169.4 (SEQ. ID. NO. 289)

ATGCTTAAACGCTTATGGATGATCTTCGGACCGGTCTTGATCGCTGGTTTGTTGGTTT
TTCTGCTCATTTTCTTTATCCTACTGAGATGCATCATAATCTAGGAGCTGAAAAGCG
TTCAGCAGTGGCTACTACTATCGATAGTTTTAAGGAGCGAAGTCAAAAAGTCAGAG
CACTATCTGATCCAAATGTGCGTTTTGTTCCCTTCTTTGGCTCTAGTGAATGGCTTCG
TTTTGACGGTGCTCATCCTGCGGTATTAGCTGAGAAATACAATCGTTCCTACCGTCCT
TATCTTTTAGGACAGGGGGGAGCTGCATCGCTTAACCAATATTTTGGAATGCAACAG
ATGTTACCACAGCTGGAGAATAAACAAGTTGTGTATGTTATCTCACCTCAGTGGTTC
AGTAAAAATGGCTATGATCCAGCAGCCTTCCAGCAGTATTTTAATGGAGACCAGTTG
ACTAGTTTTCTGAAACATCAATCTGGGGATCAGGCTAGTCAATATGCAGCGACTCGC
TTACTGCAACAGTTCCCAAACGTAGCTATGAAGGACCTGGTTCAGAAGTTGGCAAGT
AAAGAAGAATTGTCGACAGCAGACAATGAAATGATTGAATTATTGGCTCGTTTTAAT
GAACGCCAAGCTTCCTTTTTTGGTCAGTTTTCGGTTAGAGGCTATGTTAACTACGATA
AGCATGTAGCTAAGTATTTAAAAATCTTGCCAGACCAGTTTTCTTATCAGGCAATAG
AAGATGTTGTCAAAGCAGATGCTGAAAAAAATACTTCCAATAATGAGATGGGAATG
GAAAATTATTTCTATAATGAGCAGATCAAGAAGGATTTGAAGAAATTAAAGGATTC
TCAGAAAAGCTTTACCTATCTCAAGTCGCCAGAGTATAATGACTTGCAGTTGGTTTT
AACACAGTTTTCTAAATCTAAGGTAAACCCGATTTTTATCATTCCACCTGTTAATAAA
AAATGGATGAACTATGCTGGTCTACGAGAGGATATGTACCAACAAACGGTGCAGAA
GATTCGCTACCAGTTAGAAAGTCAAGGTTTTACCAATATAGCAGATTTTCTAAGGA
CGGCGGGGAGCCTTTCTTTATGAAGGACACCATTCACCTTGGTTGGTTGGGTTGGTT
GGCTTTTGACAAGGCAGTTGATCCTTTCCTATCCAATCCCACACCAGCTCCGACTTA
CCATCTGAATGAGCGCTTTTTCAGCAAAGATTGGGCGACTTATGATGGAGATGTCAA
AGAATTTCAATAG 4169.6 (SEQ. ID. NO. 290)

ATGGAGAAAAACCTCAAGGCTTTGAAACAAACAACAGACCAAGAAGGCCCAGCAA
TTGAACCTGAAAAGGCAGAGGATACCAAGACAGTCCAAAATGGTTACTTCGAGGAT
GCAGCTGTCAAGGACCGCACCTTGAGTGACTATGCAGGTAACTGGCAATCAGTTTAT
CCTTTCCTTGAAGACGGCACGTTTGACCAAGTCTTTGACTACAAGGCTAAGTTGACT
GGTAAGATGACCCAGGCTGAGTACAAGGCTTACTATACAAAAGGCTATCATACAGA
TGTGACTAAGATTAACATTACTGATAATACTATGGAATTTGTTCAAGGTGGACAAAG
CAAGAAATACACTTACAAGTATGTCGGTAAGAAAATTTTGACTTACAAGAAAGGCA
ATCGTGGCGTGCGTTTCCTCTTTGAAGCCACAGATGCTGACGCTGGACAATTCAAGT
ATGTTCAGTTTAGTGACCACAATGTTGCCCCAGTTAAGGCAGAACATTTCCATATCT
TCTTTGGAGGCACAAGCCAAGAAGCCCTCTTTGAAGAAATGGACAACTGGCCAACC
TACTACCCAGATAACCTATCTGGCCAAGAAATCGCCCAAGAAATGTTGGCGCATTGA 4170.3 (SEQ. ID. NO. 291)

ATGAAAGATGGTCATTTGCTAGCCCATCATATTCGTTTGTTGAATGGGCGGATTTTTC
AAAAGTTTACTGAGTCAAGATCCTGAGGCTCTTTATAGGGGTGAACAGGGCAAGATT
TTAGCGGTTTTATGGAATAGTGAAACTGGCTGCGCAACTGCGACAGATATCGCGCTT
GCGACTGGACTTGCGAATAATACGCTGACGACTATGATAAAAAAGCTAGAGGAACA
AAAGCTTGTAATTGTTAGTCCGTGTGGAAAAGACAAGCGTAAGAAGTATTTAGTTTT
AACGGAGTTAGGCAAGTCCCAGAAAGAAGTGGGGCATCGTGTCAGTCAGAAATTGG
ATACTATCTTTTACAAAGGATTTTCAGAGGAAGAAATTCACCCAATTTGAAGTTTTC
AAGAAAGAATTTTGGCGAATCTGAAAGAGAAGGGAAATGAGGTTTAG

TABLE 1-continued 4170.4 (SEQ. ID. NO. 292)

ATGACTAATTTAATTGCAACTTTTCAGGATCGTTTTAGTGATTGGTTGACAGCTCTAT
CTCAACATTTGCAGTTGTCGCTTTTGACCTTGTTACTAGCTATTTTGCTTGCGATTCCC
TTGGCTGTTTTTCTTCGCTATCATGAGAAGCTGGCCGACTGGGTCTTGCAGATTGCAG
GTATTTTCCAGACCATCCCGTCTCTGGCCTTGTTGGGGCTCTTATCCCTTTGATGGG
AATTGGGACCTTGCCGGCTTTGACAGCTCTAGTGATTTATGCGATTTTCCCTATTTTG
CAAAATACTATCACTGGGCTGAAGGGAATTGATCCGAACCTGCAAGAGGCTGGGAT
TGCCTTTGGGATGACCAGATGGGAACGTCTCAAGAAATTTGAAATTCCACTCGCCAT
GCCTGTTATCATGTCTGGGATTCGGACGGCAGCTGTTTTGATTATCGGTACGGCAAC
CTTGGCGGCCTTGATTGGTGCAGGGGGACTAGGTTCCTTTATTCTTTTGGGAATTGAC
CGTAATAATGCCAGTTTGATTTTGATTGGGGCACTTTCTTCTGCAGTGCTAGCCATTG
CCTTTAACTTCCTACTAAAAGTGATGGAAAAAGCAAAATTACGGACGATTTTCTCAG
GTTTTGCCTTGGTGGCTTTATTACTGGGTCTGTCTTATAGTCCAGCTCTTTTGGTTCAA
AAAGAGAAGGAAAACTTGGTTATTGCTGGGAAAATAGGTCCAGAACCAGAAATTTT
GGCCAATATGTATAAGTTGCTGATTGAAGAAAATACCAGCATGACTGCGACTGTTAA
ACCGAATTTTGGGAAGACAAGCTTCCTTTATGAAGCTCTGAAAAAAGGCGATATTGA
CATCTATCCTGAATTTACTGGTACGGTGACTGAAAGTTTGCTTCAACCATCACCCAA
GGTGAGTCATGAACCAGAACAGGTTTATCAGGTGGCGCGTGATGGCATTGCTAAGC
AGGATCATCTAGCCTATCTCAAACCCATGTCTTATCAAAACACCTATGCTGTAGCTG
TTCCGAAAAAGATTGCTCAAGAATATGGCTTGAAGACCATTTCAGACTTGAAAAAA
GTGGAAGGGCAGTTGAAGGCAGGTTTTACACTCGAGTTTAACGACCGTGAAGATGG
AAATAAGGGCTTGCAATCAATGTATGGTCTCAATCTCAATGTAGCGACCATTGAGCC
AGCCCTTCGCTATCAGGCTATTCAGTCAGGGGATATTCAAATCACGGATGCCTATTC
GACTGATGCGGAATTGGAGCGTTATGATTTACAGGTCTTGGAAGATGACAAGCAAC
TCTTCCCACCTTATCAAGGGGCTCCACTCATGAAAGAAGCTCTTCTCAAGAAACACC
CAGAGTTGGAAAGAGTTCTTAATACATTGGCTGGTAAGATTACAGAAAGCCAGATG
AGCCAGCTCAACTACCAAGTCGGTGTTGAAGGCAAGTCAGCAAAGCAAGTAGCCAA
GGAGTTTCTCCAAGAACAAGGTTTGTTGAAGAAATGA 4170.5 (SEQ. ID. NO. 293)

ATGATGCATACTTATTTGCAAAAGAAAATTGAAAATATCAAAACAACCCTAGGTGA
AATGTCAGGTGGTTACCGTCGTATGGTTGCGGCTATGGCTGATTTAGGATTTTCAGG
AACTATGAAGGCTATCTGGGATGACCTCTTTGCCCATCGTAGTTTTGCCCAGTGGAT
TTATTTGCTGGTTTTAGGAAGTTTTCCTCTCTGGCTGGAGTTGGTTTACGAACATCGT
ATTGTTGACTGGATTGGGATGATTTGTAGCTTGACAGGGATTATCTGTGTAATCTTTG
TATCGGAAGGTCGAGCAAGTAATTATCTTTTGGCTTGATTAACTCTGTTATTTACCT
TATTTGGCCCTACAGAAAGGCTTTTATGGTGAGGTGCTGACGACACTTTACTTCAC
AGTCATGCAGCCAATTGGACTTCTAGTTTGGATTTATCAGGCACAGTTTAAGAAGGA
AAAGCAGGAGTTTGTCGCGCGTAAACTGGACGGCAAGGGCTGGACAAAGTATCTTT
CCATTAGTGTGCTTTGGTGGTTGGCCTTTGGCTTCATTTATCAGTCTATTGGTGCCAA
TCGTCCCTATCGTGATTCAATCACAGATGCAACCAATGGGGTAGGGCAAATCCTCAT
GACAGCTGTTTACCGTGAACAGTGGATATTCTGGGCGGCTACCAATGTCTTTTCAAT
CTATCTCTGGTGGGGAGAAAGCCTGCAAATTCAAGGGAAATATCTAATTTATCTCAT
TAACAGTCTAGTTGGTTGGTATCAATGGAGCAAGGCAGCTAAGCAGAATACTGATTT
ACTTAACTAG 4170.6 (SEQ. ID. NO. 294)

ATGAGAAATATGAAGGCAAAATATGCTGTTTGGGTGGCTTTTTTCTTAAATTTGACT
TATGCCATTGTTGAGTTTATGCAGGTGGAGTATTTGGTTCTAGCGCTGTTCTTGCTGA
CTCTGTGCATGACTTGGGAGATGCGATTGCAATTGGAATATCAGCTTTTCTAGAAAC
AATCTCCAATCGTGAAGAAGACAATCAGTACACCTTGGGCTATAAGCGGTTTAGCCT
GCTAGGAGCCTTGGTAACAGCTGTGATTCTCGTAACGGGCTCTGTTCTAGTCATTTTG
GAAAATGTCACGAAGATTTGCATCCGCAACCAGTCAATGATGAGGGATTCTCTGGT
TAGGAATTATTGCGATTACTATCAATCTGTTAGCGAGTCTGGTGGTTGGTAAGGGAA
AGACAAAGAATGAGTCTATTCGAGTCTGCATTTTCTGGAAGATACGCTAGGGTGGG
TAGCTGTTATCCTGATGGCGATTGTTCTTCGATTTACGGACTGGTATATCCTAGATCC
TCTTTTGTCCCTTGTCATTTCTTTCTTTATTCTTTCAAAAGCCCTTCCACGTTTTTGGTC
TACACTCAAGATTTTCTTGGATGCTGTGCCAGAAGGTCTTGATATCAAGCAAGTAAA
GAGTGGCCTGGAGCGATTGGACAATGTGGCCAGCCTTAATCAGCTTAATCTCTGGAC
TATGGATGCTTTGGAAAAAATGCCATTGTCCATGTTTGTCTAAAAGAAATGGAACA
TATGGAAACTTGTAAAGAGTCTATTCGAATTTTCCTAAAAGATTGTGGTTTTCAAAA
TATTACCATTGAAATTGATGCTGACCTAGAAACTCACCAAACCCATAAGCGAAAGGT
GTGTGACTTGGAACGGAGTTATGAGCATCAACATTAG 4170.8 (SEQ. ID. NO. 295)

ATGATTGAATACAAAAATGTAGCACTGCGCTACACAGAAAAGGATGTCTTGAGAGA
TGTCAACTTACAGATTGAGGATGGGGAATTTATGGTTTTAGTAGGGCCTTCTGGGTC
AGGTAAGACGACCATGCTCAAGATGATTAACCGTCTTTTGGAACCAACTGATGGAA
ATATTTATATGGATGGGAAGCGCATCAAAGACTATGATGAGCGTGAACTCGTCTTT
CTACTGGTTATGTTTTACAGGCTATTGCTCTTTTTCCAAATCTAACAGTTGCGGAAAA
TATTGCTCTCATTCCTGAAATGAAGGGGTGGAGCAAGGAAGAAATTACGAAGAAAA
CAGAAGAGCTTTTGGCTAAGGTTGGTTTACCAGTAGCCGAGTATGGGCATCGCTTAC
CTAGTGAATTATCTGGTGGAGAACAGCAACGGGTCGGTATTGTCCGAGCTATGATTG
GTCAGCCCAAGATTTTCCTCATGGATGAACCCTTTTCGGCCTTGGATGCTATTTCGAG

TABLE 1-continued

AAAACAGTTGCAGGTTCTGACAAAAGAATTGCATAAAGAGTTTGGGATGACAACGA
TTTTTGTAACCCATGATACGGATGAAGCCTTGAAGTTGGCGGACCGTATTGCTGTCT
TGCAGGATGGAGAAATTCGCCAGGTAGCGAATCCCGAGACAATTTTAAAAGCGCCT
GCAACAGACTTTGTAGCAGACTTGTTTGGAGGTAGTGTTCATGACTAA 4171.1 (SEQ. ID. NO. 296)

ATGTCAGCAGTTGCTATTTCAGCTATGACCAAGGTTATGCAAGAAACCCACGGAAAT
CCTTCTAGTATTCATGGTCATGGTCGTCAAGCTGGCAAACTCTTGCGAGAAGCCCGT
CAGGAACTAGCCCAGTTACTAAGGACAAAACCTCAACATATCTTTTTCACTTCTGGT
GGGACTGAAGGCAATAATACTACCATCATTGGCTACTGTCTTCGTCACCAAGAACAA
GGAAAACATATCATCACAACTGCCATCGAGCACCATGCTGTCCTTGAAACAATTGAT
TACTTGGTTCAACACTTTGGGTTTGAAGCAACCATTATCCAGCCAGAAAATCAAGAA
ATCACAGCCCAGCAAATTCAAAAGGCTTTACGTGACGATACGATTTTGGTTTCTACC
ATGTTTGTCAATAATGAGACAGGAAACCTACTGCCCATCGCTGAAATTGGCCAAATA
CTCAAGCAACACCCTGCTGCCTATCATGTTGATGCAGTTCAGGCTATTGGTAAAATC
CCAATCATTCAGAAGAATTGGGCATGATTTTCTCACTGCTTCTGCCCACAAATTCC
ATGGTCCTAAGGGAATCGGTTTTCTCTACGCATCTAGCATGGACTTTGATTCCTATCT
ACATGGCGGAGACCAGGAACAGAAAAAACGTGCAGGAACTGAAAATCTGCCTGCC
ATTGTAGGCATGGTTGCAGCCCTAAAAGAAGACCTAGAAAAACAAGAAGAACATTT
TCAACATGTACAAAATCTAGAAACTGCCTTTCTGGCAGAGCTGGAGGGCATTCAGTA
TTACCTGAATAGAGGAAAACATCATCTCCCTTATGTTCTCAATATTGGATTTCCTGGT
CAGAAAAATGACCTCTTACTCCTTCGGCTAGATTTAGCTGGAATTTCAATCTCTACTG
GCTCAGCCTGTACTGCAGGCGTTGTCCAATCCAGCCATGTTTCTTGAAGCCATGTATG
GCGCAAATTCAGAACGCTTGAAGGAATCCCTTCGCATCAGTTTGTCGCCACAAAATA
CCGTTGAAGACCTACAAACCCTCGCAAAAACCTTAAAAGAAATTATCGGAGGTTAG 4172.1 (SEQ. ID. NO. 297)

ATGTTATTCAAATTATCTAAGGAAAAAATAGAGCTAGGCTTATCTCGTTTATCGCCA
GCCCGTCGTATTTTTTTGAGTTTTGCCTTGGTCATTTTACTAGGCTCTCTTCTTTTGAG
CTTGCCCTTTGTCCAAGTTGAAAGCTCACGAGCGACTTATTTTGATCATCTTTTCACT
GCTGTCTCTGCAGTCTGTGTGACGGGTCTCTCAACCCTTCCAGTAGCTCACACCTATA
ATATCTGGGGTCAAATAATCTGTTTGCTCTTGATTCAGATCGGTGGTCTAGGGCTCAT
GACCTTTATTGGGGTTTTCTATATCCAGAGCAAGCAAAAGCTTAGTCTTCGTAGCCG
TGCAACTATTCAGGATAGTTTTAGTTATGGAGAAACTCGATCTTTGAGAAAGTTTGT
CTATTCTATTTTTCTCACGACCTTTTTGGTTGAGAGCTTGGGAGCTATTTTGCTTAGTT
TTCGCCTTATTCCTCAACTTGGCTGGGGACGTGGTCTTTTTAGTTCCATTTTTCTAGC
GATCTCAGCCTTCTGTAATGCCGGTTTTGATAATTTAGGGAGCACCAGTTTATTTGCT
TTTCAGACCGATTTACTGGTCAATCTGGTGATTGCAGGCTTGATTATTACAGGCGGC
CTTGGTTTTATGGTCTGGTTTGATTTGGCTGGTCATGTAGGGAAGAAAGAAAAAAGGA
CGTCTGCACTTTCATACGAAGCTTGTACTATTATTGACTATAGGTTTGTTGTTATTTG
GAACAGCAACTACTCTCTTTCTTGAGTGGAACAATGCTGGAACGATTGGCAATCTCC
CTGTTGCCGATAAGGTTTTAGTTAGCTTTTTTCAAACAGTGACGATGCGAACAGCTG
GCTTTTTCTACGATAGATTATACTCAGGCTCATCCTGTGACTCTTTTGATTTATATCTT
ACAGATGTTTCTAGGTGGGGCACCTGGAGGAACAGCTGGGGGACTCAAGATTACGA
CATTTTTTGTCCTCTTGGTCTTTGCACGAAGTGAGCTTCTAGGCTTGCCTCATGCCAA
TGTTGCGAGACGAACGATCGCGCCGCGAACGGTTCAAAAATCCTTTAGTGTCTTTAT
TATCTTTTTGATGAGCTTCTTGATAGGATTGATTCTGCTAGGGATAACAGCCAAAGG
CAATCCTCCCTTTATCCACCTCGTATTTGAAACCATTTCAGCTCTTAGTACAGTTGGT
GTAACGGCAAATCTGACTCCTGACCTTGGGAAATTGGCTCTCAGTGTTATCATGCCA
CTTATGTTTATGGGACGAATTGGTCCCTTGACCTTGTTTGTTAGCTTGGCAGATTACC
ATCCAGAAAAGAAAGATATGATTCACTATATGAAAGCAGATATAGTATTGGTTAA 4172.2 (SEQ. ID. NO. 298)

ATGTCAGATCGTACGATTGGAATTTTGGGCTTGGGAATTTTTGGGAGCAGTGTCCTA
GCTGCCCTAGCCAAGCAGGATATGAATATTATCGCTATTGATGACTGCAGAGCGC
ATCAATCAGTTTGAGCCAGTTTTGGCGCGTGGAGTGATTGGTGACATCACAGATGAA
GAATTATTGAGATCAGCAGGGATTGATACCTGCGATACCGTTGTAGTCGCGACAGGT
GAAAATCTGGAGTCGAGTGTGCTTGCGGTTATGCACTGTAAGAGTTTGGGGGTACCG
ACTGTTATTGCTAAGGTCAAAAGTCAGACCGCTAAGAAAAGTGCTAGAAAAGATTG
GAGCTGACTCGGTTATCTCGCCAGAGTATGAAATGGGGCAGTCTCTAGCACAGACC
ATTCTTTTCCATAATAGTGTTGATGTCTTTCAGTTGGATAAAAATGTGTCTATCGTGG
AGATGAAAATTCCTCAGTCTTGGGCAGGTCAAAGTCTGAGTAAATTAGACCTCCGTG
GCAAATACAATCTGAATATTTTGGGTTTCCGAGAGCAGGAAAATTCCCCATTGGATG
TTGAATTTGGACCAGATGACCTCTTGAAAGCAGATACCTATATTTTGGCAGTCATCA
ACAACCAGTATTTGGATACCCTAGTAGCATTGAATTCGTAA 4172.3 (SEQ. ID. NO. 299)

ATGAAGTTATTGTCTATCGCAATTTCTAGCTATAATGCAGCAGCCTATCTTCATTACT
GTGTGGAGTCGCTAGTGATTGGTGGTGAGCAAGTTGGGATTTTGATTATCAATGACG
GGTCTCAGGATCAGACTCAGGAAATCGCTGAGTGTTTAGCTAGCAAGTATCCTAATA
TCGTTAGAGCCATCTATCAGGAAAATAAATGCCATGGCGGTGCGGTCAATCGTGGCT
TGGTAGAGGCTTCTGGGCGCTATTTTAAAGTAGTTGACAGTGATGACTGGGTGGATC
CTCGTGCCTACTTGAAAATTCTGAAACTTGCAGGAACTTGAGAGCAAAGGTCAAG
AGGTGGATGTCTTTGTGACCAATTTTGTCTATGAAAAGGAAGGGCAGTCTCGTAAGA
AGAGTATGAGTTACGATTCAGTCTTGCCTGTTCGGCAGATTTTTGGCTGGGACCAGG

TABLE 1-continued

TCGGAAATTTCTCCAAAGGCCAGTATACCATGATGCACTCGCTGATTTATCGGACAG
ATTTGTTGCGTGCTAGCCAGTTCTAA 4172.4 (SEQ. ID. NO. 300)

ATGAAATTCAATCCAAATCAAAGATATACTCGTTGGTCTATTCGCCGTCTCAGTGTC
GGTGTTGCCTCAGTTGTTGTGGCTAGTGGCTTCTTTGTCCTAGTTGGTCAGCCAAGTT
CTGTACGTGCCGATGGGCTCAATCCAACCCCAGGTCAAGTCTTACCTGAAGAGACAT
CGGGAACGAAAGAGGGTGACTTATCAGAAAAACCAGGAGACACCGTTCTCACTCAA
GCGAAACCTGAGGGCGTTACTGGAAATACGAATTCACTTCCGACACCTACAGAAAG
AACTGAAGTGAGCGAGGAAACAAGCCCTTCTAGTCTGGATACACTTTTTGAAAAAG
ATGAAGAAGCTCAAAAAAATCCAGAGCTAACAGATGTCTTAAAAGAAACTGTAGAT
ACAGCTGATGTGGATGGGACACAAGCAAGTCCAGCAGAAACTACTCCTGAACAAGT
AAAAGGTGGAGTGAAAGAAAATACAAAAGACAGCATCGATGTTCCTGCTGCTTATC
TTGAAAAAGCTGAAGGGAAAGGTCCTTTCACTGCCGGTGTAAACCAAGTAATTCCTT
ATGAACTATTCGCTGGTGATGGTATGTTAACTCGTCTATTACTAAAAGCTTCGGATA
ATGCTCCTTGGTCTGACAATGGTACTGCTAAAAATCCTGCTTTACCTCCTCTTGAAGG
ATTAACAAAAGGGAAATACTTCTATGAAGTAGACTTAAATGGCAATACTGTTGGTA
AACAAGGTCAAGCTTTAATTGATCAACTTCGCGCTAATGGTACTCAAACTTATAAAG
CTACTGTTAAAGTTTACGGAAATAAAGACGGTAAAGCTGACTTGACTAATCTAGTTG
CTACTAAAAATGTAGACATCAACATCAATGGATTAGTTGCTAAAGAAACAGTTCAA
AAAGCCGTTGCAGACAACGTTAAAGACAGTATCGATGTTCCAGCAGCCTACCTAGA
AAAAGCCAAGGGTGAAGGTCCATTCACAGCAGGTGTCAACCATGTGATTCCATACG
AACTCTTCGCAGGTGATGGCATGTTGACTCGTCTCTTGCTCAAGGCATCTGACAAGG
CACCATGGTCAGATAACGGCGACGCTAAAAACCCAGCCCTATCTCCACTAGGCGAA
AACGTGAAGACCAAAGGTCAATACTTCTATCAAGTAGCCTTGGACGGAAATGTAGC
TGGCAAAGAAAAACAAGCGCTCATTGACCAGTTCCGAGCAAATGGTACTCAAACTT
ACAGCGCTACAGTCAATGTCTATGGTAACAAAGACGGTAAACCAGACTTGGACAAC
ATCGTAGCAACTAAAAAAGTCACTATTAACATAAACGGTTTAATTTCTAAAGAAACA
GTTCAAAAAGCCGTTGCAGACAACGTTAAAGACAGTATCGATGTTCCAGCAGCCTA
CCTAGAAAAAGCCAAGGGTGAAGGTCCATTCACAGCAGGTGTCAACCATGTGATTC
CATACGAACTCTTCGCAGGTGATGGTATGTTGACTCGTCTCTTGCTCAAGGCATCTG
ACAAGGCACCATGGTCAGATAACGGTGACGCTAAAAACCCAGCCCTATCTCCACTA
GGTGAAAACGTGAAGACCAAAGGTCAATACTTCTATCAATTAGCCTTGGACGGAAA
TGTAGCTGGCAAGAAAAACAAGCGCTCATTGACCAGTTCCGAGCAAACGGTACTC
AAACTTACAGCGCTACAGTCAATGTCTATGGTAACAAAGACGGTAAACCAGACTTG
GACAACATCGTAGCAACTAAAAAAGTCACTATTAACATAAACGGTTTAATTTCTAAA
GAAACAGTTCAAAAAGCCGTTGCAGACAACGTTAAAGACAGTATCGATGTTCCAGCA
GCCTACCTAG 4172.5 (SEQ. ID. NO. 301)

ATGAAACTAAAAAGTTATATTTTGGTTGGATATATTATTTCAACCCTCTTAACCATTT
TGGTTGTTTTTTGGGCTGTTCAAAAAATGCTGATTGCGAAAGGCGAGATTTACTTTTT
GCTTGGGATGACCATCGTTGCCAGCCTTGTCGGTGCTGGGATTAGTCTCTTTCTCCTA
TTGCCAGTCTTTACGTCGTTGGGCAAACTCAAGGAGCATGCCAAGCGGGTAGCGGCC
AAGGATTTTCCTTCAAATTTGGAGGTTCAAGGTCCTGTAGAATTTCAGCAATTAGGG
CAAACTTTTAATGAGATGTCCCATGATTTGCAGGTAAGCTTTGATTCCTTGGAAGAA
AGCGAACGAGAAAAGGGCTTGATGATTGCCCAGTTGTCGCATGATATTAAGACTCCT
ATCACTTCGATCCAAGCGACGGTAGAAGGGATTTTGGATGGGATTATCAAGGAGTC
GGAGCAAGCTCATTATCTAGCAACCATTGGACGCCAGACGGAGAGGCTCAATAAAC
TGGTTGAGGAGTTGAATTTTTTGACCCTAAACACAGCTAGAAATCAGGTGGAAACTA
CCAGTAAAGACAGTATTTTTCTGGACAAGCTCTTAATTGAGTGCATGAGTGAATTTC
AGTTTTTGATTGAGCAGGAGAGAAGAGATGTCCACTTGCAGGTAATCCCAGAGTCTG
CCCGGATTGAGGGAGATTATGCTAAGCTTTCTCGTATCTTGGTGAATCTGGTCGATA
ACGCTTTTAAATATTCTGCTCCAGGAACCAAGCTGGAAGTGGTGGCTAAGCTGGAGA
AGGACCAGCTTTCAATCAGTGTGACCGATGAAGGGCAGGGTATTGCCCCAGAGGAT
TTGGAAAATATTTTCAAACGCCTTTATCGTGTCGAAACTTGCGTAACATGAAGACA
GGTGGTCATGGATTAGGACTTGCGATTGCGCGTGAATTGGCCCATCAATTGGGTGGG
GAAATCACAGTCAGCAGCCAGTACGGTCTAGGAAGTACCTTTACCCTCGTTCTCAAC
CTCTCTGGTAGTGAAAATAAAGCCTAA 4172.6 (SEQ. ID. NO. 302)

ATGTTTGGTCAAACGGCTCAACATGGTCTTACGAATAGCCTGAAAGACTTCTGGATT
TTTCTGCTGAATATAGGTCCACAATTGGCGTTTTTTGCCAGATGCTCCGCTGTTCCA
GATCGGTTGAGCAGGGTACTGGAAATCACCGTCGTGAGTTCAATATGATTCAGCAG
ATATTCTCGCATTTTGGGATGACTCACTTGGGACAAATCAAGTTGGTCTATCAAGAG
TCGATTGACCTTGAGTTGCTGGTCAATGCACTTAATCATCACTTGCTCATTGACAGAC
TGGTCCTCACGCCCAATCAAATAACGATAGAAATCGACAGGCAGATAGTACATGGT
CTTGACCTGCTGAAGGGGCGTAAAGACAAAGAGATTATCGACATAAAAGTATGTT
CAGGCAGTTTAGAACTGGCTAGCACGCAACAAATCTGTCCGATAAATCAGCGAGTGC
ATCATGGTATACTGGCCTTGGAGAAATTTCCGACCTGGTCCCAGCCAAAAATCTGC
CGAACAGGCAAGACTGA 4174.1 (SEQ. ID. NO. 303)

ATGGAACATTTAGCAACTTATTTTTCAACCTATGGAGGAGCTTTCTTCGCTGCATTGG
GAATTGTATTGGCGGTTGGATTAAGCGGTATGGGGTCTGCTTATGGAGTTGGTAAGG

TABLE 1-continued

```
CTGGGCAATCTGCCGCAGCTTTACTGAAAGAACAGCCTGAAAAGTTTGCCTCAGCTT
TGATATTGCAATTATTGCCCGGAACACAAGGATTATATGGTTTTGTTATTGGAATTTT
AATTTGGTTGCAATTAACTCCAGAACTTCCTTTAGAAAAAGGCGTTGCTTATTTCTTT
GTAGCTCTTCCAATTGCTATTGTAGGATACTTTTCAGCTAAGCATCAAGGAAATGTA
GCAGTAGCGGGAATGCAAATCTTGGCTAAAAGACCAAAAGAATTCATGAAGGGAGC
AATTTTAGCTGCCATGGTAGAAACCTATGCAATTCTTGCTTTTGTCGTATCATTCATT
TTTGACCCTTCGTGTATTA
```

4175.2 (SEQ. ID. NO. 304)

```
ATGTTAAAATCAGAAAAACAATCACGTTATCAAATGTTAAATGAAGAATTGTCCTTC
CTATTGGAAGGCGAAACCAATGTTTTGGCTAATCTTTCCAACGCCAGTGCTCTCATA
AAATCACGTTTTCCTAATACCGTATTTGCAGGCTTTTATTTGTTCGATGGAAAGGAAT
TGGTTTTAGGCCCCTTCCAAGGAGGTGTTTCCTGCATCCGTATTGCACTAGGCAAGG
GTGTTTGTGGTGAGGCAGCTCACTTTCAGGAAACTGTTATTGTTGGAGATGTGACGA
CCTATCTCAACTATATTTCTTGTGATAGTCTAGCTAAAAGTGAAATTGTGGTGCCGAT
GATGAAGAATGGTCAGTTACTTGGAGTTCTGGATCTGGATTCTTCAGAGATTGAGGA
TTACGATGCTATGGATCGAGATTATTTGGAACAATTTGTCGCTATTTTGCTTGAAAA
GACAGCATGGGACTTTACGATGTTTGAGGAAAAATCTTAA
```

4175.3 (SEQ. ID. NO. 305)

```
ATGTCAGTATTAGAGATCAAAGATCTTCACGTTGAGATTGAAGGAAAAGAAATTTTA
AAAGGGGTTAACCTGACCCTGAAAACAGGAGAAATTGCCGCTATCATGGGACCAAA
TGGTACAGGTAAATCGACTCTTTCTGCCGCTATCATGGGAAATCCAAACTATGAAGT
AACTAAAGGTGAAGTTTTGTTTGATGCGCTAAACATCCTTGAGTTGGAAGTGGATGA
GCGTGCGCGTATGGGACTTTTCCTTGCTATGCAATACCCATCAGAAATCCCTGGAAT
TACCAATGCTGAGTTTCTTCGTGCCGCTATGAATGCGGGTAAAGAAGATGATGAGAA
GATTTCAGTTCGTGAGTTTATTACTAAGCTAGATGAAAAAATGGAATTGCTCAACAT
GAAAGAAGAAATGGCAGAGCGTTACCTCAACGAAGGCTTCTCTGGTGGTGAGAAAA
AACGCAATGAAATTCTTCAACTTTTGATGTTGGAGCCAACATTTGCTCTTTTGGACG
AGATTGACTCAGGTCTTGATATTGACGCTCTTAAAGTTGTGTCTAAAGGTGTCAATG
CCATGCGTGGTGAAGGTTTTGGTGCTATGATCATCACTCCTACTACCAACGTCTTTTGA
ACTATATCACACCTGATGTGGTACACGTGATGATGGAAGGTCGTGTTGTCCTTTCTG
GTGGTCCAGAATTGGCTGCGCGTTTGGAACGTGAAGGATACGCAAAATTAGCTGAA
GAACTTGGCTACGACTACAAGGAAGAATTGTAA
```

4174.4 (SEQ. ID. NO. 306)

```
ATGCCCTACAAAAGACAAAGGAGTTTTTCAATGGCACTTTCTAAACTAGATAGCCTT
TATATGGCAGTGGTAGCAGACCATTCGAAAAATCCACATCACCAAGGGAAGTTAGA
AGATGCTGAGCAAATCAGTCTCAACAATCCGACTTGTGGGGATGTCATCAACCTCTC
TGTCAAGTTTGATGCAGAGGACCGTTTGGAAGATATTGCTTTTCTAAATTCAGGATG
CACGATTTCAACTGCTTCTGCTAGTATGATGACAGATGCCGTTTTAGGAAAAACCAA
ACAAGAAATTTTAGAACTGGCGACTATTTTTTCTGAAATGGTTCAAGGGCAAAAAGA
TGAGCGTCAAGACCAACTTGGAGACGCGCATTCTTGTCAGGTGTTGCCAAATTCCC
TCAAAGAATCAAGTGTGCAACCCTAGCTTGGAATGCCCTTAAGAAAACAATTGAAA
ATCAAGAAAAACAGTAA
```

4175.5 (SEQ. ID. NO. 307)

```
ATGAAAATTCAAGACCTATTGAGAAAAGATGTCATGTTGCTAGATTTGCAGGCAACT
GAAAAAACAGCTGTCATCGACGAGATGATTAAAAATTTGACAGACCACGGTTATGT
AACAGATTTTGAAACATTTAAAGAAGGAATTTTGGCGCGTGAAGCTTTGACTTCTAC
TGGTTTGGGTGATGGAATCGCAATGCCTCACAGCAAAAACGCTGCTGTCAAAGAAG
CGACAGTTCTATTTGCTAAGTCAAATAAGGGTGTTGACTACGAGAGCTTGGATGGAC
AAGCAACTGACCTCTTCTTCATGATTGCAGCTCCAGAAGGTGCCAATGATACTCACT
TGGCAGCCTTGGCAGAATTGTCTCAATACTTGATGAAAGACGGTTTTGCAGACAAAC
TTCGTCAAGCAACATCTGCAGACCAAGTTATCGAACTTTTTGACCAAGCTTCAGAAA
AAACTGAGGAACTTGTTCAAGCACCTGCTAATGACTCTGGTGACTTTATCGTAGCTG
TTACAGCTTGTACAACAGGTATTGCCCACACTTACATGGCCCAAGAAGCCCTTCAAA
AAGTAGCTGCTGAAATGGGGGTTGGTATCAAGGTCGAAACCAACGGTGCTAGCGGT
GTTGGAAATCAACTAACTGCAGAAGATATCCGTAAGGCTAAAGCTATTATCATTGCA
GCAGACAAGGCCGTTGAAATGGATCGATTTGATGGAAAACCATTGATCCATCGTCC
AGTTGCTGACGGTATCCGTAAGACAGAAGAGCTAATTAACTTGGCTCTTTCAGGAGA
TACTGAAGTCTACCGTGCCGCTAATGGTGCCAAAGCTGCAACAGCCTCTAACGAAA
AACAAAGCCTTGGTGGTGCCTTGTACAAAACACTTGATGAGTGGTGTATCTCAAATGT
TACCATTCGTTATCGGTGGTGGTATCATGATTGCCCTTGCCTTCTTGATTGACGGTGC
TTTGGGTGTTCCAAATGAAAACCTTGGCAATCTTGGTTCTTACCATGAGTTAGCTTCT
ATGTTCATGAAAATTGGTGGAGCTGCCTTTGGTTTGATGCTTCCAGTCTTTGCGGGTT
ATGTTGCCTACTCTATTGCTGAAAAACCGGGTTTGGTAGCAGGTTTCGTGGCTGGTG
CTATTGCCAAAGAAGGTTTTGCCTTTGGTAAAATTCCTTATGCCGCAGGTGGTGAAG
CAACTTCAACTCTTGCAGGTGTCTCATCTGGTTTCCTAGGTGCCCTTGTTGGTGGATT
TATCGCAGGTGCCTTGGTTCTTGCCATCAGAAATACGTTAAAGTTCCTCGTTCACTCG
AAGGTGCTAAATCAATCCTTCTATTGCCACTTCTTGGAACAATCTTGACAGGATTGT
TATGCTAGCTGTGAATATCCCAATGGCTGCAATCAACACTGCTATGAATGACTTCCT
AGGCGGTCTTGGAGGAGGTTCAGCTGTCCTTCTTGGTATCGTCCTTGGTGGAATGAT
GGCTGTTGACATGGGTGGACCAGTTAATAAAGCAGCTTATGTCTTTGGTACAGGTAC
GCTTGCAGCAACTGTTTCTTCAGGTGGTTCTGTAGCCATGGCAGCAGTTATGGCTGG
```

TABLE 1-continued

AGGAATGGTGCCACCACTTGCAATCTTTGTCGCAACTCTTCTTTTCAAAGATAAATTT
ACTAAGGAAGAACGTAACTCTGGTTTGACAAACATCATCATGGGCTTGTCATTTATC
ACTGAGGGAGCGATTCCATTTGGTGCCGCTGACCCAGCTCGTGCGATTCCAAGCTTC
ATCCTTGGTTCAGCAGTAGCAGGTGGACTCGTTGGTCTTACTGGTATCAAACTCATG
GCGCCACACGGAGGAATCTTCGTTATCGCCCTTACTTCAAATGCTCTCCTTTACCTCG
TTTCTGTCTTGGTAGGAGCAATCGTAAGTGGTGTGGTTTATGGTTACCTACGCAAAC
CACAAGCATAA 4175.6 (SEQ. ID. NO. 308)

ATGGCAAACAAGAATACAAGTACAACAAGACGGAGACCGTCTAAAGCAGAACTGG
AAAGAAAAGAAGCGATTCAACGAATGTTGATTTCGTTAGGAATTGCGATTTTATTGA
TTTTCGCAGCCTTCAAATAGGGGCTGCAGGTATAACCCTTTATAATTTAATCGCTT
GCTAGTGGGTAGCCTAGCTTATCTGGCGATATTCGGCCTATTAATCTATCTCTTCTTT
TTCAAGTGGATACGAAAACAGGAAGGACTCTTATCTGGCTTTTTCACCATATTTGCT
GGCTTACTCTTGATTTTTGAGGCCTACTTGGTTTGGAAATATGGTTTGGACAAGTCCG
TTCTAAAAGGGACCATGGCTCAGGTTGTGACAGATCTGACTGGTTTTCGAACGACTA
GCTTTGCTGGAGGGGGCTTGATCGGGGTCGCTCTTTATATTCCACAGCCTTTCTCTTT
TCAAATATCGGAACTTACTTTATTGGTTCTATCTTGATTTTAGTGGGTTCTCTCCTAG
TCAGCCCTTGGTCTGTTTACGATATTGCTGAATTTTTCAGTAGAGGCTTTGCCAAATG
GTGGGAAGGGCACGAGCGTCGAAAAGAGGAACGCTTTGTCAAACAAGAAGAAAAA
GCTCGCCAAAAGGCTGAGAAAGAGGCTAGATTAGAACAAGAAGAGACTGAAAAG
CCTTACTCGATTTGCCTCCTGTTGATATGGAAACGGGTGAAATTCTGACAGAGGAAG
CTGTTCAAAATCTTCCACCTATTCCAGAAGAAAAGTGGGTGGAACCAGAAATCATCC
TGCCTCAAGCTGAACTTAAATTCCCTGAACAGGAAGATGACTCAGATGACGAAGAT
GTTCAGGTCGATTTTTCAGCCAAAGAAGCCCTTGAATACAAACTTCCAAGCTTACAA
CTCTTTGCACCAGATAAACCAAAAGATCAGTCTAAAGAGAAGAAAATTGTCAGAGA
AAATATCAAAATCTTAGAAGCAACCTTTGCTAGCTTTGGTATTAAGGTAACAGTTGA
ACGGGCGAAATTGGGCCATCAGTGACCAAGTATGAAGTCAAGCCGGCTGTTGGTG
TAAGGGTCAACCGCATTTCCAATCTATCAGATGACCTCGCTCTAGCCTTGGCTGCCA
AGATGTCCGGATTGAAGCACCAATCCCTGGGAAATCCCTAATCGGAATTGAAGTG
CCCAACTCCGATATTGCCACTGTATCTTTCCGAGAACTATGGGAACAATCGCAAACG
AAAGCAGAAAATTTCTTGGAAATTCCTTTAGGGAAGGCTGTTAATGGAACCGCAAG
AGCTTTTGACCTTTCTAAAATGCCCCACTTGCTAGTTGCAGGTTCAACGGGTTCAGG
GAAGTCAGTAGCAGTTAACGGCATTATTGCTAGCATTCTCATGAAGGCGAGACCAG
ATCAAGTTAAATTTATGATGGTCGATCCCAAGATGGTTGAGTTATCTGTTTACAATG
ATATTCCCCACCTCTTGATTCCAGTCGTGACCAATCCACGCAAAGCCAGCAAGGCTC
TGCAAAAGGTTGTGGATGAAATGGAAAACCGTTATGAACTCTTTGCCAAGGTGGGA
GTTCGGAATATTGCAGGTTTAATGCCAAGGTAGAAGAGTCAATTCCCAGTCTGAG
TACAAGCAAATTCCGCTACCATTCATTGTCGTGATTGTGGATGAGTTGGCTGACCTC
ATGATGGTGGCCAGCAAGGAAGTGGAAGATGCTATCATCCGTCTTGGGCAGAAGGC
GCGTGCTGCAGGTATCCACATGATTCTTGCAACTCAGCGTCCATCTGTTGATGTCATC
TCTGGTTTGATTAAGGCCAATGTTCCATCTCGTGTAGCATTTGCGGTTTCATCAGGAA
CAGACTCCCGTACGATTTTGGATGAAAATGGAGCAGAAAAACTTCTTGGTCGAGGA
GACATGCTCTTTAAACCGATTGATGAAAATCATCCAGTTCGTCTCCAAGGCTCCTTT
ATCTCGGATGACGATGTTGAGCGCATTGTGAACTTCATCAAGACTCAGGCAGATGCA
GACTACGATGAGAGTTTTGATCCAGGTGAGGTTTCTGAAAATGAAGGAGAATTTTCG
GATGGAGATGCTGGTGGTGATCCGCTTTTTGAAGAAGCTAAGTCTTTGGTTATCGAA
ACACAGAAAGCCAGTGCGTCTATGATTCAGCGTCGTTTATCAGTTGGATTTAACCGT
GCGACCCGTCTCATGGAAGAACTGGAGATAGCAGGTGTCATCGGTCCAGCTGAAGG
TACCAAACCTCGAAAAGTGTTACAACAATAA 4176.1 (SEQ. ID. NO. 309)

ATGAGTTATTTTAAAAAATATAAATTCGATAAATCCCAGTTCAAACTTGGTATGCGA
ACCTTTAAAACAGGTATTGCTGTTTTTCTAGTTCTCTTGATTTTTGGCTTTTTTGGCTG
GAAAGGTCTTCAAATTGGTGCTTTGACAGCCGTTTTTAGCCTGAGGGAGAGTTTTGA
TGAGAGTGTTCATTTTGGGACTTCGCGTATTCTAGGAAATAGTATCGGTGGACTCTA
TGCCTTGGTCTTCTTCTTATAAATACCTTTTTCCACGAAGCCTTTTGGGTGACCTTG
GTAGTTGTTCCAATCTGCACCATGTTAACCATTATGACAAATGTAGCCATGAATAAC
AAAGCAGGGGTTATTGGTGGTGTAGCAGCTATGTTAATCATTACCCTATCAATTCCA
AGTGGTGAGACAATTTTGTACGTGTTTGTGCGTGTATTAGAAACGTTTATGGGAGTT
TTTGTCGCAATTATCGTAAATTACGATATTGATCGTATTCGTCTCTTTTTAGAGAAAA
AAGAAAAATAA 4178.2 (SEQ. ID. NO. 310)

ATGAATAAATCAGAACACCGCCACCAACTTATACGCGCTCTTATCACAAAAAACAA
GATTCATACACAGGCTGAGTTGCAAGCCCTTCTTGCTGAGAACGACATTCAAGTAAC
CCAGGCAACCCTCTCACGCGACATCAAAAATGAACCTATCAAAAGTCCGCGAAG
AAGATAGCGCTTATTATGTTCTTAACAATGGTTCCATCTCAAAATGGGAAAACGTC
TCGAACTCTACATGGAAGACGCCCTTGTCTGGATGCGCCCAGTTCAACACCAAGTCC
TACTAAAAACCCTTCCTGGACTGGCTCAATCCTTTGGTTCTATCATTGATACTTTGAG
CTTCCCTGACGCTATCGCTACCCTTTGTGGTAATGATGTCTGTCTTATCATCTGTGAA
GATGCAGATACTGCTCAAAAGTGCTTTGAAGAACTGAAAAAATTCGCCCCACCATTT
TTCTTTGAAGAATAA

TABLE 1-continued 4179.1 (SEQ. ID. NO. 311)

ATGAAAAGTATAAAATTAAATGCTCTATCTTACATGGGAATTCGTGTCTTGAATATT
ATTTTTCCCATCCTAACTGGAACCTATGTCGCGCGTGTCTTGGACCGAACTGACTATG
GTTACTTCAACTCAGTCGACACTATTTTGTCATTTTCTTGCCCTTTGCAACTTATGGT
GTCTATAACTACGGTTTAAGGGCTATCAGTAATGTCAAGGATAACAAAAAAGATCTT
AACAGAACCTTTTCTAGTCTTTTTTATTTGTGCATCGCTTGTACGATTTTGACCACTG
CTGTCTATATCCTAGCCTATCCTCTCTTTACTGATAATCCAATCGTCAAAAAGGT
CTACCTTGTTATGGGGATTCAACTCATTGCCCAGATTTTTTCAATCGAATGGGTCAAT
GAAGCTCTGGAAATTACAGTTTTCTCTTTTACAAAACTGCCTTCATCCGTATCCTGA
TGCTGGTCTCTATTTTCTTATTTGTTAAAAATGAACACGATATTGTTGTCTATACACT
TGTGATGAGTTTATCGACGCTGATTAACTACCTGATTAGTTATTTTTGGATTAAAAGA
GACATCAAACTTGTTAAAATTCACCTAAGTGATTTTAAACCACTCTTTCTCCCTCTGA
CAGCCATGTTAGTCTTTGCCAATGCCAATATGCTCTTCACTTTTTTAGATCGCCTCTT
CCTCGTTAAAACAGGGATTGATGTCAACGTTAGTTACTATACCATAGCTCAGCGAAT
TGTGACCGTTATAGCTGGGGTTGTAACAGGTGCAATTGGAGTGAGTGTGCCTCGTCT
CAGTTACTATCTGGGGAAAGGAGACAAAGAAGCCTATGTTTCTCTGGTTAATAGAG
GTAGTCGAATCTTTAACTTCTTTATCATTCCACTGAGTTTTGGACTCATGGTTTTAGG
ACCAAATGCCATCCTACTTTACGGTAGTGAAAAATATATCGGAGGCGGCATCTTGAC
CTCTCTCTTCGCTTTTCGTACGATTATCCTGGCCTTAGATACCATTCTTGGTCCCAA
ATTCTCTTTACCAATGGCTATGAAAAACGTATCACAGTCTATACAGTCTTTGCTGGG
CTACTCAATTTGGGCTTGAATAGTCTCCTTTTTTTCAACCATATCGTGGCTCCTGAAT
ACTACTTACTGACAACTATGCTATCAGAGACTTCTCTACTTGTTTTCTATATCATTTT
CATCCATAGAAAACAACTCATCCACTTGGGACATATCTTTAGCTATACTGTTCGATA
CTCTCTCTTTTCACTTTCCTTTGTAGCAATTTATTTCCTGATTAATTTCGTGTATCCTG
TAGATATGGTCATTAATTTGCCATTTTTGATTAATACTGGTTTGATTGTCTTGCTATC
AGCTATCTCTTATATTAGTCTACTTGTCTTCACAAAAGATAGCATTTTCTATGAATTT
TTAAACCATGTCCTAGCCTTAAAAAATAAATTTAAAAAATCATAG 4179.2 (SEQ. ID. NO. 312)

ATGAAACAACTAACCGTTGAAGATGCCAAACAAATTGAATTAGAAATTTTGGATTAT
ATTGATACTCTCTGTAAAAAGCACAATATCAACTATATTATTAACTACGGTACTCTG
ATTGGGGCGGTTCGACATGAGGGCTTTATCCCTTGGGACGACGATATTGATCTGTCC
ATGCCTAGAGAAGACTACCAACGATTTATTAACATTTTTCAAAGGAAAAAAGCAA
GTATAAGCTCCTATCCTTAGAAACTGATAAGAACTACTTTAACAACTTTATCAAGAT
AACCGACAGTACGACTAAAATTATTGATACTCGAAATACAAAAACCTATGAGTCTG
GTATCTTTATCGATATTTCCCTATAGATCGCTTTGATGATCCTAAGGTCATTGATAC
TTGTTATAAACTGGAAAGCTTCAAACTGCTGTCTTTCAGTAAACATAAAAATATTGT
CTATAAGGATAGCCTTTTAAAAGATTGGATACGAACAGCCTTCTGGTTACTCCTTCG
ACCGGTTTCTCCTCGTTATTTTGCAAATAAAATCGAGAAAGAAATTCAAAAATATAG
TCGTGAAATGGGCAATATATGGCTTTTATCCCTTCAAAATTTAAGGAAAAGGAAGT
CTTCCCAAGTGGTACCTTTGATAAAACAATCGATTTACCCTTTGAGAATTTAAGCCTT
CCTGCACCTGAAAAATTTGATACTATTTTGACACAATTTTATGGAGATTATATGACC
CTACCACCAGAAGAAAAACGCTTCTACAGTCATGAATTTCACGCTTATAAATTGGAG
GATTAG 4179.3 (SEQ. ID. NO. 313)

ATGATAAAAATCAATCATCTAACCATCACACAAAACAAAGATTTACGAGATCTTGTA
TCTGACCTAACCATGACCATCCAAGACGGGGAAAAGGTTGCTATTATTGGTGAAGA
AGGAAATGGCAAATCAACCTTACTTAAAATTTTAATGGGGGAAGCTTTGTCTGATTT
CACTATCAAGGGAAACATCCAATCTGACTATCAGTCACTGGCCTACATTCCTCAAAA
AGTCCCTGAGGACCTAAAAAAGAAAACTTTACACGACTACTTCTTTTTAGATTCTAT
TGATTTAGACTACAGTATCCTCTATCGTTTGGCGGAGGAATTGCATTTTGATAGCAA
TCGTTTCGCAAGTGACCAAGAGATTGGCAATCTATCAGGGGGCGAAGCTTTGAAAA
TTCAGCTTATCCATGAGTTAGCCAAACCCTTTGAGATTCTATTTTTAGATGAACCTTC
AAATGACCTAGACCTTGAGACAGTTGATTGGCTAAAAGGCCAGATTCAAAAGACCA
GGCAAACCGTTATTTTCATTTCCCATGATGAAGACTTTCTTTCTGAAACGGCAGACA
CTATTGTTCACTTGCGACTGGTCAAACACCGTAAAGAAGCGGAAACGCTAGTAGAG
CATTTAGACTATGATAGCTATAGTGAGCAGAGAAAGGCTAATTTTGGCAAACAAAG
TCAGCAAGCTGCTAACAACCAAAGAGCCTACGATAAAACCATGGAAAAACATCGGA
GAGTTAAGCAAAATGTAGAAACTGCGCTTCGAGCTACCAAAGATAGTACTGCCGGT
CGCCTATTGGCTAAAAAGATGAAAACTGTCCTCTCACAAGAAAACGCTACGAAAA
GGCAGCTCAGTCCATGACTCAAAAGCCACTTGAAGAGGAACAAATCCAACTTTCTT
TTCAGACATCCAACCATTACCAGCTCTAAAGTCTTAGTCCAACTGGAAAAGAAAA
TTTGTCCATTGACGACCGAGTTTTGGTTCAAAAACTACAACTAACTGTCCGTGGCCA
AGAAAAAATCGGTATTATCGGGCCAAATGGTGTTGGGAAATCAACTCTGTTAGCCA
AGTTACAGAGACTTCTGAATGATAAAAGAGAGATTTCACTTGGTTTTATGCCACAAG
ATTACCACAAAAAACTGCAATTGGATTTATCCCCAATAGCCTATCTCAGTAAAACTG
GGGAAAAAGAGGAACTACAGAAAATCCAATCTCACCTAGCTAGTCTCAATTTCAGT
TATCCAGAAATGCAGCATCAAATTCGCTCCTTATCTGGCGGACAACAGGGAAAACTC
CTGCTTTTGGATTTAGTCCTGCGCAAACCAAACTTTCTCCTGCTGGATGAACCCACAC
GAAACTTTTCTCCCACTTCTCAACCCCAAATCAGAAAACTCTTTGCTACCTATCCAG
GCGGTCTCATCACTGTTTCGCATGACCGTCGTTTCTTAAAAGAAGTCTGCTCGATCAT
CTATCGCATGACAGAACACGGTTTGAAGCTAGTTAATTTAGAAGATTTATAA

TABLE 1-continued 4179.4 (SEQ. ID. NO. 314)

ATGAAACCAAAAACATTTTACAACTTGCTTGCCGAGCAGAATCTTCCACTTTCGGAC
CAGCAAAAAGAACAATTTGAACGTTATTTTGAGCTCTTGGTCGAGTGGAATGAGAA
GATTAATTTGACGGCGATTACGGACAAGGAAGAAGTTTATCTCAAACATTTTTACGA
TTCGATTGCACCCATTCTTCAAGGTTTGATTCCCAATGAAACTATCAAACTTCTTGAT
ATCGGGGCTGGGGCAGGATTTCCTAGTCTACCAATGAAAATTCTCTATCCGGAGTTA
GATGTGACCATTATTGATTCACTCAATAAGCGCATCAACTTCCTACAACTCTTGGCTC
AAGAACTGGATTTGAACGGAGTTCATTTCTACCACGGACGTGCCGAAGATTTTGCCC
AAGACAAGAACTTCCGTGCTCAATATGATTTTGTAACAGCTCGTGCGGTTGCCCGTA
TGCAGGTCCTATCTGAATTGACTATTCCCTACCTTAAGGTTGGTGGCAAACTATTAG
CACTCAAGGCTAGCAATGCGCCTGAGGAATTTATTAGAAGCTAAGAATGCCCTCAAT
CTCCTTTTTAGTAAGGTCGAAGACAATCTCAGctACGCCCTACCGAATAGAGATCCGC
GCTATATCACAGTGGTAGAAAAGAAAAAAGAAACACCCAAATAAATATCCACGTAAG
GCTGGTATGCCAAATAAACGCCCACTTTAA 4179.6 (SEQ. ID. NO. 315)

ATGAGTATTAAACTAATTGCCGTTGATATCGACGGAACCCTTGTCAACAGCCAAAAG
GAAATCACTCCTGAAGTTTTTTCTGCCATCCAAGATGCCAAAGAAGCTGGTGTCAAA
GTCGTGATTGCAACTGGCCGCCCTATCGCAGGCGTTGCCAAACTTCTAGACGACTTG
CAGTTGAGAGACGAGGGGGACTATGTGGTAACCTTCAACGGTGCCCTTGTCCAAGA
AACTGCTACAGGACATGAGATTATCAGCGAATCCTTGACTTATGAGGATTATCTAGA
TATGGAATTCCTCAGTCGCAAGCTCGGTGTCCACATGCATGCCATTACCAAGGACGG
TATCTATACTGCAAATCGCAATATCGGAAAATACACTGTACACGAATCAACCCTCGT
CAGCATGCCTATCTTCTACCGTACCCCTGAAGAAATGGCTGGCAAAGAAATTGTTAA
ATGTATGTTTATCGATGAACCAGAAATTCTCGATGCTGCGATTGAAAAAATTCCAGC
AGAATTTTACGAGCGCTACTCCATCAACAAATCTGCTCCTTTCTACCTCGAACTCCTT
AAAAAAGAATGTAGACAAGGGTTCAGCCATTACTCACTTGGCTGAAAAACTCGGATT
GACCAAAGATGAAACCATGGCAATCGGTGATGAAGAAAATGACCGTGCCATGCTGG
AAGTCGTTGGAAACCCCGTTGTCATGGAAAATGGAAATCCAGAAATCAAAAAAATC
GCCAAATACATCACCAAAACAAATGACGAATCCGGCGTTGCCCATGCCATCCGAAC
ATGGGTACTGTAA 4179.7 (SEQ. ID. NO. 316)

ATGACTGGATTATTCTTGGAGTTATCGCTCTTATTGTTATTTTTGTGATTGTTAGCTA
TAACGGTTTGGTTAAAAATCGTATGCAAACCAAGGAGGCTTGGAGTCAGATTGATGT
TCAGTTGAAACGTCGCAATGACCTCTTGCCAAACTTGATTGAGACTGTAAAAGGTTA
TGCCAAATATGAAGGTTCTACCCTTGAAAAGGTGGCAGAACTACGTAACCAAGTGG
CGGCAGCGACTTCACCAGCAGAAGCTATGAAAGCCAGTGATGCCCTCACTCGTCAG
GTTTCAGGTATTTTTGCAGTTGCAGAAAGCTATCCAGATTTGAAAGCTAGTGCTAAC
TTTGTTAAATTGCAAGAGGAGTTGACAAACACAGAAAATAAAATTTCTTACTCTCGT
CAACTCTATAACAGTGTTGTCAGCAACTACAATGTAAAATTAGAAACTTTCCCGAGC
AATATTATCGCTGGAATGTTTGGATTTAAAGCGGCAGATTTCCTTCAAACACCTGAA
GAGGAAAAGTCGGTTCCTAAAGTTGATTTTAGCGGTTTAGGTGACTAA 4179.8 (SEQ. ID. NO. 317)

ATGTTGTTTGATCAAATTGCAAGCAATAAACGAAAAACCTGGATTTTGTTGCTGGTA
TTTTTCCTACTCTTAGCTCTTGTTGGTTATGCGGTTGGTTATCTCTTTATAAGATCGG
ACTTGGTGGTTTGGTTATTGCACTGATTATCGGCTTTATCTACGCTTTGTCTATGATTT
TTCAATCGACAGAGATTGTCATGTCCATGAATGGAGCGCGTGAGGTGGATGAGCAA
ACGGCACCAGACCTCTACCATGTAGTGGAAGATATGGCTCTGGTCGCTCAGATTCCT
ATGCCCCGTGTTTTCATCATTGATGATCCAGCCTTAAATGCCTTTGCGACAGGTTCTA
ATCCTCAAAATGCGGCTGTTGCTGCGACTTCAGGTCTACTAGCTATCATGAATCGTG
AAGAACTAGAAGCTGTTATGGGACATGAAGTCAGTCATATTCGTAATTATGATATCC
GTATTTCGACTATTGCAGTTGCCCTTGCTAGTGCTATCACCATGCTTTCTAGTATGGC
AGGTCGTATGATGTGGTGGGTGGAGCAGGTCGCAGACGAAGTGATGATGACCGAG
ATGGAAATGGTCTTGAAATCATTATGCTAGTGGTTTCCCTACTAGCTATTGTACTGGC
ACCTCTCGCTGCAACCTTGGTTCAGCTCGCTATTTCTCGTCAGAGGGAATTTCTGGCA
GATGCATCTAGTGTCGAGCTGACTCGCAATCCCCAGGGAATGATTAATGCCCTAGAT
AAGTTGGACAATAGCAAACCTATGAGTCGCCACGTCGATGATGCTAGCAGTGCCCTT
TATATCAATGATCCTAAGAAAGGTGGGGGGTTCCAAAAACTCTTTTATACCCACCCA
CCTATCTCAGAACGGATTGAACGTTTAAAACAGATGTAA 4179.9 (SEQ. ID. NO. 318)

ATGAAATTAAATATTCAAGAAATTCGTAAGCAGTCTGAAGGTTTGAACTTTGAACAA
ACGTTAGATTTAGTTGATGACCTGCGTGCACGTAATCAAGAAATTTTAGATGTAAAA
GATATCCTTGCAGTTGGGAAAGTACAATATGAAGACCGTATGTATTTCTTAGATTAT
CAACTATCTTATACCATTGTTCTTGCTTCGAGTCGCAGTATGGAGCCAGTTGAGTTAG
TTGAATCTTATCCAGTCACGGAAGTTTTCATGGAAGGCGCAACTAACCAGCTAGATC
AAGAAGTTTTAGATGATGACTTGGTCTTGCCCATCGAAAATGGGGAGCTTGACCTTG
CTGAGAGTGTATCAGACAATATCCTGCTAAACATTCCTATCAAGGTCTTGACGGCTG
AAGAAGAAGCTGGTCAAGGATTTATCTCAGGAAATGACTGGCAAATCATGACAGAG
GAAGAATACCAAGCTCAAAAAGCAGTAAAGAAAGAAGAAAACAGTCCTTTTGCTGG
CTTACAAGGACTATTTGACGGAGATGAATAA

TABLE 1-continued 4179.12 (SEQ. ID. NO. 319)

ATGGAGTTATTTATGAAAATCACAAACTATGAAATCTATAAGTTAAAAAAATCAGGT
TTGACCAATCAACAGATTTTGAAAGTGCTAGAATACGGTGAAAATGTTGATCAGGA
GCTTTTGTTGGGTGATATTGCAGATATCTCAGGTTGCCGTAATCCAGCCGTTTTTATG
GAACGTTATTTTCAGATAGACGATGCGCATTTGTCGAAAGAGTTTCAAAAATTTCCA
TCTTTCTCTATTTTAGATGACTGTTATCCTTGGGATTTGAGTGAAATATATGATGCGC
CTGTACTTTTATTTTACAAGGGAAATCTTGACCTCCTGAAATTCCCGAAGGTAGCGG
TCGTGGGCAGTCGTGCTTGTAGCAAACAGGGAGCTAAGTCAGTTGAAAAAGTCATT
CAAGGCTTGGAAAATGAACTGGTTATTGTCAGTGGTCTGGCCAAGGGCATTGACAC
AGCAGCTCTATATGGCAGCTCTTCAGAATGGCGGAAAAACCATTGCAGTGATTGGAA
CAGGACTGGATGTGTTTTATCCTAAAGCCAATAAACGCTTGCAAGACTACATCGGCA
ATGACCATCTGGTTCTAAGTGAATATGGACCTGGTGAACAACCTCTGAAATTTCATT
TTCCTGCCCGTAATCGCATCATTGCTGGACTTTGTCGTGGTGTGATTGTAGCAGAGG
CTAAGATGCGTTCAGGTAGTCTCATTACGTGTGAGCGAGCAATGGAAGAAGGACGC
GATGTCTTTGCTATTCCTGGTAGCATTTTAGATGGACTATCAGACGGTTGCCATCATT
TGATTCAAGAAGGAGCAAAATTGGTCACCAGTGGGCAAGATGTTCTTGCGGAATTT
GAATTTTAA 4181.1 (SEQ. ID. NO. 320)

ATGAAACGTCAATTAGCCTTGGTCGTCTTTAGTGGTGGTCAAGATTCAACAACCTGC
CTTTTCTGGGTCATGCAACACTATGAAACAGTCGAAGCTGTCACCTTTGCCTACGGC
CAACGTCATCACCTCGAAATTCAAATTACTAGAGAAATCGCTAAGGAACAGGGCAT
TCGTCACCATATCCTCGATATGTCTCTGCTGGGACAAATCACTGCTCAGCCAGACTTT
GCGACGATTCATATTTCCTACATTCCTGACAAGCTCTGTGTCGAGTCAAAATCCCTC
AAACTATATCTATTTAGCTACCGAAACCACGGAGATTTCCACGAAAACTGTATCAAC
ACCATCGGGAAAGACTTGGTCAACTTGCTAGACCCTCGCTATTTAGAAGTCTGGGGA
AAATTCACTCCGCGCGGTGGCATTTCAATCGACCCCTACTACAACTACGGTAAGCAA
GGAACTAAGTATGAGGGCTTGGCAGAACAACGCCTCTTCCAACACGACCTTTATCCA
GAGAAAATTGACAACCGCTAA 4181.2 (SEQ. ID. NO. 321)

ATGACCGAAACGGTAGAAGATAAAGTAAGTCATTCAATTACTGGGCTTGATATCCTC
AAGGGGATAGTTGCTGCGGGAGCTGTCATAAGTGGAACCGTTGCAACTCAAACGAA
GGTATTTACAAATGAGTCAGCAGTACTTGAAAAAACTGTAGAGAAAACGGATGCTT
TGGCAACAAATGATACAGTAGTTCTAGGTACGATATCTACAAGTAATTCAGCGAGTT
CAACTAGTTTGTCAGCTTCAGAGTCGGCAAGTACATCTGCATCTGAGTCAGCCTCAA
CCAGCGCTTCGACCTCAGCAAGTACAAGTGCATCAGAATCAGCAAGTACATCGGCT
TCGACAAGTATTTCTGCATCATCTACTGTGGTAGGTTCACAAACAGCTGCCGCTACA
GAAGCAACTGCTAAGAAGGTCGAAGAAGATCGTAAGAAACCAGCTAGTGATTATGT
AGCATCAGTTACAAATGTCAATCTCCAATCTTATGCTAAGCGACGCAAGCGTTCAGT
GGATTCCATCGAGCAATTGCTGGCTTCTATAAAAAATGCTGCTGTTTTTTCTGGCAAT
ACGATTGTAAATGGCGCCCCTGCAATTAATGCAAGTCTAAACATTGCTAAAAGTGAG
ACAAAAGTTTATACAGGTGAAGGTGTAGATTCGGTATATCGTGTTCCAATTTACTAT
AAAATTGAAAGTGACAAATGATGGTTCAAAATTGACCTTTACCTATACGGTTACGTAT
GTGAATCCTAAAACAAATGATCTTGGTAATATATCAAGTATGCGTCCTGGATATTCT
ATCTATAATTCAGGTACTTCAACACAAACAATGTTAACCCTTGGCAGTGATCTTGGT
AAACCTTCAGGTGTAAAGAACTACATTACTGACAAAAATGGTAGACAGGTTCTATCC
TATAATACATCTACAATGACGACGCAGGGTAGTGGGTATACTTGGGGAAATGGTGC
CCAAATGAATGGTTTCTTTGCTAAGAAAGGATATGGATTAACATCATCTTGGACTGT
ACCAATTACTGGAACGGATACATCCTTTACATTTACCCCTTACGCTGCTAGAACAGA
TAGAATTGGAATTAACTACTTCAATGGTGGAGGAAAGGTAGTTGAATCTAGCACGA
CCAGTCAGTCACTTTCACAGTCTAAGTCACTCTCAGTAAGTGCTAGTCAAAGCGCCT
CAGCTTCAGCATCAACAAGTGCGTCGGCTTCAGCATCAACCAGTGCCTCGGCTTCAG
CGTCAACCAGTGCGTCAGCTTCAGCAAGTACCAGTGCTTCAGTCTCAGCATCAACAA
GTGCTTCAGCCTCAGCATCGACAAGTGCCTCGGCTTCAGCAAGCACATCAGCATCTG
AATCAGCGTCAACCAGTGCTTCGGCTTCAGCAAGTACCAGTGCTTCAGCTTCAGCAT
CAACCAGCGCCTCGGCCTCAGCAAGCACCTCAGCTTCTGAATCGGCCTCAACCAGCG
CCTCGGCCTCAGCAAGCACCTCAGCTTCTGAATCGGCCTCAACCAGCGCCTCAGCCT
CAGCATCAACGAGTGCTTCGGCTTCAGCAAGCACAAGCGCCTCGGGTTCAGCATCA
ACGAGTACGTCAGCTTCAGCGTCAACCAGTGCTTCAGCCTCAGCATCAACAAGTGCG
TCAGCCTCAGCAAGTATCTCAGCGTCTGAATCGGCATCAACGAGTGCGTCTGAGTCA
GCATCAACGAGTACGTCAGCCTCAGCAAGCACCTCAGCTTCTGAATCGGCCTCAACC
AGTGCGTCAGCCTCAGCATCGACAAGCGCCTCAGCTTCAGCAAGTACCAGTGCTTCA
GCCTCAGCGTCGACAAGTGCGTCGGCCTCAACCAGTGCATCTGAATCGGCATCAACC
AGTGCGTCAGCCTCAGCAAGTACTAGTGCATCGGCTTCAGCATCAACCAGTGCCTCG
GCTTCAGCGTCAACCAGTGCGTCAGCTTCAGCAAGTACCAGTGCTTCAGTCTCAGCA
TCAACAAGTGCTTCAGCCTCAGCATCGACAAGTGCCTCGGCTTCAGCAAGCACATCA
GCATCTGAATCAGCGTCGACAAGCGCCTCAGCTTCAGCAAGTCCAGTGCGTCAGCT
TCAGCATCAACCAGCGCCTCGGCCTCAGCAAGCACCTCAGCTTCTGAATCGGCCTCA
ACCAGCGCCTCGGCCTCAGCAAGCACCTCAGCTTCTGAATCGGCCTCAACCAGCGCC
TCAGCCTCAGCATCAACGAGTGCTTCGGCTTCAGCAAGCACAAGCGCCTCGGGTTCA
GCATCAACGAGTACGTCAGCTTCAGCGTCAACCAGTGCTTCAGCCTCAGCATCAACA
AGTGCGTCAGCCTCAGCAAGTATCTCAGCGTCTGAATCGGCATCAACGAGTGCGTCT
GAGTCAGCATCAACGAGTACGTCAGCCTCAGCAAGCACCTCAGCTTCTGAATCGGC
CTCAACCAGTGCGTCAGCCTCAGCATCGACAAGCGCCTCAGCTTCAGCAAGTACCA

TABLE 1-continued

```
GTGCTTCAGCCTCAGCTCGACAAGTGCGTCGGCCTCAACCAGTGCATCTGAATCGGC
ATCAACCAGTGCGTCAGCCTCAGCAAGTACTAGTGCATCAGCTTCAGCATCAACGA
GTGCATCGGCTTCAGCATCAACCAGTGCCTCGGCTTCAGCGTCAACCAGTGCGTCAG
CTTCAGCAAGTACCAGTGCTTCAGTCTCAGCATCAACAAGTGCTTCAGCCTCAGCAT
CGACAAGTGCcTCGGCTTCAGCAAGCACATCAGCATCTGAATCAGCGTCGACAAGCG
CcTCAGCTTCAGCAAGTACCAGTGCGTCAGCCTCAGCGTCGACAAGTGCGTCAGCCT
CAGCAAGTACTAGTGCATCAGCTTCAGCATCAACGAGTGCATCGGCTTCGGCGTCAA
CCAGTGCATCAGAGTCAGCAAGTACCAGTGCGTCAGCTTCCGCATCAACAAGTGCCT
CGGCTTCAGCAAGCACCAGTGCGTCGGCTTCAGCAAGTACTAGCGCCTCAGCCTCAG
CCTCAACCAGTGCGTCAGCCTCAGCAAGTATCTCAGCGTCTGAATCGGCATCAACGA
GTGCGTCCGCTTCAGCAAGTACTAGCGCCTCAGCCTCAGCGTCAACAAGTGCATCGG
CTTCAGCGTCAACGAGTGCGTCTGAATCGGCATCAACGAGTGCGTCCGCTTCAGCAA
GTACTAGCGCCTCAGCCTCAGCGTCAACAAGTGCATCGGCTTCAGCATCAACGAGTG
CGTCCGCTTCAGCAAGTACTAGCGCCTCAGCCTCAGCGTCAACAAGTGCATCGGCTT
CAGCGTCAACGAGTGCGTCTGAGTCAGCATCAACGAGTGCGTCAGCCTCAGCAAGC
ACATCAGCTTCTGAATCTGCATCAACCAGTGCGTCAGCCTCAGCATCGACAAGCGCC
TCAGCTTCAGCAAGTACCAGTGCGTCAGCCTCAGCGTCGACAAGTGCGTCGGCTTCA
GCAAGTACCAGTGCGTCAGCCTCAGCAAGTACCAGTGCGTCAGCCTCAGCGTCGAC
AAGTGCGTCGGCCTCAACCAGTGCATCTGAATCGGCATCAACCAGTGCGTCAGCCTC
AGCAAGTACTAGCATCAGCTTCAGCATCAACGAGTGCATCGGCTTCAGCATCAAC
CAGTGCATCAGAGTCAGCAAGTACCAGTGCGTCAGTTCCGCATCAACAAGTGCCTC
GGCTTCAGCAAGTACTAG
```

4183.1 (SEQ. ID. NO. 322)

```
ATGGGGGTCGAAACTTGGTTTTATTCTAGCATCTGCTGGCTGGCCATCGGGCTTGGT
TCCGTTTGGAAGTTTCCCTACATGACTGCTGCTAATGGCGGTGGAGGCTTTTTACTAA
TCTTTCTCATTTCCACTATTTTAATCGGTTTCCCTCTCCTGCTGGCTGAGTTTGCCCTT
GGCCGTAGTGCTGGCGTTTCCGCTATCAAAACCTTTGGAAAACTGGGCAAGAATAAC
AAGTACAACTTTATCGGTGGATTGGCGCCTTTGCCCTCTTTATCCTCTTATCTTTTTA
CAGTGTTATCGGAGGATGGATTCTAGTCTATCTAGGTATTGAGTTTGGGAAATTGTT
CCAACTTGGTGGAACGGGTGATTATGCTCAGTTATTTACTTCAATCATTTCAAATCCA
GCCATTGCCCTAGGAGCTCAAGCGGCCTTTATCCTATTGAATATCTTCATTGTATCAC
GTGGGGTTCAAAAAGGGATTGAAAGAGCTTCGAAAGTCATGATGCCCCTGCTCTTTA
TCGTCTTTGTTTTATCATCGGTCGCTCTCAGTTTGCCAAATGCCATGGAAGGGGT
TCTTTACTTCCTCAAACCAGACTTTTCAAAACTGACTAGCACTGGTCTCCTCTATGCT
CTGGGACAATCTTTCTTTGCCCTCTCACTAGGGGTTACAGTCATGTTGACCTATGCTT
CTTACTTAGACAAGAAAACCAATCTAGTCCAGTCAGGAATCTCCATCGTAGCCATGA
ATATCTCGATATCCATCATGGCAGGTCTAGCCATTTTCCAAGCTCGATCCCCCTTCAA
TATCCAGTCTGAAGGGGGACCCAGCCTGCTCTTTATCGTCTTGCCTCAACTCTTTGAC
AAGATGCCTTTGGAACCATTTTCTACGTCCTCTTCCTCTTGCTCTTCCTTTTTGCGAC
AGTCACTTTTTCTGTCGTGATGCTGGAAATCAATGTAGACAATATCACCAACCAGGA
TAACAGCAAACGTGCCAAATGGAGTGTTATTTTAGGAATTTTGACCTTTGTCTTTGG
CATTCCTTCAGCCCATCTTACGGTGTCATGGCGGATGTTCACATTTTTGGTAAGACC
TTCTTTGACGCTATGGACTTCTTGGTTTCCAATCTCCTCATGCCATTTGGAGCTCTCT
ACCTTTCACTTTTTACAGGCTATATCTTTAAAAAGGCTCTTGCAATGGAGGAACTCC
ATCTCGATGAAAGAGCATGGAAACAAGGACTGTTCCAAGTCTGGCTCTTCCTTCTTC
GTTTCTTCGTTTCGTCATTCCAATCATCATCATTGTGGTCTTCATTGCCCAATTTATGT
AATCAAAAAGGACTTGAGTAG
```

4183.5 (SEQ. ID. NO. 323)

```
ATGTTGAAAAAATGGCAGTTAAAAGATGTTATCTTGCTTGCTTTCTTGTCTATCTTTT
TTGGTGGGGTTTTCGTTGGTTCAGGATATGTGTATAATATTCTCAGTCTACTCTTAAC
ACCTGTTGGTTTGCAGGCCTTTGCCAATGAAATCCTCTTCGGTCTCTGGTGTATGGCT
GCGCCCATTGCTGCCATCTTTGTTCCGAGAGTCGGAAGTGCAACGATTGGAGAAGTG
CTAGCTGCGCTTGCTGAAGTCCTTTATGGTAGCCAATTTGGTCTAGGAGCTCTTTTGT
CTGGCTTTGTTCAAGGTTTGGGAAGTGAATTTGGTTTTATCGTAACTAAGAATCGCT
ATGAAAGTTGGCTCTCTCTAACTGCTAATAGTATTGGGATTACGCTTGTTAGCTTTGT
CTATGAATACATTAAGTTAGGTTACTACGCCTTTTCCCTTCCGTTTGTCCTTTCCTTGC
TTGTGGTACGTTTTATTTCTGTTTATTTCTTCTGTACCATCTTGGTTCGTGCCATTGTC
AAACTCTATCATCAGTTTGCAACTGGAGGAAAAGCATAG
```

4183.6 (SEQ. ID. NO. 324)

```
ATGGTCAAAGTAGCAACCCAGACACCGATTATCAGTCTCTTCTTGCTGATTTTATCCT
TGGAAACATCTTTCATTCCTTCGATTGCTCTGACTCTTTCGGTAGTCGCATTTTGTATT
CTCTTTATGCTCTATTACCGTCGATTTAAAATGTTAGCTTGGATGATCATACTTGCCA
TTTTACCATCTTTTGCCAACTACTGGGCAGTTCAGTTACACGGAGATGCTTCACAGG
CAGTCATGCTTGGAACGAGGGCCTTTGTGACAGTTTGTATCGGCCTTGTCTTTGTTTC
CTCTGTTTCACTAAAAGAGCTTCTCTTGTACTTGGCTCAAAAGGGGCTATCACGCTCT
TGGTCCTATGCCTTGATTGTGGTATTCAATTCTTTTCCTCTCATTCAGCAAGAAATCA
AGTCCCTCAAAGAAGCTTGCCTATTACGTGGTCAAGAACTACATTTTTGGTCGCCCT
TGATTTACAGTAAGGTTCTGATGACAGTCTTTAGGTGGCGCCATCTTTACCTGAGAG
CTCTATCTGCTCACGGATATGACGAACATGCACAGTTGAAGAATAGCTATCGGACTT
TTTATATTCCTAAAAAAACAAAATTAATCTACCTGCTTTTCTTTTTATTGCTTCAAAC
CAGTCTATTTTTATAA
```

TABLE 1-continued 4183.7 (SEQ. ID. NO. 325)

ATGAGAAAGCACCAATTACAAGTTCACAAATTAACCATTTTATCTATGATGATTGCC
CTTGATGTAGTCCTTACACCTATCTTTCGAATTGAGGGAATGGCACCGATGTCCAGT
GTAGTCAATATTCTAGCAGGAATCATGATGGGACCTGTTTATGCCTTGGCTATGGCT
ACAGTCACAGCCTTTATCCGTATGACGACTCAAGGGATTCCGCCTTTAGCTCTCACA
GGAGCGACTTTTGGAGCCCTTCTAGCAGGTCTCTTTTATAAGTACGGTCGAAAATTT
CACTATTCTGCTCTAGGAGAGATTTTGGGAACAGGTATTATTGGTTCCATTGTTTCCT
ATCCTGTTATGGTACTCTTTACAGGATCAGCTGCTAAGCTTAGCTGGTTTATCTACAC
GCCTCGATTTTTCGGAGCAACCTTGATTGGTACAGCGATTTCCTTTATTGCCTTTCGA
TTTTTAATCAAGCAGGAATTCTTTAAAAAAGTGCAGGGATATTTCTTTAGTGAAAGG
ATAGACTGA 4183.8 (SEQ. ID. NO. 326)

ATGCAGGAATTTACAAATCCCTTTCCTATAGGCTCTAGTTCCCTCATTCACTGCATTA
CCAATGAGATTTCTTGTGAGATGCTGGCAAATGGGATTTTGGCTCTGGGATGCAAAC
CTGTCATGGCAGATGATTCCCGTGAAGTTCTTGATTTTACTAAGCAAAGTCAGGCTC
TCTTCATCAATTTGGGGCATTTGTCAGCTGAGAAGGAAAAAGCAATCCGCATGGCAG
CTTCGTATGCAAACCAATCTTCTCTCCCGATGGTAGTAGATGCGGTTGGCGTAACGA
CTTCATCCATTCGTAAGAGCTTAGTTAAAGACCTTTTAGACTATAGACCTACGGTCCT
TAAAGGAAACATGTCAGAAATTCGAAGTCTTGTTGGATTAAAGCACCACGGCGTTG
GGGTCGATGCGAGTGCTAAAGATCAAGAAACGGAGGATTTGCTTCAAGTCTTGAAA
GACTGGTGTCAGACCTATCCTGGTATGTCTTTCTTAGTCACAGGTCCCAAGGACCTC
GTCGTTTCGAAAAATCAGGTCGCTGTACTGGGAAATGGCTGTACTGAATTAGACTGG
ATAACAGGGACAGGAGACTTGGTGGAGCCTTAACAGCTGTTTTTCTCAGCCAAGGA
AAGACTGGTTTTGAAGCTTCTTGCTTAGCAGTCTCTTATCTCAATATCGCTGCTGAGA
AATAGTTGTTCAAGGAATGGGATTGGAAGAATTTCGTTACCAAGTACTCAATCAGC
TTTCGCTCCTAAGAAGAGATGAAAATTGGCTAGATACCATCAAAGGAGAGGTTTAT
GAATAG 4185.3 (SEQ. ID. NO. 327)

ATGAACCATAAAATCGCAATTTTATCAGATGTTCATGGCAATGCGACGGCGCTAGAA
GCAGTGATTGCAGATGCTAAAAATCAAGGGGCCAGTGAATATTGGCTTCTGGGAGA
TATTTTTCTTCCTGGTCCAGGCGCAAATGACTTAGTCGCCCTGCTAAAGGACCTTCCT
ATCACAGCAAGTGTTCGAGGCAATTGGGATGATCGTGTCCTTGAGGCTTTAGATGGG
CAATATGGCTTAGAAGACCCACAGGAAGTTCAGCTCTTGCGTATGACACAGTATTTG
ATGGAGCGAATGGATCCTGCAACGATTGTCTGGCTACGAAGCTTGCCTTTGCTGGAA
AAGAAAGAAATTGACGGATTGCGCTTTTCTATCTCTCATAATTTACCTGACAAAAAC
TATGGTGGTGACTTGCTAGTTGAGAATGATACAGAGAAATTTGACCAACTGCTAGAT
GCGGAAACGGACGTGGCAGTTTATGGTCATGTTCACAAGCAGTTGCTTCGTTATGGA
AGTCAAGGGCAACAAATCATCAATCCAGGGTCGATTGGCATGCCCTATTTTAATTGG
GAGGCGTTAAAAAATCACCGTTCCCAGTATGCCGTGATAGAAGTTGAAGATGGGGA
ATTACTCAATATCCAATTTCGTAAAGTTGCTTATGATTACGAAGCTGAGTTAGAATT
GGCCAAGTCCAAGGGGCTTCCCTTTATCGAAATGTATGAAGAACTGCGTCGTGACGA
TAACTATCAGGGGCACAATCTGGAATTATTAGCCAGCTTAATAGAAAAGCATGGGT
ATGTAGAGGATGTGAAGAATTTTTTTGATTTTTTGTAA 4186.1 (SEQ. ID. NO. 328)

ATGAATGTAAATCAGATTGTACGGATTATTCCTACTTTAAAAGCTAATAATAGAAAA
TTAAATGAAACATTTTATATTGAAACCCTTGGAATGAAGGCCTTGTTAGAAGAATCG
GCCTTTCTGTCACTAGGTGACCAAACGGGTCTTGAAAAGCTGGTTTTAGAAGAAGCT
CCCAGTATGCGTACTCGTAAGGTAGAGGGAAGAAAAAAACTAGCTAGATTGATTGT
CAAGGTGGAAAATCCCTTAGAAATTGAAGGAATCTTATCTAAAACAGATCGATTCA
TCGATTATATAAAGGTCAAAATGGCTACGCTTTTGAAATTTTCTCACCAGAAGATGA
TTTGATTTTGATTCATGCGGAAGATGACATAGCAAGTCTAGTAGAAGTAGGAGAAA
AGCCTGAATTTCAAACAGATTTGGCATCAATTTCTTTAAGTAAATTTGAGATTTCTAT
GGAATTACATCTCCCAACTGATATCGAAAGTTTCTTGGAATCATCTGAAATTGGGGC
ATCCCTTGATTTTATTCCAGCTCAGGGGCAGGATTTGACTGTGGACAATACGGTTAC
CTGGGACTTATCTATGCTCAAGTTCTTGGTCAATGAATTAGACATAGCAAGTCTTCG
CCAGAAGTTTGAGTCTACTGAATATTTTATTCCTAAGTCTGAAAATTCTTCCTTGGT
AAAGATAGAAATAATGTTGAATTGTGGTTTGAAGAAGTATGA 4186.2 (SEQ. ID. NO. 329)

ATGAAGTGGACCAAGATTATTAAAAAATAGAAGAACAAATCGAGGCAGGGATTTA
TCCCGGAGCCTCTTTTGCGTATTTTAAGGACAATCAATGGACAGAGTTCTATTTAGG
CCAGAGTGACCCAGAGCATGGCTTGCAGACTGAGGCAGGACTAGTTTATGACCTAG
CTAGTGTCAGCAAGGTTGTTGGGGTTGGCACAGTTTGTACCTTCTTGTGGGAAATAG
GTCAATTAGATATTGATAGACTGGTAATAGATTTTTTACCTGAGAGTGATTATCCAG
ACATCACTATTCGCCAGCTCTTGACTCATGCAACAGACCTTGATCCTTTTATTCCTAA
TCGTGATCTTTTAACAGCCCCTGAATTAAAGGAAGCGATGTTTCATCTCAACAGACG
AAGTCAGCCAGCCTTTCTTATTCGGATGTCCATTTTTTGCTGTTGGGCTTATTTTGG
AAAGAATTTTTAATCAAGATTTGGATGTGATTTTAAAGGATCAAGTCTGGAAACCTT
GGGGAATGACGGAAACTAAGTTTGGGCCAGTTGAGCTTGCTGTTCCAACAGTAGA
GGTGTAGAGGCAGGCATAGTGCATGATCCCAAGGCTCGTCTCCTGGGTAGACATGCT

TABLE 1-continued

GGGAGTGCTGGTTTATTTTCGACTATAAAGGATTTACAAATCTTTTTAGAACACTATT
TAGCAGATGATTTTGCAAGAGACTTAAATCAAAATTTTTCTCCTTTGGATGACAAGG
AACGTTCTTTAGCATGGAATTTGGAAGGAGATTGGCTAGACCATACGGGCTATACAG
GTACCTTTATCATGTGGAATCGTCAGAAGCAAGAAGCCACTATTTTCCTATCGAATC
GTACCTATGAAAAGGACGAGAGAGCTCAATGGATATTAGACCGCAATCAAGTGATG
AACTTGATTCGCAAAGAAGAGTAA 4187.2 (SEQ. ID. NO. 330)

ATGATGAAGAAGACTTATAATCATATTTTGGTCTGGGGAGTCATTTTCTATAGCATTT
GCATTGTCTGTTTTTGCTTTACTCCTCAAGAACAATCTACCGTGGGAGTGGGAACTCC
AGGTATTCAGCATCTTGGACGCCTGGTTTTTCTTTTGACTCCTTTCAATTCTCTCTGG
AAACTGGGCGAAGTGAGTGACATTGGACAATTATGTTGGATTTTTTTACAAAATATC
CTCAATGTCTTCTTGTTTTTTCCTCTGATTTTCCAACTCCTTTATCTATTTCCAAATTT
GCGGAAAACAAAAAAGGTCCTTCTTTTTAGTTTTCTTGTGAGTCTTGGAATCGAGTG
TACGCAATTAATCTTGGACTTTTTCTTTGATTTCAATCGCGTCTTTGAGATTGATGAT
TTGTGGACCAACACTTTGGGTGGCTATCTGGCTTGGCTCCTTTATAAACGATTACATA
AAAACAAGGTAAGGAATTAA 4188.1 (SEQ. ID. NO. 331)

ATGAAGATTCCTCTCTTAACTTTTGCAAGGCATAAATTTGTTTATGTCTTGCTTACTT
TGCTTTTTCTTGCTTTGGTTTATCGTGATGTTTTGATGACTTATTTCTTTTTTGATATTC
ATGCGCCCGATCTAGCTAAATTCGATGGACAAGCAATTAAAAATGACTTATTAAAAT
CAGCATTAGATTTTCGTATTCTCCAGTTCAATCTAGGTTTTTTATCAATCATTTATTATT
CCAATCATCATTGTTTTGCTAGGTTTTCAATATATTGAGCTGAAAAATAAAGTTTTAC
GATTGAGTATTGGAAGAGAAGTGAGTTATCAAGGGTTAAAAAGAAAGTTGACTTTG
CAAGTTGCAAGTATCCCTTGTTTGATATATTTAGTGACTGTGCTGATAATTGCAATTA
TAACCTATTTCTTTGGGACTTTTTCTCCTCTTGGATGGAATTCTCTATTTTCTGATGGA
AGTGGTTTACAAAGACTCCTAGATGGAGAGATAAAAAGCTATTTGTTCTTTACTTGT
GTCCTACTAATCGGTATTTTCATCAATGCAATCTATTTTTTACAAATAGTTGATTATG
TGGGGAATGTGACTCGTTCGGCAATCACCTATTTGATGTTTCTTTGGCTTGGTTCTAT
GCTGCTTTATAGTGCCTTGCCTTACTATATGGTTCCTATGACGAGTTTGATGCAAGCT
AGCTATGGGGATGTAAGTTTGATGAAACTCTTTACTCCTTATATCCTTTATATTGTCC
CTTACATGGTGCTTGAAAAATATGAAGATAATGTTTAA 4188.2 (SEQ. ID. NO. 332)

ATGAAGATAATGTTTAAGAATTTTAACATATTTTGCTAAATAGAAAGATTGTTTTA
CTACTTCGTATAGTTCTGATGATGATTTTGATAAACCATCTATTGTCAACAGCGGTTC
AAAGCAGGATGCTGTTATCTTTTTCAAGAGAATTGATTTCAATTTTTTCCTATAT
GACTATTCTGAAGCGAATTTAGAAATCCCCAAACTATTGTTAAACCTTTCGCTTTTCA
TGGTAGGATGGCTCTCTGTCATTTTACTTGAAAGTGATTGGCAGACCATTACCATC
ACTTGATTCGCTATCAATCAAGCTCCTTTTTCGATTATACAAGGAAACGATTGGTTGT
CATTTCTAAATTTTTTACTCAAGATTTGTTTGTCTGGTTTCTTGGTTTACTTCCTCTAG
GAATTCATTTCAAAACAGTCGCACTTTTCTTTTTACTTGCTCAGTTAATGATGTTGTA
CTTACTACTGTCTTATCTGATAGCACTGATTAGTGCGGGCGCTGGTTTTTCCTTTTTTC
TCTATTTTTTAGCATTTGTGGGACAAGAATGGATGATGGATCATATTGTAACAGTGT
ATTTAGTACTCTTAAGTTTATTAGTTATGTTGATTGTTAGTCGCTTGGAAGAGAAATT
TAAGAAAGGATAA 4188.5 (SEQ. ID. NO. 333)

ATGGGCAAAGGAGAGATGGGCAAAGGAGTTATTGGCTTGGAGTTCGACTCAGAAGT
ATTGGTCAACAAGGCTCCAACCCTTCAATTGGCAAATGGTAAAACAGCGACTTTCCT
AACCCAGTATGATAGCAAGACCTTGTTGTTTGCAGTAGATAAGGAAGATATCGGAC
AGGAAATTATTGGTATAGCTAAAGGAAGCATCGAAAGTATGCATAATCTTCCTGTAA
ATCTAGCAGGTGCCAGAGTTCCTGGCGGAGTAAATGGTAGCAAAGCAGCGGTGCAT
GAAGTTCCAGAATTTACAGGGGGAGTTAATGGTACAGAGCCAGCTGTTCATGAAAT
CGCGAGAGTATAAGGGATCTGATTCGCTTGTAACTCTTACTACAAAAAAAGATTATAC
TTACAAAGCTCCTCTTGCTCAGCAGGCACTTCCTGAAACAGGAAACAAGGAGAGTG
ACCTCCTAGCTTCACTAGGACTAACAGCTTCTTCCTTGGTCTGTTTACGCTAGGGAA
AAAGAGAGAACAATAA 4188.10 (SEQ. ID. NO. 334)

ATGTTTAAAGTTTTACAAAAAGTTGGAAAAGCTTTTATGTTACCTATAGCTATACTTC
CTGCAGCAGGTCTACTTTTGGGGATTGGTGGTGCACTTTCAAACCCAACCACGATAG
CAACTTATCCAATACTAGACAATAGTATTTTTCAATCAATATTCCAAGTAATGAGCT
CTGCAGGAGAGGTTGTATTCAGTAATTTGTCACTACTCTCTGTGTGGGATTATGTAT
TGGCTTAGCGAAACGAGATAAAGGAACCGCTGCGTTAGCAGGAGTAACTGGTTACT
TAGTTATGACTGCAACGATCAAAGCTTTGGTAAAACTTTTTATGGCAGAAGGATCTG
CAATTGATACTGGAGTTATTGGAGCATTAGTTGTCGGAATAGTTGCCGTATATTTGC
ACAACCGATATAACAATATTCAATTACCTTCCGCTTTAGGATTCTTTGGAGGTTCAC
GCTTCGTTCCTATTGTTACATCGTTCTCTTCTATCTTGATTGGCTTTGCTTCTTCTTGTT
ATTTGGCCACCTTTCCAACAACTTCTTGTTTCTACAGGTGGATATATTTCTCAGGCGG
GTCCAATTGGAACTTTTCTATATGGATTTTTAATGAGACTTTCTGGAGCAGTAGGCTT
ACATCATATAATTTACCCTATGTTTTGGTATACTGAACTTGGTGGTGTTGAAACTGTT
GCAGGACAAACAGTGGTTGGAGCTCAAAAAATATTTTTTGCTCAATTAGCCGATTTG

TABLE 1-continued

GCCCATTCTGGATTATTTACAGAAGGAACAAGGTTTTTTGCAGGTCGTTTCTCAACA
ATGATGTTCGGTTTACCGGCTGCCTGTTTAGCGATGTACCATAGTGTTCCTAAAAATC
GTCGTAAAAAATACGCGGGTTTGTTTTTTGGAGTTGCTTTAACATCTTTTATTACCGG
TATTACAGAACCAATTGAATTTATGTTTCTATTCGTCAGTCCGGTTCTATATGTTGTT
CACGCATTCCTTGATGGTGTTAGCTTCTTTATTGCAGACGTCTTAAATATTTCAATAG
GAAACACATTTTCAGGAGGTGTAATCGATTTCACTTTATTTGGAATTTTGCAGGGGA
ACGCTAAGACGAATTGGGTTCTTCAGATTCCATTTGGACTTATTTGGAGTGTTTTGTA
TTATATTATTTTTAGATGGTTCATTACTCAATTCAACGTTCTAACGCCAGGGCGAGGA
GAAGAAGTAGATTCTAAAGAAATTTCTGAATCCGCAGATTCAACTTCAAATACTGCA
GATTATTTAAAACAGGATAGCCTACAAATTATCAGAGCCTTGGGTGGATCAAATAAT
ATAGAAGATGTAGATGCTTGTGTGACACGTTTACGTGTAGCTGTAAAAGAAGTTAAT
CAAGTTGATAAAGCACTTTTAAAACAAATTGGTGCAGTTGATGTCTTAGAAGTGAAG
GGTGGCATTCAAGCAATCTATGGAGCAAAAGCAATCTTATATAAAAATAGTATTAAT
GAAATTTTAGGTGTAGATGATTAA 4188.11 (SEQ. ID. NO. 335)

ATGAAATTTAGAAAATTAGCTTGTACAGTACTTGCGGGTGCTGCGGTTCTTGGTCTT
GCTGCTTGTGGCAATTCTGGCGGAAGTAAAGATGCTGCCAAATCAGGTGGTGACGG
TGCCAAAACAGAAATCACTTGGTGGGCATTCCCAGTATTTACCCAAGAAAAAACTG
GTGACGGTGTTGGAACTTATGAAAAATCAATCATCGAAGCGTTTGAAAAAGCAAAC
CCAGATATAAAAGTGAATTGGAAACCATCGACTTCAAGTCAGGTCCTGAAAAAAT
CACAACAGCCATCGAAGCAGGAACAGCTCCAGACGTACTCTTTGATGCACCAGGAC
GTATCATCCAATACGGTAAAAACGGTAAATTGGCTGAGTTGAATGACCTCTTCACAG
ATGAATTTGTTAAAGATGTCAACAATGAAAACATCGTACAAGCAAGTAAAGCTGGA
GACAAGGCTTATATGTATCCGATTAGTTCTGCCCCATTCTACATGGCAATGAACAAG
AAAATGTTAGAAGATGCTGGAGTAGCAAACCTTGTAAAAGAAGGTTGGACAACTGA
TGATTTTGAAAAAGTATTGAAAGCACTTAAAGACAAGGGTTACACACCAGGTTCATT
GTTCAGTTCTGGTCAAGGGGGAGACCAAGGAACACGTGCCTTTATCTCTAACCTTTA
TAGCGGTTCTGTAACAGATGAAAAAGTTAGCAAATATACAACTGATGATCCTAAATT
CGTCAAAGGTCTTGAAAAAGCAACTAGCTGGATTAAAGACAATTTGATCAATAATG
GTTCACAATTTGACGGTGGGCAGATATCCAAAACTTTGCCAACGGTCAAACATCTT
ACACAATCCTTTGGGCACCAGCTCAAATGGTATCCAAGCTAAACTTTTTAGAAGCAA
GTAAGGTAGAAGTGGTAGAAGTACCATTCCCATCAGACGAAGGTAAGCCAGCTCTT
GAGTACCTTGTAAACGGGTTTGCAGTATTCAACAATAAAGACGACAAGAAAGTCGC
TGCATCTAAGAAATTCATCCAGTTTATCGCAGATGACAAGGAGTGGGGACCTAAAG
ACGTAGTTCGTACAGGTGCTTTCCCAGTCCGTACTTCATTTGGAAAACTTTATGAAG
ACAAACGCATGGAAACAATCAGCGGCTGGACTCAATACTACTCACCATACTACAAC
ACTATTGATGGATTTGCTGAAATGAGAACACTTTGGTTCCCAATGTTGCAATCTGTA
TCAAATGGTGACGAAAAACCAGCAGATGCTTTGAAAGCCTTCACTGAAAAAGCGAA
CGAAACAATCAAAAAGCTATGAAACAATAG 4188.12 (SEQ. ID. NO. 336)

ATGCAATCTACAGAAAAAAAACCATTAACAGCCTTTACTGTTATTTCAACAATCATT
TTGCTCTTGTTGACTGTGCTGTTCATCTTTCCATTCTACTGGATTTTGACAGGGGCAT
TCAAATCACAACCTGATACAATTGTTATTCCTCCTCAGTGGTTCCCTAAAATGCCAA
CCATGGAAAACTTCCAACAACTCATGGTGCAGAACCCTGCCTTGCAATGGATGTGGA
ACTCAGTATTTATCTCATTGGTAACCATGTTCTTAGTTTGTGCAACCTCATCTCTAGC
AGGTTATGTATTGGCTAAAAAACGTTTCTATGGTCAACGCATTCTATTTGCTATCTTT
ATCGCTGCTATGGCGCTTCCAAAACAAGTTGTCCTTGTACCATTGGTACGTATCGTC
AACTTCATGGGAATCCATGATACTCTCTGGGCAGTTATCTTGCCTTTGATTGGATGGC
CATTCGGTGTCTTCCTCATGAAACAGTTCAGTGAAAATATCCCTACAGAGTTGCTTG
AATCAGCTAAAATCGACGGTTGTGGTGAGATTCGTACCTTCTGGAGTGTAGCCTTCC
CGATTGTGAAACCAGGGTTTGCAGCCCTTGCAATCTTTACCTTCATCAATACTTGGA
ATGACTACTTCATGCAATTGGTAATGTTGACTTCACGTAACAATTTGACCATCTCACT
TGGGGTTGCGACCATGCAGGCTGAAATGGCAACCAACTATGGTTTGATTATGGCAG
GAGCTGCCCTTGCTGCTGTTCCAATCGTCACAGTCTTCCTAGTCTTCCAAAAATCCTT
CACACAGGGTATTACTATGGGAGCGGTCAAAGGATAA 4191.1 (SEQ. ID. NO. 337)

ATGAAAAAAACTTTTTTCTTACTGGTGTTAGGCTTGTTTTGCCTTCTTCCACTCTCTGT
TTTTGCCATTGATTTCAAGATAAACTCTTATCAAGGGGATTTGTATATTCATGCAGAC
AATACGCAGAGTTTAGACAGAAGATAGTTTACCAGTTTGAGGAGGACTTTAAGGG
CCAAATCGTGGGACTTGGACGTGCTGGTAAGATGCCTAGCGGGTTTGACATTGACCC
TCATCCAAAGATTCAGGCCGCGAAAAACGGTGCAGAACTAGCAGATGTGACTAGCG
AAGTAACAGAAGAAGCGGATGGTTATACTGTGAGAGTCTATAATCCAGGTCAGGAG
GGCGACATAGTTGAAGTTGACCTCGTCTGGAACTTAAAAAATTTACTTTTCCTTTATG
ATGATATCGCTGAATTAAATTGGCAACCTCTGACAGATAGTTCAGAGTCTATTGAAA
AGTTTGAATTTCATGTAAGGGGAGACAAGGGGGCTGAAAAACTCTTTTTCCATACAG
GGAACTTTTTAGAGAGGGAACGATTGAAAAGAGTAACCTTGATTATACTATCCGTT
TAGACAATCTTCCGGCTAAGCGTGGAGTTGAGTTGCATGCCTATTGGCCTCGGACCG
ATTTTGCTAGCGCTAGGGATCAGGGATTGAAAGGGAATCGTTTAGAAGAGTTTAATA
AGATAGAAGACTCGATTGTTAGAGAAAAAGATCAGAGTAAACAACTCGTTACTTGG
GTCCTCCCTTCGATCCTTTCCATCTCCTTGTTATTGAGTGTCTGCTTCTATTTTATTTA
TAGAAGAAAGACCACTCCTTCAGTCAAATATGCCAAAAATCATCGTCTCTATGAACC
ACCAATGGAATTAGAGCCTATGGTTTTATCAGAAGCAGTCTACTCGACCTCCTTGGA
GGAAGTGAGTCCCTTGGTCAAGGGAGCTGGAAAATTCACCTTTGATCAACTTATTCA

TABLE 1-continued

AGCTACCTTGCTAGATGTGATAGACCGTGGGAATGTCTCTATCATTTCAGAAGGAGA
TGCAGTTGGTTTGAGGCTAGTAAAAGAAGATGGTTTGTCAAGCTTTGAGAAAGACTG
CCTAAATCTAGCTTTTTCAGGTAAAAAGAAGAAACTCTTTCCAATTTGTTTGCGGA
TTACAAGGTATCTGATAGTCTTTATCGTAGAGCCAAAGTTTCTGATGAAAACGGAT
TCAAGCAAGAGGGCTTCAACTCAAATCTTCTTTTGAAGAGGTATGAACCAGATGCA
AGAAGGAGTGAGAAAACGAGTTTCCTTCTGGGGGCTCCCAGATTATTATCGTCCTTT
AACTGGTGGGGAAAAGGCCTTGCAAGTGGGTATGGGTGCCTTGACTATCCTGCCCCT
ATTTATCGGATTTGGTTTGTTCTTGTACAGTTTAGACGTTCATGGCTATCTTTACCTCC
CTTTGCCAATACTTGGTTTTCTAGGGTTAGTTTTGTCTGTTTTCTATTATTGGAAGCTT
CGACTAGATAATCGTGATGGTGTTCTAAATGAAGCGGGAGCTGAGGTCTACTATCTC
TGGACCAGTTTTGAAAATATGTTGCGTGAGATTGCACGATTGGATCAGGCTGAACTG
GAAAGTATTGTGGTCTGGAATCGCCTCTTGGTCTATGCGACCTTATTTGGCTATGCG
GACAAGGTTAGTCATTTGATGAAGGTTCATCAGATTCAAGTGGAAAATCCAGATATC
AATCTCTATGTAGCTTATGGCTGGCACAGTACGTTTTATCATTCAACAGCACAAATG
AGCCATTATGCTAGTGTCGCAAATACAGCAAGCACCTACTCTGTATCTTCTGGAAGT
GGAAGTTCTGGTGGTGGCTTCTCTGGAGGCGGAGGTGGCGGCAGTATCGGTGCCTTT
TAA 4191.2 (SEQ. ID. NO. 338)

ATGAAAAAAGTAAGAAAGATATTTCAGAAGGCAGTTGCAGGACTGTGCTGTATATC
TCAGTTGACAGCTTTTTCTTCGATAGTTGCTTTAGCAGAAACGCCTGAAACCAGTCC
AGCGATAGGAAAAGTAGTGATTAAGGAGACAGGCGAAGGAGGAGCGCTTCTAGGA
GATGCCGTCTTTGAGTTGAAAAACAATACGGATGGCACAACTGTTTCGCAAAGGAC
AGAGGCGCAAACAGGAGGAAGCGATATTTCAAACATAAAACCTGGGACATACACCT
TGACAGAAGCCCAACCTCCAGTTGGTTATAAACCCTCTACTAAACAATGGACTGTTG
AAGTTGAGAAGAATGGTCGGACGACTGTCCAAGGTGAACAGGTAGAAAATCGAGA
AGAGGCTCTATCTGACCAGTATCCACAAACAGGGACTTATCCAGATGTTCAAACACC
TTATCAGATTATTAAGGTAGATGGTTCGGAAAAAAACGGACAGCACAAGGCGTTGA
ATCCGAATCCATATGAACGTGTGATTCCAGAAGGTACACTTTCAAAGAGAATTTATC
AAGTGAATAATTTGGATGATAACCAATATGGAATCGAATTGACGGTTAGTGGGAAA
ACAGTGTATGAACAAAAAGATAAGTCTGTGCCGCTGGATGTCGTTATCTTGCTGAT
AACTCAAATAGTATGAGTAACATTCGAAACAAGAATGCTCGACGTGCGGAAAGAGC
TGGTGAGGCGACACGTTCTCTTATTGATAAAATTACATCTGATTCAGAAAATAGGGT
AGCGCTTGTGACTTATGCTTCCACTATCTTTGATGGGACCGAGTTTACAGTAGAAAA
AGGGGTAGCAGATAAAAACGGAAAGCGATTGAATGATTCTCTTTTTTGGAATTATGA
TCAGACGAGTTTTACAACCAATACCAAAGATTATAGTTATTTAAAGCTGACTAATGA
TAAGAATGACATTGTAGAATTAAAAAATAAGGTACCTACCGAGGCAGAAGACCATG
ATGGAAATAGATTGATGTACCAATTCGGTGCCACTTTTACTCAGAAAGCTTTGATGA
AGGCAGATGAGATTTTGACACAACAAGCGAGACAAAATAGTCAAAAGTCATTTTC
CATATATTACGGATGGTGTCCCAACTATGTCGTATCCGATTAATTTTAATCATGCTACGT
TTGCTCCATCATATCAAAATCAACTAAATGCATTTTTTAGTAAATCTCCTAATAAAG
ATGGAATACTATTAAGTGATTTTATTACGCAAGCAACTAGTGGAGAACATACAATTG
TACGCGGAGATGGGCAAAGTTACCAGATGTTTACAGATAAGACAGTTTATGAAAAA
GGTGCTCCTGCAGCTTTCCCAGTTAAACCTGAAAAATATTCTGAAATGAAGGCGGCT
GGTTATGCAGTTATAGGCGATCCAATTAATGGTGGATATATTTGGCTTAATTGGAGA
GAGAGTATTCTGGCTATCCGTTTAATTCTAATACTGCTAAAATTACCAATCATGGTG
ACCCTACAAGATGGTACTATAACGGGAATATTGCTCCTGATGGGTATGATGTCTTTA
CGGTAGGTATTGGTATTAACGGAGATCCTGGTACGGATGAAGCAACGGCTACTAGTT
TTATGCAAAGTATTTCTAGTAAACCTGAAAACTATACCAATGTTACTGACACGACAA
AAATATTGGAACAGTTGAATCGTTATTTCCACACCATCGTAACTGAAAAGAAATCAA
TTGAGAATGGTACGATTACAGATCCGATGGGTGAGTTAATTGATTTGCAATTGGGCA
CAGATGGAAGATTTGATCCAGCAGATTACACTTTAACTGCAAACGATGGTAGTCGCT
TGGAGAATGGACAAGCTGTAGGTGGTCCACAAAATGATGGTGGTTTGTTAAAAAAT
GCAAAAGTGCTCTATGATACGACTGAGAAAAGGATTCGTGTAACAGGTCTGTACCTT
GGAACGGATGAAAAGTTACGTTGACCTACAATGTTTCGTTTGAATGATGAGTTTGTA
AGCAATAAATTTTATGATACCAATGGTCGAACAACCTTACATCCTAAGGAAGTAGA
ACAGAACACAGTGCGCGACTTCCCGATTTCCTAAGATTCGTGATGTGCGGAAGTATCC
AGAAATCACAATTTCAAAAGAGAAAAAACTTGGTGACATTGAGTTTATTAAGGTCA
ATAAAAATGATAAAAAACCACTGAGAGGTGCGGTCTTTAGTCTTCAAAAACAACAT
CCGGATTATCCAGATATTTATGGAGCTATTGATCAAAATGGCACTTATCAAATGTG
AGAACAGGTGAAGATGGTAAGTTGACCTTTAAAAATCTGTCAGATGGGAAATATCG
ATTATTTGAAAATTCTGAACCAGCTGGTTATAAACCCGTTCAAAATAAGCCTATCGT
TGCCTTCCAAATAGTAAATGGAGAAGTCAGAGATGTGACTTCAATCGTTCCACAAGA
TATACCAGCGGGTTACGAGTTTACGAATGATAAGCACTATATTACCAATGAACCTAT
TCCTCCAAAGAGAGAATATCCTCGAACTGGTGGTATCGGAATGTTGCCATTCTATCT
GATAGGTTGCATGATGATGGGAGGAGTTCTATTATACACACGGAAACATCCGTAA 4191.3 (SEQ. ID. NO. 339)

ATGAAATCAATCAACAAATTTTTAACAATGCTTGCTGCCTTATTACTGACAGCGAGT
AGCCTGTTTTCAGCTGCAACAGTTTTTGCGGCTGGGACGACAACAACATCTGTTACC
GTTCATAAACTATTGGCAACAGATGGGGATATGGATAAAATTGCAAATGAGTTAGA
AACAGGTAACTATGCTGGTAATAAAGTGGGTGTTCTACCTGCAAATGCAAAAGAAA
TTGCCGGTGTTATGTTCGTTTGGACAAATACTAATAATGAAATTATTGATGAAAATG
GCCAAACTCTAGGAGTGAATATTGATCCACAAACATTTAAACTCTCAGGGGCAATGC
CGGCAACTGCAATGAAAAAATTAACAGAAGCTGAAGGAGCTAAATTTAACACGGCA
AATTTACCAGCTGCTAAGTATAAAATTTATGAAATTCACAGTTTATCAACTTATGTC
GGTGAAGATGGAGCAACCTTAACAGGTTCTAAAGCAGTTCCAATTGAAATTGAATT

TABLE 1-continued

```
ACCATTGAACGATGTTGTGGATGCGCATGTGTATCCAAAAAATACAGAAGCAAAGC
CAAAAATTGATAAAGATTTCAAAGGTAAAGCAAATCCAGATACACCACGTGTAGAT
AAAGATACACCTGTGAACCACCAAGTTGGAGATGTTGTAGAGTACGAAATTGTTAC
AAAAATTCCAGCACTTGCTAATTATGCAACAGCAAACTGGAGCGATAGAATGACTG
AAGGTTGGCATTCAACAAAGGTACAGTGAAAGTAACTGTTGATGATGTTGCACTTG
AAGCAGGTGATTATGCTCTAACAGAAGTAGCAACTGGTTTTGATTTGAAATTAACAG
ATGCTGGTTTAGCTAAAGTGAATGACCAAAACGCTGAAAAAACTGTGAAAATCACT
TATTCGGCAACATTCAATGACAAAGCAATTGTAGAAGTACCAGAATCTAATGATGTA
ACATTTAACTATGGTAATAATCCAGATCACGGGAATACTCCAAAGCCGAATAAGCC
AAATGAAAACGGCGATTTGACATTGACCAAGACATGGGTTGATGCTACAGGTGCAC
CAATTCCGGCTGGAGCTGAAGCAACGTTCGATTTGGTTAATGCTCAGACTGGTAAAG
TTGTACAAACTGTAACTTTGACAACAGACAAAAATACAGTTACTGTTAACGGATTGG
ATAAAAATACAGAATATAAATTCGTTGAACGTAGTATAAAAGGGTATTCAGCAGAT
TATCAAGAAATCACTACAGCTGGAGAAATTGCTGTCAAGAACTGGAAAGACGAAAA
TCCAAAACCACTTGATCCAACAGAGCCAAAAGTTGTTACATATGGTAAAAAGTTTGT
CAAAGTTAATGATAAAGATAATCGTTTAGCTGGGGCAGAATTTGTAATTGCAAATGC
TGATAATGCTGGTCAATATTTAGCACGTAAAGCAGATAAAGTGAGTCAAGAAGAGA
AGCAGTTGGTTGTTACAACAAAGGATGCTTTAGATAGAGCAGTTGCTGCTTATAACG
CTCTTACTGCACAACAACAAACTCAGCAAGAAAAAGAGAAAGTTGACAAAGCTCAA
GCTGCTTATAATGCTGCTGTGATTGCTGCCAACAATGCATTTGAATGGGTGGCAGAT
AAGGACAATGAAAATGTTGTGAAATTAGTTTCTGATGCACAAGGTCGCTTTGAAATT
ACAGGCCTTCTTGCAGGTACATATTACTTAGAAGAAACAAAACAGCCTGCTGGTTAT
GCATTACTAACTAGCCGTCAGAAATTTGAAGTCACTGCAACTTCTTATTCAGCGACT
GGACAAGGCATTGAGTATACTGCTGGTTCAGGTAAAGATGACGCTACAAAAGTAGT
CAACAAAAAATCACTATCCCACAAACGGGTGGTATTGGTACAATTATCTTTGCTGT
AGCGGGGGCTGCGATTATGGGTATTGCAGTGTACGCATATGTTAAAAACAACAAAG
ATGAGGATCAACTTGCTTAA
```

4191.4 (SEQ. ID. NO. 340)

```
ATGACAATGCAGAAAATGCAGAAAATGATTAGTCGTATCTTCTTTGTTATGGCTCTG
TGTTTTTCTCTTGTATGGGGTGCACATGCAGTCCAAGCGCAAGAAGATCACACGTTG
GTCTTGCAATTGGAGAACTATCAGGAGGTGGTTAGTCAATTGCCATCTCGTGATGGT
CATCGGTTGCAAGTATGGAAGTTGGATGATTCGTATTCCTATGATGATCGGGTGCAA
ATTGTAAGAGACTTGCATTCGTGGGATGAGAATAAACTTTCTTCTTTCAAAAAGACT
TCGTTTGAGATGACCTTCCTTGAGAATCAGATTGAAGTATCTCATATTCCAAATGGT
CTTTACTATGTTCGCTCTATTATCCAGACGGATGCGTTTCTTATCCAGCTGAATTTC
TTTTTGAAATGACAGATCAAACGGTAGAGCCTTTGGTCATTGTAGCGAAAAAAACA
GATACAATGACAACAAAGGTGAAGCTGATAAAGGTGGATCAAGACCACAATGCTT
GGAGGGTGTCGGCTTTAAATTGGTATCAGTAGCAAGAGATGTTTCTGAAAAAGAGG
TTCCCTTGATTGGAGAATACCGTTACAGTTCTTCTGGTCAAGTAGGGAGGAACTCTCT
ATACTGATAAAAATGGAGAGATTTTTGTGACAAATCTTCCTCTTGGGAACTATCGTT
TCAAGGAGGTGGAGCCACTGGCAGGCTATGCTGTTACGACGCTGGATACGGATGTC
CAGCTGGTAGATCATCAGCTGGTGACGATTACGGTTGTCAATCAGAAATTACCACGT
GGCAATGTTGACTTTATGAAGGTGGATGGTCGGACCAATACCTCTCTTCAAGGGGCA
ATGTTCAAAGTCATGAAAGAAGAAAGCGGACACTATACTCCTGTTCTTCAAAATGGT
AAGGAAGTAGTTGTAACATCAGGGAAAGATGGTCGTTTCCGAGTGGAAGGTCTAGA
GTATGGGACATACTATTTATGGGAGCTCCAAGCTCCAACTGGTTATGTTCAATTAAC
ATCGCCTGTTTCCTTTACAATCGGGAAAGATACTCGTAAGGAACTGGTAACAGTGGT
TAAAAATAACAAGCGACCACGGATTGATGTGCCAGATACAGGGGAAGAAACCCTTG
TATATCTTGATGCTTGTTGCCATTTTGTTGTTTGGTAG
```

4191.5 (SEQ. ID. NO. 341)

```
ATGAGCCACATATACTTATCTATTTTCACAAGTCTCTFTGCTGATGCTAGGACTTGTCA
ATGTTGCTCAAGCCGATGAATATTTACGCATCGGTATGGAAGCAGCATATGCTCCCT
TTAACTGGACCCAGGATGATGATAGCAACGGAGCTGTCAAAATCGATGGGACCAAT
CAGTATGCCAACGGATACGATGTTCAAATCGCCAAGAAAATCGCTAAGGACTTAGG
TAAAGAACCTTTGGTTGTTAAAACCAAGTGGGAAGGTCTAGTCCCTGCCCTTACTTC
TGGTAAGATTGACATGATTATCGCAGGTATGAGTCCAACTGCAGAACGCAAACAAG
AAATTGCCTTTTCGAGCAGTTACTATACTAGCGAACCAGTTTTGCTTGTCAAAAAAG
ATTCTGCCTACGCAAGTGCTAAATCTTTGGATGACTTTAACGGTGCAAAAATCACTT
CTCAACAAGGGGTCTACCTTTATAACTTGATTGCACAAATCCCAGGTGCTAAAAAAG
AAACAGCCATGGGAGACTTCACTCAAATGCGACAAGCTCTTGAGGCTGGTGTCATTG
ATGCTTATGTTTCTGAACGTCCAGAAGCACTGACTGCTGAAGCTGCGAACTCTAAGT
TCAAGATGATTCAAGTAGAACCTGGTTTCAAAACTGGGGAAGAAGATACAGCTATC
GCTATCGGGCTTCGTAAAAATGACAATCGTATTAGCCAAATCAATGCCAGCATTGAA
ACCATTTCAAAAGATGACCAAGTTGCCTTGATGGATCGTATGATCAAGGAACAACCT
GCCGAAGCTACAACAACTGAAGAGACTAGCAGTAGTTTCTTTAGCCAAGTTGCTAA
AATTCTTTCTGAAAACTGGCAACAACTCTTGCGTGGTGCTGGTATCACTCTTTTAATC
TCTATCGTCGGAACCATCATAGGTCTCATTATTGGACTTGCCATTGGTGTCTTCCGTA
CTGCTCCTCTCTCTGAAAACAAAGTCATTTACGGCCTACAAAACTAGTCGGCTGGG
TTCTCAATGTCTACATTGAAATTTTCCGTGGTACGCCAATGATTGTTCAATCGATGGT
TATCTACTATGGAACTGCCCAAGCTTTCGGGATCAACCTTGACCGTACACTGGCTGC
TATCTTCATCGTTTCAATCAATACCGGTGCCTACATGACTGAAATCGTCCGTGGTGGT
ATCCTAGCAGTTGACAAGGGACAATTTGAAGCTGCGACTGCTCTTGGTATGACCCAT
AACCAGACCATGCGTAAGATTGTCCTACCTCAGGTAGTCCGTAACATCCTACCTGCA
ACTGGTAATGAATTTGTCATCAATATCAAAGATACATCTGTATTGAACGTTATCTCT
GTTGTCGAACTTTATTTCTCAGGAAATACCGTGGCAACACAAACCTATCAATACTTC
```

TABLE 1-continued

CAGACATTTACAATCATCGCCGTGATTTACTTTGTCCTCACCTTCACCGTAACACGTA
TCCTACGCTTTATCGAGCGCAGAATGGACATGGATACCTACACTACAGGTGCTAACC
AAATGCAAACGGAGGATTTGAAATAA 4191.6 (SEQ. ID. NO. 342)

ATGACACAAGCAATCCTTGAAATTAAACACCTCAAAAAATCCTATGGACAAAACGA
AGTGCTAAAAGACATTTCACTCACTGTCCACAAGGGAGAGGTCATCTCTATCATCGG
AAGCTCTGGAAGCGGAAAATCGACCTTCCTACGCTCCATTAACCTACTTGAAACACC
AACTGATGGACAAATCCTTTATCATGGACAAAACGTCCTCGAAAAAGGCTATGACCT
CACGCAATACCGTGAAAAGTTGGGGATGGTTTTCCAATCCTTTAACCTCTTTGAAAA
TCTCAATGTTCTTGAAAACACAATCGTCGCTCAGACAACTGTCCTAAAACGCGAACG
CACAGAAGCTGAAAAGATTGCCAAAGAAAACCTGGAAAAGGTCGGCATGGGAGAA
CGCTACTGGCAAGCCAAACCAAAACAACTCTCAGGTGGTCAAAAACAACGTGTGGC
CATCGCTCGTGCCCTCTCCATGAATCCGGACGCTATTCTCTTTGATGAACCAACATC
AGCTCTCGATCCAGAAATGGTTGGAGAAGTCCTCAAAATCATGCAGGACCTGGCTC
AGGAAGGCTTGACCATGATTGTCGTAACCCATGAAATGGAATTTGCCCGTGATGTCT
CTCACCGTGTTATCTTTATGGATAAGGGCGTGATCGCTGAAGAAGGTAAACCAGAA
GACCTCTTCACCAATCCTAAAGAAGACCGAACAAAAGAGTTCCTTCAACGCTATCTC
AAATAA 4192.3 (SEQ. ID. NO. 343)

ATGAAAAAGTATCAACTTCTATTCAAAATAAGTGCAGTCTTCTCTTACTTATTTTTCG
TATTTAGTCTTTCTCAGCTGACGCTTATCGTCCAAAACTATTGGCAATTTTCTTCTCA
GATAGGCAATTTATTCTGGATTCAAAATATCTTGAGTTTACTTTTTATTGGAGTCATG
ATTGTGGTTCTTGTTAAGACAGGCCATGGTTATCTCTTCCGCATTCCAAGAAAAAAA
TGGCTTTGGTATTCGATTTTGACAGTATTAGTGCTAGTGTTCCAGATCTCTTTTAACG
TTCAGACAGCTAAACATGTTCAGTCAACTGCGGAAGGTTGGGCTGTATTGATTGGTT
ATAGTGGGACTAACTTTGCAGAGCTAGGTATTTATATAGCCCTGTTCTTTCTGGTTCC
ACTGATGGAAGAATTGATTTATAGAGGATTACTGCAACATGCTTTTCTTTAAGCATTC
GCGATTTGGTCTTGATTTGCTTCTTCCTTCTATTTTATTTGCTCTCCCTCATTTTTCAA
GCCTGCCTAGTCTGTTAGATATCTTCGTCTTTGCAACAGTTGGAATCATCTTTGCTGG
TTTGACCCGCTATACCAAGAGCATTTATCCATCCTATGCGGTGCATGTGATCAATAA
TATTGTAGCGACCTTCCCGTTTTTGCTCACTTTTCTACATAGGGTCTTGGGGTAA 4193.1 (SEQ. ID. NO. 344)

ATGAACAAGAAACAATGGCTAGGTCTTGGCCTAGTTGCAGTGGCAGCAGTTGGACT
TGCTGCATGTGGTAACCGCTCTTCTCGTAACGCAGCTTCATCTTCTGATGTGAAGAC
AAAAGCAGCAATCGTCACTGATACTGGTGGTGTTGATGACAAATCATTCAACCAATC
AGCTTGGGAAGGTTTGCAGGCTTGGGGTAAAGAACACAATCTTTCAAAAGATAACG
GTTTCACTTACTTCCAATCAACAAGTGAAGCTGACTACGCTAACAACTTGCAACAAG
CGGCTGGAAGTTACAACCTAATCTTCGGTGTTGGTTTTGCCCTTAATAATGCAGTTA
AAGATGCAGCAAAAGAACACACTGACTTGAACTATGTCTTGATTGATGATGTGATTA
AAGACCAAAAGAATGTTGCGAGCGTAACTTTCGCTGATAATGAGTCAGGTTACcTTG
CAGGTGTGGCTGCAGCAAAAACAACTAAGACAAAACAAGTTGGTTTTGTAGGTGGT
ATCGAATCTGAAGTTATCTCTCGTTTTGAAGCAGGATTCAAGGCTGGTGTTGCGTCA
GTAGACCCATCTATCAAAGTCCAAGTTGACTACGCTGGTTCATTTGGTGATGCGGCT
AAAGGTAAAACAATTGCAGCCGCACAATACGCAGCCGGTGCAGATATTGTTTACCA
AGTAGCTGGTGGTACAGGTGCAGGTGTCTTTGCAGAGGCAAAATCTCTCAACGAAA
GCCGTCCTGAAAATGAAAAGTTTGGGTTATCGGTGTTGATCGTGACCAAGAAGCA
GAAGGTAAATACACTTCTAAAGATGGCAAAGAATCAAACTTTGTTCTTGTATCTACT
TTGAAACAAGTTGGTACAACTGTAAAAGATATTTCTAACAAGGCAGAAGAGGAGA
ATTCCCTGGCGGTCAAGTGATCGTTTACTCATTGAAGGATAAAGGGGTTGACTTGGC
AGTAACAAACCTTTCAGAAGAAGGTAAAAAAGCTGTCGAAGATGCAAAAGCTAAA
TCCTTGATGGAAGCGTAAAAGTTCCTGAAAAATAA 4193.3 (SEQ. ID. NO. 345)

ATGTCTAAAAAATTACAACAAATTTCGGTTCCCTTGATTTCTGTATTCCTAGGAATTT
TACTCGGAGCCATTGTCATGTGGATCTTCGGTTATGATGCTATTTGGGGCTACGAAG
AATTGTTCTATACAGCCTTTGGCAGTCTGCGTGGGATTGGAGAAATCTTCCGTGCTA
TGGGTCCTCTGGTCTTGATTGGTCTTGGTTTTGCCGTTGCCAGTCGAGCTGGTTTCTT
TAACGTCGGACTTCCTGGTCAGGCTTTGGCAGGTTGGATTCTCAGTGGTTGGTTTGCC
CTGTCGCATCCAGATATGCCCCGTCCCTTGATGATTCTAGCAACCATCGTGATTGCCT
TGATTGCTGGTGGGATTGTCGGAGCGATTCCAGGTATTCTTAGGGCCTATCTAGGGA
CGTCAGAGGTTATTGTAACCATCATGATGAACTACATTGTCTTGTATGTAGGGAATG
CCTTTATCCATGCTTTCCCTAAAGACTTCATGCAAAGTACAGATTCGACCATTCGTGT
TGGGGCTAATGCAACCTATCAGACACCTTGGTTGGCTGAGTTGACTGGTAACTCACG
GATGAATATTGGTATTTTCTTTGCCATCATTGCCGTTGCAGTTATTTGGTTCATGCTC
AAGAAAACAACTCTTGGTTTTGAAATCCGTGCAGTTGGTCTTAATCCACATGCTTCA
GAATATGCTGGTATTTCTGCCAAGCGGACTATTATCCTATCTATGATTATTTCAGGTG
CCTTGGCAGGTCTTGGTGGAGCTGTTGAAGGTTTGGGAACCTTCCAGAACGTCTATG
TTCAAGGTTCGTCATTAGCTATCGGATTTAACGGAATGGCGGTTAGTTTGCTTGCGG
CCAACTCACCAATTGGTATACTCTTTGCAGCCTTCCTATTTGGCGTTCTCCAAGTTGG
GGCTCCTGGTATGAATGCGGCGCAGGTACCATCTGAGCTTGTCAGCATTGTAACAGC
GTCTATTATCTTCTTTGTCAGTGTTCATTACCTTATCGAACGCTTTGTCAAACCGAAA
AAACAAGTTAAAGGAGGTAAGTAA

TABLE 1-continued 4194.1 (SEQ. ID. NO. 346)

ATGGGAGTGAAAAAGAAACTAAAGTTGACTAGTTTGCTAGGACTGTCTCTGTTAATC
ATGACAGCCTGTGCGACTAATGGGGTAACTAGCGATATTACAGCCGAATCGGCTGA
TTTTTGGAGTAAATTGGTTTACTTCTTTGCGGAAATCATTCGCTTTTTATCGTTTGATA
TTAGTATCGGAGTGGGGATTATTCTCTTTACGGTCTTGATTCGTACAGTCCTCTTGCC
AGTCTTTCAGGTGCAATGGTGGCTTCTAGGAAAATGCAGGAAGCTCAGCCACGCA
TTAAGGCGCTTCGAGAACAATATCCAGGTCGAGATATGGAAAGCAGAACCAAACTA
GAGCAGGAAATGCGTAAAGTATTTAAAGAAATGGGTGTCAGACAGTCAGACTCTCT
TTGGCCGATTTTGATTCAGATGCCGGTTATTTTGGCCCTGTTCCAAGCCCTATCAAGA
GTTGACTTTTTAAAGACAGGTCATTTCTTATGGATTAACCTTGGTAGTGTGGATACA
ACCCTTGTTCTTCCGATTTTAGCAGCAGTATTCACCTTTTTAAGTACTTGGTTGTCCA
ACAAAGCTTTGTCTGAGCGAAATGGCGCTACGACTGCGATGATGTATGGGATTCCAG
TCTTGATTTTTATCTTTGCAGTTTATGCGCCAGGTGGAGTCGCCCTATACTGGACAGT
GTCTAATGCTTATCAAGTCTTGCAAACCTATTTCTTGAATAATCCATTCAAGATTATC
GCAGAGCGCGAGGCCGTAGTACAGGCACAAAAGATTTGGAAAATAGAAAAAGAA
AAGCCAAGAAAAAGGCTCAGAAAACGAAATAA 4194.4 (SEQ. ID. NO. 347)

ATGGTTATCGATCCATTTGCTATCAACGAACTAGACTATTACTTAGTTTCACACTTCC
ACAGTGATCATATCGACCCATACACAGCTGCAGCAATTCTCAATAATCCTAAGTTAG
AGCATGTTAAGTTTATCGGTCCTTACCACTGTGGACGAATCTGGGAAGGATGGGGTG
TTCCAAAAGAACGTATCATCGTTGTTAAACCAGGTGACACTATCGAATTAAAAGATA
TGAAGATTCATGCAGTAGAATCATTTTGACCGTACTTGCTTGGTAACTCTCCCAGTGA
ACGGTGCTGATGAGACAGGCGGTGAACTTGCTGGCTTGGCTGTTACAGATGAAGAA
ATGGCTCAAAAGGCTGTTAACTATATCTTTGAAACACCAGGTGGAACCATCTATCAT
GGTGCAGATTCTCACTTCTCAAACTATTTTGCAAAACATGGTAAAGACTTTAAAATT
GATGTTGCTTTGAATAACTATGGTGAAAATCCGGTAGGTATCCAAGACAAAATGAC
ATCTATCGACCTTCTTCGTATGGCAGAAAATCTGCGTACCAAAGTCATTATCCCAGT
TCACTATGATATCTGGTCTAACTTCATGGCTTCTACTAATGAGATTCTAGAACTTTGG
AAAATGCGAAAAGATCGCTTGCAATACGATTTCCATCCATTTATCTGGGAAGTTGGC
GGTAAGTACACTTATCCTCAAGATCAACACTTAGTAGAATACCATCATCCACGTGGT
TTTGATGATTGTTTTGAACAAGACTCTAACATTCAATTTAAAGCTTTGCTATAA 4196.2 (SEQ. ID. NO. 348)

ATGTTCCTTTCAGGCTGGTTGTCTAGTTTTGCTAATACTTATATCCATGATTTACTGG
GGGTTCTTTTCCCAGATAGTCCATTTTTAAATGCCTTTGAAAGTGCTATTGCGGCTCC
TTTGGTAGAAGAACCCTTGAAATTATTGTCACTTGTTTTTGTTTTGGCTTTGATTCCT
GTGCGAAAATTAAAATCTTTGTTTTTACTTGGAATTGCTTCCGGTTTGGGATTCCAAA
TGATTAAGGATATTGGTTATATTCGTACGGATTTGCCAGAGGGCTTTGACTTTACTAT
TTCGCGAATTTTAGAGCGTATCATCTCAGGAATTGCCTCTCACTGGACTTTTTCAGGT
CTAGCTGTAGTAGGTGTTTACTTGCTTTACAGAGCCTATAAAGGACAGAAGGTTGGC
AAGAAACAGGGCCTTATTTTCTAGGTTTAGCCTTGGGAACTCACTTCTTGTTTAACT
CTCCTTTTGTGGAGTTGGAAACAGAGTTGCCTTTAGCGATTCCAGTGGTTACGGCTA
TTGCTCTCTATGGTTTTTATCATGCTTATTGCTTGTTGAGAAACACAATGAGTTGAT
GACCTAG 4197.1 (SEQ. ID. NO. 349)

ATGAAGGTGGAACCACGTTGCGACGTCCTTTCGAGGATGTCGCATTTTTTTATTAGG
ATACTAATTATGGAGTTGCAAGAATTAGTGGAGCGCAGTTGGGCAATCCGACAAGC
TTATCACGAACTGGAAGTTAAGCATCATGATTCCAAGTGGACGGTAGAAGAAGACC
TCTTGGCTTTATCTAATGATATTGGAAATTTCCAACGACTGGTGATGACAAGCAAG
GACGCTACTATGATGAAACACCCTACACACTGGAACAAAAACTTCAGAAAATATC
TGGTGGCTATTAGAACTTTCTCAACGTTTGGATATAGACATTCTGACGGAAATGGAA
AACTTCCTCTCTGATAAAGAAAAGCAATTGAACGTTAGGACTTGGAAGTAG 4197.4 (SEQ. ID. NO. 350)

ATGCTTGATTGGAAACAATTTTTCTAGCCTATCTGCGCTCCCGTAGTCGTCTTTTTA
TCTATCTGCTTTCTTTGGCATTTCTTGTCTTACTCTTCAGTTTTTATTTGCCAGTCTA
GGAATTTACTTCCTCTACTTTTTCTTCTTGTGTTGCTTTGTAACCATATTATTTTTCAC
TTGGGACATATTGGTGGAAACGCAGGTCTATCGCCAGGAACTTCTCTATGGAGAGA
GGGAAGCCAAGTCTCCTTTGGAAATAGCTTTAGCAGAAAAATTAGAAGCGCGTGAG
ATGGAACTCTATCAGCAGAGGTCAAAAGCAGAAAGAAAACTGACGGATTTGCTGGA
TTACTATACCTTGTGGGTCCATCAGATAAAGACCCCCATTGCAGCCAGTCAACTCTT
AGTTGCAGAAGTGGTCGACCGCCAACTGAAGCAGCAGCTAGAACAGGAAATTTTCA
AAATCGACTCCTATACCAACCTAGTTTTACAGTACCTGCGTTTAGAAAGTTTCCATG
ATGATTTGGTCTTAAAGCAGGTTCAAATTGAGGACTTGGTCAAGGAAATAATTCGTA
AATATGCTCTTTTCTTTATCAAAAAGGCTTAAATGTCAATCTACATGACCTTGATAA
AGAAATCGTGACGGATAAAAAGTGGCTGCTAGTGGTTATTGAGCAAATCATCTCAA
ACAGTCTCAAGTACACCAAGGAAGGTGGTCTGGAGATTTATATGGATGACCAAGAG
CTTTGTATCAAAGATACGGGAATCGGGATAAAAAACAGTGATGTCCTCCGAGTATTT
GAACGTGGCTTTTCAGGATACAATGGCCGTTTGACCCAGCAGTCCTCTGGACTTGGC

TABLE 1-continued

CTTTATCTATCTAAGAAAATTTCTGAAGAACTGGGGCACCAGATTCGTATCGAGTCT
GAGGTCGGAAAAGGAACGACAGTGCGGATTCAGTTTGCTCAAGTGAACTTAGTCCT
TGAGTAA 4211.2 (SEQ. ID. NO. 351)

ATGGAACTTAATACACACAATGCTGAAATCTTGCTCAGTGCAGCTAATAAGTCCCAC
TATCCGCAGGATGAACTGCCAGAGATTGCCCTAGCAGGGCGTTCAAATGTTGGTAA
ATCCAGCTTTATCAACACTATGTTGAACCGTAAGAATCTCGCCCGTACATCAGGAAA
ACCTGGTAAAACCCAGCTCCTGAACTTTTTTAACATTGATGACAAGATGCGCTTTGT
GGATGTGCCTGGTTATGGCTATGCTCGTGTTTCTAAAAAGGAACGTGAAAAGTGGGG
GTGCATGATTGAGGAGTACTTAACGACTCGGGAAAATCTCCGTGCGGTTGTCAGTCT
AGTTGACCTTCGTCATGACCCGTCAGCAGATGATGTGCAGATGTACGAATTTCTCAA
GTATTATGAGATTCCAGTCATCATTGTGGCGACCAAGGCGGACAAGATTCCTCGTGG
TAAATGGAACAAGCATGAATCAGCAATCAAAAAGAAATTAAACTTTGACCCGAGTG
ACGATTTCATCCTCTTTTCATCTGTCAGTAAGGCAGGGATGGATGAGGCTTGGGATG
CAATCTTAGAAAAATTGTGA 4211.3 (SEQ. ID. NO. 352)

ATGACAAAGAAACAACTTCACTTGGTGATTGTGACAGGGATGAGTGGCGCAGGGAA
AACTGTAGCCATTCAGTCCTTCGAGGATCTAGGTTATTTCACCATTGATAATATGCC
GCCAGCTCTCTTGCCTAAGTTTTTGCAGCTGGTTGAAATTAAGGAAGACAATCCTAA
GTTGGCCTTGGTAGTGGATATGCGTAGCCGTTCTTTCTTTTCAGAGATTCAAGCTGTT
TTGGATGAGTTGGAAAATCAAGATGGTTTGGATTTCAAAATCCTCTTTTTGGATGCG
GCTGATAAGGAATTCCTCGCTCGTTACAAGGAAACCAGACGGAGTCACCCACTAGC
AGCAGACGGTCGTATTTTAGATGGAATCAAGTTGGAACGTGAACTCTTGGCACCTTT
GAAAAATATGAGCCAAAATGTGGTGGATACGACTGAACTCACTCCACGTGAGcTGC
GCAAAACCCTTGCAGAGCAGTTTTCAGACCAAGAACAAGCCCAGTCTTTCCGTATCG
AAGTCATGTCTTTCGGATTTAAGTATGGAATCCCGATTGATGCGGACTTGGTCTTTG
ATGTCCGTTTCTTGCCAAATCCCTATTATTTACCAGAACTGAGAAACCAAACGGGTG
TGGATGAACCTGTTTATGATTATGTCATGAACCATCCTGAGTCAGAAGACTTTTATC
AACATTTATTGGCCTTGATTGAGCCGATTCTGCCAAGTTACCAAAAGGAAGGTAAGT
CCGTTTTGACCATTGCCATGGGATGTACGGGTGGACAACACCGTAGTGTGGCATTTG
CTAAACGCTTGGCGCAGGACTTATCCAAGAATTGGTCTGTTAATGAAGGGCATCGCG
ACAAAGACCGCAGAAAGGAAACGGTAAACCGTTCATGA 4211.4 (SEQ. ID. NO. 353)

ATGAGAAAACCAAAGATAACGGTGATTGGTGGAGGGACTGGAAGTCCCGTCATTCT
AAAAAGTCTGCGGGAAAAAGATGTGGAAATCGCAGCTATCGTGACGGTGGCAGATG
ATGGTGGTTCTTCAGGTGAACTCCGAAAAAATATGCAACAGTTGACACCGCCAGGT
GATCTTCGTAATGTCCTTGTGGCCATGTCGGATATGCCTAAGTTTTATGAGAAGGTCT
TTCAGTATCGGTTCTCTGAGGATGCCGGAGCCTTTGCTGGCCATCCATTGGGAAATC
TCATCATTGCTGGCTTGTCAGAAATGCAGGGTTCAACCTATAATGCCATGCAGTTAT
TGAGCAAATTTTTCCATACAACAGGGAAAATTTATCCTTCCAGTGACCATCCTTTGA
CCCTTCATGCAGTCTTTCAGGATGGGACAGAAGTGGCTGGAGAGAGTCATATTGTAG
ACCATCGAGGCATAATTGACAATGTCTATGTGACCAATGCCCTAAACGATGATACGC
CTCTGGCCAGCCGTCGAGTAGTGCAGACCATCCTTGAAAGTGACATGATTGTCCTAG
GGCCAGGTTCCCTCTTTTACCTCTATTTTGCCCAATATCGTGATTAAGGAAATTGGGCG
GGCTCTTTTGGAAACCAAGGCAGAAATTGCCTATGTCTGCAATATCATGACCCAACG
TGGGGAGACGGAACACTTTTACAGATAGCGACCACGTGGAAGTCTTGCATCGTCACC
TTGGTCGCCCTTTTATCGACACTGTCTTGGTGAATATTGAAAAAGTGCCTCAGGAAT
ACATGAATTCCAACCGTTTTGATGAATACTTAGTGCAAGTGGAACACGATTTTGTAG
GTCTTTGTAAGCAAGTTTCGCGCGTGATTCATCTAACTTCCTTCGTCTGGAAAATGG
CGGTGCCTTCCACGATGGAGATTTGATTGTGGACGAGTTGATGCGCATTATACAGGT
GAAAAAATGA 4213.1 (SEQ. ID. NO. 354)

ATGAAAAATTTGATAAAGTTGCTAATAATTAGATTGATTGTTAACTTAGCAGACAGT
GTATTTTATATAGTAGCATTGGCACGTTAGCAATAATTATTCTTCGAGCATGTTCT
TAGGAATATTTATTGCAGTAAATTATCTACCGGATTTGTTACTAATCTTTTTTGGACC
AGTTATTGACAGAGTAAATCCGCAAAAAATTCTTATAATATCAATTTTGGTTCAATT
AGCAGTGGCTGTAATATTTTTATTATTATTAAACCAAATATCATTTTGGGTGATAATG
AGTCTAGTGTTTATTTCAGTAATGGCTAGCTCCATAAGTTACGTGATAGAAGATGTG
TTGATTCCTCAAGTGGTAGAATATGATAAGATTGTATTTGCAAATTCTCTTTTTAGTA
TTTCGTATAAAGTATTAGATTCTATTTTTAATTCATTCGCATCATTTTTACAGGTGGC
AGTAGGATTTATTTATTGGTTAAGATAGATATAGGCATATTTTACTTGCTCTATTT
ATATTGTTGTTGTTAAAATTTAGAACTAGCAATGCGAATATAGAAAACTTCTCTTTC
AAATATTACAAGAGAGAAGTGTTGCAAGGTACAAAGTTTATTTTAAATAATAAATTA
TTATTTAAAACCAGTATTTCTTTAACGCTTATAAACTTTTTTATTCATTTCAGACAGT
AGTTGTACCGATTTTTTCTATTCGATATTTTGATGGTCCGATTTTTTATGGTATTTTTT
TAACTATTGCTGGTTTGGGTGGTATATTGGGAAATATGCTAGCGCCAATCGTAATAA
AATATTTAAAATCGAATCAAATTGTTGGTGTATTTCTTTTTTTGAACGGCTCAAGTTG
GTTAGTAGCAATTCTTATAAAAGACTATACTTTATCACTTATTTATTTTTCGTTTGTT
TTATGTCTAAAGGAGTCTTCAATATTATTTTAATTCGTTGTACCAACAAATACCTCC
ACATCAACTTCTTGGTAGGGTAAATACTACCATTGATTCTATTATTTCTTTTGGAATG
CCAATTGGTAGTTTAGTTGCAGGAACGCTTATTGATTTGAATATTGAATTAGTGTTA

TABLE 1-continued

ATTGCTATTAGCATACCTTATTTTTTGTTTTCTTATATTTTTTATACGGATAATGGATT
GAAAGAATTTAGTATATATTAG 4213.2 (SEQ. ID. NO. 355)

ATGATGTCTAACAAAAATAAGGAAATTCTGATTTTTGCGATTCTCTATACAGTCCTCT
TTATGTTTGATGGCGTTAAATTGCTGGCTTCTTTAATGCCATCTGCCATTGCAAATTA
TCTTGTTTATGTAGTTTTAGCTCTATATGGCTCCTTCTTGTTCAAGGATAGATTGATC
CAACAATGGAAGGAGATTAGAAAGACTAAAAGAAAATTCTTCTTTGGAGTCTTAAC
AGGATGGCTCTTTCTCATTCTGATGACTGTTGTCTTTGAATTTGTATCAGAGATGTTG
AAGCAGTTTGTGGGACTAGATGGACAAGGTCTAAATCAGTCTAATATTCAAAGTACC
TTTCAAGAACAACCACTACTGATAGCTGTTTTTGCTGTGTCATTGGACCTCTGGTAG
AAGAATTATTTTTCCGTCAGGTCTATTGCATTACTTGCAGGAACGGTTGTCAGGTTT
ACTAAGCATTATTCTGGTAGGACTTGTTTTTGCTCTGACTCATATGCACAGTTTGGCT
CTATCAGAGTGGATTGGTGCAGTTGGTTACTTAGGTGGAGGCCTTGCCTTTTCTATTA
TTTATGTGAAAGAAAAAGAGAATATCTACTATCCCCTACTTGTTCACATGTTAAGCA
ACAGCCTCTCCTTAATCATTTTAGCTATCAGTATAGTAAAATGA 4224.1 (SEQ. ID. NO. 356)

TTGAAAAAGCCAATTATCGAATTCAAAAACGTCTCTAAAGTTTTTGAAGACAGCAAC
ACCAAGGTTCTCAAAGACATCAACTTTGAGTTGGAAGAAGGGAAATTCTACACCCTT
CTAGGTGCATCTGGTTCGGGGAAATCAACTATCCTAAACATTATTGCAGGTTTACTG
GATGCGACGACAGGAGATATCATGCTAGACGGTGTTCGTATCAATGATATTCCAACC
AACAAGCGCGACGTACATACCGTCTTCCAATCCTATGCCTTGTTCCCACATATGAAT
GTGTTTGAAAATGTTGCCTTTCCACTTCGCTTGCGTAAAATTGATAAGAAAGAAATC
GAGCAGCGTGTAGCGGAAGTTCTCAAGATGGTTCAGTTGGAAGGTTATGAAAAACG
TTCCATCCGCAAACTTTCTGGAGGACAACGTCAGCGTGTGGCCATCGCCCGTGCTAT
CATCAACCAACCCCGTGTGGTCTTGTTGGACGAGCCTTTATCAGCGCTGGACTTGAA
ATTGAGAACAGACATGCAGTACGAATTGCGTGAATTACAACAACGATTGGGCATTA
CCTTTGTCTTTGTCACTCACGATCAGGAAGAAGCTCTTGCCATGAGTGACTGGATTTT
CGTTATGAATGATGGCGAGATTGTCCAGTCTGGAACCCCTGTGGACATCTACGATGA
GCCAATCAACCACTTTGTTGCCACCTTTATCGGGGAGTCAAACATCTTGCCAGGTAC
CATGATTGAGGACTACTTGGTCGAATTTAACGGCAAACGCTTTGAAGCGGTTGATGG
TGGGATGAAGCCAAATGAACCTGTTGAGGTCGTTATTCGTCCAGAGGACTTGCGCAT
TACCCTTCCTGAAGAAGGCAAGCTCCAAGTTAAGGTCGATACCCAGCTTTTCCGTGG
AGTTCATTATGAAATTATCGCCTATGACGAACTTGGAAATGAATGGATGATCCACTC
AACCCGTAAGGCTATCGTGGGTGAGGAAATCGGTCTGGACTTTGAACCAGAAGACA
TCCACATCATGCGTCTCAATGAAACCGAAGAAGAGTTCGATGCTCGTATTGAGGAGT
ACGTAGAAATCGAAGAGCAAGAAGCAGGTTTGATCAATGCAATCGAGGAGGAAAG
AGATGAAGAAAACAAGCTCTAA 4252.1 (SEQ. ID. NO. 357)

ATGAAATCAATGAGAATCTTATTTTTGTTAGCTTTAATTCAAATCAGTTTGAGTAGCT
GTTTCCTATGGAAGGAATGCATCTTGTCCTTTAAACAAAGTACAGCTTTTTTCATCGG
AAGCATGGTTTTCGTTTCAGGAATCTGTGCTGGAGTAAATTATCTTTATACCCGTAA
GCAAGAAGTCCATAGTGTCCTAGCCAGTAAGAAGTCGGTGAAGCTTTTTTACAGTAT
GTTACTCTTAATTAATTTGTTAGGAGCTGTTCTTGTTTTGTCAGATAACTTGTCATC
AAAAATACGCTGCAGCAAGAATTAGTTGACTTTTTATTGCCATCCTTCTTTTTCCTAT
TTGGGCTAGATTTGCTGATTTTTTACCCTTGAAAAAATACGTGCGCGATTTTCTTGC
TATGCTGGACAGAAAAAAGACAGTGTTGGTTGACTATTTTAGCAACACTTCTTTTCTT
AAGAAATCCAATGACCATTGTCTCACTTCTGATTTATATTGGACTGGGCTTGTTTTTT
GCAGCCTATCTTGTCCCAAATTCGGTTAAGAAGGAAGTTTCCTTTTTATGGTCATATT
TTCCGAGATCTTGTATTGGTCATTGTTACGCTCATTTTCTTTTAG 4252.2 (SEQ. ID. NO. 358)

ATGGTTAAAAAAATTATTGGAATGGTGCTAGCTTTACTTTCTGTAACTGTAGTAGGA
GTAGGTGTTTTTGCTTATACTATTTATCAACAAGGGACAGAAACCTTAGCTAAAACC
TATAAAAAAATCGGTGAAGAAACCAAGGTTATTGAAGCGACTGAACCTCTAACCAT
TCTGTTAATGGGAGTGGACACCGGAAATGTTGAACGAACTGAAACTTGGGTCGGTA
GAAGTGATAGCATGATCTTGATGACAGTGAATCCTAAAACGAAAAAAACAACAATG
ATGAGTTTAGAGCGGGATATTCGACGCGCATTGAATCAGGGAATGGTCAGGCTCAT
GAAGCGAAACTGAACTCAGCATATGCAGATGGTGGAGCGAAGCTTGCTATAGAAAC
CATTCAAAAAATGATGAATATCCATATTGATCGCTATGTGATGGTCAATATGAGAGG
ATTGCAAAAACTAGTGGATGCAGTAGGAGGTATTACAGTCAATAATATCCTAGGTTT
CCCAATTTCTATCAGTGACCAAGAAGAATTTAATACTATTTCTATCGGTGTTGGGGA
GCAACATATTGGGGAGAAGAAGCCCTAGTCTATGCACGAATGCGTTACCAAGATC
CTGAGGGGATTATGGTCGTCAAAAACGTCAACGTGAAGTTATTCAAAAAGTCATG
GAAAAAGCTCTCAGTTTAAATAGCATTGGTCATTATCAAGAGATTCTAAAAGCTTTG
AGTGACAATATGCAGACCAATATTGATTTGTCTGCAAAAAGTATCCCTAACTTGCTA
GGCTATAAAGATTCATTTAAAACCATTGAAACTCAGCAGTTGCAGGGTGAAGGAGA
GATACTTCAAGGTGTTTCTTACCAGATTGTTTCGAGAGCACATATGTGGAAATGCA
AAATCTACTCCGACGTTCTTTGGGACAAGAAGAAGTTACTCAGCTTGAAACCAATGC
GGTTTTATTTGAAGATTTATTTGGCAGAGCACCTGTTGGTGATGAAGATAATTAA

TABLE 1-continued 4256.2 (SEQ. ID. NO. 359)

ATGAAAAAACAAGCCTATGTCATTATTGCTCTCACCTCCTTCCTATTTGTCTTTTTTTT
CTCCCACAGCTTGCTGGAAATACTTGATTTTGACTGGTCTATCTTTTTGCACGATGTC
GAAAAAACAGAAAAATTTGTCTTTTATTGTTGGTTTTCAGCATGTCCATGACCTGTC
TCTTAGCCCTGTTTGGCGAGGGATCGAAGAGCTTTCTCTAAGAAAAATGCAGGCTA
ATCTCAAGCGTTTATTAGCAGGGCAAGAAGTGGTTCAGGTTGCAGATCCAGATTTGG
ATGCCAGTTTCAAGTCCTTATCAGGTAAACTTAACCTTTTGACAGAGGCTCTTCAAA
AAGCTGAAAATCAGAGCCTTGCTCAGGAAGAGGAAATCATCGAGAAGGAACGGAA
GCGAATTGCTCGGGATTTGCACGATACAGTCAGTCAGGAGTTGTTTGCGGCCCACAT
GATTTTATCGGGTATCAGTCAGCAGGCTTTGAAATTGGATAGAGAAAAGATGCAGA
CCCAGTTGCAGAGTGTCACAGCTATTTTAGAAACAGCCCAGAAGGATTTGCGGGTTT
TGCTCTTGCATTTGCGACCAGTTGAACTGGAGCAGAAGAGCTTGATAGAAGGGATTC
AAATTCTTTTAAAAGAGCTTGAGGACAAGAGTGATCTTAGGGTTAGTCTCAAGCAGA
ATATGACGAAATTGCCTAAGAAAATCGAGGAGCATATCTTCCGTATCCTGCAAGAGT
TGATTAGCAATACCCTCCGCCATGCCCAGGCATCTTGCCTAGATGTCTACCTCTATC
AGACAGATGTTGAATTGCAACTGAAGGTGGTGGACAATGGGATTGGTTTCCAGTTA
GGGAGCTTAGACGACTTGAGTTATGGACTGCGAAATATCAAGGAGCGGGTTGAAGA
TATGGCTGGAACAGTTCAACTCTTGACAGCTCCCAAGCAAGGGCTGGCGGTTGATAT
CCGTATTCCCCTGTTAGATAAGGAATGA 4263.1 (SEQ. ID. NO. 360)

ATGATTGTTTCCATTATTTCTCAAGGATTTGTCTGGGCTATTCTAGGTCTGGGAATCT
TTATGACATTTAGGATTTTAAACTTTCCAGATATGACGACAGAAGGTTCCTTCCCTCT
TGGGGGAGCTGTTGCTGTCACTTTGATAACCAAAGGCGTGAACCCATTTTTAGCGAC
ACTTGTTGCTGTAGGAGCAGGTTGTTTGGCTGGAATGGCAGCAGGCCTTCTTTATAC
AAAAGGGAAGATCCCAACCTTGCTCTCAGGGATTTTGGTGATGACTTCTTGTCACTC
AATCATGCTCTTGATTATGGGACGTGCGAATTTAGGCCTGCTTGGAACCAAGCAAAT
TCAGGATGTTTTGCCTTTTGATTCGGATTTGAATCAACTCTTGACAGGTCTCATCTTT
GTGAGTATTGTTATTGCTCTCATGCTCTTTTTCTTGGACACTAAACTCGGACAAGCCT
ATATTGCTACAGGGGATAATCCTGATATGGCTAGAAGTTTCGGGATTCATACTGGAC
GCATGGAGCTCATGGGCTTGGTCTTATCAAATGGTGTGATTGCCCTTGCAGGTGCCC
TCATTGCTCAGCAAGAAGGTTATGCCGATGTGCTCGAGGGATCGGGGTTATCGTTG
TGGGGCTTGCAAGTTTGATTATTGGAGAAGTTATTTTCAAGAGTTTGAGCTTGGCAG
AGCGTTTGGTTACTATCGTTGTAGGTTCTATCGCTTATCAATTTTAGTGTGGCAGT
TATCGCACTTGGCTTTAATACAAGTTACCTTCGTTTATACAGTGCCTTGATTTTAGCA
GTCTGCCTCATGATTCCAACATTTAAGCAAACAATCTTGAAAGGAGCCAAGTTAAGC
AAATGA 4346.1 (SEQ. ID. NO. 361)

ATGAAAAAAATGAAAGTTTGGTCTACTGTACTTGCAACGGGAGTTGCTCTTACTACA
CTTGCTGCTTGCTCTGGAGGTTCAAATTCTACGACTGCTTCTTCATCTGAAGAAAAA
GCTGATAAAAGTCAAGAATTAGTTATCTATTCGAACTCAGTCTCAAATGGTCGTGGT
GATTGGTTAACTGCTAAAGCAAAAGAAGCTGGTTTTAATATAAAAATGGTTGATATC
GCTGGCGCTCAATTAGCAGACCGTGTTATTGCTGAGAAGAATAATGCAGTTGCAGAT
ATGGTATTTGGAATTGGTGCTGTTGATTCAAATAAAATTAGAGATCAAAAATTACTA
GTACAGTACAAGCCTAAATGGTTAGATAAAATTGATCAATCTTTATCAGATAAAGAT
AATTATTATAATCCTGTGATTGTTCAACCATTAGTTTTAATTGGGGCGCCTGATGTAA
AAGAAATGCCTAAAGATTGGACTGAATTAGGGTAGTAAGTATAAAGGTAAATATTCA
ATTTCTGGTCTTCAAGGAGGTACAGGACGGGCAATTCTAGCAAGTATCTTAGTTCGA
TACCTTGATGATAAAGGTGAATTAGGTGTTTCCGAAAAAGGTTGGGAAGTAGCAAA
AGAATATTTGAAAAATGCATACACTCTTCAAAAGGGAGAAAGTTCAATTGTTAAGA
TGTTAGACAAAGAAGATCCAATACAATATGGAATGATGTGGGGTTCTGGTCATTA
GTTGGACAAAAGAACAAAATGTTGTTTTCAAAGTATGACTCCTGAGATTGGTGTA
CCATTTGTAACTGAACAAACTATGGTTTTAAGCACTAGTAAAAAACAAGCGTTGAGCT
AAAGAATTTATTGATGGTTTGGTCAATCAGAAATTCAAGTAGAATATAGTAAGAAC
TTTGATCTATTCCTGCAAATAAAGATGCCCTCAAAGATCTACCTGAAGATACGAAG
AAATTTGTTGATCAAGTGAAACCACAAAATATTGACTGGGAAGCTGTTGGAAAGCA
TTTGGATGAATGGGTAGAAAAAGCTGAATTAGAATACGTACAATAA 4346.2 (SEQ. ID. NO. 362)

ATGATTAAATTTGATAATATTCAAATTAAATATGGTGATTTTGTTGCAATTGATAATC
TGAATTTAGATATACATGAAGGGGAATTTTTTACATTTCTTGGGCCTTCAGGATGTG
GTAAATCAACTACTTTGAGAGCATTGGTAGGTTTTCTAGATCCATCATCAGGAAGTA
TTGAAGTTAATGGAACAGATGTCACTCATTTGGAACCTGAAAAGCGTGGAATTGTA
TTGTATTTCAATCTTATGCGCTATTTCCAACTATGACTGTTTTTGATAATATTGCATTT
GGTTTAAAGTTAAGAAGGTAGCTCCAGATGTTATTAAAGCTAAAGTATCAGCAGTG
GCAGCAAAAATTAAGATCTCTGATCAACAGTTACAGCGTAATGTATCAGAATTATCT
GGGGGTCAACAACAAAGGGTAGCATTGGCTCGTGCTCTGGTTCTTGAACCTAAAATT
CTTTGTCTAGATGAACCATTGTCAAACCTTGACGCAAATTACGTGTAGATTTGAGA
AAAGAGTTGAAAAGACTTCAAAAAGAGTTAGGTATTACTACTTTATATGTTACTCAT
GATCAAGAGGAAGCCTTGACTTTATCTGATAGAATTGCAGTCTTTAACAATGGATAC
ATCGAACAGGTCGGTACACCAGTAGAGATTTATCATAATTCTCAAACTGAATTTGTA
TGTGATTTTATTGGAGATATTAATGTTTTGACCGATGAAACAGTCCACGAAGTATTA
TTGAAAAATACAAGCGTTTTCTTAGAGGATAAAAAAGGATACATTCGATTAGAGAA

TABLE 1-continued

```
AGTTCGATTCAATCGTGAAACTGAACAAGATTTTATTCTAAAAGGGACAATTATTGA
TGTTGAGTTTTCTGGAGTTACAATTCACTATACAATAAAAGTTTCTGAAAGTCAGAT
TCTTAATGTAACAAGTATTGATAGTCAGGCTGCTATTAGATCTGTCGGAGAAAGTGT
GGAATTATTTATCACACCATCAGACGTTCTGCAATTTTAA
```

4346.3 (SEQ. ID. NO. 363)

```
ATGCGTCATAAATTAAATTTAAAAGATTGGCTTATTCGTTTAGGGTTAATCTGGTTCT
TAGTAACATTTATTATTTATCCAAACTTTGATCTAGTAGTGAATGTATTTGTAAAAGG
AGGAGAATTTTCCCTTGATGCTGTACATCGTGTTCTAAAATCTCAGAGGGCACTTCA
GAGTATTATGAACAGTTTTAAGTTAGCATTTTCACTCATTATTACAGTTAATGTCGTA
GGTATTCTTTGTGTTCTATTTACAGAGTACTTTGATATTAAAGGTGCTAAAATTTTAA
AATTAGGTTATATGACCTCTTTAATTTATGGAGGAGTGGTTTTAGCGACTGGATATA
AATTTGTCTATGGTCCTTATGGATTGATTACAAAATTTTTACAAAATGTTATCCCTTC
TTTAGACCCTAACTGGTTTATGGGTATGGTGCAGTCTTATTCATTATGACATTTTCA
GGAACTGCTAATCATACATTGTTTTTAACAAATACAATTCGAAGCGTTGACTATCAC
ACTATTGAGGCTGCTCGAAATATGGGAGCAAAACCATTTACTGTTTTCCGAAAAGTA
GTGTTACCAACCTTAATTCCAACTCTATTTGCACTTACTATTATGGTTTTTCTTAGTG
GTTTATCTGCAGTAGCAGCACCCATGATTGTTGGTGGTAAAGAATTTCAAACTATAA
ATCCAATGATTATTACATTTGCAGGGATGGGAATTCTCGTGATTTAGCTGCCCTAC
TTGCAATTATTTTAGGTATTGCAACTACAATTTTGCTTACTATCATGAATAAGATAGA
AAAAGGTGGAAATTATATTTCTATCTCTAAGACTAAAGCGCCTCTTAAAAAACAAAA
AATTGCGTCTAAGCCTTGGAATATCATTGCTCACATTGTAGCATATGGATTGTTCAC
AGTTTTCATGCTCCACTAATTTTTTATAGTATTATACTCATTTACAGATCCAGTTGCA
ATTCAAACAGGTAACTTAACATTATCAAACTTTACTTTAGAAAATTATCGCTTATTCT
TTAGTAATAGTGCGGCATTCTCTCCATTCTTGGTCAGCTTTATTTATTCTATTATTGCT
GCGACAACAGCAACAATTCTCGCAGTTGTATTTGCTCGTGTTGTCAGAAAACATAAA
TCTCGTTTTGATTTCTTATTTGAATATGGTGCTCTACTTCCTTGGTTACTACCAAGTAC
ACTTTTAGCAGTAAGTTTATTATTTACTTTTAATCAGCCACAATTTCTTGTCTTGAAT
CAGATTTTGGTAGGTAGTTTGGTAATTCTACTTATTGCATATATAGTTGTAAAAATCC
CATTTTCTTATAGAATGGTACGTGCTATTTTATTTAGTGTTGATGATGAGATGGAAGA
TGCAGCAAGAAGTATGGGTGCTTCACCTTTTTATACTATGATGAAGGTTATCATTTCC
ATTTATTTTACCGGTTGTTCTCTCTGTTATTGCTTTAAACTTTAACTCTTTATTAACTG
ACTTCGACTTATCTGTATTCCTTTACCATCCCCTAGCTCAACCATTAGGTATTACGAT
TCGATCTGCAGGTGATGAAACAGCAACATCTAATGCACAAGCTCTGGTATTTGTTTA
TACAATTGTTCTGATGATTATTTCTGGAACGGTATTATACTTCACACAAAGACCGGG
CGTAAAGTAAGGAAATAA
```

TABLE 2

(SEQ ID. NO. 1)
```
MEELVTLDCLFIDRTKIEANANKYSFVWKKTTEKFSAKLQEQIQVYFQEEITPLLIKYAM
FDKKQKRGYKESAKNLANWHYNDKEDSYTHPDGWYYRFHHTKYQKTQTDFQQEIKV
YYADEPESAPQKGLYMNERYQNLKAKECQALLSPQGRQIFAQRKIDVEPVFGQIKASLG
YKRCNLRGKRQVRIDMGLVLMANNLLKYSKMKZ
```

(SEQ ID. NO. 2)
```
MGKGHWNRKRVYSIRKFAVGACSVMIGTCAVLLGGNIAGESVVYADETLITHTAEKPK
EEKMIVEEKADKALETKNIVERTEQSEPSSTEAIASEKKEDSAVTPKEEKVSAKPEEKAP
RIESQASNQEKPLKEDAKAVTNEEVNQMIEDRKVDFNQNWYFKLNANSKEAKPDADVS
TWKKLDLPDWSIFNDFDHESPAQNEGGQLNGGEAWYRKTFKLDEICDLKKNVRLTFD
GVYMDSQVYVNGQLVGHYPNGYNQFSYDITKYLQKDGRENVIAVHAVNKQPSSRWYS
GSGIYRDVTLQVTDKVHVEKNGTTILTPKLEEQQHGKVETHVTSKIVNTDDKDHELVAE
YQIVERGGHAVTGLVRTASRTLKAHESTSLDAILEVERPKLWTVLNDKPALYELITRVY
RDGQLVDAKKDLFGYRYYHWTPNEGFSLNGERIKFHGVSLHHDHGALGAEENYKAEY
RRLKQMKEMGVNSIRTTHNPASEQTLQIAAELGLLVQEEAFDTWYGGKKPYDYGRFFE
KDATHPEARKGEKWSDFDLRTMVERGKNNPAIFMWSIGNEIGEANGDAHSLATVKRLV
KVIKDVDKTRYVTMGADKFRFGNGSGGHEKIADELDAVGFNYSEDNYKALRAKHPKW
LIYGSETSSATRTRGSYYRPERELKHSNGPERNYEQSDYGNDRVGWGKTATASWTFDR
DNAGYAGQRWTGTDYIGEPTPWHNQNQTPVKSSYFGIVDTAGIPKHDFYLYQSQWVSV
KKKPMVHLLPHWNWENKELASKVADSEGKIPVRAYSNASSVELFLNGKSLGLKTFNKK
QTSDORTYQEGANANELYLEWKVAYQPGTLEAIARDESGKEIARDKITTAGKPAAVRLI
KEDHAIAADGKDLTYIYYEIVDSQGNVVPTANNLVRPQLHGQGQLVOVDNGEQASRER
YKAQADGSWIRKAFNGKGVAIVKSTEQAGKFTLTAHSDLLKSNQVTVFTGKKEGQEKT
VLGTEVPKVQTIIGEAPEMPTTVPFVYSDGSRAERPVTWSSVDVSKPGIVTVKGMADGR
EVEARVEVIALKSELPVVKRIAPNTDLNSVDKSVSYVLIDGSVEEYEVDKWEIAEEDKA
KLAIPGSRIQATGYLEGQPIHATLVVEEGNPAAPAVPTVTVGGEAVTGLTSQKPMQYPX
LAYGAKLPEVTASAKNAAVTVLQASAANGMRASIIIQPKDGGPLQTYAIQFLEEAPKIAH
LSLQVEKADSLKEDQTVKLSVRAHYQDGTQAVLPADKVTFSTSGEGEVAIRKGMLELH
KPGAVTLNAEYEGAKDQVELTIQANTEKKIAQSIRPVNVVTDLHQEPSLPATVTVEYDK
GFPKTHKVTWQAIPKEKLDSYQTFEVLGKVEGIDLEARAKVSVEGIVSVEEVSVTTPIAE
APQLPESVRTYDSNGHVSSAKVAWDAIRPEQYAKEGVVVNGRLEGTQLTTKLHVRVSA
QTEQGANISDQWTGSELPLAFASDSNPSDPVSNVNDKLISYNNQPANRWTNWNRTNPE
ASVGVLFGDSGILSKRSVDNLSVGFHEDHGVGVPKSYVIEYYVGKTVPTAPKNPSFVGN
EDHVFNDSANWKPVTNLKAPAQLKAGEMNHFSFDKVETYAVRIRMVKADNKRGTSIT
EVQIFAKQVAAAKQGQTRIQVDGKDLANFNPDLTDYYLESVDGKVPAVTASVSNNGLA
```

TABLE 2-continued

```
TVVPSVREGEPVRVLAKAENGDILGEYRLHFTKDKSLLSHKPVAAVKQARLLQVGQAL
ELPTKVPVYFTGKDGYETKDLTVEWEEVPAENLTKAGQFTVRGRVLGSNLVAEITVRV
TDKLGETLSDNPNYDENSNQAYASATNDIDKNSHDRVDYLNDGDHSENRRWTNWSPTP
SSNPEVSAGVIFRENGKIVERTVTQGKVQFFADSGTDAPSKLVLERYVGPEFEVPTYYSN
YQAYDADHPFNNPENWEAVPYRADKDIAAGDEINVTFKAIKAKAMRWRMERKADKSG
VAMIEMTFLAPSELPQESTQSKILVDGKELADFAENRQDYQITYKGQRPKVSVEENNQV
ASTVVQSGEDSFPVLVRLVSESGKQVKEYRIHLTKEKPVSEKTVAAVQEDLPKIEFVEKD
LAYKTVEKKDSTLYLGETRVEQEGKVGKERIEFAINPDGSKEEKLREVVEVPTDRIVLVG
TKPVAQEAKKPQVSEKADTKPIDSSEASQTNKAQLPSTGSAASQAAVAAGLTLLGLSAG
LVVTKGKKEDZ (SEQ ID. NO. 3)
MKIMKXKYWTLAILFFCLFNNSVTAQEIPKNLDGNITHTQTSESFSESDEKQVDYSNKN
QEEVDQNKFRIQIDKTELPVTTDKHLEKNCCKLELEPQINNDIVNSESNNLLGEDNLDNK
IKENVSHLDNRGGNIEHDKDNLESSIVRXYEWDIDKVTGGGESYKLYSKSNSKVSIAILD
SGVDLQNTGLLKNLSNMSKNYVPNKGYLGKEEGEEGIISDIQDRLGHGTAVVAQIVGDD
NINGVNPHVNINVYRIFGKSSASPDWIVKAWDAVDDGNDHNLSTGQYLMIDGEYEDGT
NDFETFLKYKKAIDYANQKGVIIVAALGNDSLNVSNQSDLLKLISSRIZKVRKPGLVVDV
PSYFSSTISVGGIDRIGNLSDFSNKGDSDAIYAPAGSTLSLSELGLNNFINAEKYKEDWIFS
ATLGGYTYLYGNSFAAPKVSGAIAMIIDKYLKDQPYNYMFVKKFWKKHYQZ (SEQ ID. NO. 4)
MKKTWKVFLTLVTALVAVVLVACGQGTASKDNKEAELKXVDFILDWTPNTNHTGLYV
AKEKGYFKEAGVDVDLKLPPEESSSDLVINGKAPFAVYFQDYMAKKLEKGAGITAVAAI
VEHNTSGILSRKSDNVSSPKDLVGKKYGTWNDPTELAMLKTLVESQGGDFEKVEKVPN
NDSNSITPIANGVFDTAWIYYGWDGILAKSQGVDANFMYLKDYVKEFDYYSPVIIANND
YLKDNKEEARKVIQAIKKGYQYAMEHPEEAADILIKNAPELKEKRDFVIESQKYLSKEY
ASDKEKWGQFDAARWNAFYKWDKENGILKEDLTDKGFTNEFVKZ (SEQ ID. NO. 5)
MKRTWRNSFVTNLNTPFMIGNIEJPNRTVLAPMAOVTNSAFRTIAKELGAGLVVMEMV
SDKGIQYNNEKTLHMLHIDEGENPVSIQLFGSDEDSLARAAEFIQENTKTDIVDINMGCP
VNKIVKNEAGAMWLKDPDKIYSIINIVQSVLDIPLTVKMRTGWADPSLAVENALAAEAA
GVSALAMHGRTREQMYTGHADLETLYKVAQALTICIPFLANGDIRTVQEAKQRIEEVGA
DAVMIGRAAMGNPYLFNQINHYFETGEILPDLTFEDKMKIAYEHLKRLINLKGENVAVR
ERGLAPHYLRGTSGTSGAAKLRGAISQASTLAEIETLLQLEKAZ (SEQ ID. NO. 6)
MIKNPKLLTKSFLRSFAILGGVGLVIHIAIYLTFPFYYIQLEGEKFNESARVFTEYLKTKTS
DEIPSLLQSYSKSLTISAHLKRDIVDKRLPLVHDLDIKDGKLSNYIVMLDMSVSTADGKQ
VTVQFVHGVDVYKEAKNILLLYLPYTFLVTIAPSFVFSYFYTKRLLNPLFYISEVTSKMQ
DLDDNIRFDERJCDEVGEVGKQINGMYEELLKVIYELESRNEQIVKLQNQKVSFVRGAS
HELKTPLASLRMLENMQHNIGDYKDHPKYIAKSINKIDQMSHLLEEVLESSKFQEWTEC
RETTVKPVLVDILSRYQELAHSIGVTIENQLTDATRVVMSLRALDKVLTNLISNAIKYSD
KNGRVHSEQDGYLSIKNTCAPLSDQELEHLFDFYHSQIVTDKDESSGLGLY1VNNILESY
QMDYSFLPYEHGMEFKISLZ (SEQ ID. NO. 7)
MYLGDLMEKAECGQFSILLQESQTTVKAVMEETGFSKATLTKYVTLLNDKALDSGLEL
AIHSEDENLRLSIGAATKGRDIRSLFLESAVKYQILVYLLYHQQFLAHQLAQELVISEATL
GRHLAGLNQILSEFDLSIQNGRWRGPEHQIHYFYFCLFKVWSSQEWEGHMQKPERKQEI
ANLEEICGASLSAGQKLDLVLWAHISQQRLRVNACQFQVIEEKMRCYPDNIFYLRLLRK
VPSFFAGQHIPLGVEDGEMMIFFSFLLSHRILPLHTMEYILGFGGQLADLLTQLIQEMKKE
ELLGDYTEDHVTYELSQLCAQVYLYKGYILQDRYKYQLENRHPYLLMEHDFKETAEEIF
HALPAFQQGTDLDKKILWEWLQLIEYMAEGGQHMRIGLDLTSGFLVFSRMAAILKRYL
EYNRFITTIEAYDPSRHYDLLVTNNPIHKKEQTPVYYLKNDLDMEDLVAIRQLLFTZ (SEQ ID. NO. 8)
MEFSKKTRELSIKKMQERTLDLLHGGGITGAGVALQAAASGLETGLIEMQDFAEGTSSR
STKLVHGGLRYLKQFDVEVVSDTVSERAVVQQIAPHIPKSDPMLLPVYDEDGATFSLFR
LKVAMDLYDLLAGVSNTPAANKVLSKDQVLERQPNLKKEGLVGGGVYLDFRNNDARL
VIENIKRANQDGALANHKAEGFLFDESGKITGVVARDLLTDQVFEIKARLVINTTGPWSD
KVRNLSNKGTQPSQMRKGVHLVVDSSKIKVSQPVYFDTGLGDGRMVFVLPRENKTYEG
TTDTDYTGDLEHPKVTQEDVDYLLGIVNNRFPESNITIDDIESSWAGLRPLIAGNSASDY
NGGNNGTISDESFDNLIATVESYLSKEKTREDVESAVSKLESSTSEKHLDPSAVSRGSSLD
RDDNGLLTLAGGKITDYRKMAEGAMERVVDIICAEFDRSFKLINSKTYPVSGGELNPAN
VDSEIEAFAQLGVSRGLDSKEAHYLANLYGSNAPKVFALAHSLEQAPLSLADTLSHYAM
RNELLTLSPVDFLLRRTNHMLFMRDSLDSIVEPILDEMGRFYDWTEEEKATYRADVEAA
LANNDLAELKNZ (SEQ ID. NO. 9)
MMNELFGEFLGTLIILLGNGVVAGVVLPKTKSNSSGWIVITMGWGIAVAVAVFVSGKLS
PAYLNPAVTIGVALKGGLPWASVLPYILAQFAGAMLGQILVWLQFKPHYEAEENAGNIL
ATFSTGPAIKDTVSNLISEILGTFVLVLTIPALGLYDFQAGIGTFAVGTLIVGIGLSLGGTTG
YALNPARDLGPRIMHSILPIPNKGDGDWSYAWIPVVGPVIGAALAVLVFSLFZ (SEQ ID. NO. 10)
```

TABLE 2-continued

```
MTKKKERISVIHREKILWLKWYFMRDKEQPKYSVLERKMFDAAKNQDMLAYQKYATI
KQTSEADIRVQTSEADILEAVKEVYVYNHMNVIGACQRILFISQSPAYDKLNKWPNIYSD
LYFSVVPLPKMGVYHEMVGIZ (SEQ. ID. NO. 11)
MKNSNEAEMKLLYTDIRTSLTEILTREAEELVAAGKRVFYIAPNSLSFEKERAVLEYLSQ
QASFSITVTRFAQMARYLVLNDLPAKTTLDDIGLGLAFYKCLAELDPKDLRVYGAIKQD
PQLIQQLIELYHEMTKSQMSFLDLENLTDEDKRADLLLIFEKVTAYLNQGQLAQESQLSH
LIEAIENDKVSSDFNQIALVIDGFTRFSAEEERVVDLLHGKGVEWIGAYASKKAYTSPFSE
GNLYQAVKFLHHLASKYQTPAQDCSQTHEKMDSFDKASRLLESSYDFSELALDVDEKD
RENLQIWSCLTQKEELELVARSIRQKLHENSDLSYKHFRJLLGDVASYQLSLKTIFDQYQI
PFYLGRSEAMAHHPLTQFVESILALKRYRPRQEDLINLLRTDLYTDLSQSDIDAFEQYIRY
LGINGLPAFQQTFTKSHHGKFNLERLNVLRLRILAPLETLFASRKQKAEKLLQKWSVFLK
EGAVTKQLQDLTITLEAVEQERQAEVWKAFCNVLEQFATVFAGSQVSLEDFLALLHSG
MSLSQYRTIPATVDTVLVQSYDLIAPLTADFVYAIGLTQDNLPKISQNTSLLTDEERQNL
NQATEEGVQLLIASSENLKKNRYTMLSLVNSARKQLFLSAPSLFNESESKESAYLQELIH
FGFRRREKRMNHKGLSKEDMGSYHSLLSSLVAYHQQGEMSDTEQDLTFVKVLSRVIGK
KLDQQGLENPAIPTSPSSKTLAKDTLQALYPAKQEFYLSTSGLTEFYRNEYSYFLRYVLG
LQEELRLHPDARSHGNFLHRFEALQLPNEDSFDQRLEQAIQETSQERBFSAIYQESLEAQI
TKEVLLDVARTTGHILRHNPALETIKEEANFGGKDQAFIQLDNGRSVFVRGKVDRIDRLK
ANGAIGVVDYKSSLTQFQFPHFFNGLNSQLPTYLAALKREGEQNFFGAMYLEMAEPVQ
SLMAVKSLAGAVVEASKSMKYQGLFLEKESSYLGEFYNKNKANQLTDEEFQLLLDYNA
YLYKKAAEKILAGRFAINPYTENGRSIAPYVQQHQAITGFEANYHLGQARFLEKIDLAD
GKRLVGEKLKQAWLEKIREELNRZ (SEQ. ID. NO. 12)
MKLIPFLSEEEIQKLQEAEANSSKEQKKTAEQIEAIYTSAQNILVSASAGSGKTFVMAERL
DQLARGVEISQLFISTFTVKAATELKERLEKJCISKKIQETDDVDLKQHLGRQLADLPNA
AIGTMDSFTQKFLGKHGYLLDIAPNFRILQNQSEQULENEVFPHEVFEAHYQGKQKETFS
HLLKNEAGRGKDERGLRQQVYKIYDFLQSTSNPQKWLSESFLKGFEKADFTSEKEKLTE
QIKQALWDLESFFRYHLDNDAKEIAKAAYLENVQLILDEEGSLNQESDSQAYQAVLARV
VAISKEKNGRALTNASRKADLKPLADAYNEERKTQFAKLGQISDQIAILDYQERYHGDT
WKLAKTFQSFMSDFVEAYRQRKRQENAPEFADISHYTIEILENFPQVRESYQERFHEVM
VDEYQDTNHIQERMLELLSNGHNRFMVGDIKQSIYRFRQADPQCFNEKFQRYAQNPQE
GRLIILKENFRSSSEVLSATNDVFERLMDQEVGEINYDNKHQLVFANTKLTPNPDNKAAF
LLYDKDDTGEEEESQRETKLTGEMRLVIKEILKLHQEKGVAFKRIALLTSSRSRNOQILL
ALSEYGEPVKTDGEQNNYLQSLEVQVMLDTLRVIHNPLQDYALVALMKSPMFGFDEDE
LARLSLQKAEDGVHENLYEKLVNAQKMASSQKGLIHTALAEKLKQFMDILASWRLYA
KTHSLYDLIWKIYNDRFYYDYVGALPNGPARQANLYALALRADQFEKSNFEKGLSRFIR
MIDQVLEAQHDLASVAVAPPKDAVELMTIHKSKGLEFPYVFILNMDQDINKQDSMSEVI
LSRQNGLGVKYIAKMETGAVEDHYPKTIKLSIPSLTYRQNEEELQLASYSEQMRLLYVA
MTRAEKKLYLVGKGSREKLESKEYPAAKNGKLNSNTRLQARNFQDWLWAISKVFTKD
KLNFSYRFIGEDQLTREAIGELETKSPLQDSSQADNRQSDTIKEALEMLKEVEVYNTLHR
AAIELPSVQTPSQUCKPYEPVMDMEGVEIAGQGQSVGKKISFDLPDFSTKEKVTGAEIGS
ATHELMQRIDLSQQLTLASLTETLKQVQTSQAVRDKINLDKILAFFDTVLGQEILANTDH
LYREQPFSMLKRDQKSQEDFVVRGILDGYLLYENKIVLFDYKTDRYDEPSQLVDRYRG
QLALYEEALSRAYSIENIEKYLILLGKDEVQVKVZ (SEQ. ID. NO. 13)
MELARHAESLGVDALATIPPIYFRLPEYSVAKYWNDISSAAPNTDYVCYNIPQLAGVAL
TPSLYTEMLKNPRVIGVKNSSMPVQDIQTFVSLGGEDMIVFNGPDEQFLGGRLMGARAG
IGGTYGAMPELFLKLNQLIADKDLETARELQYAINAHGKITSAHGNMYGVIKEVLKINB
GLNIGSVRSPLTPVTEEDRPVVEAAAALIRETKERFLZ (SEQ. ID. NO. 14)
MYKTKCLREKLVLFLKIFFPIUYQFANYSASFVDTAMTGQYNTMDLAGVSMATSTWNP
PFTPLTGIVSALVPIIGHHLGRGKKEEVASDFYQFIYLALGLSVVLLGMVLPLAPIILNHIG
LEAAVAAVAVRYLWFLSIGIIPLLLFSVIRSLLDSLGLTKLSMYLMLLLLPLNSGFNYLLI
YGAFGVPELGGAGAGLGTSLAYWVLLGISVLVLFKQEKLKALHLEKRIPLNMDKIKEGV
RLGLPIGGTVFAEVAIFSVVGLIMAKFSPLIIASHQSAMNFSSLMYAFPMSISSAMAIVVS
YEVGAKRFDDAKTYIGLGRWTALIFAAFTLTFLYIFRGNVASLYGNDPKFIDLTVRFLTY
SLFFQLADTFAAPLQGILRGYKDTVIPFYLGLLGYWGVAIPVYAIZ (SEQ. ID. NO. 15)
MSTLAKIEALLFVAGEDGIRVRQLAELLSLPPTGIQQSLGKLAQKYEKDPDSSLALIETSG
AYRLVTKPQFAEILKEYSKAPINQSLSRALETLIIAYKQPITRIEIDAIRGVNSSGALAKLQ
AFDLIKEDGKKEVLGRPNLYWITDYFLDYMGLNHLEELPVIDELEIQAQESQLFGERIEED
ENQZ (SEQ. ID. NO. 16)
MDTMISRFFRHLPEALKSLKRNGWMTVAAVSSVMITLTLVAIFASVIFNTAKLATDIENN
VRVVVYIRKDVEDNSQTIEKEGQTVTNNDYHKVYDSLKNMSTVKSVTFSSKEEQYEKL
TEIMGDNWKIFEGDANPLYDAYIVEANTPNDVKTIAEDAKKIEGVSEVQDGGANTERLF
KLASFIRVWGLGIAALLIFIAVFLISNTIRITIISRSREIQLMRLVGAKNSYIRGPFLLEGAFIG
LLGAIAPSVLVFIVYQIVYQSVNKSLVGQNLSMISPDLFSPLMIALLFVIGVFIGSLGSQGIS
MRRFLKIZ
```

TABLE 2-continued (SEQ. ID. NO. 17)
MKKVRFIFLALLFFLASPEGAMASDGTWQGGQYLKEDGSQAANEWVFDTHYQSWFYI
KADANYAENEWLKQGDDYFYLKSGGYMAKSEWVEDKGAFYYLDQDGKMKRNAWV
GTSYVGATGAKVIEDWVYDSQYOAWFYIKADGQHAEKEWLQIKGKDYYFKSGGYLLT
SQWINQAYVNASGAKVQQGWLFDKQYQSWFYIKBNGNYADKEWIFENGFHYYYLKS
GGYMAANEWEWDKESWFYLKFDGKMAEKEWVYDSHSQAWYYFKSGGYMTANEWI
WDKESWFYLKSDGKIAEKEWVYDSHSQAWYYFKSGGYMTANEWIWDKESWFYLKSD
GKIAEKEWVYDSHSQAWYYFKSGGYMAKNETVDGYQLGSDGKWLGGKTTNENAAY
YQVVPVTANVYDSDGEKLSYISQGSVVWLDKDRKSDDKRLAITISGLSGYMKTEDLQA
LDASKDFIPYYESDGHRFYHVAQNASIPVASHLSDMEVGKKYYSADGLHFDGFKLEN
PPLFICDLTEATNYSAEELDKVFSLLNTNNSLLENKGATFKEAEEHYHINALYLLAHSALE
SNWGRSKIAKDKNNFFGITAYDITPYLSAKTFDDVDKGILGATKWIKENYIDRGRTFLGN
KASGMNVEYASDPYWGEKIASVMMKINEKLGGKDZ (SEQ. ID. NO. 18)
MKKVLQKYWAWAFVVIPLLLQAIPFYVPMFQGAFYSFTNWTGLTYNYKFVGLNNFKL
LFMDPKFMNAIGFTAIIALAMVVEIALCLARVLNSKIKGQTFFRAWFFFPAVLSGLTVALIF
KQVFNYGLPAIGNALHIEFFQTSLLGTKWGAIFAAVFVLLWQOVAMPEIIFLAGLQSIPTE
ITEAARIDGATSKQVFWNIELPYLLPSVSMVFELALKGGLTAFDQVFAMTGGGPNNATT
SLGLLVYNYAFKNNQFGYANAIAVILFFLIVVISHQLRVSKKFEIZ (SEQ. ID. NO. 19)
MMKQDERKALIGKYILLILGSVLILVPLLATLFSSFKPTKDIVDNFFGFFTNFTWDNFSRL
LADGIGGYYWNSVVITVLSLLAVMIFIPMAAYSIARNMSKRKAFTIMYTLLILGLFVPFQV
IMIPITVMMSKLGLANTPGLILLYLTYAIPQTLFLYVGYIKISIPESLDEAAEIDGANQFTTY
FRIIFPMMKPMHATTMIINALWFWNDFMLPLLVLNRDSKMWTLPLFQYNYAGQYFNDY
GPSFASYVVGIISITIVYLFFQRHIHSGMSNGAVKZ (SEQ. ID. NO. 20)
MKSILQKMGEHPMLLLFLSYSTVISILAQNWMGLVASVGMFLFTIFFLHYQSILSHKFFR
LILQFVLFGSVLSAAFASLEHPQIVKKPNYAPLSPNMQVWHQNRAEVTFFNPNYYGIICC
FCIMIAPYLFTTTKLNWLKVFCVIAGPVNLFGLNFTQNRTAFPAIIAGAIIYLFTTTKNWK
AFWLSIGVFAIGLSFLFSSDLGVRMGTLDSSMEERISIWDAGMALFKQNPFWGEGPLTY
MNSYPRIHAPYHEHAHSLYIDTILSYGIVGTILLVLSSVAPVRLMMDMSQESGKRPIIGLY
LSFLTVVAVHGIFDLALFWIQSGFIFLLVMCSIPLEHRMLVSDMTDZ (SEQ. ID. NO. 21)
MSKMDVQKIIAPMMKFVNMRGIIALIKDGMLAILPLTVVGSLFLIMGQLPFEGLNKSIAS
VFGANWTEPPMQVYSGTFAIMGLISCFSIAYSYAKNSGVEALPAGVLSVSAFFILLRSSYI
PKQGEAIGDAISKVWFGGQGHGAHIGLVVGSIYTFFIKRKIVIKMPEQVPQAIAKQFEAMI
PAVIFLSSMIVYILAKSLTNGGTFIEMIYSAIQVPLQGLTGSLYGAIGIAFFISFLWWFGVH
GQSVVNGVTALLLSNLDANKAMLASANLSLENGAHIVTQQFLDSFLILSGSGITFGLVVA
MLFAAKSQYQALGKVAAFPAIFNVNEPVVFGFPEVMNPVMFVPFILVPVLAAVIVYGA
IATGFMQPFSGVTLPWSTPAILSGFLVGGWQGVETQLVILAMSTLVYFPFFKVQDRLAY
QNEIKQSZ (SEQ. ID. NO. 22)
MKKKDLVDQLVSEIETGKVRTLGIYGHGASGKSTFAQELYQALDSTTVNLLETDPYITS
GRHLVVPKDAPNQKVTASLPVAHELESLQRDILACRRVWMSZ (SEQ. ID. NO. 23)
MKKRYLVLTALLALSLAACSQEKTKNEDGETKTEQTAKADGTVGSKSQGAAQKKAEV
VNKGDYYSIQGKYDEIIVANKHYPLSKDYNPGENPTAKAELVKLIKAMQEAGPPISDHY
SGFRSYETQTKLYQDYVNQDGKAAADRYSARPGYSEHQTGLAFDVIGTDGDLVTEEKA
AQWLLDHAADYGFVVRYLKGKEKETGYMAEEWHLRYVGKEAIKEIAASGLSEEYYG
FEGGDYVDZ (SEQ. ID. NO. 24)
MREPDFLNHFLKKGYFKKHAKAVLALSGGLDSMFLFKVLSTYQKELEEELILAHVNHK
QRIESDWEEKELRKIAAEAELPIYISNFSGEPFSEARARNFRYDFFQEVMKKTGATALVTA
HHADDQVETIFMRLIRGTRLRYLSGIKEKQVVGEIEIIRPFLHFQKKDFPPFHFEDTSNQE
NHYFRNRIRNSYLPELEKENPRFRDAILGIGNEILDYDLAIAELSNNINVEDLQQLPSYSES
TQRVLLQTYLNRFPDLNLTKAQFAEVQQILKSKSQYRHPIKNGYELEKEYQQFQICKISP
QADEKBDELVLHYQNQVAYQGYLFSFGLPLEGELIQQIPVSRETSIHIRHRKTGDVLIKN
GHRKKLRRLFIDLKIPMEKRNSALIIEQFGEIVSILGIATNNLSKKTKNDIMNTVLYIEKID
RZ (SEQ. ID. NO. 25)
MRKPLIILLLPSFLTISKVVSTEKEVVYTSKEIYYLSQSDFGIYFRBKLSSPMVYGEVPVYA
NEDLVVESGKLTPKTSFQITEWRLNKQGIPVPKLSNHQFIAADKRFLYDQSEVTPTIICKV
WLESDFKLYNSPYDLKEVKSSLSAYSQVSIDKTMFVEGREFLHIDQAGWVAKESTSEED
NRMSKVQEMLSEKYQKDSFSIYVKQLTTGKSAGINQDEKMYAASVLKLSYLYYTQEKI
NEGLYQLDTTVKYVSAVNDFPGSYKPEGGSLPKKEDNKEYSLKDUTKVSKESDNVAH
NLLGYYISNQSDATFKSKMSAIMGDDWDPKEKLISSKMAGKFMEAIYNQNGFVLESLT
KTDFDSQRIAKGVSVKVAHKIGDADEFKHDTGVVYADSPFILSIFTKNSDYDTISKIAKD
VYEVLKZ TABLE 2-continued (SEQ. ID. NO. 26)
MKKQNNGLIKNPFLWLLFIFFLVTGFQYFYSGNNSGGSQQINYThLVQEITDGNVKELTY
QPNGSVIEWSGVYKNPKSTKEETGIQFFTPSVTKVEKFTSTILPADITVSELQKLATDHKA
EVTVKHBSSSGIWINLLVSWPFGILFFFLFSNIMGNMGGGNGRNPMSFGRSKAXANKBDI
KVRFSDVAGAEEEKQELVEVVEFLKDPKRFKLGARIPAGVLLEGPPGTGKLLLAKAVAG
EAGVPFFSDSGSDLVEMFVGVGASRVRSLFEDAKKAAPAIIFIDEIDAVGRQRGVGLGGG
NFRTRQTLNQLLIEMDGFEGNEGIIVIAATNSDVLDPALLRPGRFDRKVLVGRPDVKGEA
ILKVHAKNKPLAEDVDLKLVAQQTPGFGFVGADLENVLNEAALVAARRNSIIDASDIDE
AEDRVIAGPSKKKDKTVSQKERELVAYHEAGHIVGLVLSNARVVHKVTIVPRGRAGGY
MIALPKEDQMLEDMKEQLAGLMGGRVAEEIIFNVQITGASNDFEQATQMARAMVTEYG
MSEKLGPVQYEGNHAMLGAQSPQSEQTAYEIDEEVRSLLNEARNKAAEHQSNRETHKL
LEALLKYETLDSTQIKALYETGKMPEAVEEESHALSYDEVKSKMNDEKZ (SEQ. ID. NO. 27)
MKRSSLLVRMVISIFLVFLILLALVGTFYYQSSSSAIEATIEGNSQSQTSHFIQSYIKKLETT
STGLTQQTDVLAYAENPSQDKVEGIRDLFLTILKSDKDLKTVVLVTKSGQVISTDDSVQ
MKTSSDMMAEDWYQKAIHQGAMPVLTPARKSDSQWVISVTQELVDAKGANLGVLRL
DSYETLEAYLNQLQLGQQGFAFIINENHEFVYHPQHTVYSSSSKMEAMKPYDTGQYTP
GHKSYVSQEKIAGTDWTVLGVSSLEKLDQVRSQLLWTLLGASVTSLLVCLCLVWFSLK
RWIAPLKDLRETMLEIASGAQNLRAKEVGAYELREVTRQFNAMLDQIDQLMVALIRSQEE
TTRQYQLQALSSQINPHFLYNTLDTIIWMAEFHDSQRVVQVTKSLATYFRLALNQGKDLI
CLSDEINHVRQYLFIQKQRYGDKLEYEINENVAFDNLVLPKLVLQPLVENALYHGIKEKE
GQGHIKLSVQKQDSGLVIREDDGVGFQDAGDSSQSQLKRGGVGLQNVDQRLKLHPGA
NYHMKIDSRPQKGTKVEIYINRIETSZ (SEQ. ID. NO. 28)
MKRSSLLVRMVISIFLVFLILLALVGTIYYQSSSSAIEATIEGNSQTTISQTSHFIQSYIKKLE
TTSTGLTQQTDVLAYAENPSQDKVEGIRDLFLTILKSDKDLKTVVLVTKSGQVISTDDSV
QMKTSSDMMAEDWYQKAIHQGAMPVLTPARKSDSQWVISVTQELVDAKGANLGVLR
LDISYETLEAYLNQLQLGQQGFAFIINENHEFVYHPQHTVYSSSSKMEAMKPYIDTGQGY
TPGHKSYVSQEKIAGTDWTVLGVSSLEKLDQVRSQLLWTLLGASVTSLLVCLCLVWFSL
KRWIAPLKDLRETMLEIASGAQNLRKEVGAYELREVTRQFNAMLDQIDQLMVA1RSQE
ET1RQYQLQALSSQINPHFLYNTLDTUWMAEFHDSQRVVQVTKSLATYFRLALNQGKD
LICLSDENHVRQYLPIQKQRYGDKLEYEINENVAFDNLVLPKLVLQPLVENALYHGIKEK
EGQGHIKLSVQKQDSGLVIRIEDDGVGFQDAGDSSQSQLKRGGVGLQNVDQRLKLHFG
ANYHMKIDSRPQKGTKVEIYINRIETSZ (SEQ. ID. NO. 29)
MEFKLLREALKVKQVRSKILETIFWLVFRIGTSITVPGVNANSLNALSGLSFLNMLSLVSG
NALKNFSIFALGVSPYITASIVVQLLQMDILPKFVEWGKQGEVGRRKLNQATRYIALVLA
FVQSIGITAGFNTLAGAQLIKTALTPQVFLTIGIILTAGSMIVTWLGEQETDKGYGNGVSM
HFAGWSSIPEMIQGIYVDYFVNVPSSRITSSIIFVHLIITVLLIIYFTTYVQQAEYKIPIQYTK
VAQGAPSSSYLPLKVNPAGVIPVIFASSITAAPAAILQFLSATGHDWAWVRVAQEMLAT
TSPTGIAMYALLIILFTFFYTFVQINPEKAAERYKRVVPISMEFVLVKVQKNICLNFFVVL
QLLVPSSLVZ (SEQ. ID. NO. 30)
MDIRQVTETIAMIEEQNFDIRTITMGISLLDCIDPDENRAAEKIYQKATTKAANLVAVGDEI
AAELGIPIVNKRVSVTPISLIGAATDATDYVVLAKALDKAAKE1GVDFIGGFSALVQKGY
QICGDEILINSIPRALAETDKVCSSVNIGSTKSGINMTAVADMGRIIKETANLSDMGVAKL
VVFANAVEDNPFMAGAFHGVGEADVIIVGVSGPGVVKRALEKVRGQSPDVVAETVK
KTAFKITRIGQLVGQMASERLGVEFGIVDLSLAPTPAVGDSVARVLEEMGLETVGTHGT
TAALALLNDQVKKGGVMACNQVGGLSGAFIPVSEDEGMEAAVQNGSLNLEKLEAMTA
ICSVGLDMIAIPEDTPAETIAAMIADEAAIGVINMKTTAVRIIPKGKEGDMIEIGGLLGTAP
VMKVNGASSVDFISRGGQIPAPIHSFKNZ (SEQ. ID. NO. 31)
MTQIIDGKALAAKLQGQLAEKTAKLKEETGLVPGLVVILVGDNPASQVYVRNKERSAL
AAGFRSEVVRVPETITQEELLDLIAKYNQDPAWHGILVQLPLPKHIDEEAVLLAIDPEKD
VDGFHPLNMGRLWSGHPVMIPSTPAGIMEMPHEYGIDLEGKNAVVIGRSNIVGSKPMAQ
LLLAKNATVTLTHSRTHNLSKVAAXADILVVAIGRAKFVTADFVKPGAVVIDVGMNRD
ENGKLCGDVDYEAVAPLASHITPVPGGVGPMTITMLMEQTYQAALRTLDRKZ (SEQ. ID. NO. 32)
MSKFNRIHLVVLDSVGIGAAPDANNFVNAGVPDGASDTLGHISKTVGLNVPNMAKIGL
GNIPRETPLKTVAAESNPTGYATKLEEVSLGKDTTGHWEIMGLNITEPPFDTFWNGFPEE1
LTKIEEFSGRKVIREANKPYSGTAVIYDFGPRQMSTGELHYTSADPVLQIAAHEDIIPLDE
LYRICEYARSITLERPALLGRIIARPYVGEPGNFTRTANRRDLAVSPFFPTVLDKLNEAGI
DTYAVGKINDIFNGAGINHDMGHNKSNSHGIDTLLKTMGLAEFEKGFSFTNLVDFDALY
GHRRNAHGYRDCLHEPDERLPEHAAMRENDLLLITADHGNDPTYAGTDHTREYIPLLA
YSPAFKGNGLIPVGHFADISATVADNFGVETAMIGESFLDKLVZ (SEQ. ID. NO. 33)
MFISISAGLVTFLLTLVEPAFIQFYRKAQITGQQMNEDVKQHQAKAGTPTMGGLVPLITS
VLVAFFFALFSSQFSNNVGMILFILVLYGLVGFLDDFLKVFRKINEGLNPKQKLALQLLG
GVIFYLFYERGGDILSVPGYPVHLGFFYIPFALFWLVGFSNAVNLTDGVDGLASISVVISL TABLE 2-continued

```
SAYGVIAYVQGQMDLLLVILAMIGGLLGFFIPNHKPAKVFMGDVGSLALGGMLAAISM
ALHQEWTLLUGIVYVFEFTSVMMQVSYFKLTGGKPIFRMTPVHHHFELGGLSGKGNPW
SEWKVDFFFWGVGLLASLLTLAILYLMZ
```

(SEQ. ID. NO. 34)
```
LFKKNKDELNIALPAMGENFLQMLMGMVDSYLVAHLGLIAISGVSVAGNIMYQAIRAL
GAAISSVLSKSIGQKDQSKLAYNVTEALKITLLLSILLGFLSIFAGKSMIGLLGTERDVAES
GGLYLSLVGGSIVLLGLMTSLGALIRATHNPRLPLYVSFLSNALNILFSSLAIFVLDMGIA
GVAWGTIVSRLVGLVILWSQLKIPYGKPTFGLDKELLTLALPAAGERLMMRAGDVVHA
LVVSFGTEAVAGNAIGEVLTQFNYMPAFGVATATVMLLARAVGEDDWKRVASLSKQT
LFLSLFMLPLSFSIYVLGVPLTHLYTDSLAVEASVLVTLFSLLGTPMTTGTVIYTAVWQG
LGNARLPFYATSIGMWCIRIGTGYLMGIVLGWGLPGIWAGSLLDNGFRWLFLRYRYQR
YMSLKGZ
```

(SEQ. ID. NO. 35)
```
MQTQEKRSQAAVLGLQHLAMYSGSILVPIMIATALGYSAEQLTYLISTDIFMCGVATFLQ
LQLNKYFGIGLPVVLGVAFQSVAPLIMIGQSHGSGAMFGALIASGLYVVLVSGIFSKVAN
LFPSIVTGSVITTIGLTLIPVAIGNMGNNVPEPTGQSLLAAITVLIILINIFTKGFIKSISILIGL
VVGTAIAATMGLVDFSPVAVAPLVHPTPLYFG,PTFEISSIVMMCIIATVSMVESTGVYLA
LSDITKDPIDSTRLRNGYREGLAVLLGGIFNTFPYTGFSQNVGLVKLSGIKKRLPIYYAAG
FLVLLGLLPKFGALAQIIPSSVLGGAMLVMFGFVSIQGMQILARVDFANNEHNFLIAAVSI
AGVGLNNSNLFVSMPTAFQMFFSNGIVVASLLAIVLNAVLNHKKKZ
```

(SEQ. ID. NO. 36)
```
MKDRKEYLQDKGKVTVNDLAQALGKDSSKDFRELIKTLLMERKHQIRFEEDGSLTLEIK
KKHEITLKGIFHAHKNGFGFVSLEGEEDDLFVGKNDVNYAIDGDTVEVVHCKVADRNK
GTAAEAKIIDILEHSLTTVVGQIVLDQEKPKYAGYISKNQK1SQPIYVKKPALKLEGTEVL
KVPEDKYPSKKHDFFVASVLDVVGHSTDVGIDVLEVLESMDIVSEFPEAVVKEAESVPD
APSQKDMEGRLDLRDEDGADAKDLDOAVHIKALKNGNLEPGVHADVSYYEGSALDKE
ALNRTSVYVTDRVVPMLPERSNGICSLNPQVDRLTQSAIMEIDKHGRVVNTQTVIKTSFR
MTYSDVNDILAGDEEKEYHKIVSSIELMAKLHETLENMRVKRGALNFDTNEAKILVDKQ
GKPVDIVLRQRGIAERMIESFMLMANETVAEHFSKLDLPRYIHEBPKAEKVQKFIDYASS
FGLRIYGTASELSQEALQDIMRAVEGBPYADVLSMMLRSMQQARYSEHNHGHYGLAA
DYYTHFTSPIRRYPDLLVHRMIRDYGRSKEIAEHFEQVIPEIATQSSNRERRAIEAEREVE
AMKKAEYMEEYVGEEYDAVSSIVKFGLFVELPNTVEGLINTNLPEFYHFNERDLTLRG
EKSGITFRVGQQIRIRVERADKMTGEIDFSFVPSEDFDVIEKGLKQSSRSGRGRDSNRRSD
KKEDKRKSGRSNDKRKHSQKDKKKKGKKPFYKEVAKKGAKHGKGRGKGRRTKZ
```

(SEQ. ID. NO. 37)
```
MGTTGFTIIDLIILIVYLLAVLVAGIYFSKKEMKGKEFFKGDGSVPWYVTSVSIFATMLSPI
SPFLGLAGSSYAGSWLWFPAQLGMVVAIPLTHIILPIFARDIDTAYDLYDKRFNSKALRISAL
LFIIYQLGRMSUMYLPSAGLSVLTGIDINILIILMGVVAIVYSYTGGLKSVLWTDFIQGVIL
JSGVVLALFVLIANIKGGFGAVAETLANGKFLAANEKLFDPNLLSNSIFLIVMGSGPTILSS
YASSQDLVQRFTTTQNIKKLNKMLFTNGVLSLATAVFYLIGTGLYVFYQVQNADSAASN
IPQDQIFMYFIAYQLPVGITGLILAAIYAASQSTISTGLNSVATSWTLDIQDVISKNMSDNR
RTKIAQFVSLAVGLPSIGVSIVMAHSDIKSAYEWFNSFMGLVLGLLGGVRLGVSKKANK
QGAYAALPIVMVFICYFLPPTAVSYWAYSLISISVSVVSGYIVSVLTGNKVSAPKYTTIED
ITEIKADSSWEVRMZ
```

(SEQ. ID. NO. 38)
```
MKFSKKYAGSAVIVSLSLCAYALNQHRSQENKDNNRVSYVDGSQSSQKSENLTPDQVS
QKEGIQAEQAEQIVIKITDQGYVTSHGDHYHYYNGKVPYDALFSEELLMKDPNYQLKD
ADIVNEVKGGYUKVDGKYYVYLKDAAHADNVRTKDEINRQKQEHVKDNEKVNSNVA
VARSQGRYTNDGYVPNPADIIEDTGNAYIVPHGGHYHYIPKSDLSASELAAAKAHLGKN
MQPSQLSYSSTASDNNTQSVAKGSTSKPANKSENLQSLLKELYDSPSAQRYSESDGLVID
PAKIISRTPNGVAIPHGDHYHPIPYSKLSALEEKTARVPISGTGSTVSTNAKPNEVVSSLGS
LSNPSSLTTSKELSSASDGYIFNPKDIVEETATAYWRHGDHFHYIPKSNQIGQPTLPNNSL
ATPSPSLPINPGTSHEKHEEDGYGFDANRIIAEDESGFVMSHGDHNHYFFKKDLTEEQIK
VRKNIZ
```

(SEQ. ID. NO. 39)
```
MKKRAIVAVIVLLLIGLDQLVKSYIVQQIPLGEVRSWIPNFVSLTYLQNRGAAPSILQDQQ
LLFAVITLVVVIGAIWYLHKHMEDSFWMVLGLTLUAGGLGNFIDRVSQGPVVDMFHLD
FINFAIFNVADSYLTVGVIILLIAMLKEEINGNZ
```

(SEQ. ID. NO. 40)
```
MNTNLASFIVGLHDENDRFYFVQKDGQTYALAKEEGQHTVGDTVKGFAYTDMKQLR
LTTLEVTATQDQFGWGRVTEVRKDLGVFVDTGLPDKEIVVSLDILPELKELWPKXGDQL
YIRLEVDKKDRIWGLLAYQEDFQRLARPAYNNMQNQNWPAIVYRKLSGTFVYLPENNN
MLGFIHPSERYAEPRLGQVLDARVIGFREVDRTLNLSLKPRSFEMLENDAQMILTYLSSN
GGFMTLNDKSSPDDIKATFGISKGQFKKALGGLMKAGKIKQDQFGTELIZ
```

(SEQ. ID. NO. 41)
```
MKDVSLFLLKKVFKSRLNWIVLALFVSVLGVTFYLNSQTANSHSLESRLESR1AANERAI
NENEEKLSQMSDTSSEEYQFAXNNLDVQKNLLTRKTEILTLLKEGRWKEAYYLQWDE
BKNYEFVSNDPTASPGLKMGVDRERKIYQALYPLNIKAHTLEFPTHGIDQIVILEVIIPS
LFVVAIIFMLTQLFAERYQNHLDTAHLYPVSKVTFAISSLGVGVGYVTVLFIGICGFSPLV
```

TABLE 2-continued

GSLISGFGQLDYPYNYSLVNQEVTIGKIQDVLFPGLLLAFLAFIVIVEVVYLIAYPFKQKM
PVLFLSLIGIVGLLFGIQTIQPLQRIAHLIPFTYLRSVEILSGRLPKQIDNVDLNWSMGMVL
LPCLIIFLLLGILFISRWGSSQKICEFFNRFZ (SEQ. ID. NO. 42)
MMKFILDIVSTPAILVALIAILGLVLQKKKLPDIIKGGIKTFVGFLVVSGGAGIVQNSLNPF
GTMPEHAPHLSOVVPNNEAIVAVAUITYGSATAMIMFAGMVFNILIARFTRFKYIFLTGH
HTLYMACMIAVILSVAGFTSLPLILLGGLALGUMSISPAFVQKYMVQLTGNDKVALGHF
SSLGYWLSGFTGSLIGDKSKSTEDIICPPKSLAPLRDSTVSITLSMAVIYUVAIFAGSEYIEK
EISSSGTSGLVYALQLAGQFAAGVFVLAGVRLILGEIVPAPKGISERLVPNSKPALDCPIVY
TYAPNAVLIGFTSSFVGGLVSMVIMIASGTVVILPGVVPHFFCGATAGVTGNASGGVRG
ATIGAPLQGILISFLPVFLMPVLGGLGFQGSTFSDADFGLSGIILGMLNQFGSQAGIVIGLV
LILAVMFGVSPIKKPSATEEZ (SEQ. ID. NO. 43)
MIKTFLSALSVILFSIPIITYSFPPSSNLNZWLSTQPILAQIYAFPLATATMAAILSFLFFFLSF
YKKNKQIRFYSGILLLLSLILLLFGTDKTLSSASNKTKTLKLVTWNVANQIEAQHIERIFS
KFDADMAIFPELATNIRGEQENQRIKLLFHQVGLSMANYDIFTSPPTNSGIAPVTVIVKXS
YGFYTEAKTPHTFRFGTIVLHSRKQNIPDIIALHTAPPLPGLMEIWKQDLNIIHNQLASKY
PKAIIAGDFNATMRHGALAKISSHRDALNALPPFERGTWNSQSPKLFNATIDHILLPKNH
YYVKDLDIVSFQNSDHRCIFTEITFZ (SEQ. ID. NO. 44)
MNPIQRSWAYVSRKRLRSFLILLVLLAGISACLTLMKSNKTVESNLYKSLNTSPSIKKIEN
GQTFKLSDLASVSKIKGLENVSPELEVAKLKDKEAVTGEQSVERDDLSAADNNLVSLTA
LEDSSKDVTFTSSAFNLKEGRLHLQKGDSKKILHEELAKKNGSLHDKIGLDAGQSESGK
GQTVEFEIIGWSGKKQEKFTGLSSDFSENQVFTDYESSQTLLGNSEAQVSAARFYVENPK
EMDGLMKQVENIALENQGYQVEKENKAFEQIKDSVATFQTPLTIFLYGMLIAGAGALIL
VLSLWLRERVYEVGILLALGKGKSS1FLQFCLEVVLVSLGALLPAFVAGNAITTYLLQTL
LASGDQASLQDTLAKASSLTSILSFAESYVFLVLLSCLSVALCFLFLFRKSPKEILSSISZ (SEQ. ID. NO. 45)
MLHNAFAYVTRKFFKSIVTFLIILLMASLSLVGLSIKGATAKASQETFKNITNSFSMQINR
RVNQGTPRGAGNEKGEDIKKITENKAIESYVKRINAIGDLTGYDLIETPETKKNLTADRA
KRFGSSLMITGVNDSSKEDKFVSGSYKLVEGEHLTNDDKDKILLHKDLAAKHGWKVGD
KVKLDSNIYDADNEKGAKETVEVTIKGLFDGHNKSAVTYSQELYENTAITDIHTAAKLY
GYTEDTAIYGDATFFVTADKNLDDVMKELNGISGINWKSYTLVKSSSNYPALEQSISGM
YXMANLLFWGSLSPSVLLLALLLSLWINARRKEVGILLSIGLKQASILGQFITESILIAIPAL
VSAYFLANYTARAIGNTVLANVTSGVAKQASKAAQASNLGGGAEVDGFSKTLSSLD1SI
QTSDFIIIFVLALVLVVLVMALASSNLLRKQPKELLLDGEZ (SEQ. ID. NO. 46)
MSQDKQMKAVSPLLQRVINISSIVGGVGSLIFCIWAYQAGILQSKETLSAFIQQAGIWGPP
LFIFLQILQTVVPIIPGALTSVAGVFIYGHIIGTIYNYIGIVIGCAIIFYLVRLYGAAFVQSVV
SKRTYDKYIDWLDKGNRFDRFFIFMMIWPISPADFLCMLAALTKMSFKRYMTIIILTKPF
TLVVYTYGLTYIIDFEWQMLZ (SEQ. ID. NO. 47)
MRNMWVIKETYLRHVESWSFFFMVISPFLFLGISVGIGHLQGSSMAKNNKVAVVTTVPS
VAEGLKNVNGVNFDYKDEASAKEEAIKEEKLKGYLTIDQEDSVLKAVYHGETSLENGIKF
EVTGTLNELQNQLNRSTASLSQEQEKRLAQTIQFTEKIDEAKENXKFIQTIAAGALGFFLY
MILITYAGVTAQEVASEKGTKIMEVVFSSIRASHYFYARMMALFLVILTHIGIYVVGGLA
AVLLFKDLPFLAQSGILDHLGDAISLNTLLFILISLFMYVVLAAFLGSMVSRPEDSGKALS
PLMILIMGGFFGVTALGAAGDNLLLKIGSYIPFISTFFMPFRTINDYAGGAEAWISLALTV
WAVVATGFIGRMYASLVLQTDDLGIWKTFKRALSYKZ (SEQ. ID. NO. 48)
MTETIKLMIKAHTSVRRFKEQEIPQVDLNEILTAAQMASSWKNFQSYSVIVVRSQEKKD
ALYELVPQEAIRQSAVFLLFVGDLNRAEKGARLHTDTFQPQGVEGLLISSVDAALAGQN
ALLAAESLGYGGVHGLVRYKSEEVAELFNLPDYYTYSVFGMALGVPNQHHDMKPRLP
LENVVFEEEYQEQSTEAIQAYDRVQADYAGARATTSWSQRLAEQFGQAEPSSTRKNLE
QKKLLZMLKLIAIVGTNSKRSTNRQLLQYMQKHFTDKAEIELVEIKAIPVFNKPADKQVP
AEILEIAAKIEEADGVHGTPEYDHSIPAVLMSALAWLSYGIYPLLNKPIMITGASYGTLGS
SRAQLQLRQILNAPEIKANVLPDEFLLSHSLQAYNPSGDLVDLDVIKKLDAIFDDPRIFVKI
TEKLRNAQELLRKDAEDFDWENLZ (SEQ. ID. NO. 49)
MNTYQLNNGVEIPVLGFGTFICAKDGEEAYRAVLEALKAGYRHIDTAAIYQNEESVGQA
IKDSGVPREEMFVTTKLWNSQQTYSQTRQALEKSIEKLGLDYLDLYLIHWPNPKPLREN
DAWFTRNAEVWRAMEDLYQEGKIRAIGVSNFLPHHLDALLETATIVPAVNQVRLAPGV
YQDQVVAYCREKGILLEAWGPPGQGELFDSKQVQEIAANHGKSVAQLALAWSLAEGFL
PLPKSVTTSRIQANLDCFGIELSHEERETLKTIAVQSGAPRVDDVDFZ (SEQ. ID. NO. 50)
MRCKMLDPIAIQLGPLAIRWYALCIVTGLILAVYLTMKEAPRKKIIPDDLDPILVAFPLAIL
GARLYYVIFRFDYYSQNLGEIFAIWNGGLAIYGGLITGALVLYIFADRKLINTWDFLDIAA
PSVMIAQSLGRWGNFFNQEAYGATVDNLDYLPGRRDQMYIEGSYRQPTFLYESLWNLL
GFALILIFRRKWKSLRRGHITAFYLIWYGFGRMVIEGMRTDSLMFFGFRVSQWLSVVLIG
LGIMIVIYQNRKKAPYYITEEENZ

TABLE 2-continued (SEQ. ID. NO. 51)
MGKLSSILLGTVSGAALALFLTSDKGKQVCSQAQDPLDDLREDPEYAKEQVCEKLTEVK
EQATDFVLKTKEQVESGEITVDSILAQTKSYAFQATEASKNQLNNLKEQWQEKAEALD
DSEEIVIDITEEZ (SEQ. ID. NO. 52)
MKTKLIFWGSMLFLLSLSILLTIYLAWLFYPMEIQWLNLTNRVYLKPETIQYNFHILMNYL
TNPFSQVLQMPDFRSSAAGLNHFAVVKNLFHLVQLVALVTLPSFYVFVNRIVKKDFLSL
YRKSLLALVVLPVMIGLGGVLIGFDQFFTLFHQILFVGDDTWLFDPAKDPVIMILPETFFL
HAFLLFFALYENFFGYLYLKSRRKZ (SEQ. ID. NO. 53)
MTYHFTEEYDHVIGAGHAGVEASLAASRMGCKVLLATINIEMLAFMPCNPSIGGSAKGI
VVREVDALGGEMAKTIDKTYIQMKMLNTGKGPAVRALRAQADKELYSKEMRKTVEN
QENLTLRQTMIDEILVEDGKVVGVRTATHQEYAAKAVNTTGTALRGEIIIGDLKYSSGPN
HSLASINLADNLKELGLEIGRFKTGTPPRVKASSINYDVTEIQPGDEVPNHFSYTSRDEDY
VKDQVPCWLTYTNGTSHEUQNNLHRAPMFTGVVKGVGPRYCPSIEDKIVRIFADKERHQ
LFLEPEGRNTEEVYVQGLSTSLPEDVQRDLVHSIKGLENAEMMRTGYAIEYDMVLPHQL
RATLETKKISGLFTAGQTNGTSGYEEAAGQGUAGINAALKIQGKPELILKRSDGYIGVMI
DDLVTKGTIEPYRLLTSRAEYRLILRHDNADMRLTEMGREIGLVDDERWARFEIKICNQF
DNEMKRLDSIKLKPVKETNAKVEEMGFKPLTDAVTAKEFLRRPEVSYQDVVAFIGPAAE
DLDDKIIELIETEIKYEGYISKAMDQVAKMKRMEEKRIPANIDWDDIDSIATEARQKFKU
NPETIGQASRISGVNPADISILMVYLEGKNRSISKTLQKSKZ (SEQ. ID. NO. 54)
MTKQVLLVDDEEHILKLLDYHLSKEGFSTQLVTNGRKALALAETEPFDFILLDIMLPQLD
GMEVCKRLRAKGVKTPIMMVSAKSDEFDKVLALELGADDYLTKPFSPRELLARVKAVL
RRTKGEQEGDDSDNIADDSWLFGTLKVYPERHEVYKANKLLSLTPKEFESDKNPFFEVF
KVSKVTAQZ (SEQ. ID. NO. 55)
MTTFKDGFLWGGAVAAHQLEGGWQEGGKGISVADVMTAGRHGVAREITLGVLEGKY
YPNHEAIDFYHRYKEDIALFAEMGFKCPRTSIAWTRFPKGDELEPNEEGLQFYDNLPDEC
LKNGIEPVITLSHFEMPYHLVTEYGGWKNRKLIDFPAREAEVVFKRYKDKVKYWMTFN
EINNQANYQEDFAPFTNSGIVYEEGDNREAIMYQAAHYELVASARAVKIGHEINPDFQIY
YMSFAIDSHRENNPYDYLETEDLVKNNYVKASEWEWQIDPEGLRYALNWFTDHYHLPL
FNENGFGMDQVAADGMVHDDYREYLGAHIREMKKAVVEDGVDLMGYTPWGCIDLVS
AGTGEMRKRYGFIYVDKDDNGKGSYNRSPKKFGWYKEVISSNGESVEZ (SEQ. ID. NO. 56)
MDQQNGLFGFLENHVMGPMGKLAQPKVVLTAAGMAAVPFWGSMFLVFSILPQAPSPP
WADIFSASFDKFTSLYMVANYATMGSLSLYFVLSLAYELTKIYAEEEELNMNPLNGALL
ALMAFVMTVPQUFDGGMMKTSLKEGAVIADGWAMGNVVARFGTTGIFTAHMAIVTV
LIYRMCVKHNWVIKMPEAVPEGVSRGPTALVPGFVVAFVVIFINGLLVAMGTDIKVLMP
FGFVSNLTNSWIGLMUYLLTQLLWWGIHGANIVFAFVSPIALANMAENAAGGHFAVAG
EFSNMFLVIAGGSGATLGLCLYIAFASKSEQLKIGRSVVPALFNINEPLILGLPIIYNPALAI
PFILAPMVTATIYYVANSLNFIKPIIAQVPWPTPVGIGAFLGTADLRAVLVALVCAFAAPL
VYLPFTRVYDQKLVKEEQGIZ (SEQ. ID. NO. 57)
MKKFYVSPIFPILVGLIAFGVLSTFIIFVNNNLLTVLILPLFVGGYVFLFKKLRVHYTRSDV
EQIQYVNHQAEESLTALLEQMPVGVMKLNLSSGEVEWFNPYAELILTKEGDFDLEAVQT
IIKASVGNPSTYAKLGEKRYAVHMDASSGVLYFVDNSREQAITDELVTSRPVIGVSVDN
YDDLEDETSESDISQENSFVANFISEFSEKHMMFSRRVSMDRFYLFTDYTVLEGLMNDK
FSVIDAFREESKQRQLPLTLSMGFSYGDGNHDEIGKVALLNLNLAEVRGGDQVVVKEN
DSTKNPVYFGGGSAASTIKRTRTRTRAMMTASDKIRSVDQVFVVGHKNLDMDALGSAV
GMQLFASNVIENSYALYDEEQMSPDIERAVSFIEKEGVTKLLSVKDAMGMVTNRSLLIL
VDHSKTALTLSKEFYDLFTQTIVIDHHRRPQDFPDNAVITYIESGASSASELVTELIQPQNS
KKNRLSRMQASVLMAOMMLDTKNFTSRVTSRTFDVASYLRTGSDSIAIQEIAATDFEE
YREVNEULQGRKLGSDVLIAEAKDMKCYDTVVISKAADAMLAMSGIEASFVLAKNTQO
FISLSARSRSKLNVQR1MEELGGGHFNLAAAQIKDVTLSEAGEKLTEIVLNEMKEKEKE
EZ (SEQ. ID. NO. 58)
MKEKNMWKELLNRAGWILVFLLAVLLYQVPLVVTSILTLKEVALLQSGLIVAGLSIVVL
ALFIMGARKTKLASFNFSFFRAKDLARLGLSYLVIVGSNILGSILLQLSNETTTANQSQIN
DMVQNSSIISSFFLLALLAPICEEILCRGIVPKKIFRGKENLGFVVGTIVFALLHQPSNLPSL
LIYGGMSTVLSVIAYKTQRLEMSILLHMIVNGLAFCLLALVVIMSRTLGISVZ (SEQ. ID. NO. 59)
MKEKNMWKELLNRAGWILVFLLAVLLYQVPLVVTSILTLKEVALLQSGLIVAGLSIVVL
ALFIMGARKTKLASFNFSFFRAKDLARLGLSYLVIVGSNLGSILLQLSNETITANQSQIND
MVQNSSLISSPFLLALLAPICEEILCRGIVPKKIPRGKENILGFVVGTWFALLHQPSNLPSL
LIYGGMSTVLSWAYKTQRLEMSILLHMIVNGIAFCLLALVVIMSRTLGISVZ (SEQ. ID. NO. 60)
MDTQKIEAAVKMUEAVGEDANREGLQETPARVARMYQEIFSGLGQTAEEHLSKSFEIID
DNMVVEKDIFFHTMCEHHFLPFYGRAHIAYIPDGRVAGLSKLARTVEVYSKKPQIQERL TABLE 2-continued

```
NIEVADALMDYLGAKGAFVVIEAEHMCMSMRGVRKPGTATUTVARGLFETDKDLRDQ
AYRLMGLZMKDLFLKRKQAFRKECLGYLRYVLNDHFVLFLLVLLGFLAYQYSQLLQHF
PENHWPILLFVGITSVLLLLWGGTATYMEAPDKLFLLVGEEEIKLHLKRQTGISLVFWLF
VQTLFLLLFAPLFLAMGYGLPVFLLYVLLLGVGKYFHFCQKASKFFTETGLDWDYVISQ
ESKRKQVLLRFFALFTQVKGISNSVKRRAYLDFILKAVQKVPGKIWQNLYLRSYLRNGD
LFALSLRLLLLSLLAQVFIEQAWIATAVVVLFNYLLLPQLLALYHAFDYQYLTQLFPLDK
GQKEKGLQEVVRGLTSFVLLVELVVGLITFQEKLALLALLGAGLVLLVLYLPYQVKRQ
MQDZ
```
(SEQ. ID. NO. 61)
```
MRKSIVLAADNAYLIPLETTIKSVLYHNRDVDFYILNSDIAPEWFKLLGRKMEVVNSTIR
SVHIDKELFESYKTGPHINYASYFRFFATEVVESDRVLYLDSDIIVTGELATLFEIDLKGYS
IGAVDDVYAYEGRKSGFNTGMLLMDVAKWKEHSIVNSLLELAAEQNQVVNLGDQSIL
NIYFEDNWLALDKTYNYMVGIDEYHLAQECERLDDNPPTIVHYASHDKPWNTYSISRLR
ELWWVYRDLDWSEIAFQRSDLNYFERSNQSKKQVMLVTWSADIKHLEYLVQRLPDWH
PHLAAPCDCSEELTSLSQYTNVTVYQNVLHSRIDWLLDDSEVYLDINTGGEVFNVVTRA
QESGKICIFAFDITRKSMDDGLYDGIFSVERPDDLVDRMKNIEIEZ
```
(SEQ. ID. NO. 62)
```
MTKIYSSIAVKKGLFTSFLLFIYVLGSRIILPFVDLNTKDFLGGSTAYLAFSAALTOGNLRS
LSIFSVGLSPWMSAMILWQMFSFSKRLGLTSTSIEIQDRkKMYLTLLIAVIQSLAVSLRLP
VQSSYSAILVVLMNTILLIAGTFFLVWLSDLNASMGIGGSIVILLSSMVLNIPODVLETFQT
VHIPTGHVLLALLTLVFSYLLALMYRARYLVPVNKIGLHNRFKRYSLEIMLNPAGGMP
YMYVMSFLSVPAYLFILLGFIFPNHSGLAALSKEIMVGKPLWVYVYISVLFLFSIIFAFVT
MNGEEIADRMKKSGEYIYGIYPGADTSRFINRLVLRFSVIGGLFNVIMAGGPMLFVLFDE
KLLRLAMIPGLFMMFGGMIFTIRDEVKALRLNETYRPLIZ
```
(SEQ. ID. NO. 63)
```
MSSLSDQELVAKTVEFRQRLSEGESLDDILVEAFAVVREADKRILGMFPYDVQVMGAIV
MHYGNVAEMNTGEGKTLTATMPVYLNAPSGEGVMVVTPNEYLSKRDAEEMGQVYRF
LGLTXGVPFTEDPKKEMKASEKKLIYASDWTTINSNLGPDYLNDNLASNEEGKFLRPFN
YVUDEIDDILLDSAQTPLIIAGSPRVQSNYYAIIDTLVTTLVEGWYIPKEEKEEVWLTTKG
AKSAENELGIDNLYKEEHASFARHLVYAIRAHKLFTKDKDYHRGNEMVLVDKGTGRL
MEMTKLQGGLHQAIEAKEHVKLSPETRAMASITYQSLPKMFNKISGMTGTGKVAEKEFI
ETYNMSVVRIPTNRPRQRIDYPDNLYITLPEKVYASLEYIKQYHAKGNPLLVFVGSVEMS
QLYSSLLFREGIAHNVLNANNAAREAQIISESGQMGAVTVATSMAGRGTDCKLGKGVA
ELGGUVIGTERMESQRIDLQIRGRSGRQGDPGMSKFFVSLEDDVIKKFGPSWVHKKYKD
YQVQDMTQPEVLKGRKYRKLVEKAQHASDSAGRSARRQTLEYAESMNIQRDIVYKER
NRLIDGSRDLEDVVVDIIERYTEEVAADHYASRELLFWPIVTNISPHVKEVPDYIDVTDKT
AVRSFMKQVIDKELSEKKELLNQHDLYEQPLRLSLLKAIDDNWVEQVDYLQQLSMAIG
GQSASQKNPEVEYYQEAYAGFEAMKEQIHADMVRNLLMGLVEVTPKGEIVTHFPZ
```
(SEQ. ID. NO. 64)
```
MIGTFAAALVAVLANRVPIEITPNSANTEIAPPDGIGQVLSNLLLKLVDNPVNALLTANYI
RILSWAVIFGLAMREASKNSQELLKTIADVTSKIVEWIINLAPFGILGLVFKISDKGVGSLA
NYGILLVLLVTTMLPVAPVVNPLIAPFFMRRNPYPLVWNCLRVSGVTAPFTRSSATNTPV
NMKLCMDLGLNPDTYSVSIPLOSTINMAGVAITINLLTLAAVNTLGTPVDFATAFVLSVV
AAISSCDASGIAGGSLLUPVACSLFGISNDIAIQIVGVGPVIGVQDSCETALNSSTDVLFTA
VAEYAATRKKZ
```
(SEQ. ID. NO. 65)
```
MSISQRTTKLILATCLACLLAYFLNLSSAVSAGIIALLSLSDTRRSTLKIARNRLFSMLLA
LAIGVLAFHLSGFHIWSLGLYLAVPLAYKMGWEIGITPSTVLVSHLLVQESTSPDLLVNE
FLLFAIGTGFALLVNLYMPSREEEIQHYHTLVEEKDILQRFKYYLSRGDGRNRAQLVAEL
DTLLKEALRLVYLDHSDHLFHQTDYHIHYFEMRQRQSRILRNMAQQINTCHLAASESLIL
AQLFSKAGQLSQTNPASDLLDEIERYLEVFRNRSLPKTREEPETRATLLQLLREAKTFIQV
KVDFYQKYRQZ
```
(SEQ. ID. NO. 66)
```
MEIMSLAIAVFAVIIGLVIGYVSISAKM1SSQEAAELMLLNAEQEATNLRGQAEREADLL
VNEAKRESKSLKKEALLEAKEEARKYREEVDAEFKSERQELKQIESRLTERATSLDRXD
DNLTSKEQTLEQKEQSISDRAKNLDAREEQLEEVERQKEAELERIGALSQAEARDIILAQ
TSENLTREIASRIREAEQEVKERSDKMAKDILVQAMQRIAGEYVAESTNSTVHLPDDTM
KGRIIGREGRNIRTFESLTGVDVIIDDTPEVVTLSGFDPIRREIARMTMEMLLKDGRIHPAR
IEELVEKNRQEIDNKIREYGEAAAYEIGAPNLHPDLMKIMGRLQPRTSYGQNVLRHSIEV
AKLAGIMASELGENAALARRAGFLHDIGKAIDHEVEGSHVELIGMELARKYKEPPVVVNT
IASHHGDVEAESVIAVIVAAADALSAARPGARSESLESYIKRLHDLEEIANGFEGVQTSFA
LQAGREIRIMVNPGKIKDDKVTILAHKVRKKIENNLDYPGNIKVTVIRELRAVDYAKZ
```
(SEQ. ID. NO. 67)
```
MMLKPSIDTLLDKVPSKYSLVILBAKRAHELEAGAPATQGFKSEKSTLRALEEIESGNVTI
HPDPEGKREAVRRRIEEEKRRKEEEEKKIKEQIAKEKEDGEKIZ
```
(SEQ. ID. NO. 68)
```
MSAYQLPTVWQDEASNQGAFTGLNRPTAGARFEQNLPKGEQAFQLYSLGTPNGVKVTI
LLEELLEAGFKEAAYDLYKIAIMDGDQFGSDPFKLNPNSKIPALLDQSGTENVRVFESAH
ILLYLAEKFGAFLPSNPVEKVEVLNWLFWQAGAAPFLGGGFGHFFNYAPEKLEYPINRF
TMEVKRQLDLLDKELAQKPYIAGNDYTIADIAIWSWYGQLVQGNLYQGSAKFLDASSY
QNLVKWAEKANRPAVKRGLEVTYTEIKZ
```

TABLE 2-continued (SEQ. ID. NO. 69)
LASLITSIIMFYVGFDVLRDTIQKILSREETVIDPLGATLGIISAAIMFVVYLYNTRLSKKSN
SNALKAAAKDNLSDAVTSLGTAIAILASSFNYPIVDKLVAIIITFFILKTAYDIFIESSFSLSD
GFDDRLLEDYQKAIMEIPKISKVKSQRGRTYGSNIYLDITLEMNPDLSVFESHEIADQVES
MLEERPGVFDTDVHIEPAPIPEDEILDNVYKKLLMREQLIDQGNQLEELLTDDFVYIRQD
GEQMDKEAYKTKKELNSAIKDIQITSISQKTKLICYELDGIIHTSIWRRMETWQNIFHQET
KKEZ (SEQ. ID. NO. 70)
MTIKLVATDMDGTFLDGNGRFDMDRLKSLLVSYKEKGIYFAVASGRGFLSLEKLFAGV
RDDIIFIAENGSLVEYQGQDLYEATMSRDFYLATFEKLKTSPYVDINKLLLTGKKGSYVL
DTVDETYLKVSQHYNENIQKVASLEDITDDIFKFTTNFTEETLEDGEAWVNENVPGVKA
MTTGFESIDIVLDYVDKGVAIVELVKKLGITMDQVMAFGDNLNDLHMMQVVGHPVAP
ENARPEILELAKTVIGHHKERSVIAYMHGLZ (SEQ. ID. NO. 71)
MADIKLIALDLDGTLLITDKRLTDRTKETLQAARDRGIKVVLTTGRPLKAMDFFLHELG
TDGQEDEYTITFNGGLVQKNTGEILDKTVFSYDDVARLYEETEKLSLPLDAISEGTVYQI
QSDQELYAKFNPALTFVPVDFEDLSSQMTYNKCVTAFAQEPLDAAEQKISPELFDQYEIF
KSREMLLEWSPKNVHKATGLAKLISHLGIDQSQVMACGDEANDLSMIEWAGLGVAMQ
NAVPEVKAAANVVTPMTNDEEAVAWAIEEYVLKENZ (SEQ. ID. NO. 72)
MESLLILLLIANLAGLFLIWQRDRQEKHLSKSLEDQADHLSDQLDYRFDQARQASQLD
QKDLEVVVSDRLQEVRKELHQGLTQVRQEMTDNLLQTRDKTQRLQALQESNEQRLE
QMRQTVEEKLEKTLQTRLQASFETVSKQLESVNRGLDEMQTVARDVGALNKVLSGTKT
RGALGELQLGQHEDIMTPAQYEREYATVENSSERVEYAIKLPGQGDQEYVYLPIDSKFP
LADYYRLEEAYETGDKDEIERCRKSLLASVKRFARDIRNKYIAPPRTTNFGVLFVPTEGL
YSEIVRNPVFFDDLRREEQIWAGPSTLSALLNSLSVGFKTLNIQKSADHISKTLASVKTEF
GKFGGILVKAQKHLQHASGNIDELLNRRTIAIERTLRHIELSEGEPALDLLHFQENEEEYE
DZ (SEQ. ID. NO. 73)
MKISHMKKDELFEGFYLIKSADLRQTRAGKNYLAFTFQDDSGEIDGKLWDAQPHNIEAF
TAGKVVHMKGRREVYNNTPQVNQITLRLPQAGEPNDPADFKVKSPVDVIKEIRDYMSQ
MIFKIENPVWQRIVRNLYTKYDKEFYSYPAAICTNHHAFETGLAYHTATMVRLADALSE
VYQLNKSLLYAGIMLHDLAKVIELTGPDQTEYTVRGNLLGHIALIDSEITKTVMELGIDD
TKEEVVLLRHVILSHHGLLEYGSPVRPRIMEAEIIHMIDNLDASMMMSTALALVDKGE
MTNKIFAMDNRSFYKPDLDZ (SEQ. ID. NO. 74)
MSEKAKKGFKMPSSKTVLLIIIAIMAVLTFIPAGAPIEGIYETQPQNPQGIWDVLMAPIRA
MLGTHPEEGSLIKBTSAAIDVAPRLMVGGFLGIVNKTGALDVGIASIVKKYKGREKMLIL
VLMPLFALGGTTYGMGEETMAFYPLLVPVMMAVGFDSLTGVAIILLGSQIGCLASTLNP
FATGIASATAGVGTGDGVLRLIFWVTLTALSTWFVYRYADKIQKDPTKSLVYSTRKEDL
KHFNVEESSSVESTLSSKQKSVLFLPVLTFILMVLSRPWTDLGVTIPDDFNTWLTGLPVIG
NIVGSSTSALGTWYFPEGAMLFAFMGILIGVIYGLKEDKUSSFMNGAADLLSVALIVAIA
RGIQVIMNDGMITDTILNWGKEGLSGISSQVFIVVTYIFYLPMSFLIPSSSGLASATMGIM
APLGEFVNVRPSLIITAYQSASGVLNLIAPTSGIVMGALALGRINIGTWWKFMGKLVVAII
VVTIALLLLGTPLPFLZ (SEQ. ID. NO. 75)
MSNSFVKLLVSQLFANLADIFFRVTIIANIYUSKSVIATSLVPILIGISSFVASLLVPLVTKR
LALNRVLSLSQFGKTILLAILVGMPTVMQSVAPLVTYLFVVAISILDGFAAPVSYAIVPRY
ATDLGKANSALSMTGEAVQLIGWGLGGLLFATIGLLPTTCINLVLYIISSFLMLFLPNAEV
EVLESETNLEILLKGWKLVARNPRLRLIWSANLLEFSNTIWVSSHLVFVTELLNKTESYW
GYSNTAYSIGIIISGLLRISEKFLAAKWEPQLFTPNLIVFIQNPCLSLDPGWFLFSPNGCFLL
DKKEFPLYGISVEKNTKRKETHMNSLPNHHIQNKSFYQLSFDGGHLTQYGGLIFFQELFS
QLKLKERISKYLVTNDQRRYCRYSDSDILVQPLPQLLTGYGTDYACKELSADAYFPKLL
EGGQLASQPRFSRTDEETVHSLRCLNLELVEFFLQPHQLNQLIVDEDSTHFTTYGKQEGV
AYNAHYRAHGYHPLYAFEGKTGYCFNAQLRPGNRYCSEEADSFTTPVLERFNQLLFRM
DSGFATPKLYDLIEKTGQYYUKLKKNTVLSRLGDLSLPCQDEDLTILPHSAYSETLYQAG
SWSHKRRVCQFSERKEONLPYDVISLVTNMTSGTSQDQFQLYRGRGQAENFIKEMKBG
FFGDKTDSSTLIKNEVRMMMSCIAYNLYLFLKHLAGGDFQTLTIKRFRMLHVVGKCVR
TGRKQLLKLSSLYAYSELFSALYSRIRKVNLNLPVPYEPPRRKASLMMHZ (SEQ. ID. NO. 76)
MMEFFQQLPHLEPYGNPQYFVYIAATLPIFIGLFFKKRFAWYEVLVSLFFIVTMLVGGK
TNQLAALGIYLCWEILLLLFYKHYRKDGKWVFYLVSFLSLLPIIFVKVQPAINGTQSLLGF
LGISYLTPRSVGIVIELRDGVIKDPTLWEFLRFLLFMPTFSSGPIDRFKRFNENYQAIPERD
ELMDMLDESVRYIMWGFLYKFILAHVLGETLLPPLKNLALQSGGFFNLYALAVMYTFG
LELFFDFAGYSMPALAISNLMGIRSPINFNKPFLSRDLKEFWNRWHMSLSFWFRDFVPM
RMVMVLTRKKVFKNRNVTSSMAYIVNMLMGFWHGVTWYYIAYGLFHGLGLVINDAW
VRKKKTLNKERKKAGKAALPENRWIQLLGMVVTFHVVMLSFLIFSGFLNNLWFKKZ (SEQ. ID. NO. 77)
MLKRLWMIFGPVLIAGLLVFLLIFFYPTEMHHNLGAEKRSAVATTIDSFKERSQKVRALS
DPNVRFVPFFGSSEWLRFDGAHPAVLAEKYNRSYRYLLGQGGAASLNQYFGMQQMLP TABLE 2-continued QLENKQVVYVISPQWFSKNGYDPAAPQQYPNGDQLTSFLKHQSGDQASQYAATRLLQQ
PPNVAMKDLVQKLASKEELSTADNEMIELLARFNERQASFFGQFSVRGYVNYDKHVAK
YLKILPDQPSYQAIEDVVKADAEKTSNNEMGMENYPYNEQIKKDLKKLKDSQKSPTYL
KSPEYNDLQLVLTQFSKSKVNPIFIIPPVNKKWMNYAGLREDMYQQTVQKIRYQLESQG
FTNIADFSKDGGEPFFMKDTIHLGWLGWLAFDKAVDPFLSNPTPAPTYHLNERFFSKDW
ATYDGDVKEFQZ (SEQ. ID. NO. 78)
MEKNLKALKQTTDQEGPAIEPEKAEDTKTVQNGYFEDAAVKDRTLSDYAGNWQSVYP
FLEDGTFDQVFDYKAKLTGKMTQAEYKAYYTKGYHTDVTKINITDNTMEFVQGGQSK
KYTYKYVGKKILTYKKGNRGVRFLFEATDADAGQFKYVQFSDHNVAPVKAEHFHIFFG
GTSQEALFEEMDNWPTYYPDNLSGQEIAQEMLAHZ (SEQ. ID. NO. 79)
MKDGHLLAHHIRLLNGRIFQKLLSQDPEALYRGEQGKILAVLWNSETGCATATDIALAT
GLANNTLTTMIKKLEEQKLVIVSPCGKDKRKKYLVLTELGKSQKEVGHRVSQKLDTIFY
KGFSEEEIHQFEGFQERILANLKEKGNEVZ (SEQ. ID. NO. 80)
MTNLIATFQDRFSDWLTALSQHLQLSLLTLLLAILLAIPLAVFLRYHEKLADWVLQIAGIF
QTIPSLALLGLFIPLMGIGTLPALTALVLYAIFPILQNTGLKGIDPNLQEAGIAFGMTRWER
LKIFEIPLAMPVIMSGIRTAAVLIGTATLAALIGAGGLGSPILLGIDRNNASLILIGALSSAV
LAIAFNFLLKVMEKKLRTSGFALVALLLGLSYSPALLVQKEKENLVIAGKIGPEPEILAN
MYKLLIEENTSMTATVKPNPGKTSFLYEALKKGDIDIYPEETGTVTESLLQPSPKVSHEPE
QVYQVARDGIAKQDHLAYLICPMSYQNTYAVAVPKKIAQEYGLKTISDLKKVEGQLKA
GFTLEFNDREDGNKGLQSMYGLNLNVATIEPALRYQAIQSGDIQITDAYSTDAELERYDL
QVLEDDKQLFPPYQGAPLMKEALLKKHPELERVLNTLAGKITESQMSQLNYQVGVEGK
SAKQVAKEFLQEQGLLKKZ (SEQ. ID. NO. 81)
MMHTYLQKKIENIKTTLGEMSGGYRRMVAAMADLGFSGTMKAIWDDLPAHRSFAQWI
YLLVLGSFPLWLELVYEHRIVDWIGMICSLTGIICVIFVSEGRSNYLFGLINSVIYLILALQ
KGFYGEVLTTLYFTVMQPIGLLVIYQAQFKKEKQEFVARKLDGKGWTKYLSISVLWWL
AFGFIYQSIGANRPYRDSITDATNGVGQILMTAVYREQWIFWAATNVFSIYLWWGESLQI
QGKYLIYLINSLVGWYQWSKAAKQNTDLLNZ (SEQ. ID. NO. 82)
MRNMKAKYAVWVAPFLNLTYAIVEFIAGGVFGSSAVLADSVHDLGDAIAIGISAFLETIS
NREEDNQYTLGYKRFSLLGALVTAVILVTGSVLVILENVTKILHPQPVNDEGILWLGILTI
NLLSLVVGKGKTKNESILSLHFLEDTLGWVAVILMAIVLRFTDWYILDPLLSLVISFFILS
KALPRFWSTLKIFLDAVPEGLDIKQVKSGLERDNVASLNQLNLWTMDALEKNAIVHVC
LKEMEHMETCKESIRIFLKDCGFQNITIEIDADLETHQTHKRKVCDLERSYEHQHZ (SEQ. ID. NO. 83)
MIEYKNVALRYTEKDVLRDVNLQIEDGEFMVLVGPSGSGKTTMLKMINPLLEPTDGNIY
MDGKRIKDYDERELRLSTGYVLQAIALIPNLTVAENIALIPEMKGWSKEEITKKTEELLA
KVGLPVAEYGHRLPSELSGGEQQRVGIVLRAMIGQPICIFLMDEPFSALDAISRKQLQVL
TKELIEFGMTTIFVTHDTDEALKLADRJAVLQDGEIRQVANPETILKAPATDFVADLPGG
SVHDZ (SEQ. ID. NO. 84)
MSAVAISAMTKVMQETHGNPSSIHGHGRQAGKLLREARQELAQLLRTKPQHIFFTSGGT
EGNNTTIIGYCLRHQEQGKHIITTAIEHHAVLETIDYLVQHFGFEATIIQPENQEITAQQIQ
KALRDDTILVSTMFVNNETGNLLPIAEIGQILKQHPAAYHVDAVQAIGKIPHSEELGIDFL
TASAHKFHGPKGIGFLYASSMDFDSYLHGGDQEQKRAGTENLPAIVGMVAALKEDLEK
QEEHFQHVQNLETAFLAELEGIQYYLNRGKHHLPYVLNIGFPGQKNDLLLLRLDLAGIST
GSACTAGVVQSSHVLEAMYGANSERLKESLRISLSPQNTVEDLQTLAKTLKEUGGZ (SEQ. ID. NO. 85)
MLFKLSKEKIELGLSRLSPARRIFLSFALVILLGSLLLSLQFVQVESSRATYFDHLFTAVSA
VCVTGLSTLPVAHTYNIWGQIICLLLIQIGGLGLMTFIGVFYIQSKQKLSLRATIQDSFSYG
SLRFVYSIFLTTFLVESLGAILLSFRLIPQLGWGRGLFSSIPLAISAFCNAGPDNLGSTSLFA
FQTDLLVNLVIAGLIITGGLGPMVWFDLAGHVGRKKKGRLHFHTKLVLLLTIGLLLFGT
ATTLFLEWNNAGTIGNLPVADKVLVSFFQTVTMRTAGFSTIDYTQAHPVTLLIYILQMFL
GGAPGGTAGGLKITTFFVLLVFARSELLGLPHANVARRTIAPRTVQKSFSFIIFLMSFLIGI
LLGITAKGNPPFIHLVPETISALSTVGVTANLTPDLGKLALSVIMPLMFMGRIGPLTLFVS
LADYXPEKKDMIHYMKADISIGZ (SEQ. ID. NO. 86)
MSDRTIGILGLGIFGSSVLAALAKQDMNIIAIDDHAERINQFEPVLARGVIGDITDEELLRS
AGIDTCDTVVVATGENLESSVLAVMHCKSLGVPTVIAKVKSQTAKKVLEKIGADSVISP
EYEMGQSLAQTILFHNSVDVFQLDKNVSIVEMKIPQSWAGQSLSKLDLRGKYNLNILGF
REQENSPLDVEFGPDDLLKADTYILAVNNQYLDTLVALNSZ (SEQ. ID. NO. 87)
MKLLSIAISSYNAAAYLHYCVESLVIGGEQVGILIINDGSQDQTQEIAECLASKYPNIVRAI
YQENKCHGGAVNRGLVEASGRYFKVVDSDDWVDPRAYLKILETLQELESKGQEVDVF
VTNFVYEKEGQSRKKSMSYDSVLPVRQIFGWDQVGNFSKGQYTMMHSLIYRTDLLRAS
QFZ TABLE 2-continued (SEQ. ID. NO. 88)
MKFNPNQRYTRWSRRLSVGVASVVVASGFFVLVGQPSSVRADGLNPTPGQVLPEETSG
TKEGDLSEKPGDTVLTQAKPEGVTGNTNSLPTPTERTEVSEETSPSSLDTLPBKDEEAQK
NPELTDVLXETVDTADvDGTQASPAERRPEQVKGGVKENTKDSIDVPAAYLEKAEGKG
PPFTAGVNQVIPYELFAGDGMLTRLLLKASDNAPWSDNGTAKNPALPPLEGLTICGKYFY
EVDLNGNTVGKQGQAUDQLRANGTQTYKATVKVYGNKDGKADLTNLVATKNVDINI
NGLVAKETVQKAVADNVKDSIIDVPAAYLEKGEGPTAGVNHVIPYELFAGDGMLTRLL
LLSDKAPWSDNGDAKNPALSPLGENVKTKGQYFYQVALDGNVAGKEKQALIDQFRAN
GTQTYSATVNVYGNKDGKPDLDNIVATKKVTLNNGLSKETVQKAVADNVKDSIDVPA
AYLEKAKGEGPFTAGVNHVIPYELFAGDGMLTRLLLKASDKAPWSDNGDAKNPALSPL
GENVKTKGQYFYQLALDGNVAGKEKQALIDQFRANGTQTYSATVNVYGNKDGKPDLD
NIVATKXVTININGLISKETVQKAVADNVKTVSMFQQPTZ (SEQ. ID. NO. 89)
MKLKSYILVGYIISTLLTILVVFWAVQKMLIAKGEIYFLLGMTIVASLVGAGISLFLLLPVF
TSLGKLKEHAKRVAAKDFPSNLEVQGPVEFQQLGQTFNEMSHDLQVSFDSLEESEREGL
MIAQLSHDIKTPITSIQATVEGILDGIIKESEQAHYLATIGRQTERLNKLVEELNFLTLNTA
RNQVETTSKDSIFLDKLLIECMSEFQFLIEQERRDVHLQVIPESARIEGDYAKLSRJLVNEI
TVSSQYGLGSTETLVLNLSGSENKAZ (SEQ. ID. NO. 90)
MFGQTAQHGLTNSLKDFWIFLLNIGPQLAFFCQMLRCSRSVEQGTGNHRREFNMIQQIFS
HFGMTHLGQIKLVYQESIDLELLVNALNHHLLIDRLVLTPNQITIEIDRQIVHGLDLLKGR
XDKEIIDIKSMFRQLELASTQQICPNQRVHHGILAFGEISDLVPAKNLPNRQDZ (SEQ. ID. NO. 91)
MEHLATYPSTYGGAPAALGWLAVGLSGMGSAYGVGKAGQSAAALLKEQPEKFASALI
LQLLPGTQOLYGFVIGLIWLQLTPSLPLEKGVAYFVALPIA1VGYFSAKHQGNVAVAGM
QILAKRPKEFMKGAILAAMVETYALLAIWVSFILTLRVZ (SEQ. ID. NO. 92)
MLKSEKQSRYQMLNEELSFLLEGETNVLANLSNASALIKSRFPNTVFAGFYLFDGKELV
LGPFQGGVSCIIRIALGKGVCGEAAGHFQETVIVGDVTTYLNYISCDSLAKSEIVVPMMK
NGQLLGVLDLDSSEIEDYDAMDRDYLEQFVAILLEKTAWDFTMFEEKSZ (SEQ. ID. NO. 93)
MSVLEKDLHVEIEGKEILKGVNLTLTGEAAIMGPNGTGKSAAIMGNPNYEVTKGEVLFD
GVNILELEVDERARMGLFLAMQYPSEIPGITNAEFLRAAMNAGKEDDEKISVREFITKLD
EKMELLNMKEEMAERYLNEGFSGGEKKRNEILQLLMLEPTFALLDEIDSGLDIDALKVV
SKGVNAMRGEGFGAMIITTHYQRLLNYITPDVVHVMMEGRVVLSGGPELAARLEREGY
AKLAEELGYDYKEELZ (SEQ. ID. NO. 94)
MPYKRQRSFSMALSKLDSLYMAVVADHSKNPHHQGKLEDAEQISLNNPTCGDVINLSV
KFDAEDRLEDIAFLNGCTISTASASMMTDAVLGKKQEILELAT1FSEMVQGQKDERQDQ
LGDAAGVAKFPQPJKCATWNALKIENQEKQZ (SEQ. ID. NO. 95)
MKIQDLLRKDVMLLDLQATEKTAVIDEMIKNLTDHGYVTDEFETFKEGILAREALTSTG
LGIAMPHSKNAAVKEATVLFAKSNKGVDYESLDGQATDLFFMIAAPEGANDTHLAALA
ELSQYLMKDGFADKIRQATSADQVIELFDQASEKTEELVQAPANDSGDFIVAVTACTTG
IAHTYMAQEALQKVAAEMGVGIKVETNGASGVGNQLTAEDIRKAKAIIIAADKAVEMD
RFDGKPLINRPVADGIRKTEELINLALSGDTEVYRANGAJ(AATASNEKQSLGGALYLMS
GVSQMLPFVIGGGIMIALAFLIDGALGVPNENLGNLGSYHELASMFMKIGGAAFGLMLP
VFAGYVAYSIAEKPGLVAGFVAGALAKEGFAFGKIPNDFLGGLGGGSAVLLGIVLGGM
MAVDMGGPVNKAAYVFGTGTLAATVSSGGSVAMAAVMAGGMVPPLAIFVATLLFVL
VGAIVSGVVYGYLRKPQAZ (SEQ. ID. NO. 96)
MANKNTSTTRRRPSKAELERKEAIQRMLISLGIAILLIFAAFKLGAAGITLYNLIRLLVGSL
AYLAIFGLLIYLFFFKWIRKQEGLLSGFFTIFAGLLLIFEAYLVWKYGLDKSVLKGTMAQ
VVTDLTGFRTTSFAGGGLIGVALYPTAFLFSNIGTYFIGSLILVGSLLVSPWSVYDIAEFSR
GFAKWWEGHERRXEERFVKQEEKARQKAEKEARLEQEETEKALLDLPPVDMETGEILT
EEAVQNLPPIPEEKWVEPEIILPQAELKFPEQEDDSDDEDVQVDFSAKEALEYKLPSLQLF
APDKPKDQSKEKKWRENIKILEATFASFGIKVTVERAEIGPSVTKYEVKPAVGVRVNRIS
NLSDDLALALAAKDVRIEAPIPGKSUGTEVPNSDIATVSFELWEQSQTKAENFLEIPLGK
AVNGTARAFDLSKMPHLLVAGSTGSGKSVAVNGIIASILMKARPDQVKFMMVDPKMV
ELSVYNDIPILLJPVVTNPRKASKALQKVVDEMENRYELFAKVGVRNIAGFNAKVEEFN
SQSEYKQIPLPFIVVIVDELADLMMVASKBVEDAIIRLGQKARAAGIHMILATQRPSVDVI
SGUKANVPSRVAFAVSSGTDSRTLDNGAEKLLGRGDMLFKPIDENHPVRLQGSFISDDD
VERIVNPIKTQADADYDESFDPGEVSENEGEFSDGDAGGDPLFEEAXSLVIETQKASASM
IQRRLSVGFNRATRLMEELEIAGVIGPAEGTKPPJCVLQQZ (SEQ. ID. NO. 97)
MSYFKKYKFDKSQFKLGMRTKTGIAVFLVLLIFGFGWKGLQIGALTAVFSLRESFDESV
HFGTSRILGNSIGGLYALVFLLNTFFWEAWVTLVVVPICTMLTIMTNVAMNNCAGVIGG
VAAMLHTLSPSGETILYVFVRVLETFMGVFVAUVNYDIDRLRLFLEKKEKZ TABLE 2-continued (SEQ. ID. NO. 98)
MNKSEHRHQLIRAUTKNKIHTQAELQALLAENDIQVTQATLSRDIKNMNLSKVREEDSA
YYVLNNGSISKWEKRLELYMEDALVWMRPVQHQVLLKTLPGLAQSFGSHDTLSFPDAA
TLCGNDVCLIICEDADTAQKCFEELKKFAPPFFFEEZ (SEQ. ID. NO. 99)
MCSIKLNALSYMGRVLNIFPItTGTYVARVLDRTDYGYFNSVDTILSFELPPATYGVYNY
GLRAISNVKDNKKDLNRTFSSLFYLCIACTILTRAVYILAYPLFFTDNPIVKKVYLVMGIQ
LIAQFSIEWVNBALENYSILFYKTAFRILMLVSIFLPVKNEHDEVVYTLVMSLTLINYLSY
FWKRDIKLVKIHLSDFKPLFLPLTAMLVANANMLFTTLDRLFLVICTGIDVNVSYAQRJV
TVIAGVVTGAIGVSVPRLSYYLGKGDKEAYVSLVNRCSRIFNPFHPLSFGLMVLGNAILL
YGSEKYIGGGILTSLFAFRTULALDTILGSQILFTNGYHKRTVYTVFAGLLNLGLNSLLFF
NHVAPEYYLLTRMLSETSLLVFYIIFEHRKQLIHLGHIFSYTVRYSLFSLSWAIYFUNFVY
PVDMVINLPFLINTGLIVLLSAISYISLLVFRKDStFYEFLNHVLALKNKFKKSZ (SEQ. ID. NO. 100)
MELFMKITNYEIYXLKKSGLTNQQILICVLEYGENVDQELLLGDIADISGCRNPAVFMER
YPQIDDAHLSKEFQKFPSPSILDDCYPWDLSEIYDAPVLLFYKGNLDLLKFPKVAVVGSR
ACSKQGAKSVEKVIQGLENELVIVSGLAXGDTAAHMAALQNGGKTAVIGTGLDVFPKA
NKRLQDYIGNDHLVLSEYGPGEQPLKHFPARNRIAGLCRGVIVAEAKMRSGSLTCERAM
EEGRDVFAIPGSILDGLSDGCIIMLIQEGAKLVTSGQDVLAEFEPZ (SEQ. ID. NO. 101)
MKQLTVEDAKQIELEILDYIDTLCKKIININYIINYGTLIGAVRHEGFIPWDDDIDLSMPRB
DYQRFINIFQKEKSKYKLLSLERDKNYNNFIKTDSTRKIIDTRNTKTYESGIIDIEPDRFDD
PKVIDTCYKESKLLSFSKHKNWYKDSLLKDWIRTAFWLLLRPVSPRYFANKIEKEIQKYS
RENGQYMAFIPSKFKEKEVFPSGTFDKTIDLPPENLSLPAPEKPDTILTQFYGDYMTLPPE
EKRFYSHEFHAYKLEDZ (SEQ. ID. NO. 102)
MIKINHLTITQNKDLRDLVSDLTMTIQDGEKVAIIGEEGNGKSTLLKLMGEALSDFTIKG
NIQSDYQSLAYPQKVPEDLKKKTLHDYFFLDSIDLDYSILYRLAEELHFDSNRFASDQEIG
NLSGGEALKIQLIHELAICPFEILFLDEPSNDLDLETVDWLKGQIQKTRQTVTFISHDEDPL
SETADTIVLRLVKHRKEAETHVEHLDYDSYSEQRKANFAKQSQQAANNQRAYDKTME
KIRRVKQNVETALRATKDSTAGRLLAKKMKTVLSQEKRYEKAAQSMTQKPLEEEQIQL
FFSDIQPLPASKVLVQLEKENLSIDDRVLVQKLQLTVRGQEKIGIIGPNGVGKSTLLAKLQ
RLLNDKREISLGIMPQDYHXJCLQLDLSPIAYLSKTGEKEELQKQSHLASLNFSYPMQHQ
RSLSGGQQGKLLLLDLVLRKPNFLLLDEPTRNPSPTSQPQIRKLFATYPGGLITVSHDRRF
LKEVCSIIYRMTEHGLKLVNLEDLZ (SEQ. ID. NO. 103)
MKPKTFYNLLAEQNLPLSDQQKEQFERYFELLVEWNEKINLTAITDKEEVYLKNFYDSI
APILQGLIPNETIKLLDIGAGAGFPSLPMKILYPELDVTIIDSLNKRINFLQLLAQELDLNGV
HFYHGRAEDFAQDKNFRAQYDFVTARAVARMQVLSELTIPYLKVGGKLLALKASNAPE
ELLEAKNALNLLFSKVEDNLSYALPNRDPRYITVVEKKKETPNKYPRKAGMPNKRPLZ (SEQ. ID. NO. 104)
MSIKUAVDIDGTLVNSQKEITPEVFSAIQDAKEAGVKVVIATGRPIAGVAICLLDDLQLR
DEGDYVVTFNGALVQETATGHEIISSLTYEDYLDMEFLSRKLGVHMHAITKDGIYTANR
NIGKYTVHESTLVSMPYRTPEEMAGKJVKCMFIDEPEIPEIKKIAKYITKTNDESGVAHAI
RTWVLZ (SEQ. ID. NO. 105)
MTWIILGVIALIVIIVSYNGLVKNRMQTKEAWSQIDVQLKRRNDLLPNLIETVKGYAYEG
LEKVAELRNQVTSPAEAMKASDALTRQVSGIFAVAESYPDLKASANPVICLQEELTNTE
NKSYSRQLYNSVVSNYNVKLETFSNIIAGMFGFKAADFLQTPEEEKSVPKVDPSGLGDZ (SEQ. ID. NO. 106)
MLFDQIASNKRKTWILLLVFFLLLALVGYAVGYLIRSGLGGLVIALIIGFIYALSMIFQSTE
VMSMNGAREVDEQTAPDLYHVVEDMALVAQIPMPRVFIIDDPALNAFATGSNPQNAAV
AATSGLLAIMNREELEAVMGHEVSHIRNYDIRISTIAVALASAITMLSSMAGRMMWWG
GAGRRRSDDDRDGNGLEIIMLVVSLLAIVLAPLAATLVQLAISRQREFLADASSVELTRN
PQGMINALDKLDNSKPMSRHVDDASSALYINDPKKGGGFQKLFYTHPPtSERIERLKQM
Z (SEQ. ID. NO. 107)
MKLNIQEIRKQSEGLNFEQTLDLVDDLRARNQEILDVKDILAVGKVQYEDRMYFLDYQL
SYTIVLASSRSMEPVELVESYPVTEVFMEGATNQLDQEVLDDDLVLPIENGELDLAESVS
DNLLNIPIKVLTAEEBAGQCPISGNDWQIMTEEEYQAQKAVKKEENSPFAGLQGLFDGD
EZ (SEQ. ID. NO. 108)
MKRQLALVVPSGGQDSRTCLWVMQHYETVEAVTFAYGQRMHLEQRRREIAKEQGRH
HILDMSLLGQITAQPDFATIHSYLPDKLCVESKSLKLYLFSYRNHGDFHENCNTIGKDLV
NLLDPRYLEVWGKFTPRGGISDPYYNYGKQGTKYEGLAEQRLFQHDLYPEKIDNRZ (SEQ. ID. NO. 109)
MTETVEDKVSHSn*GLDILKGIVAAGAVISGTVATQTKVFTNESAVLEKTVEKTDALAT
NDTVVLGTISTSNSASSTSLSASESASTSASESASTSASTSASTSASESASTSASTSISASST TABLE 2-continued

```
VVGSQTAAATEATAKXVEEDRKKPASDYVASVTNVNLQSYAgRRKRSVDSIEQLLASIK
NAAVSGNTVNGAPAINASLNLAKSETKVYTGEGVDSVYRVPIYYKLKVTNDGSKLTFT
YTVTYVNPKTNDLGNISSMRPGYSYNSGTSTQTMLTLGSDLGKPSGVKNYITDKNGRQ
VLSYNTSTMTRQGSGYTWGNGAQMNGFFAKXGYGLTSSWTVPITGTDTSFTFTPYAAR
TDRIGINYFNGGGKVVESSITSQSLSQSKSLSVSASQSASASASTSASASASTSASASASTS
ASASASTSASVSASTSASASASTSASASASTSASESASTSASASASASTSASASASTSASASAS
TSASESASTSASASASTSASESASTSASASASTSASASASTSASGSASTSTSASASTSASAS
ASTSASASASISASESASTSASESASTSTSASASTSASESASTSASASASTSASASASTSASA
SASTSASASASTSASESASTSASASASTSASASASTSASASASTSASASASTSASVSASTSASA
SASTSASASASTSASESASTSASASASTSASASASTSASASASTSASESASTSASASASTSA
SESASTSASASASTSASASASTSASGSASTSTSASASTSASASASTSASASASISASESASTS
ASESASTSASESASTSASASASTSASASASTSASASASTSASASARQVRRPQPVHLNRMQP
VRQPQQVLVHQLQHQRVHRLQHQPVPRLQRQPVRQLQQVPVLQSQHQQVLQPQHRQV
PRLQQAHQHLNQRRQAPQLQQVPVRQPQRRQVRQPQQVLVHQLQHQRVHRLRRQPVH
QSQQVPVRQLPHQQVPRLQQAPVRRLQQVLAPQPQPQPVRQPQQVSQRLNRIIQRVRPL
QQVLAPQPQRQQVHRLQRQRVRLNRHQRVRPLQQVLAPQPQQQVHRLQHQRVRPLQ
QVLAPQPQRQQVHRLQRQRVRLSQHQRVRQPQQAHQLLNLHQPVRQPHRQAPQLQQ
VPVRQPQRRQVRRLQQVPVRQPQQVVRQPQRRQVRRPQPVHLNRNQPVRQPQQVLV
HQLQMQRVHRLQHQPVHQSQQVPVRQPRINKCLGFSKYZ
```

```
                                                     (SEQ. ID. NO. 110)
MGVETWFYSSICWLALGLGSVWKFPYMTAANGGGGFLLIFLLSTILIGPLLLAEALGRSA
GVSAIKTFGKLGKNNKYNIGWIGAFALFLLSFYSVIGGWTLVYLGIEFGKLFQLGGTGDY
AQLFTSfLSNPAIALGAQAAPILLNIFIVSRGVQKGIERASKVMMPLLFIVFVFIIGRSLSLP
NAMEGVLYPDSKLTSTGLLYALGQSFALSLGVTVMLTYASYLDKXTNLVQSGISIVAM
NISISIMAGLAFQARSPFNQSEGGPSLLVLPQLIDKMPFGTUYVLFLLLFLFATVTFSVVM
LEINVDNITNQDNSKRAXWSVILGLTFVFGTPSALSYGVMADVHIFGKTFFDAMDFLVS
NLLMPFGALYLSLTGYTFKKALAMEELHLDERAWKQGLFQVWLFLLRFFVSSFQSSSL
WSSLPNLCNQKGLEZ
```

```
                                                     (SEQ. ID. NO. 111)
MLKKWQLKDVILLAFLSIFFC3GVFVGSGYVYNELSLLLTPLGLQAFANEILFGLWCMA
APIAAIFVPRVGSATIGEVLAALAEVLYGSQFGLGALLSGFVQGLGSEFGFIVTKNRYES
WLSLTANSIGITLVSFVYEYIKLGYYAFSLPFVLSLLVVRFISVYFFCTILVRAIVKLYHQF
ATGGKAZ
```

```
                                                     (SEQ. ID. NO. 112)
MVKVATQTPHSLLLILSLETSFIPSIALTLSVVAPCILFMLYYRRFKMLAWMLLLAILPSF
ANYWAVQLHGDASQAVMLGTRAFVTVCIGLVFVSSVSLKELLLYLAQKGLSRSWSYAL
IVVFNSFPLQQEIKSLKEACLLRGQELHFWSPLIYSKVLMTVFRWRHLYLRALSAHGYD
EHAQLKNSYRTFYPKKTKLIYLLFFLLLQTSLLZ
```

```
                                                     (SEQ. ID. NO. 113)
MRKHQLQVHKLTLSMMALDVVLTPRIEGMAPMSSVVNLAGIMMGPVYALAMATVRA
FXRNfFRQGIPPLALTGATFGALLAGLFYKYGRKFHYSALGEILGTGUGSIVSYPVMVLF
TGSAAKLSWFEYTPREFGATLIGTALSFIAFRFLKQEFFKKVQGYFFSERIDZ
```

```
                                                     (SEQ. ID. NO. 114)
MQETNPFPIGSSSLIHCFLNEISCEMLANGILALGCKPVMADDSREVLDFIKQSQALNLGH
LSAEKEKJJRMAASYANQSSLPMVVDAVGVRSSIRKSLVKDLLDYRPRVLKGNMSEIRS
LVGLKHHGVGVDASAJCDQETEDLLQVLKDWCQTYPGMSFLVTGPKDLVVSKNQVAV
LGNGCTELDWITGTGDLVGALTAVFLSQGKTGPEASCLAVSYLNIAAEKIVVQOMGLEE
FRYQVLNQLSLLRRDENWLDTIKGEVYEZ
```

```
                                                     (SEQ. ID. NO. 115)
MNHKAILSDVMGNATALEAVL&DAXNQGASEYWLLGDIFLPGPGANDLVALLKDLPP
ASVRGNWDDRVLEALDGQYGLEDPQEVQLLRMTQYLMERMDPATIVWLRSLPLLEKK
EIDGLRFSISHNLPDKNYGGDLLVENDTEKFDQLLDAETDVAVYGHVHKQLLRYGSQG
QQIINPGSIGMPYFNWEALKNHRSQYAVIEVEDGELLNIQFRKVAYDYEAELELAKSKG
LPFIEMYEELRRDDNYQGHNLELLASLIEKHGYVEDVKNFFDFLZ
```

```
                                                     (SEQ. ID. NO. 116)
MNVQIVRIIPTLKANNRKLNETFYIETLGMKALLEESAFLSLGDQTGLEKLVLEEAPSMR
TRKVEGRKKLARLIVKVENPLEIEGTTDSIHRLYKGQNGYAFEIPSPEDDLILIHAEDDIAS
LVEVGEKPEQTDLASKEISMELHLDIFLESSEIGASLDFIPAQGQDLTVDNTVTWDLSML
KFLVNELDLSLRQKFESTEYFIPKSEKGKDNVELWEVZ
```

```
                                                     (SEQ. ID. NO. 117)
MKWTKHIIKKIEEQIEAGIYPGASFAYFKDNQWTEFYLGQSDPEHGLQTEAGLVYDLAS
VSKVVGVGTVCTFLWEIGQLDIDRLVIDFLPESDYPDTIRQLLTRATDLDPPIPNRDLLTA
PELKEAMFHLNRSQPAFLYSDVHPLLLGFLEFNQDLDVILKDQVWKPWGMTETKFGPV
ELAVPTVRGVEAGIVHDPKARLLGREAGSAGLFSTIKDLQIFLEHYLADDFALNQNFSPL
DDKERSLAWNLEGDWLDHTGYTGTFIMWNRQKQEATFLSNRTYEKDERAQWILDRNQ
VMNLIEEZ
```

```
                                                     (SEQ. ID. NO. 118)
MMKKTYNHILVWGVIFYSICIVCFCFTPQEQSTVGVGTPGIQHLGRLVFLLTPFNSLWKL
GEVSDIGQLCWIFLQNILNVFLFFPLIFQLLYLFPNLRKTKKVLLFSFLVSLGIECTQLILDF
FFDFNRVFEIDDLWTNTLGGYLAWLLYKRLHKVRNZ
```

TABLE 2-continued (SEQ. ID. NO. 119)
MKIPLLTFLARHKFVYVLLTLLFLALVYRDVLMYFFDIHAPDLAKFDGQAIKNDLLKSA
LDFRILQNLGQSFIIPIIIVLLGFQYIELKNXVLRLSRBVSYQGLKRKLTLQVASIPCLIYLV
TVLUAHTYFFGTFSPLGWNSLSDGSGLQRLLDGEIKSYLFFTCVLLIGIFINAIYFLQIVDY
VGNVTRSAITYLMFLWLGSMLLYSALPYYMVPMTSLMQASYGDVSLMKLPYILYIVPY
MVLEICYEDNVZ (SEQ. ID. NO. 120)
MFKVLQKVGKAFMLPIAILPAAGLLLGLGGALSNPRTIATYPILDNSIFQSIFQVMSSAGE
VVFSNLSLLLCVGLCIGLAKRDKGTAALAGVTGYLVMTATUALVKLFMAEGSAIDTGVI
GALVVGIVAVYLHNRYNNIQLPSALGGGSPPISFSSILIGFVFFVWPPFQQLLVSTGGYSQ
AGPIGTLYGFLMRLSGAVGLHHIIYPMTYTELGGVETVAGQTVGAQKIPAQLADLAHSG
LFREGTREAGRFSTMMFGLPAACLAMYHSVPKNRRKKYAGLFGVALTSFITGITEPIEFM
FLPVSPVLYVHAFLDGVSPFIADVLNISIGNTFSGGVIDFRLFGILQGNAKTNWVLQIPGLI
WSVLYYIIFRWFTQNVLTRGEEVDSKEISESADSTSNTADYLKQDSLQIIRALGGSNNIED
VDACVTRLRVAVEVNQVDKALLKQIGAVDVIEVKGGIQAIYGAKAILYKNSINEILGVD
DZ (SEQ. ID. NO. 121)
MKFRKLACVLAGAAVLGLAACGNSGGSKDAAKSGGDGAKTEITWWAFPVFTQEKTGD
GVGTYEKSUEAFEKANPDIKVKLETDFKSGPEKNTAIEAGTAPDVLFDAPGRIIQYGKNG
KLAELNDLFTDEFVKDVNNENRVQASKAGDKAYMYPISSAPFYMAMNKKMLEDAGV
ANLVKEGWITDDFEKVLKALKDKGYTPGSLFSSSGQGGDQGTRAFISNLYSGSVTDEKVS
KYTRDDPKFVKGLEKATSWIKDNLINNGSQFDGGADIQNFANGQTSYTILWAPAQNGIQ
AKLLEASKVEVVEVPFPSDEGKPALEYLVNGFAVNNKDDKKVAASKKIQFIADDKEWG
PKDVVRTGAFPVRTSFGKLYEDKRMETSGWTQSPYYNTIDGFAEMRThWPMLQSVSNG
DEKPADALKAFTEKANETIKKAMKQZ (SEQ. ID. NO. 122)
MQSTEKKPLTAFTVISTIILLLLTVLFIPPFYWILTGAFKSQPDTIVIPPQWFPKMPTMENF
QQLMVQNPALQWMWNSVFISLVTMFLVCATSSLAGYVLAKKRFYGQRILFAIFIAAMA
LPKQVVLVPLVRIVNFMGHDTLWAVILPLIGWPFGVFLMKQFSENIPTELLESAKIDGCG
EIRTFWSVAPPVKPGFAALAIPTFINTWNDYFMQLVMLTSRNNLTISLGVATMQAEMAT
NYGLMAGAALAAVPIVTVFLVFQKSTQGITMGAVKGZ (SEQ. ID. NO. 123)
MKIMFKNFNNILLNRCIVLLLRIVLMMILINHLLSTAVQKQDAVIFFKRELSFSYNDYSEA
NLEIPICLLLNLSIFMVGWLSVILLESDLADHYHHLIRYQSSSFFDYTRKRLVVISKFFTQD
LFVWFLGLLPLGIHFKTVALFFLLAQLMMLYLLLSYUALISAGAGFSFFLYPLAFVGQE
WMMDHIVTVYLVLLSLLVMLVSRLESKFKKGZ (SEQ. ID. NO. 124)
MGKGEMGKGVIGLEFDSEVLVNKAPTLQLANGKTATFLTQYDSICTLLPAVDKEDIGQE
IIGIAKGSIESMHNLPVNLAGARVPGVNGSKAAVHEVPEFTGGVNGTEPAVHEIAEYKGS
DSLVTLTTGKDYTYKAPLAQQALPETGNKESDLLASLGLTAFLGLFTLGKXREQZ (SEQ. ID. NO. 125)
MKKTFFLLVLGLFCLLPLSVIAIDFKINSYQGDLYIHADNTAEFRQKIVYQFEEDFKGQIV
GLGRAGKMPSGFDIDPHPKIQAAKNGAELADVTSEVTEADGYTVRVYNPGQEGDIVEV
DLVWNL,KNLLPLYDDIAELNWQPLTDSSESIEKFEFHVRGDKGAEKLFFTGKLBGTIEK
SNLDYTIRLDNLPAKRGVELHAYWPRTDFASARDQGLKGNRLEENKIEDSIVREKDQSK
QLVTWVLPSILSISLLLSVCYFIYRRKTRPSVKYAKNHRLYEPPMELEPMVLSEAVY5TSL
EEVSPLVKGAGKFTFDQLIQATLLDVIDRGNVSIISEGDAVGLRLVKEDGLSSFEKDCLN
LAFSGKICEETLSNLFADYKVSDSLYRRAKVSDEKRIQARGLQLKSSPEEVLNQMQEGV
RKRVSFWGLPDYYRPLTGGEKALQVGMGALTLPLFIGFGLFLYSLDVNGYLYLPLPILG
FLGLVLSVFYYWKLRLDNRDGVLNBAGAEVYYLWTSFENMLRIARLDQAELESVVWN
RLLVYATLFGYADKVSHLMKVNQIQVENPDINLYVAYGWHSTYHSTAQMSHYASVAN
TASTYSVSSGSGSSGGGFSGGGGGGSIGAFZ (SEQ. ID. NO. 126)
MKKVRKIFQKAVAGLCCISQLTASSIVALAETPETSPAIGKVVIKBTOEGGALLGDAVFE
LKNNTDGTTVSQRTEAQTGEAIFSNIKPGTYTLTEAQPPVGYKPSTKQWTVEVEKNGRT
TVQGEQVENREEALSDQYPQTGTYPDVQTPYQUCVDGSEKNGQHKALNPNPYERVPEG
TLSKRIYQVNNLDDNQYGIELTVSGKTVYEQKDKSVPLDVVILLDNSNSMSNIRNKNAR
RAERAGEATRSLIDKTSDSENRVALVTYASTIFDGTEFTVBKGVADKNGKRLNDSLFwN
YDQTSVITNTKDYSYLKLTNDKNDIVELKNKVPTEAEDHDGNRLMYQFGATFTQKALM
KADEILTQQARQNSQKVLFHITDGVPTMSYPINFNHATFAPSYQNQLNAFFSKSPNKDGL
LSDRTQATSGEITIVRGDGQSYQMFTDKTVYEKGAPAAFPVKPEKYSEMKAAGYAVGD
PNGGYWLNWRESILAYPFNSNTAKITNHGDPTRWYYNGNIAPDGYDVFTVGIGNGDPG
TDEATATSFMQSISSKPENYTNVTDTRKILEQLNRYFHTIVTEKKSENGTITDPMGELIDL
QLGTDGRFDPADYTLTANDGSRLENGQAVGGPQNDGGLLKNAKVLYDRREKRIRVTG
LYLGTDEKVTLTYNVRLNDEFVSNKFYDTNGIfLRLHPKEVEQNTVRDFPIPKIRDVRKY
PEITSKEKKLGDIBFIKVNKNDKKPLRGAVFSLQKQHPDYPDIYGAIDQNGTYQNVRTGE
DGKLTFKNLSDGKYRLFENSEPAGYKPVQNKPIVAFQIVNGEVRDVTSVPQDIPAGYEFT
NDKHYRRNEPIPPKREYPRTGGIGMLPFYLIGCMMMGGVLLYRRKHPZ TABLE 2-continued (SEQ. ID. NO. 127)
MKSINKFLTMLAALLLTASSLFSAATVFAAGTTTTSVTVHKLLATDGDMDKIANELETG
NYAGNKVGVLPANAKEIAGTLTGSKAVPIEIELPLNDVVDAHVYPKNTEAKPKIDKDFK
GKANPDTPRVDKDTPVNHQVGDVVEYEIVTKIPALANYATANWSDRMTEGLAFNKGT
VVTVDDVALEAGDYALTEVATGFDLKLTDAGLAKVNDQNAEKTVKITYSATLNDKAIV
EVPESNDVTINYGNNPDHGNTPKPNKPNENGDLTLTKTWVDATGAPIPAGAEATFDLVN
AQTGKVVQTVTLDKNTVTVNGLDKNTEYKFVERSIKGYSADYQEITTAGEIAVKNWKD
ENPKPLDTEPKVVTYGKKFVKVNDKDNRIAGAEFEWVADKDNENVVKLVSDAQGRFEI
TGLLAGTYYLEETKQPAGYALLTSRQKFEVTATSYSATGQGIEYTAGSGKDDATKVVN
KKITIPQTGGIGTIIFAVAGAAIMGIAVYAYVKNNKDEDQLAZ (SEQ. ID. NO. 128)
MTMQKMQKMSRJFFVMALCPSLVWGAHAVQAQEDHTLVLQLENYQEVVSQLPSRDG
HRLQVWKLDDSYSYDDRVQIVRDLHSWDENKLSSFKKTSFEMTFLENQLEVSHIPNGLY
YVRSUQTDAVSYPAEPLFEMTDQTVEPLVIVAKJCTDTMVKLIKVDQDHNRLEGVGFKL
VSVARDVSEKEVPLIGEYRYSSSGQVGRTLYTDKGEIPVRNLPLGNYRYKEVELAGYAV
TTLDTDVQLVDHQLVTITVVNQKLPRGNVDFMKVDORTNTSLQGAMFKVMKEESGHY
TPVLQNGKEVVVTSGKDGRFRVEGLEYGTYYLWELQAPTGYVQLTSPVSFTIGKDTRK
ELVTVVKNNKRRJDVPDTGEETLVYLDACCHVVWZ (SEQ. ID. NO. 129)
MSHIYLSIFTSLLLMLGLVNVAQADEYLRIGMEAAYAPFNWTQDDDSNGAVKIDGTNQ
YANGYDVQIAKKAKDLGKEPLVVKTKWEGLVPALTSGKIDMIIAGMSAERICQEIAFSSS
YYTSEPVLLVKKDSAYAS&YLDDPNGAKITSQQGVYLYNLL4QIPGAKICITAMGDFAQ
MRQALEAGVDAYVSERPEALTAEAANSKFKMIQVEPGFKGEEDTAIAIGLRKNDNRISQI
NASIETSKDDQVALMDRMIKEQPAEATITEETSSSFFSQVAKILSENWQQLLRGAGITLLI
SVGTIIGLIIGLAIGVFRTAPLSENKVIYGLQKLVGWVLNVYIEIRGTPMVQSMVIYYGTA
QAFGINLDRTLAAIFIVSINTGAYMTEVRGGILAVDKGQFEAATALGMTHNQTMRKWLP
QVVRNILPATGNEFVINIKDTSVLNVISVVELYFSGNTVATQTYQYFQTFRIIAVIYFVLTF
TVTRILRFIERRMDMDTYTROANQMQTEDLKZ (SEQ. ID. NO. 130)
MTQAILEIKHLKKSYGQNEVLKDSLTHKGEVISIIGSSGSGKSTFLRINLLETPTDGQYHG
QNVLEKGYDLTQYREKLGMVFQSFNLFENLNVLENTIVAQTRVLKRERTEAEKIAKENL
EKVGMGERYWQAKPKQLSGGQKQRVALARALSMNPDAILFDETSALDPEMVGEVLKI
MQDLAQEGLTMIVVTHEMEFARDVSHRVFMDKGVLAEEGKPEDLFTNPKEDRTKEFLQ
RYLKZ (SEQ. ID. NO. 131)
MKKYQLLFSAVFSYLFFVFSLSQLTLIVQNYWQFSSQGNLPWIQNILSLLFIGVMIVVLV
QGHGYLFPJPPJCKWLWYSLTVLVLVQISFNVQTAKHVQSTAEGWAVLIGYSGTNFAEL
GIYALFFLVPLMEELYRGLLQHAFFKRFGLDLLLPSILFALPHFSSLPSLLDIFVFATVGIIF
AGLTRYTKSIYPSYAVHVINNIVATFPPFLLTFLHRVLGZ (SEQ. ID. NO. 132)
MNKKQWLGLGLVAVAAVGLAACGNRSSRNAASSSDVKTKIVTDTGGVDDKSFNQSA
WEGLQAWGKEHNKDNGFTYFQSTSEADYANNLQQAAGSYNLIFGVGFALNNAVKDA
AKEHTDLNYYLIDDVIKDQKNVASVTFADNESGYLAGVAAAKTTKTKQVGFVGGIESE
VISRFEAGFKAGVASVDPISKVQVDYAGSFGDAAKGKTIAAQYAAGADIVYQVAGGTG
AGVFAEAKSLNESRPENEKVWIGVDRDQEAEGKYTSKDGKESNFVLVSTLKQVGTTVK
DISNKAERGEFPGGQVIVYSLKDKGVDLAVTNLEEGKKAVEDAKAKILDGSVKYEKZ (SEQ. ID. NO. 133)
MSKKLQQISVPLISVFLGILLGAIVMWIFGYDAIWGYEELPYTAFGSLRGIGEIFRAMGPL
VLIGLGFAVASRAGFPNVGLPGQALAGWILSGWFALSHPDMPRPLMILATIVIALIAGGI
VGAIPGILRAYLGTS2VIVTIMMNYIVLYVGNAPIHAPPKDFMQSTDSTIRVGANATYQT
PWLAELTGNSRMNIGIFFAIIAVAVIWFMLKKTRLGFEIRAVGLNPMASEYAGISAKRTH
LSMIISGALAGLGGAVEGLGTFQNVYVQGSSLAIGFNGMAVSLLAANSPIGILPAAFLFG
VLQVGAPGMNAAQVPSELVSIVTASIIFFVSVEYLIERPVKPKKQVKGGKZ (SEQ. ID. NO. 134)
MGVKKLKLTSLLGSLLITACATNGVTSDITAESADWSKLVYFFAEIIRYLSFDISIGVGuLF
RVLIRTVLLPVQVQMVASRKMQEAQPRIKALREQYPGRDMESRTKLEQEMRKVFKEM
GVRQSDSLWPILIQMPVILALFQALSRVDFLKTGHFLWINLGSVDTRLVLPILAAVFTFLS
TWLSNKALSERNGATTAMMYGIPVLIRPAVYAPGGVALYWTVSNAYQVLQTYFLNNPF
KIIAEREAVVQAQKDLENRKRKAKKKAQKTKZ (SEQ. ID. NO. 135)
MVIDPFANELDYYLVSHFHSDHIDPYTAAAILNNPKLEHVKFIGPYHCGRIWEGWGVKE
RFLVVKPGDTIELKDMKIHAVESFDRTCLVTLPVNGADETGGELAGLAVTDEEMAQKA
VNYIPETPGGTIYHGADSHESNYFAJCHGKDFKIDVALNNYGENPVGIQDKMTSIDLLRM
AENLRTKVIIPVHYDIWSNFMASTNEILELwKMRKDRLQYDFHPFIwEVGGKYTYPQDQ
HLVEYHHPRGFDDCFEQDSNIQFKALLZ TABLE 2-continued (SEQ. ID. NO. 136)
MFLSGWLSFANYIHDLLVLFPDSPFLNAFESAIAAPLVEELSCVFVTM4PVRXKSTLTGIA
SOLCFQMIKNGYIRTDLPEGFDFTISRILERJISGIASHWTFSGLAVVGVYLLYRAYKC3Q
KVGKKQGLIFLGLALGTHFLFNSPFVELETEIPLAIPVVTAIALYGFYMAYCFVEKHNEL
MTZ (SEQ. ID. NO. 137)
MKVEPRCDVLSRMSHFFIRILIMLQELVERSWAIRQAYHELEVKHHDSKVRRVEEDLLA
LSNDIGNPQRLVMTKQGRYYDETPYTLEQKLSENIWWLLELSQRLDIDILTEMENFLSDK
EKQLNVRTWKZ (SEQ. ID. NO. 138)
MLDWKQFFLAYLRSRSRLFIYLLSLAFLVLLFQFLASLGIYFLYFPPLCCFVTILFRWDILV
ETQVYRQELLYGEREAKSPLEIALAEKLEAREMELYQQRSKAERKLTDLLDYYTLWVH
QIKTPIAASQLLVAEVVDRQLKQQLEQEIFICIDSYTNLVLQYLRLESPHDDLVLKQVQIE
DLVKEIIRKYALFRQKGLNVNLHDLDKEIVTDKJCwLLVVIEQIISNSLKYTKEGGLEIYM
DDQELCIKDTGIGIKNSDVLRVFERGFSGYNGRLTQQSSGLGLYLSKKISEELGHQIRIESE
VGKGTRVRIQFAQVNLVLEZ (SEQ. ID. NO. 139)
MELNTHNAEILLSAANKSHYPQDELPEIALAGRSNVGKSSFINTMLNRXNLARTSGKPG
QLLNFFNIDDKMRFVDVPGYGYARVSKKEREKWGCMIEEYLTRRENLAVVSLVDLRHD
PSADDVQMYEFLKYYEIPVIRVATKADKIPRGKWNKHESAIKKKLNFDPSDDFILFSSVS
KAGMDEAWDAILEKLZ (SEQ. ID. NO. 140)
MTKKQLHLVVTGMSGAGKTVAIQSFBDLGYFEDNMPPALLPKELQLVEIKEDNPKLAL
VVDMRSRSFFSEIQAVLDELENQDGLDPKILLDAADKELVARYKETRRSHPLAADGRLD
GIgLRELLAPLKNMSQNVVDRRELTPRELRITLAEQFSDQEQAQSFPJEVMSFGIKYGIPID
ADLVFDVRFLPNPYYLPELRNQTGVDEPVYDYVMNHPESEDFYQHLLALIEPILPSYQKE
GKSVLTIAMGCTGGQMRSVAFAKRLAQDLSKNWSVNEGHPDKDRRKETVNRSZ (SEQ. ID. NO. 141)
MRKPKITVIGGGTGSPVTLKSLREKDVEAAIVTVADDGGSSGELRKNMQQLTPPGDLRN
VLVAMSDMPKFYEKVFQYRFSEDAGAFAGHPLGNLUAGLEMQGSTYNAMQLLSKFPH
RGKYPSSDHPLTLVFQTEVAGHIVDMRGIIDNEVLHRLRPFIDTVLVNEKVPEYMNSNRP
DEYLVQVEHDFVGLCKQVSRVISSNPLPENGGAIDLIVDELMRIQVKKZ (SEQ. ID. NO. 142)
MKNLIKLLIUVNLADSVFYIVALWHVSNNYSSSMFLGFIAVNYLPDLLLIGPVDRVNPQK
ILIILVQLAVAVIFTLLLNQISFWVIMSLVFSVMASSISYVIEDVLIQVVEYDKIVFANSLFSI
SYKVLDSFNSFFLQVAVGILLVKIDIGIPLLALFILLLLKRTSNANIENFSFKYYKREVLQG
THFILNNGLLFTSISLTLINFFYSFQTVVVPFSIRYGPIJYGIPLTGLGGILGNMLAPIVIKYL
KSNQVGVFLFLNGSSWLVAIVIKDYTLSLILFFVCFMSKGVNIINSLYQQIPPHQLLGRVN
TTIDSIISFGMPIGSLVAGTLIDLNIELVLIAISIPYFLFSYLFYTDNGLKEFSIYZ (SEQ. ID. NO. 143)
MMSNKNKEILIFAILYTVLFMFDGVKLLASLMPSAIANYLVYVVLALYGSFLFKDRLIQQ
WKEIRKTKRKFFFGVLTGWLFLILMTVVFEFVSEMLKQFVGLDGQGLNQSNIQSTFQEQ
PLLIAVFACVIGPLVEELFFRQVLLHYLQERLSGLLSIILVGLVFALTHMHSLALSEWIGA
VGYLGGGLAFSIIYVKEKENIYYPLLVHMLSNSLSLIILAISLVKZ (SEQ. ID. NO. 144)
LKKPIIEFKNVSKVFEDSNTCVLKDNFELEEGICYTLLGASGSGKSTILNHAGLLDATRGD
IMLDGVRINDPTIKRDVHTVFQSYALFPHMNVFENVAFPLRLRKIDKKEIEQRVAEVLK
MVQLEGYEKRSLRKLSGGQRQRVAIARAIINQPRVVLLDEPLSALDLKLRTDMQYELRE
LQQRLGITFVFVTHDQEALAMSDWTVMNDGETVQSGTPVDIYDEPINHFVATFGB
SNILPGTMIEDYLVEFNGKREAVDGGMKPNEPVEVVIRPEDLRTLPEEGKLQVKVDTQL
FRGVHYEUAYDELGNEWMIHSTRKAVGEEGLDFBPEDIHIMRLNETEEEFDAPJEEYVEI
EEQEAGLINAIEEERDEENKLZ (SEQ. ID. NO. 145)
MKSMRILFLLALIQISLSSCFLWKECILSFKQSTAFFIGSMVFVSGICAGVNYLYTRKQEV
HSVLASKKSVKLFYSMLLLNLLGAVLVLSDNLFKNLQQELVDFLLPSFFLFGLDLLIFLP
LKXYVRDFLAMLDRXTVLVTILATLLFLRNPMTVSLLIYIGLGLFFAAYLVPNSVKKEVS
FYGHIRDLVLVIVTLIFFZ (SEQ. ID. NO. 146)
MVKKIIGMVLALLSVTVVGVGVFAYTIYQQGTETLAIZTYKKIGEETKVIEATEPLTILLM
GVURGNVERTETWVGRSDSMILMTVNPKTKRITMMSLERDILTRIESGNGQAHEAKLNS
AYADGGAELAIETIQKMMNIHIDRYVMVNMRGLQKLVDAVGGRRVNNLGFPISSDQEE
NTSIGVGEQHIGGEEALVYARMRYQDPEGDYGRQKRQREVIQKVMEKALSLNSIGHYQ
EILKALSDNMQTNIDLSAKSPNLLGYPZDSFKTIETQQLQGEGEILQGVSYQIVSRAHMLE
MQNLLRRSLGQEEVTQLETNAVLFEDLFGRAPVGDEDNZ (SEQ. ID. NO. 147)
MKKQAYVUALTSFLFVFFFSHSLLEILDFDWSIFLHDVEKTEKTVFLLLVFSMSMTCLLA
LFwRGIEELSLRKMQANLKRLLAGQEVVQVADPDLDASFKSLSGKLNLLTEALQKAEN TABLE 2-continued

```
QSLAQEEEIIEKERKRIARDLHDTVSQELFAAHMILSGISQQALKLDREKMQTQLQSVTAI
LETAQKDLRVLLLHLRPVELEQKSLIEGIQILLKELEDKSDLRVSLKQNMTKLPKKLEEHI
FRJLQELSNTLRHAQASCLDVYLYQTDVELQLKVVDR4GIGFQLGSLDDLSYGLRNIKER
VEDMAGTVQLLTAPKQGLAVDIRIPLLDKEZ
```

(SEQ. ID. NO. 148)
```
MIVSIISQGFVWAILGLGIFMTFRILNFPDMTTEGSIPLGGAVAVTLITKGVNPFLATLVAV
GAGCCLAGMAAGLLYTKGKIPTLLSGILVMTSCHSIMLLIMGRANLGLLGTKQIQDVLPF
DSDLNQLLTGLRFVSRVXALMLPLLDTKLGQAYIATGDNPDMARSFGHTGRMELMGL
VLSNGVIALAOALAQQEGYADVSRGGVIVVGLASLIIGEVISLAEPVTIVVGSIAYQFLV
WAVIAIOFNTSYLRLYSALILAVCLMUTFKQTILKGAJCLSKZ
```

(SEQ. ID. NO. 149)
```
MKKMKVWSTVLATGVALTRLAACSGGSNSTTASSSEEKADKSQELVIYSNSVSNGRGD
WLTAXAEAGFNIKMVDIAGAQLADRVLAEKNNAVADMVFGIGAVDSNKIRDQKLLVQ
YKPKWLDKIDQSLSDKDNYYNPVIVQPLVLIGAPDVKEMPKDWTELGSKYKGKYSISGL
QGGTGRALASILVRYLDDKGELGVSEKGWEVAICEYLKNAYTLQKOESSIVKMLDKED
PIQYGMMWGSGALVGQKEQNVVPKVMTPEIGVPFVTEQTMVLSTSKKQALAKEFIDWF
GQSEIQVEYSKNFGSIPANKDALKDLPEDTKKFVDQVKPQNIDWEAVGKHLDEWVEKA
ELEYVQZ
```

(SEQ. ID. NO. 150)
```
MIKFDNIQIKYGDFVAIDNLNLDHEGEFTFLGPSGCGKSTLRALVGFLDPSSGSIEVNGTD
VTHLEPEKRGIGVFQSYALFPTMTVDNIAFGLKVKKVAPDVIKAKVSAVAAKIKISDQQL
QRNVSELSGGQQQRVALARLVLEPKILCLDEPLSNLDAKLRVDLRKELKRLQKELGRIT
LYVTHDQEEALTLSDRIAVFNNGYIEQVGTPVEIYHNSQTEVCDPIGDNVLTDETVHEVL
LKNTSVFLEDKKGYIRLEKVRFNRETEQDFLKGTUDVEFSGVTEHYTIKVSESQILNVTSI
DSQAARSVGESVELFITPSDVLQFZ
```

(SEQ. ID. NO. 151)
```
MRHKLNLKDWLRLGLRWFLVTRIYPNFDLVVNVFVKGGESLDAVHRVLKQPALQSMN
SPSLIVNVVGILCVLFTEYFDIKGAKZLKLGYMTSLIYGGVVLATGYKFVYGPYGLITKF
LQNVIPSLDPNWPIGYGAVLFIMTFSGTANHTLFLTNTHSVDYTIEARNMGKPVFRICVV
LPTLITLFALTIMVFLSGLSAVAAPMIVGGKEFQTINPMIITFAGMGNSRDLAALLAIILGI
ATTILLLTIMNKIEKGGNYISISKTKAPLKKQKIASKPWNIIAHIVAYGLFTVFMLPLIFIVLY
SPTDPVVIALNFNSLLTDFDLSVFLYHPLAQPLGITIPSAGDETATSNAQALVF/RYTIVLM
IISGTVLYPTQPJGPJVPJ CZ
```

TABLE 3

ID201 - 4106.4

(SEQ. ID. NO. 168)
```
ATGATAAAAAATCCTAAATTATTAACCAAGTCTTTTTTAAGAAGTTTTGCAATTCTA
GGTGGTTGGTCTAGTCATTCATATAGCTATTTATTTGACCTTTCCTTTTTATTATATTC
AACTGGAGGGGAAAAGTTTAATGAGAGCGCAAGAGTGTTTACGGAGTATTAAAG
ACTAAGACATCTGATGAAATTCCAAGCTTACTCCAGTCTTATTCAAAGTCCTTGACC
ATATCTGCTCACCTTAAAAGAGATATTGTAGATAAGCGGCTCCCTCTTGTGCATGAC
TTGGATATTAAAGATGGAAAGCTATCAAATTATATCGTGATGTTAGATATGTCTGTT
AGTACAGCAGATGGTAAACAOGTAACCGTGCAATTTGTTCACGGGGTGGATGTCTA
CAAAGAAGCAAAGAATATTTTGCTTTTGTATCTCCCATATACATTTTTGGTTACAATT
GCTTTTTCCTTTGTTTTTCTTATTTTATACTAAACGCTTGCTCAATCCTCTTTTTTAC
ATTTCAGAAGTGACTAGTAAAATGCAAGATTTGGATGACAATATTCGTTTTGATGAA
AGTAGGAAAGATGAAGTTGGTGAAGTTGGAAAACAGATTAATGGTATGTATGAGCA
CTTGTTGAAGGTTATTTATGAGTTGGAAAGTCGTAATGAGCAAATTGTAAAATTGCA
AAAATCAAAAGGTTTCCTTTGTCCGCGGAGCATCACATGAGTTGAAAACCCCCTTTAGC
CAGTCTTAGAAATTATCCTAGAGAATATGCAGCATAATATTGGAGATTCAAAGATCA
TCCAAAATATATTGCAAAGAGTATAAATAAGATTGACCAGATGAGCCACTTATTAG
AAGAAGTACTGGAGTCTTCTAAATTCCAAGAGTGGACAGAGTGTCGTGAGACCTTG
ACTGTTAAGCCAGTTTTAGTAGATATTTTATCACGTTATCAAGAATTAGCTCATTCAA
TAGGTGTTACAATTGAAATCAATTGACAGATGCTACCAGGGTCGTCATGAGTCTTA
GGGCATTGGATAAGGTTTTGACAAACCTGATTAGTAATGCAATTAAATATTCAGATA
AAAATGGGCGTGTAATCATATCCCAGCAAGATGGCTATCTCTCTATCAAAAATACAT
GTGCGCCTCAAGTGACCAAGAACTAGAACATTTATTTGATATATTCTATCATTCTCA
AATCGTGACAGATAAGGATGAAAGTTCCGGTTTGGGTCTTTACATTGTGAATAATAT
TTTAGAAAAGCTATCAAATGGATTATAGTTTTCTCCCTTATGAACACGGTATCGAATTT
AAGATTACCTTATAG
```

(SEQ. ID. NO. 152)
```
MIKNPKLLTKSFLRSFAILGGVGLVIHIAIYLTFPFYYIQLEGEKFNESARVFTEYLKTKTS
DEIPSLLQSYSKSLTISAHLKRDIVDKRLPLVHDLDIKDGKLSNYIVMLDMSVSTADGKQ
VTVQFVHGVDVYKEAKNILLLYLPYTFLVTIAFSFVFSYFYTKRLLNPLFYISEVTSKMQ
DLDDDNIRFDESRKDEVGEVGKQINGMYEHLLKVIYELESRNEQIVKLQNQKVSFVRGAS
HELKTPLASLRIILENMQHNIGDYKDHPKYIAKSINKIDQMSHLLEEVLESSKFQEWTECR
```

TABLE 3-continued

ETLTVKPVLVDILSRYQELAHSTGVTTENGLTDATRVVMSLRALDKVLTNLTSNATTCY
SDJGRVIISEQDGYLSIKNTCAPLSDQELEHLFDIFYHSQIVTDKDESSGLGLYIVNNILESY
QMDYSFLPYEHGMEFKISLZ

ID202 - 41069

(SEQ. ID. NO. 169)
ATGGATAAAATTATTAAAACTATATCAGAAAGCGGAGCCTTTCGTGCTTTTGTCCTT
GATAGCACTGAAACCGTCCGCACTGCTCAAGAAAAACATCAAACCCAAGCTAGCTC
AACTGTAGCGCTTGGTCGAACTCTTATCGCTAGCCAGATTCTCGCAGCCAATGAAAA
AGGAAATACCAAACTTACAGTTAAGGTGTTGGGATCTAGCTCTCTAGGTGCTATTAT
CACCGTCGCTGATACCAAGGGGAACGTCAAAGGCTATGTTCAAAATCCTGGTGTTGA
CATCAAAAAGACTGCGACTGGTCAAGTCCTAGTCGGACCTTTTGTTGGAAATGGTCA
ATTCCTCGTTATCACAGACTACGGTACTGGAAATCCTTACAACTCTATAACTCCCCTC
ATCTCTGGAGAAATCGGTGAAGACCTTGCCTTTTACCTTACTGAAAGCCAACAAACG
CCTTCAGCGGTCGGCCTCAATGTCCTTTTGGACGAGGAAGACAAGGTCAAGGTTGCA
GGTGGTTTCCTAGTTCAAGTCTTGCCAGGAGCCAAGAAAGAAGAGATTGCTCGCTTT
GAAAAACGCATCCAAGAAATGCCAGCTATCTCTACTCTTCTCGAAACGTTTCCAATG
TGACTGTAGCCATGAACGCTTTATGAACGCTCTTGCCAGCCTTCCAAGCTCAGACTT
ACAGGAAATGAAAGAGGAAGACCACGGGGCAGAAATCACTTGTCAATTCTGCCAAA
CTACTTACAACTTTGATGAAAGGACCTGGAGGAACTCATTCGTGACAAATCTTAA (SEQ. ID. NO. 153)
MDKIIKTISESGAFRAFVLDSTETVRTAQEKHQTQASSTVALGRTLIASQILAANEKGNTK
LTVKVLGSSSLGAIITVADTKCNV1CGYVQPCVDTKKTATGEVLVGPFVGNGQFLVTTD
YGTG&PYNSTTPLTSGETGEDLAFYLTESQQTPSAVGLNLLDEEDKVKVAGGFLVQVLP
GAKKEETARFETCRTQEMPATSTLLESDDHIEALLKATYGDEAYKRLSEEEIRFQCDCSH
ERFMNALASLPSSDLQEMKEEDHGAEITCQFCQTTYNFDEKDLEELIRDKSZ

ID203 - 4115

(SEQ. ID. NO. 170)
ATGAAATCAATAACTAAAAAGATTAAAGCAACTCTTGCAGGAGTAGCTGCCTTGTTT
GCAGTATTTGCTCCATCATTTGTATCTGCTCAAGAATCATCAACTTACACTGTTAAAG
AAGGTGATACACTTTCAGAAATCGCTGAAACTCACAACACAACAGTTGAAAAATTG
GCAGAAAACAACCACATTGATAACATTCATTTGATTTATGTTGATCAAGAGTTGGTT
ATCGATGGCCCTGTAGCGCCTGTTGCAACACCAGCGCCAGCTACTTATGCGGCACCA
GCCGCTCAAGATGAAACTGTTTCAGCTCCAGTAGCAGAAACTCCAGTAGTAAGTGA
AACAGTTGTTTCAACTGTAAGCGGATCTGAAGCAGAAGCCAAAGAATGGATCGCTC
AAAAAGAATCAGGTGGTAGTATACAGCTACAAATGGACGTTATATCGGACGTTACC
AATTAA (SEQ. ID. NO. 154)
MKSITKKIKATLAGVAALFAVFAPSFVSAQESSTYTVKEGDTLSEIAETHNTTVEKLAEN
NHTDNTHLTYVDQELVIDGPVAPVATPAPATYAAPAAQDETVSAPVAETPVVSETVVST
VSGSEAEAKEWIAQKESGGSIQLQMDVISDVTNZ

ID204 - 4111.7

(SEQ. ID. NO. 171)
ATGAATTTAGGAGAATTTTGGTACAATAAAATAAATAAGAACAGAGGAAGAAGGTT
AATGAAGAAAGTAAGATTTATTTTTTTAGCTCTGCTATTTTTCTTAGCTAATCCAGAG
GGTGCAATGGCTAGTGATGGTACTTGGCAAGGAAAACAGTATCTGAAAGAAGATGG
CAGTCAAGCAGCAAATGAGTGGGTTTTGATACTCATTATCAATCTTGGTTCTATAT
AAAAGCAGATGCTAACTATGCTGAAAATGAATGGCTAAAGCAAGGTGACGACTATT
TTTACCTCAAATCTGGTGGCTATATGGCCAAATCAGAATGGGTAGAAGACAAGGA
GCCTTTTATTATCTTGACCAAGATGGAAAGATGAAAAGAAATGCTTGGGTAGGAACT
TCCTATGTTGGTGCAACAGGTGCCAAAGTAATAGAAGACTGGGTCTATGATTCTCAA
TACGATGCTTGGTTTTATATCAAAGCAGATGGACAGCACGCAGAGAAAGAATGGCT
CCAAATTAAAGGGAAGGACTATTTATTTCAAATCCGGTGGTTATCTACTGACAAGTCA
GTGGATTAATCAAGCTTATGTGAATGCTAGTGGTGCCAAAGTACAGCAAGGTTGGCT
TTTTGACAAACAATACCAATCTTGGTTTTACATCAAAGAAAATGGAAACTATGCTGA
TAAAGAATGGATTTTCGAGAATGGTCACTATTATTATCTAAAATCCGGTGGCTACAT
GGCAGCCAATGAATGGATTTGGGATAAGGAATCTTGGTTTTATCTCAAATTTGATGG
GAAAATGGCTGAAAAGAATGGGTCTACGATTCTCATAGTCAAGCTTGGTACTACTT
CAAATCCGGTGGTTACATGACAGCCAATGAATGGATTTGGGATAAGGAATCTTGGTT
TTATCTCAAATCTGATGGGAAAATAGCTGAAAAGAATGGGTCTACGATTCTCATAG
TCAAGCTTGGTACTACTTCAAATCCGGTGGTTACATGACAGCCAATGAATGGATTTG
GGATAAGGAATCTTGGTTTTACCTCAAATCTGATGGGAAAATAGCTGAAAAGAAT
GGGTCTACGATTCTCATAGTCAAGCTTGGTACTACTTCAAATCTGGTGGCTACATGG
CGAAAAATGAGACAGTAGATGGTTATCAGCTTGGAAGCGATGGTAAATGGCTTGGA
GGAAAAACTACAAATGAAAATGCTGCTTACTATCAAGTAGTGCCTGTTACAGCCAAT
GTTTATGATTCAGATGGTGAAAAGCTTTCCTATATATCGCAAGGTAGTGTCGTATGG
CTAGATAAGGATAGAAAAAGTGATGACAAGCGCTTGGCTATTACTATTTCTGGTTTG
TCAGGCTATATGAAAACAGAAGATTTACAAGCGCTAGATGCTAGTAAGGACTTTATC
CCTTATTATGAGAGTGATGGCCACCGTTTTTATCACTATGTGGCTCAGAATGCTAGT
ATCCCAGTAGCTTCTCATCTTTCTGATATGGAAGTAGGCAAGAAATATTATTCGGCA
GATGGCCTGCATTTTGATGGTTTTAAGCZTGAGAATCCCTTCCTTTTCAAAGATTTAA
CAGAGGCTACAAACTACAGTGCTGAAGAATTGGATAAGGTATTTAGTTTGCTAAAC

TABLE 3-continued

```
ATTAACAATAGCCTTTTGGAGAACAAGGGCGCTACTTTTAAGGAAGCCGAAGAACA
TTACCATATCAATGCTCTTTATCTCCTTGCCCATAGTGCCCTAGAAAGTAACTGGGG
AAGAAGTAAAATTGCCAAAGATAAGAATAATTTCTTTGGCATTACAGCCTATGATAC
GACCCCTTACCTTTCTGCTAAGACATTTGATGATGTGGATAAGGGAATTTTAGGTGG
AACCAAGTGGATTAAGGAAAATTATATCGATAGGGGAAGAACTTTCCTTGGAAACA
AGGCTTCTGGTATGAATGTGGAATATGCTTCAGACCCTTATTGGGCGAAAAAATTG
CTAGTGTGATGATGAAAATCAATGAAAGCTAGGTGGCAAAGATTAG
```

(SEQ. ID. NO. 155)
```
MNLGEFWYNKINKNRGRRLMKKVRFIFLALLFFLASPEGAMASDGTWQGKQYLKEDG
SQAANEWVFDTHYQSWFYIKADANYAENEWLKQGDDYFYLKSGGYMAKSEWVEDK
GAFYYLDQDGKMKRNAWVGTSYVGATGAKVIEDWVYDSQYDAWFYIKADGQHAEK
EWLQIKGKDYYFKSGGYLLTSQWINQAYVNASGAKVQQGWLFDKQYQSWFYTKENG
NYADKEWIFENGHYYYLKSGGYMAANEWIWDKESWFYLKFDGKMAEKEWVYDSHS
QAWYYFKSGGYMTANEWTWDKESWFYLKSDGKIAEKEWVYDSHSQAWYYFKSGGY
MTANEWIWDKESWFYLKSDGKIAEKEWVYDSHSQAWYYFKSGGYMAKNETVDGYQL
GSDGKWLGGKTTNENAAYYQVVPVTANVYDSDGEKLSYISQGSVVWLDKDRKSDDK
RLAITISGLSGYMKTEDLQALDASKDFIPYYESDGHRFYHYVAQNASIPVASHLSDMEV
GKKYYSADGLHFDGFKLENPFLFKDLTEATNYSAEELDKVFSLLNINNSLLENKGATFK
EAEEHYHINALYLLAHSALESNWGRSKIAKDKNNFFGITAYDTTPYLSAKTFDDVDKGI
LGATKWIKENYIDRGRTFLGNKASGMNVEYASDPYWGEKIASVMMKINEKLGGKDZ
```

ID205 - 41181.1

(SEQ. ID. NO. 172)
```
ATGAAAAAATTAGGTACATTACTCGTTCTCTTTCTTTCTGCAATCATTCTTGTAGCAT
GTGCTAGCGGAAAAAAAGATACAACTTCTGGTCAAAAACTAAAAGTTGTTGCTACA
AACTCAATCATCGCTGATATTACTAAAAATATTGCTGGTGCAAAATTGACCTTCATA
GTATCGTTCCGATTGGGCAAGACCCACACGAATACGAACCACTTCCTGAAGACGTTA
AGAAAACTTCTGAGGCTAAATTTGATTTTCTATAACGGTATCAACCTTGAAACAGGT
GGCAATGCTTGGTTTACAAAATTGGTAGAAAATGCCAAGAAACTGAAAACAAAGA
CTACTTCGCAGTCAGCGACGGCGTTGATGTTATCTACCTTGAAGGTCAAATGAAAA
AGGAAAAGAAGACCCACACGCTTGGCTTAACCTTGAAAACGGTATTATTTTTGCTAA
AAATATCGCCAAACAATTGAGCGCCAAAGACCCTAACAATAAAGAATTCTCATGAA
AAAAATCTCAAAGAATATACTGATAAGTTAGACAAACTTGATAAAGAAGTAAGGA
TAAATTTAATAAGATCCCTGCTGAAAAGAAACTCCATTGTAACCAGCGAAAGGAGC
ATTCAAATACTTCTCTAAAGCCTATGGTGTCCCAAGTGCTTTACATCTGGGAAATCA
ATACTGAAGAAGAAGGAACTCCTGAACAAATCAAGACCTTGGTTGAAAAACTTCGC
CAAACAAAACTTCCATCACTCTTTGTAGAATCAAGTGTGGATGACCGTCAATGAAA
ACTGTTTCTCAAGCACACAAACATCCCAATCTACGCTCAAATCTTTACTGACTCTATCG
CAGAACAAGGTCCCGAAGGCGACAGCTACTACAGCATGATGAAATACAACCTTGAC
AAGATTGCTGAAGGATTGGCAAAATAA
```

(SEQ. ID. NO. 156)
```
MKKLGTLLVLFLSAIILVACASGKKDTTSGQKLKVVATNSIIADITKNIAGDKIDLHSIVPI
GQDPHEYEPLPEDVKKTSEANLIFYNGINLETGGNAWFTKLVENAKKTENKDYFAVSD
GVDVIYLEGQNEKGKEDPHAWLNLENGIIFAKNIAKQLSAKDPNNKEFYEKNLKEYTDK
LDKLDKESKDKFNKIPAEKKLIVTSEGAFKYFSKAYGVPSAYIWEINTEEEGTPEQIKTLV
EKLRQTKVPSLFVESSVDDRPMKTVSQDTNIPIYAQIFTDSIAEQGKEGDSYYSMMKYNL
DKIAEGLAKZ
```

ID206 - 41191.1

(SEQ. ID. NO. 173)
```
ATGGAATGGTATAAAAAAATCGGACTTCTTGCAACTACAGGTTTAGCTTTGTTTGGG
CTCGGCGCTTGCTCCAACTATGGTAAATCTGCGGATGGCACAGTGACCATCGAGTAT
TTCAACCAGAAAAAAGAAATGACCAAAACCTTGGAAGAAATCACTCGTGATTTTGA
GAAGGAAAACCCTAAGATCAAGGTCAAGTCGTCAATGTACCAAATGCTGGTGAAG
TATTGAAGCACGCGTTCTCGCAGGAGATGTGCCTGATGTGGTCAATATTTACCCAC
AGTCCATCGAACTGCAAGAATGGGCAAAAGCAGGTGTTTTTGAAGATTGACCAACA
AAGACTACCTGAAACGCGTGAAAATGGCTACGCTGAAAAATATGCTGTAAACGAAA
AAGTTTACAACGTTCCTTTTACAGCTAATGCTTATGGAATTTACTACAACAAAGATA
AATTCGAAGAACTGGGCTTGAAGGTTCCTGAAACCTGGGATGAATTTGAACAGTTA
GTCAAAGATATCGTTGCTAAAGGACAAACACCATTTGGAATTGCAGGTGCAGATGC
TTGGACACTCAATGGTTACAATCAATTAGCCTTTGCGACAGCAACAGGTGGAGGAA
AAGAACAAATCAATACCTTCGTTATTCTCAACCAAATGCCATTAAATTGTCGGATC
CGATTATGAAAGATGATATCAAGGTCATGGACATCCTTCGCATCAATGGATCTAAGC
AAAAGAACTGGGAAGGTGCTGGCTATACCGATGTTATCGGAGCCTTCGCACGTGGG
GATGTCCTCATGACACCAATGGTCTTGGCGATCACAGCGATTAATGAACAAAAA
CCGAACTTTAAGATTGGGACCTTCATGATTCCAGGAAAGAAAAAGGACAAAGCTT
AACCGTTGGTGCGGAGACTTGGCATGGTCTATCTCAGCCACCACCAAACATCCAA
AAGAAGCCAATGCCTTTGTGGAATATATGACCCGTCCAGAAGTCATGCAAAAATAC
TACGATGTGGACGGATCTCCAACAGCGATCGAAGGGGTCAAACAAGCAGGAGAAG
ATTCACCGCCTTGCTGGTATGACCGAATATGCCTTTACGGATCGTCACTTGGTCTGGT
TGCAACAATACTGGACCAGTGAAGCAGACTTCCATACCTTGACCATGAACTATGTCT
TGACCGGTGATAAACAAGGCATGGTCAATGATTTGAATGCCTTCTTTAACCCGATGA
AAGCGGATGTGGATTAG
```

TABLE 3-continued (SEQ. ID. NO. 157)
MEWYKKIGLLATTGLALFGLACSNYGKSADGTVTIEYFNQKKEMTKTLEEITRDFEKE
NPKIKVKVVNVPNAGEVLKTRVLAGDVPDVVNIYPQSIELQEWAKAGVFEDLSNKDYL
KRVKNGYAEKYAVNEKVYNVPFTANAYGIYYNKDKFEELGLKVPETWDEFEQLVKDI
VAKGQTPFGIAGADAWTLNGYNQLAFATATGGGKEANQYLRYSQPNAIKLSDPIMKDD
IKVMDILRTNGSKQKNWEGAGYTDVIGAFARGDVLMTPNGSWAITAINEQKPNFKIGTF
MIPGKEKGQSLTVGAGDLAWSISATTKHPKEANAFVEYMTRPEVMQKYYDVDGSPTAI
EGVKQAGEDSPLAGMTEYAFTDRHLVWLQOYWTSEADFHTLTMNYVLTGDKQGMVN
DLNAFFNPMKADVDZ

ID207 - 4123.1

(SEQ. ID. NO. 174)
ATGAAGAAAATCAAACCGCATGGACCGTTACCAAGTCAGACTCAGCTAGCTTATCT
GGGAGATGAACTAGCAGCTTTTATCCACTTCGGTCCTAATACCTTTTATGACCAAGA
ATGGGGGACTGGACAGGAGGATCCTGAGCGCTTTAACCCGAGTCAGTTGGATGCGC
GTGAGTGGGTTCGTGTGCTCAAGGAAACGGGCTTCAAAAAGTTGATTTTGGTGGTCA
AGCACCACGATGGCTTTGTCCTTTATCCGACAGCTCACACAGATTATTCGGTTAAGG
TCAGTCCTTGGAGGAGAGGAAAGGGCGAGTTGCTCCTTGAAGTATCCCAAGCTGCC
ACAGAGTTTGATATGGATATGGGGGTCTACCTGTCACCGTGGGATGCCCATAGTCCC
CTCTATCATGTGGACCGAGAAGCGGACTACAATGCCTATTATCTGGCTCAGTTGAAG
GAAATCTTATCAAATCCTAACTATGGGAATGCTGGTAAGTTCGCTGAGGTTTGGATG
GATGGTGCCAGAGGAGAGGGCGCGCAAAAGGTTAATTATGAATTTGAAAAATGGTT
TGAAACCATTCGTGACCTGCAGGGCGATTGCTTGATTTTTTCAACAGAAGGCACCAG
TATCCGCTGGATTGGCAATGAACGAGGGTATGCAGGTGATCCACTGTGGCAAAAGG
TGAATCCTGATAAACTAGGAACAGAAGCAGAGCTGAACTATCTTCAGCACGGGGAT
CCCTCGGGCACGATTTTTTCAATCGGAGAGGCAGATGTTTCCATCCGTCCAGGCTGG
TTCTACCATGAGGATCAGGATCCTAAGTCTCTCGAGGAGTTGGTCGAAATCTACTTT
CACTCAGTAGGGCGAGGAACTCCACTCTTGCTTAATATTCCGCCGAATCAAGCTGGG
CTCTTTGATGCAAAGGATATTGAACGACTTTATGAATTTGCGACCTATCGCAATGAG
CTCTATAAAGAAGATTTGGCTCTGGGAGCTGAGGTATCTGGTCCAGCTCTTTCCGCA
GACTTTGCTTGTCGCCATTTGACAGACGGCCTTGAGACCAGCTCTTGGGCAAGCGAT
GCAGACTTGCCCATCCAGTTAGAACTCGACTTAGGTTCTCCTAAAACTTTTGATGTA
ATTGAGTTAAGAGAAGATTTGAAGCTAGGGCCCGAATCGCTGCTTTTCATGTGCAAG
TAGAGGTGGATGGTGTCTGGCAGGAGTTTGGTTCGGGTCATACTGTTGGTTACAAAC
GTCTCTTACGAGGAGCAGTTGTTGAGGCACAGAAGATACGTGTAGTCATTACAGAAT
CACAGGCCTTTGCCTTTGTTGACCAAGATTTCCCTTTATAAAACTCCTGGATTATCAA
AAAAAGAAGTTGTTCAGGAACTAGCATTTGCAGAAAAAAGCCTAGCTGTGGCAAAG
GGAGAAAATGCCTATTTTACAGTTAAGCGCAGAGAATGTAGTGGTCCTTTAGAAGCT
AAGATTTCGATTCAACCGGGGACAGGTGTCCATGGTGTCGCCTATCAGGATGAGATT
CAAGTCCTTGCGTTTCAAACTGGTGAGACTGAAAAAAGTCTGACGCTACCAACCTTG
TATTTCGCAGGAGATAAAACCTTGGATTTCTATCTGAACCTAACGGTGGATGGTCAG
CTTGTGGATCAACTTCAAGTCCAAGTTTCATAA (SEQ. ID. NO. 158)
MKKIKPHGPLPSQTQLAYLGDELAAFIHFGPNTFYDQEWGTGQEDPERFNPSQLDAREW
VRVLKETGFKKLILVVKHHDGFVLYPTAHTDYSVKVSPWRRGKGDLLLEVSQAATEFD
MDMGVYLSPWDAHSPLYHVDREADYNAYYLAQLKEILSNPNYGNAGKFAEVWMDGA
RGEGAQKVNYEFEKWFETIRDLQGDCLIFSTEGTSIRWIGNERGYAGDPLWQKVNPDKL
GTEAELNYLQHGDPSGTIFSIGEADVSIRPGWFYHEDQDPKSLEELVEIYFHSVGRGTPLL
LNIPPNQAGLFDAKDIERLYEFATYRNELYKEDLALGAEVSGPALSADFACRHLTDGLET
SSWASDADLPIQLELDLGSPKTFDVIELREDLKLGQRIAAFHVQVEVDGVWQEFGSGHT
VGYKRLLRGAVVEAQKTRVVTTESQALPLLTKTSLYKTPGLSKKEVVQELAFAEKSLA
VAKGENAYFTVKRRECSGPLEAKISIQPGTGVHGVAYQDEIQVLAFQTGETEKSLTLPTL
YFAGDKTLDFYLNLTVDGQLVDQLQVQVSZ

ID208 - 4125.12

(SEQ. ID. NO. 175)
ATGCTTGAAAGACTGAAAAGAATACATTATATGTTTTGGATCAGTTTAATTTTTATG
ATTTTCCCCATCCTGTCTGTAGTGACTGGGTGGCTTTCTGCCTGGCATTTATTGATTG
ATATTCTATTTGTAGTGGCATATTTGGGTGTTTTAACAACTAAGAGCCAGCGCCATC
TTGGCTATATTGGGGCCTCATGCTGACTTATGTAGTTGGGAATACTGCCTTTGTTGCT
GTTAATTATATCTGGTTTTTCTTTTTCCTATCCAATCTCTTAAGTATCATTTCAGCGT
ACGTAGTTTAAAGTCTTTACATGTCTGGACTTTTCTTCTTGCTCAAGTCCTTGTTGTG
GGGCAACTGTTGATTTTTCAGAGAATCGAAGTTGAGTTTCTATTCTATCTACTTGTAA
TTCTTACTTTTGTCGATTTAATGACTTTTGGATTGGTTCGGATTCGTATTGTCGAGGA
TTTGAAAGAAGCTCAGGTCAAGCAAAATGCTCAGATAAATCTATTGCTTGCTGAAAA
TGAACGTAGTCGTATCGGTCAGGATTTGCATGATAGTCTGGGACATACCTTTGCTAT
GCTGAGTGTCAAGACAGATTTAGCCTTGCAGTTATTTCAGATGGAGCTTATCCACAG
GTGGAAAGGAATTAAAGAAATTCACCAGATAGCAGGATCCATGA (SEQ. ID. NO. 159)
MLERLKRTHYMFWTSLTFMTFPPTLSVVTGWLSAWHLLTDTLFVVAYLGVLTTKSQRLS
WLYWGLMLTYVVGNTAFVAVNYIWFFFLSNLLSYHFSVRSLKSLHVWTFLLAQVLVV
GQLLIFQRIEVEFLFYLLVILTFVOLMTFGLVRIRIVEDLKEAQVKQNAQINLLLAENERS
RIGQDLHDSLGHTFAMLSVKTDLALQLFQMEAYPQVEKELKEIHQISKDPZ

TABLE 3-continued

ID209 - 4126.3

(SEQ. ID. NO. 176)
ATGAATGATAAGTTAAAAATCTTCTTGTTGCTAGGAGTATTTTTTCTAGCCATAACCG
GTTTCTATGTTCTATTGATACGAAATGCAGGGCAGACAGATGCCTCGCAAATTGAAA
AGGCGGCAGTTAGCCAAGGAGGAAAAGCAGTGAAAAAAACAGAAATTAGTAAAGA
CGCAGACTTGCACGAAATTTATCTAGCTGGAGGTTGTTTCTGGGGAGTGGAGGAATA
TTTCTCACGTGTTCCCGGGGTGACGGATGCCGTTTCAGGCTATGCAAATGGTAGAGG
AGAAACAACCAAGTACGAATTGATTAACCAAACAGGTCATGCAGAAACCGTCCATG
TCACCTATGATGCCAAGCAAATTTCTCTCAAGGAAATCCTGCTTCACTATTTCCGCAT
TATCAATCCAACCAGCAAA)*ATAAACAAGGAAATGATGTGGGGACCCAGTACCGTA
CTGGTGTTTATTACACAGATGACAAGGATTTGGAAGTGATTAACCAAGTCTTTGATG
AGGTGGCTAAGAAATACGATCAACCTCTAGCAGTTGAAAAGGAAAACTTGAAGAAT
TTTGTGGTGGCTGAGGATTACCATCAAGACTATCTAAAGAAAAATCCAAATGGCTAC
TGCCATATCAATGTTAATCAGGCGGCCTATCCTGTCATTGATGCCAGCAAATATCCA
AAACCAAGTGATGAGGAATTGAAAAAGACCCTGTCACCTGAGGAGTATGCAGTTAC
CCAGGAAAATCAAACAGAACGAGCTTTCTCAAACCGTTACTGGGATAAATTTGAAT
CCGGTATCTATGTGGATATAGCAACTGGGGAACCTCTCTTTTCATCAAAAGACAAAT
TTGAGTCTGGTTGTGGCTGGCCTAGTTTTACCCAACCCATCAGTCCAGATGTTGTCAC
CTACAAGGAAGATAAGTCCTACAATATGACGCGTATGGAAGTGCGGAGCCGAGTAG
GAGATTCTCACCTTGGGCATGTCTTTACGGATGGTCCACAGGACAAGGGCGGCTTAC
GTTACTGTATCAATAGCCTCTCTATCCGCTTTATTCCCAAAGACCAAATGGAAGAAA
AAGgcTACGCTTATTTACTAGATTATGTTGATAA (SEQ. ID. NO. 160)
MNDKLKIFLLLGVFFLAITGFYVLLIRNAGQTDASQIEKAAVSQGGKAVKKTEISKDADL
HETYTAGGCFWGVEEYFSRVPGVTDAVSGYANGRGETTKYELINQTGHAETVHVTYD
AKQISLKEILLHYFRIINPTSKNKQGNDVGTQYRTGVYYTDDKDLEVINQVFDEVAKKY
DQPLAVEKENLKNFVVAEDYHQDYLKKNPNGYCHINVNQAAYPVIDASKYPKPSDEEL
KKTLSPEEYAVTQENQTERAFSNRYWDKFESGIYVDIATGEPLFSSKDKFESGCGWPSFT
QPISPDVVTYKEDKSYNMTRMEVRSRVGDSHLGMVFTDGPQDKGGLRYCINSLSIRFIP
KDQMEEKGYAYLLDYVDZ

ID210 - 4127.1

(SEQ. ID. NO. 177)
ATGAAAAAGAAATGGATGTATTATGCTGCTTGTTCTTCTAATGAATCTGCCGATGAC
AGTTCATCTGATAAAGGAGACGGCGGTTCGCTAGTCGTTTATTCACCAAACTCAGAG
GGCTTAATTGGAGCAACTATTCCTGCCTTTGAAGAAAATATGGTATCAAAGTAGAA
CTGATTCAAGCTGGTACTGGAGAACTTTTCAAAA)ACTAGAGTCAGAAAAAGAAGTT
CCTGTAGCTGATGTTATCTTTGGTGGTTCTTATACAACATATACTACCCACGGAGAA
CTCTTTGAAAACTATACTTCAAAAGAAAATGATAATGTTATCAAAGAATATCAAAAC
ACAACTGCTACTCTACTCCTTATACACTAGATGGTAGTGTTTTAATCGTCAACCCTG
ATTTAACTAAAGGCATGAACATCGAAGGATATAACGATCTTTTCAAACCTGAACTAA
AAGGAAAAATCGCAACTGCTGACCCAGCAAACTCTTCTAGCGCCTTTGCTCATTAA
CAAATATGCTACAAGCTCAAGGTGGTTAACAAAGATGATAAGGCTTGGTCTTATGTA
AAAGATCTTTTCACACTTATTGATGGTAAAATCGGTTCAGTTCATCAGTGTCTATAA
AGTAGTCGCTGATGGAGAAATGGCTGTTGGTCTCTCTTATGAAGATCCAGCAGTTAA
ACTCTTAAATGACGGAGCTAACATTAAGGTAGTCTATCCAAAAGAAGGAACCGTCTT
CCTACCTGCTAGTGCTGCTATCGTTAAAAAATCTAAAAATATGGAAAATGCCAAGAA
ATTTATCGATTTTATTATCTCTCAAGAAGTACAAGATACACTTGGTACAACCACTACT
AACCGTCCTGTTCGTAAAAATGCTAAAACAAGCGAAAACATGAAACCAATTGACAA
AATCAAAACACTCACTGAAGATTATGATTATGTCATCAAGAATAAATCAGATATCGT
TAAGAAATACAACGAAGTCTTTACAGATATCCAATCTAAACAGTAA (SEQ. ID. NO. 161)
MKKKWMYYAACSSNESADDSSSDKGDGGSLVVYSPNSEGLIGATIPAFEEKYGIKVELI
QAGTGELFKKLESEKEVPVADVIFGGSYTQYTTHGELFENYTSKENDNVIKEYQNTTGY
STPYTLDGSVLIVNPDLTKGMNIEGYNDLFKPELKGKIATADPANSSSAFAQLTNMLQA
QGGYKDDKAWSYVKDLFTLIDGKIGSSSSSVYKVVADGEMAVGLSYEDPAVKLLNDG
ANIKVVYPKEGTVFLPASAAIVKKSKNMENAKKFIDFIISQEVQDTLGTTTTNRPVRKNA
KTSENMKPIDKIKTLTEDYDVIKNKSDIVKKYNEVFTDIQSKQZ

ID211 - 4127.2

(SEQ. ID. NO. 178)
ATGAGTGAGATCAAAATTATTAACGCCAAAAAAATCTACCACGATGTCCCTGTTATT
GAGAATTTGAACATTACAATTCCAAAAGGAAGTCTCTTTACCCTTCTTGGAGCTTCA
GGATGTGGGAAAACGACCCTTCTTCGTATGATTGCAGGTTTCAACAGTATCGAAGGT
GGAGAATTTTACTTCGATGATACAAAAATCAATAATATGGAACCCAGCAAACGCAA
TATCGGATGGTTTTCCAAAACTACGCTATTTTCCCACATTTGACTGTCCGAGACAA
CGTTGCTTTTGGTCTTATGCAAAAGAAGGTTCCAAAAGAAGAATTGATTCAACAGAC
CAACAAGTATCTTGAACTCATGCAAATTGCTCAATATGCGGATCGAAAGCCCGATAA
ACTCAGTGGTGGACAACAACGTGTCACCTTGGCATGCGCCTTAGCGGTTAATCC
AAGTGTTCTCCTCATGGACGAGCCACTTAGTAATCTGGAGGCCAAACTTCGCTTGGA
TATGCGTCAAGCCATCCGAGAATCCAACACGAAGTGGGAATTACAACTGTTTATGT
AACCCACGACCAAGAAGAAGCCATGGCTATTTCAGACCAAATTGCTGTTATGAAAG
ATGGGGTGATCCAACAAATCGGCCGACCAAAAGAACTCTATCATAAACCAGCTAAT
GAGTTTGTGGCAACCTTTATCGGACGCACAAATATTATCCCTGCCAATCTTGAAAAA

TABLE 3-continued

```
CGGAGCGACGGCGCTTATATCGTCTTTTCAGATGGCTATGCCCTTCGAATGCCAGCT
CTTGATCAGGTTGAGGAGCAAGCTATTCATGTAAGCATTCGTCCCGAAGAGTTTATC
AAAGATGAATCTGGAGATATTGAAGGAACTATTAGAGATAGCGTCTATCTTGGACT
AAATACGGATTATTTCATTGAGACAGGTTTTGCCTCAAAAATTCAAGTTAGTGAAGA
ATCAACTTTTGAAGAAGATCTACAAAAAGGCAATCGTATTCGTCTACGAATCAATAC
GCAAAAATTAAACATCTTTTCTGCAGATGGTTCCCAAAACCTGATAAAAGGAGTCAA
CCATGGAACGTAA
```

(SEQ. ID. NO. 162)
```
MSEIKIINAKKIYHDVPVIENLNITIPKGSLFTLLGASGCGKTTLLRMIAGFNSIEGGEFYFD
DTKINNMEPSKRNIGMVFQNYAIFPHLTVRDNVAFGLMQKKVPKEELIQQTNKYLELM
QIAQYADRKPDKLSGGQQQRVTLACALAVNPSVLLMDEPLSNLEAKLRLDMRQAIREIQ
HEVGITTVYVTHDQEEAMAISDQIAVMKDGVIQQIGRPKELYHKPANEFVATFIGRTNIIP
ANLEKRSDGAYIVFSDGYALRMPALDQVEEQAIHVSIRPEEFIKDESGDIEGTIRDSVYLG
LNTDYFIETGFASKIQVSEESTFEEDLQKGNRIRLRINTQKLNIFSADGSQNLIKGVNHGTZ
```

ID212 - 4136.1

(SEQ. ID. NO. 179)
```
ATGAAGAAAAAATTATTGGCAGGTGCCATCACACTATTATCAGTAGCAACTTTAGCA
CGTTGTTCGAAAGGGTCAGAAGGTGCAGACCTTATCAGCATGAAAGGGGATGTCAT
TACAGAACATCAATTTTATGAGCAAGTGAAAACGAACCCTTCAGCCCAACAAGTCTT
GTTAAATATGACCATCCAAAAAGTTTTTGAAAAACAATATGGCTCAGAGCTTGATGA
TAAAGAGGTTGATGATACTATTGCCGAAGAAAAAAAACAATATGGCGAAAACTACC
AACGTGTCTTGTCACAAGCAGGTATGACTCTTGAAACACGTAAAGCTCAAATTCGTA
CAAGTAAATTAGTTGAGTTGGCAGTTAAGAAGGTAGCAGAAGCTGAATTGACAGAT
GAAGCCTATAAGAAAGCCTTTGATGAGTACACTCCAGATGTAACGGCTCAAATCATC
CGTCTTAATAATGAAGATAAGGCCAAAGAAGTTCTCGAAAAAGCCAAGGCAGAAGG
TGCTGATTTTGCTCAATTAGCCAAAGATAATTCAACTGATGAAAAAACAAAAGAAA
ATGGTGAGAAATTACCTTTGATTCTGCTTCAACAGAAGTACCTGAGCAAGTCAAAA
AAGCCGCTTTCGCTTTAGATGTGGATGGTGTTTGTGATGTGATTACAGCAACTGGCA
CACAAGCCTACAGTAGCCAATATTACATTGTAAAACTCACTAAGAAAACAGAAAAA
TCATCTAATATTGATGACTACAAAGAAAATTAAAAACTGTTATCTTGACTCAAAA
CAAAATGATTCAACATTTGTTCAAAGCATTATCGGAAAAGAATTGCAAGCAGCCAA
TATCAAGGTTAAGGACCAAGCCTTCCAAAATATCTTTACCCAATATATCGGTGGTGG
AGATTCAAGCTCAAGCAGTAGTACATCAAACGAATAG
```

(SEQ. ID. NO. 163)
```
MKKKLLAGAITLLSVATLAACSKGSEGADLISMKGDVITEHQFYEQVKSNPSAQQVLLN
MTIQKVFEKQYGSELDDKEVDDTIAEEKKQYGENYQRVLSQAGMTLETRKAQIRTSKL
VELAVKKVAEAELTDEAYKKAFDEYTPDVTAQIIRLNNEDKAKEVLEKAKAEGADGAQ
LAKDNATDEKTKENGGEITFDSASTEVPEQVKKAAFALDVDGVSDVITATGTQAYSSQY
YIVKLTKKTEKSSNIDDYKEKLKTVILTQKQNDSTFVQSIIGKELQAANIKVKDQAFQNIF
TQYIGGGDSSSSSSTSNEZ
```

ID213 - 4137.3

(SEQ. ID. NO. 180)
```
ATGAAAAAAAATATTAAACAATATGTAACCTTAGGTACTGTAGTGGTATTATCAGCA
TTTGTTGCTAACTCAGTTGCAGCTCAGGAGACTGAAACTTCTGAAGTATCAACACCA
AAGTTGGTGCAACCTGTTGCACCAACGACTCCGATTTCGGAAGTACAACCTACATCG
GATAACTCTTCGGAAGTTACTGTACAACCTCGAACAGTTGAAACTACTGTTAAGGAT
CCATCTTCTACAGCGGAAGAAACTCCTGTCTTAGAAAAAAATAATGTTACTTTAACA
GGGGGCGGAGAAAATGTTACTAAAGAGTTAAAGGATAAATTTACTAGCGGTGACTT
TACTGTAGTGATTAAGTACAATCAGTCAAGTGAGAAAGGCTTACAAGCTCTGTTTGG
AATATCTAATTCCAAACCCGGTCAACAAAATAGTTATGTAGATGTGTTCCTAGAGA
CAATGGTGAGTTGGGGATGGAAGCGCGTGATACTTCTTCCAATAAAAATAACCTAGT
ATCCAGACCTGCTTCAGTTTGGGGTAAGTACAAACAAGAGGCTGTGACTAACACTGT
TGCAGTAGTAGCAGATTCAGTCAAAAAAACATATTCTTTATACGCAAATGGTACAAA
AGTAGTAGAAAAGAAAGTGGATAATTTCCTAAACATCAAGGATATTAAAGGTATTG
ATTACTATATGCTTGGGGGAGTGAAACGTGCAGGAAAACGGCGTTTGGTTTTAACG
GAACACTAGAAAATATCAAATTCTTTAATAGTGCATTGGATGAAGAAACTGTTAAA
AAGATGACAACAAACGCTGTTACTGGACATTTAATTTATACGGCTAATGATACAACA
GGTTCTAACTATTTCCGTATTCCAGTTCTGTATACTTTTAGCAATGGTCGGGTATTTT
CAACGATTGACGCTCGTTACGGTGGAACTCATGATTTCTTGAATAAAAATTAATATTG
CTACAAGTTATAGTGATGATAATGGTAAGACATGGACTAAACCAAAATTAACATTG
GCATTCGATGATTTTGCGCCAGTACCATTAGAATGGCCTCGTGAAGTTGGTGGACGT
GACTTACAAATCAGCGGTGGTGCAACCTATATTGACTCTGTTATTGTTGAAAAAAG
AACAAACAAGTACTCATGTTTGCTGATGTGATGCCTGCTGGAGTAAGTTTTAGAGAA
GCAACTAGAAAAGATTCAGGTTATAAACAAATTGATGGTAATTATTACCTTAAATTA
AGGAAACAAGGTGATACTGATTACAATTATACTATTCGTGAGAATGGTACTGTATAC
GACGATCGTACCAACAGACCAACTGAATTTTCAGTAGATAAAAATTTCGGTATTAAA
CAAAATGGTAATTATTTGACGGTAGAGCGG
```

(SEQ. ID. NO. 164)
```
MKKNIKQYVTLGTVVVLSAFVANSVAAQETETSEVSTPKLVQPVAPTTPISEVQPTSDNS
SEVTVQPRTVETTVKDPSSTAEETPVLEKNNVTLTGGGENVTKELKDKFTSGDFTVVIK
YNQSSEKGLQALFGISNSKPGQQNSYVDVFLRDNGELGMEARDTSSNKNNLVSRPASV
WGKYKQEAVTNTVAVVADSVKKTYSLYANGTKVVEKKVDNFLNIKDIKGIDYYMLGG
```

TABLE 3-continued

VKRAGKTAFGFNGTLENIKFFNSALDEETVKKMTTNAVTGHLIYTANDTTGSNYFRIPV
LYTFSNGRVFSSIDARYGGTHDFLNKINIATSYSDDNGKTWTKPKLTLAFDDFAPVPLE
WPREVGGRDLQISGGATYIDSVIVEKKNKQVLMFADVMPAGVSFREATRKDSGYKQID
GNYYLKLRKQGDTDYNYTIRENGTVYDDRTNRPTEFSVDKNFGIKQNGNYLTVER

ID214 - 4185

(SEQ. ID. NO. 181)
ATGAAAAAATTTAGCCTATTACTAGCTATCCTACCATTTTTGGTTGCCTGTGAGAATC
AAGCTACACCCAAAGAGACTAGCGCTCAAAAGACAATCGTCCTTGCTACAGCTGGC
GACGTGCCACCATTTGACTACGAAGACAAGGGCAATCTGACAGGCTTTGATATCGA
AGTTTTAAAGGCAGTAGATGAAAAACTCAGCGACTACGAGATTCAATTCCAAAGAA
CCGCCTGGGAGAGCATCTTCCCAGGACTTGATTCTGGTCACTATCAGGCTGCGGCCA
ATAACTTGAGTTACACAAAAGAGCGTGCTGAAAAATACCTTTACTCGCTTCCAATTT
CCAACAATCCCCTCGTCCTTGTCAGCAACAAGAAAAATCCTTTGACTTCTCTTGACC
AGATCGCTGGTAAAACAACACAAGAGGATACCGGAACTTCTAACGCTCAATTCATC
AATAACTGGAATCAGAAACACACTGATAATCCCGCTACAATTAATTTTTCTGGTGAG
GATATTGGTAAACGAATCCTAGACCTTGCTAACGGAGAGTTTGATTTCCTAGTTTTT
GACAAGGTATCCGTCAAAAGATTATCAAGGACCGTGGTTTAGACCTCTCAGTCGTT
GATTTACCTTCTGCAGATACGGGGAGCAATTATATCATTTTCTCAAGCGACCAAAAA
GAGTTTAAAGAGCAATTTGATAAAGCGCTCAAAGAACTCTATCAAGACGGAACCCT
TGAAAAACTCAGCAATACCTATCTAGGTGGTTCTTACCTCCCAGATCAATCTCAGTT
ACAATAA (SEQ. ID. NO. 165)
MKKFSLLLAILPFLVACENQATPKETSAQKTIVLATAGDVPPFDYEDKGNLTGFDIEVLK
AVDEKLSDYEIQFQRTAWESIFPGLDSGHYQAAANNLSYTKERAEKYLYSLPISNNPLVL
VSNKKNPLTSLDQIAGKTTQEDTGTSNAQFINNWNQKHTDNPATINFSGEDIGKRILDLA
NGEFDFLVFDKVSVQKIIKDRGLDLSVVDLPSADSPSNYIIFSSDQKEFKEQFDKALKELY
QDGTLEKLSNTYLGGSYLPDQSQLQZ

ID215 - 4211.1

(SEQ. ID. NO. 182)
ATGAAAAAAAATAGTTTATATATCATATCCTCACTCTTTTTTGCTTGTGTCTTATTTG
TCTATGCTACGGCGACGAATTTTCAAAACAGTACCAGTGCTAGGCAGGTAAAAACG
GAAACCTATACTAATACAGTAACAAATGTCCCTATTGACATACGCTATAATAGTGAT
AAGTATTTTATTAGCGGTTTTGCTTCAGAAGTATCAGTGGTCTTGACTGGTGCAAATC
GCCTATCGCTAGCTAGTGAAATGCAAGAAAGTACACGTAAATTCAAGGTTACTGCTG
ACCTAACAGATGCCGGTGTTGGAACGATTGAAGTTCCTTTGAGCATTGAAGATTTAC
CCAATGGGCTGACCGCTGTGGCGACTCCGCAAAAAATTACAGTCAAGATTGGTAAG
AAGGCTCAGAAGGATAAGGTAAAGATTGTACCAGAGATTGACCCTAGTCAAATTGA
TAGTCGGGTACAAATTGAAAATGTCATGGTGTCAGATAAAGAAGTGTCTATTACGA
GTGACCAAGAGACATTGGATAGAATTGATAAGATTATCGCTGTTTTGCCAACTAGCG
AACGTATAACAGGTAATTACAGTGGTTCAGTACCTTTGCAGGCAATCGACCGCAATG
GTGTTGTCTTACCGGCAGTTATCACTCCGTTTGATACAATAATGAAGGTGACTACAA
AACCAGTAGCACCAAGTTCAAGCACATCAAATTCAAGTACAAGCAGTTCATCGGAG
ACATCTTCGTCAACGAAACGAACTAGTTCAAAAACGAATTAA (SEQ. ID. NO. 166)
MKKNSLYIISSLFFACVLFVYATATNFQNSTSARQVKTETYTNTVTNVPIDIRYNSDKYFI
SGFASEVSVVLTGANRLSLASEMQESTRKFKVTADLTDAGVGTIEVPLSIEDLPNGLTAV
ATPQKITVKIGKKAQKDKVKIVPEIDPSQIDSRVQIENVMVSDKEVSITSDQETLDRIDKII
AVLPTSERITGNYSGSVPLQAIDRNGVVLPAVITPFDTIMKVTTKPVAPSSSTSNSSTSSSS
ETSSSTKATSSKTNZ

ID216 - 4127.3

(SEQ. ID. NO. 183)
ATGTTGATTGGCGAAGGGTATCGGACTTTCCCTGTCCTGATTTATACCCAATTTATTA
GCGAGGTTGGAGGAAATTCTGCTTTTGCAATTATGGCGATTATCATTGCCTTGGCAA
TTTTCCTTATCCAAAAACACATTGCAAACCGCTACAGTTTCAGCATGAATCTGCTCC
ATCCAATGAGCCTAAAAAACTACAAAAGGAAAAATGGCTGCCATTTATGCAACA
GTCTACGGAATTATCTTTATCTCTGTTTTACCTCAAATCTACTTAATTTATACCTCTTT
CCTAAAAACATCAGGTATGGTATCTGTTAAAGGTTATTCTCCAAACAGTTACAAGGT
AGCTTTTCCATCGTATGGGATCTGCTATTTTCAATACCATTCGTATCCCTTTGATGCC
TTAGTTCTAGTTGTTCTATTTGCGACATTTATCTCCTACCTAGCCGTTAGAAAACGGA
ATTTGTTTACAAACTTAATTGACAGCCTCAGTATGGTACCTTATATTGTACCAGGAA
CCGTTCTAGGGATTGCCTTCATTTCTTCCTTCAATACTGGTCTATTTGGAAGTGGATT
TCTTATGATTACAGGGACTGCTTTCATCTTGATTATGTCTCTATCTGCCAGAAGATTA
CCTTATACTATTCGCTCATCTGTTGCTAGCTTACAACAAATAGCACCAAGTATTGAA
GAAGCTGCTGAAAGCTTAGGAAGTAGTCGTCTCAATACCTTTGCTAAGATTACAACT
CCAATGATGCTATCTGGTATCATTTCTGGAGCCATCTTATCTTGA

TABLE 3-continued (SEQ. ID. NO. 167)
MLIGEGYRTFPVLIYTQFISEVGGNSAFAIMAIIIALAIFLIQKHIANRYSFSMNLLHPIEPK
KTTKGKMAAIYATVYGIIFISVLPQIYLIYTSFLKTSGMVSVKGYSPNSYKVAFHRMGSAI
FNTIRIPLIALVLVVLFATFISYLAVRKRNLFTNLIDSLSMVPYIVPGTVLGIAFISSFNTGLF
GSGFLMITGTAFILIMSLSARRLPYTIRSSVASLQQIAPSIEEAAESLGSSRLNTFAKITTPM
MLSGIISGAILSZ

TABLE 4

ID301

(SEQ. ID. NO. 196)
ATGAATAAGAAAAAAATGATTTTAACAAGTCTAGCCAGCGTCGATATCTTAGGGGC
TGGTTTTGTTACGTCTCAGCCTACTTTTGTAAGAGCAGAAGAATCTCCACAAGTTGTC
GAAAAATCTTCATTAGAGAAGAAATATGAGGAAGCAAAAGCAAAAGCTGATACTGC
CAAGAAAGATTACGAAACGGCTAAAAAGAAAGCAGAAGACGCTCAGAAAAAGTAT
GAAGATGATCAGAAGAGAACTGAGGAGAAAGCTCGAAAAGAAGCAGAAGCATCTC
AAAAATTGAATGATGTGGCGCTTGTTGTTCAAAATGCATATAAAGAGTACCGAGAA
GTTCAAAATCAACGTAGTAAATATAAATCTGACGCTAATATCAGAAAAAATTAAC
AGAGGTCGACTCTAAAATAGAGAAGGCTAGGAAAGAGCAACAGGACTTGCAAAAT
AAATTTAATGAAGTAAGAGCAGTTGTAGTTCCTGAACCAAATGCGTTGGCTGAGACT
AAGAAAAAAGCAGAAGAAGCTAAAGCAGAAGAAAAAGTAGCTAAGAGAAAATATG
ATTATGCAACTCTAAAGGTAGCACTAGCGAAGAAAGAAGTAGAGGCTAAGGAACTT
GAAATTGAAAAACTTCAATATGAAATTTCTACTTTGGAACAAGAAGTTGCTACTGCT
CAACATCAAGTAGATAATTTGAAAAAACTTCTTGCTGGTGCGGATCCTGATGATGGC
ACAGAAGTTATAGAAGCTAAATTAAAAAAAGGAGAAGCTGAGCTAAACGCTAAAC
AAGCTGAGTTAGCAAAAAAACAAACAGAACTTGAAAAACTTCTTGACAGCCTTGAT
CCTGAAGGTAAGACTCAGGATGAATTAGATAAAGAAGCAGAAGAAGCTGAGTTGGA
TAAAAAAGCTGATGAACTTCAAAATAAAGTTGCTGATTTAGAAAAAAGAAATTAGTA
ACCTTGAAATATTACTGGAGGGGCTGATCCTGAAGATGATACTGCTGCTCTTCAAA
ATAAATTAGCTGCTAAAAAAGCTGAGTTAGCAAAAAAACAAACAGAACTTGAAAAA
CTTCTTGACAGCCTTGATCCTGAAGGTAAGACTCAGGATGAATTAGATAAAGAAGC
AGAAGAAGCTGAGTTGGATAAAAAAAGCTGATGAACTTCAAAATAAAGTTGCTGATT
TAGAAAAAAGAAATTAGTAACCTTGAAATATTACTTGGAGGGGCTGATTCTGAAGAT
GATACTGCTGCTCTTCAAAATAAATTAGCTACTAAAAAAGCTGAATTGGAAAAAACT
CAAAAAGAATTAGATGCAGCTCTTAATGAGTTAGGCCCTGATGGAGATGAAGAAGA
AACTCCAGCGCCGGCTCCTCAACCAGAGCAACCAGCTCCTGCACCAAAACCAGAGC
AACCAGCTCCAGCTCCAAAACCAGAGCAACCAGCTCCTGCACCAAAACCAGAGCAA
CCAGCTCCAGCTCCAAAACCAGAGCAACCAGCTCCAGCTCCAAAACCAGAGCAACC
AGCTAAGCCGGAGAAACCAGCTGAAGAGCCTACTCAACCAGAAAAACCAGCCACTC
CAAAAACAGGCTGGAAACAAGAAAACGGTATGTGGTATTTCTACAATACTGATGGT
TCAATGGCAATAGGTTGGCTCCAAAACAACGGTTCATGGTACTACCTAAACGCTAAC
GGCGCTATGGCAACAGGTTGGGTGAAAGATGGAGATACCTGGTACTATCTTGAAGC
ATCAGGTGCTATGAAAGCAAGCCAATGGTTCAAAGTATCAGATAAATGGTACTATG
TCAACAGCAATGGCGCTATGGCGACAGGCTGGCTCCAATACAATGGCTCATGGTACT
ACCTCAACGCTAATGGTGATATGGCGACAGGATGGCTCCAATACAACGGTTCATGGT
ATTACCTCAACGCTAATGGTGATATGGCGACAGGATGGGCTAAAGTCAACGGTTCAT
GGTACTACCTAAACGCTAACGGTGCTATGGCTACAGGTTGGGCTAAAGTCAACGGTT
CATGGTACTACCTAAACGCTAACGGTTCAATGGCAACAGGTTGGGTGAAAGATGGA
GATACCTGGTACTATCTTGAAGCATCAGGTGCTATGAAAGCAAGCCAATGGTTCAAA
GTATCAGATAAATGGTACTATGTCAATGGCTTAGGTGCCCTTGCAGTCAACACAACT
GTAGATGGCTATAAAGTCAATGCCAATGGTGAATGGGTTTAA (SEQ. ID. NO. 184)
MNKKKMILTSLASVAILGAGFVTSQPTFVRAEESPQVVEKSSLEKKYEEAKAKADTAKK
DYETAKKKAEDAQKKYEDDQKRTEEKARKEAEASQKLNDVALVVQNAYKEYREVQN
QRSKYKSDAEYQKKLTEVDSKIEKARKEQQDLQNKFNEVRAVVVPEPNALAETKKKAE
EAKAEEKVAKRKYDYATLKVALAKKEVEAKELEIEKLQYEISTLEQEVATAQHQVDNL
KKLLAGADPDDGTEVIEAKLKKGEAELNAKQAELAKKQTELEKLLDSLDPEGKTQDEL
DKEAEEAELDKKADELQNKVADLEKEISNLEILLGGADPEDDTAALQNKLAAKKAELA
KKQTELEKLLDSLDPEGKTQDELDKEAEEAELDKKADELQNKVADLEKEISNLEILLGG
ADSEDDTAALQNKLATKKAELEKTQKELDAALNELGPDGDEEETPAPAPQPEQPAPAPK
PEQPAPAPKPEQPAPAPKPEQPAPAPKPEQPAPAPKPEQPAKPEKPAEEPTQPEKPATPKT
GWKQENGMWYFYNTDGSMAIGWLQNNGSWYYLNANGAMATGWVKDGDTWYYLE
ASGAMKASQWFKVSDKWYYVNSNGAMATGWLQYNGSWYYLNANGDMATGWLQY
NGSWYYLNANGDMATGWAKVNGSWYYLNANGAMATGWAKVNGSWYYLNANGSM
ATGWVKDGDTWYYLEASGAMKASQWFKVSDKWYYVNGLGALAVNTTVDGYKVNA
NGEWVZ

ID302

(SEQ. ID. NO. 197)
ATGTTTGCATCAAAAAGCGAAAGAAAAGTACATTATTCAATTCGTAAATTTAGTGTT
GGAGTAGCTAGTGTAGTTGTTGCCAGTCTTGTTATGGGAAGTGTGGTTCATGCGACA
GAGAACGAGGGAGCTACCCAAGTACCCACTTCTTCTAATAGGGCAAATGAAAGTCA

TABLE 4-continued

```
GGCAGAACAAGGAGAACAACCTAAAAAACTCGATTCAGAACGAGATAAGGCAAGG
AAAGAGGTCCAGGAATATGTAAAAAAATAGTGGGTGAGAGCTATGCAAATCAAC
TAAAAAGCGACATACAATTACTGTAGCTGCCAGTCTTGTTATGGGAAGTGTGGTTCA
TGCGACAGAGAACGAGGGAGCTACCCAAGTACCCACTTCTTCTAATAAGATACTGA
TGATGGAGAGTCGATCAAAAGTAGATGAAGCTGTGTCTAAGTTTGAAAAGGACTCA
TCTTCTTCGTCAAGTTCAGACTCTTCCACTAAACCGGAAGCTTCAGATACAGCGAAG
CCAAACAAGCCGACAGAACCAGGAGAAAAGGTAGCAGAAGCTAAGAAGAAGGTTG
AAGAAGCTGAGAAAAAAGCCAAGGATCAAAAAGAAGAAGATCGTCGTAACTACCC
AACCATTACTTACAAAACGCTTGAACTTGAAATTGCTGAGTCCGATGTGGAAGTTAA
AAAAGCGGAGCTTGAACTAGTAAAAGTGAAAGCTAACGAACCTCGAGACGAGCAA
AAAATTAAGCAAGCAGAAGCGGAAGTTGAGAGTAAACAAGCTGAGGCTACAAGGT
TAAAAAAAATCAAGACAGATCGTGAAGAAGCAGAAGAAGAAGCTAAACGAAGAGC
AGATGCTAGATGCGAAGTCTTCAGATTCTAGCGTAGGTGAAGAAACTCTTCCAAGCC
CATCCCTGAAACCAGAAAAAAAGGTAGCAGAAGCTGAGAAGAAGGTTGAAGAAGC
TAAGAAAAAAGCCGAGGATCAAAAAGAAGAAGATCGCCGTAACTACCCAACCAAT
ACTTAGAAAACGCTTGAACTTGAAATTGCTGAGTCCGATGTGGAAGTTAAAAAAGC
GGAGCTTGAACTAGTAAAAGAGGAAGCTAAGGAACCTCGAAACGAGGAAAAAGTT
AAGCAAGCAAAAGCGGAAGTTGAGAGTAAAAAAGCTGAGGCTACAAGGTTAGAAA
AAATCAAGACAGATCGTAAAAAAGCAGAAGAAGAAGCTAAACGAAAAGCAGCAGA
AGAAGATAAAGTTAAAGAAAAACCAGCTGAACAACCACAACCAGCGCCGGCTCCA
AAAGCAGAAAAACCAGCTCCAGCTCCAAAACCAGAGAATCCAGCTGAACAACCAA
AAGCAGAAAAACCAGCTGATCAACAAGCTGAAGAAGACTATGCTCGTAGATCAGAA
GAAGAATATAATCGCTTGACTCAACAGCAACCGCCAAAAACTGAAAAACCAGCACA
ACCATCTACTCCAAAAACAGGCTGGAAACAAGAAAACGGTATGTGGTACTTCTACA
ATACTGATGGTTCAATGGCGACAGGATGGCTCCAAAACAATGGCTCATGGTACTACC
TCAACAGCAATGGCGCTATGGCGACAGGATGGCTCCAAAACAATGGTTCATGGTAC
TATCTAAACGCTAATGGTTCAATGGCAACAGGATGGCTCCAAAACAATGGTTCATGG
TACTACCTAAACGCTAATGGTTCAATGGCGACAGGATGGCTCCAATACAATGGCTCA
TGGTACTACCTAAACGCTAATGGTTCAATGGCGACAGGATGGCTCCAATACAATGGC
TCATGGTACTACCTAAACGCTAATGGTGATATGGCGACAGGTTGGGTGAAAGATGG
AGATACCTGGTACTATCTTGAAGCATCAGGTGCTATGAAAGCAAGCCAATGGTTCAA
AGTATCAGATAAATGGTACTATGTCAATGGCTCAGGTGCCCTTGCAGTCAACACAAC
TGTAGATGGCTATGGAGTCAATGCCAATGGTGAATGGGTAAACTAA
```

(SEQ. ID. NO. 185)
MFASKSERKVHYSIRKFSVGVASVVVASLVMGSVVHATENEGATQVPTSSNRANESQA
EQGEQPKKLDSERDKARKEVEEYVKKIVGESYAKSTKKRHTITVALVENELNNIKNEYL
NKIVESTSESQLQILMMESRSKVDEAVSGEKDSSSSSSSDSSTKPEASDTAKPNKPTEPGE
KVAEAKKKVEEAEKKAKDQKEEDRRNYPTITYKTLELEIAESDVEVKKAELELVKVKA
NEPRDEQKIKQAEAEVESKQAEATRLKKIKTDREEAEEEAKRRADAKEQGKPKGRAKR
GVPGELATPDKKENDAKSSDSSVGEETLPSPSLKPEKKVAEAEKKVEEAKKKAEDQKEE
DRRNYPTNTYKTLELEIAESDVEVKKAELELVKEEAKEPRNEEKVKQAKAEVESKKAE
ATRLEKIKTDRKKAEEEAKRKAAEEDKVKEKPAEQPQPAPAPKAEKPAPAPKPENPAEQ
PKAEKPADQQAEEDYARRSEEEYNRLTQQQPPKTEKPAQPSTPKTGWKQENGMWYFY
NTDGSMATGWLQNNGSWYYLNSNGAMATGWLQNNGSWYYLNANGSMATGWLQNN
GSWYYLNANGSMATGWLQYNGSWYYLNANGSMATGWLQYNGSWYYLNANGDMAT
GWVKDGDTWYYLEASGAMKASQWFKVSDKWYYVNGSGALAVNTTVDGYGVNANG
EWVNZ

ID303

(SEQ. ID. NO. 198)
```
ATGGTAAAAAGACGTATAAGGAGAGGGACGAGAGAACCTGAAAAAGTTGTTGTTCC
TGAGCAATCATCTATTCCTTCGTATCCTGTATCTGTTACATCTAACCAAGGAACAGAT
GTAGCAGTAGAACCAGCTAAAGCAGTTGCTCCAACAACAGACTGGAAACAAGAAAA
TGGTATGTGGTATTTTTATAATACTGATGGTTCCATGGCAACAGGTTGGGTACAAGT
TAATAGTTCATGGTACTACCTCAACAGCAACGGTTCTATGAAAGTCAATCAATGGTT
CCAAGTTGGTGGTAAATGGTATTATGTAAATACATCGGGTGAGTTAGCGGTCAATAC
AAGTATAGATGGCTATAGAGTCAATGATAATGGTGAATGGGTGCGTTAA
```

(SEQ. ID. NO. 186)
MVKRRIRRGTREPEKVVVPEQSSIPSYPVSVTSNQGTDVAVEPAKAVAPTTDWKQENG
MWYFYNTDGSMATGWVQVNSSWYYLNSNGSMKVNQWFQVGGKWYYVNTSGELAV
NTSIDGYRVNDNGEWVRZ

ID304

(SEQ. ID. NO. 199)
```
CTGAATACAAGTTTTGTTCATGCTGCTGATGGGATTCAATATGTCAFAGATGATACT
AGAGATAAAGAAGAGGGAATAGAGTATGATGACGCTGACAATGGGGATATTATTGT
AAAAGTAGCGACTAAACCTAAGGTAGTAACCAAGAAAATTTCAAGTACGCGAATTC
GTTATGAAAAGATGAAACAAAAGACCGTAGTGAAATCCTGTTACAATTGATGGA
GAGGATGGCTATGTAACTACGACAAGGACCTACGATGTTAATCCAGAGACTGGTTA
TGTTACCGAACAGGTTACTGTTGATAGAAAAGAAGCCACGGATACAGTTATCAAAG
TTCCAGCTAAAAGCAAGGTTGAAGAAGTTCTTGTTCCATTTGCTACTAAATATGAAG
CAGACAATGACCTTTCTGCAGGACAGGAGCAAGAGATTACTCTAGGAAAGAATGGG
AAAACAGTTACAACGATAACTTATAATGTAGATGGAAAGAGTGGACAAGTAACTGA
GAGTACTTTAAGTCAAAAAAAGACTCTCAAACAAGAGTTGTTAAAAAAAGAACCA
AGCCCCAAGTTCTTGTCCAAGAAATTCCAATCGAAACAGAATATCTCGATGGCCCAA
```

TABLE 4-continued

CTCTTGATAAAAGTCAAGAAGTAGAAGAAGTAGGAGAAATTGGTAAATTACTCTTA
CTACAATCTATACTGTAG (SEQ. ID. NO. 187)
LNTSFVHAADGIQYVRDDTRDKEEGIEYDDADNGDIIVKVATKPKVVTKKISSTRIRYEK
DETKDRSENPVTIDGEDGYVTTTRTYDVNPETGYVTEQVTVDRKEATDTVIKVPAKSKV
EEVLVPFATKYEADNDLSAGQEQEITLGKNGKTVTTTTYNVDGKSGQVTESTLSQKKDS
QTRVVKKRTKPQVLVQEIPIETEYLDGPTLDKSQEVEEVGEIGKLLLLQSILZ

ID305

(SEQ. ID. NO. 200)
ATGAAGCTTTTGAAAAAAATGATGCAAATCGCACTAGCCACATTTTTCTTCGGTTTG
TTAGCGACAAATACAGTATTTGCAGATGATTCTGAAGGATGGCAGTTTGTCCAAGAA
AATGGTAGAACCTACTACAAAAAGGGGGATCTAAAAGAAACCTACTGGAGAGTGAT
AGATGGGAAGTACTATTATTTTGATCCTTTATCCGGAGAGATGGTTGTCGGCTGGCA
ATATATACCTGCTCCACACAAGGGGGTTACGATTGGTCCTTCTCCAAGAATAGAGAT
TGCTCTTAGACCAGATTGGTTTTATTTTGGTCAAGATGGTGTATTACAAGAATTTGTT
GGCAAGCAAGTTTTAGAAGCAAAAACTGCTACGAATACCAACAAACATCATGGGGA
AGAATATGATAGCCAAGCAGAGAAACGAGTCTATTATTTTGAAGATCAGCGTAGTT
ATCATACTTTAAAAACTGGTTGGATTTATGAAGAGGGTCATTGGTATTATTTACAGA
AGGATGGTGGCTTTGATTCGCGCATCAACAGATTCACGGTTGGAGAGCTAGCACGTG
GTTGGGTTAAGGATTACCCTCTTACGTATGATGAAGAGAAGCTAAAAGCAGCTCCAT
GGTACTATCTAAATCCAGCAACTGGCATTATGCAAACAGGTTGGCAATATCTAGGTA
ATAGATGGTACTACCTCCATTCGTCAGGAGCTATGGCAACTGGCTGGTATAAGGAAG
GCTCAACTTGGTACTATCTAGATGCTGAAAATGGTGATATGAGAACTGGCTGGCAAA
ACCTTGGGAACAAATGGTACTATCTCCGTTCATCAGGAGCTATGGCAACTGGTTGGT
ATCAGGAAAGTTCGACTTGGTACTATCTAAATGCAAGTAATGGAGATATGAAAACA
GGCTGGTTCCAAGTCAATGGTAACTGGTACTATGCCTATGATTCAGGTGCTTTAGCT
GTTAATACCACAGTAGGTGGTTACTACTTAAACTATAATGGTGAATGGGTTAAGTAA (SEQ. ID. NO. 188)
MKLLKKMMQIALATFFFGLLATNTVFADDSEGWQFVQENGRTYYKKGDLKETYWRVI
DGKYYYFDPLSGEMVVGWQYIPAPHKGVTIGPSPRIEIALRPDWFYFGQDGVLQEFVGK
QVLEAKTATNTNKHHGEEYDSQAEKRVYYFEDQRSYHTYLHSSGAMATGWYKEGST
WYYLDAENGDMRTGWQNLGNKWYYLRSSGAMATGWYQESSTWYYLNASNGDMKT
GWFQVNGNWYYAYDSGALAVNTTVGGYYLNYNGEWVKZ

ID306

(SEQ. ID. NO. 201)
TTGGCTGGTAGATATGGTTCTGCTGTTCAGTGTACAGAAGTGACTGCCTCAAACCTT
TCAACAGTTAAAACTAAAGCTACGGTTGTAGAAAAACCACTGAAAGATTTTAGAGC
GTCTACGTCTGATCAGTCTGGTTGGGTGGAATCTAATGGTAAATGGTATTTCTATGA
GTCTGGTGATGTGAAGACAGGTTGGGTGAAAACAGATGGTAAATGGTACTATTTGA
ATGACTTAGGTGTCATGCAGACTGGATTTGTAAAATTTTCTGGTAGCTGGTATTACTT
GAGCAATTCAGGTGCTATGTTTACAGGCTGGGGAACAGATGGTAGCAGATGGTTCT
ACTTTGACGGCTCAGGAGCTATGAAGACAGGCTGGTACAAGGAAAATGGCACTTGG
TATTACCTTGACGAAGCAGGTATCATGAAGACAGGTTGGTTTAAAGTCGGACCACAC
TGGTACTATGCCTACGGTTCAGGAGCTTTGGCTGTGAGCACAACAACACCAGATGGT
TACCGTGTAAATGGTAATGGTGAATGGGTAAACTAG (SEQ. ID. NO. 189)
LAGRYGSAVQCTEVTASNLSTVKTKATVVEKPLKDFRASTSDQSGWVESNGKWYFYES
GDVKTGWVKTDGKWYYLNDLGVMQTGFVKFSGSWYYLSNSGAMFTGWGTDGSRWF
YFDGSGAMKTGWYKENGTWYYLDEAGIMKTGWFKVGPHWYYAYGSGALAVSTTTPD
GYRVNGNGEWVNZ

ID307

(SEQ. ID. NO. 200)
ATGAAAATTTTGAAAAAAACTATGCAAGTTGGACTGACAGTATTTTTCTTTGGTTTG
CTAGGGACCAGTACAGTATTTGCAGATGATTCTGAAGGATGGCAGTTTGTCCAAGAA
AACGGAAGAACCTACTACAAAAAGGGGGACCTCAAAGAAACCTACTGGCGAGTGAT
TGATGGTAAGTACTATTATTTTGATTCTATCTGGAGAGATGGTTGTCGGCTGGCA
ATATATCCCGTTTCCATCTAAAGGTAGTACAATTGGTCCTTACCCAAATGGTATCAG
ATTAGAAGGTTTTCCAAAGTCAGAGTGGTACTACTTCGATAAAAATGGAGTGCTACA
AGAGTTTGTTGGTTGGAAACATTAGAGATTAAAACTAAAGACAGTGTTGGAAGAA
AGTACGGGGAAAAACGTGAAGATTCAGAAGATAAAGAAGAGAAGCGTTATTATAC
GAACTATTACTTTAATCAAAATCATTCTTTAGACACACGTTCGCTTTATGATCAGTCT
AACTCGTATTATCTAGCTAAGACGGAAATTAATGGAGAAAACTACCTTGGTGGTGA
AAGACGTGCGGGTGGATAAACGATGATTCGACTTGGTACTACCTAGATCCAACAA
CTGGTATTATGCAAACAGGTTGGCAATATCTAGGTAATAAGTGGTACTACCTCCGTT
CCTCAGGAGCAATGGCCACTGGCTGGTATCAGGAAGGTACCACTTGGTATTATTTAG
ACCACCCAAATGGCGATATGAAAACAGGTTGGCAAAACCTTGGGAACAAATGGTAC
TATCTCCGTTCATCAGGAGCTATGGCAACTGGTTGGTATCAAGATGGTTCAACTTGG
TACTACCTAAATGCAGGTAATGGAGACATGAAGCAGGTTGGTTCCAGGTCAATGG
CAACTGGTACTATGCTTAT

TABLE 4-continued (SEQ. ID. NO. 190)
MKILKKTMQVGLTVFFFGLLGTSTVFADDSEGWQFVQENGRTYYKKGDLKETYWRVI
DGKYYYFDSLSGEMVVGWQYIPFPSKGSTIGPYPRGIRLEGFPKSEWYYFDIOGVLQEFV
GWKTLEILKTISVGRKYGEKREDSEDKEEKRYYTNYYFNQNHSLETGWLYDQSNWYYL
AKTEINGENYLGGERRAGWINDDSTWYYLDPTTGIMQTGWQYLGNKWYYLRSSGAM
ATGWYQEGTTWYYLDHPNGDMKTGWQNLGNKWYYLRSSGAMATGWYQDGSTWYY
LNAGNGDMKTGWFQVNGNWYYAYSSGALAVNTTVDGYSVNYNGEWVRZ

ID308

(SEQ. ID. NO. 203)
ATGAAAAAGAAATTAACTAGTTTAGCACTTGTAGGCGCTTTTTTAGGTTTGTCATGG
TATGGGAATGTTCAGGCTGAAGAAAGTTCAGGAAATAAAATCCACTTTATCAATGTT
CAAGAAGGTGGCAGTGATGCGATTATTCTTGAAAGCAATGGACATTTTGCCATGGTG
GATACAGGAGAAGATTATGATTTCCCAGATGGAAGTGATTCTCGCTATCCATGGAGA
GAAGGAATTGAAACGTCTTATAAGCATGTTCTAACAGACCGTGTCTTTCGTCGTTTG
AAGGGAATTGGGTGTCCAAAAACTTGATTTTATTTTGGTGACCCATACCCACAGTGAT
CATATTGGAAATGTTGATGAATTACTGTCTACCTATCCAGTTGACCGAGTCTATCTTA
AGAAATATAGTGATAGTCGTATTACTAATTCTGAACGTCTATGGGATAATCTGTATG
GCTATGATAAGGTTTTACAGACTGCTGCAGAAAAAGGTTTCAGTTATTCAAAATA
TCACACAAGGGGATGCTCATTTTCAGTTTGGGGACATGGATATTCAGCTCTATAATT
ATGAAAATGAAACTGATTCATCGGGTGAATTAAAGAAAATTTGGGATGACAATTCC
AATTCCTTGATThGCGTGGTGAAAGTCAATGGCAAGAAAATTTACCTTGGGGCGAT
TTAGATAATGTTCATGGAGCAGAAGACAAGTATGGTCCTCTCATTGGAAAAGTTGAT
TTGATGAAGTTTAATCATCACCATGATACCAACAAATCAAATACCAAGGATTTCATT
AAAAAATTTGAGTCCGAGTTTGATTGTTCAAACTTCGGATAGTCTACCTTGGAAAAT
GGTGTTTGATAGTGAGTATGTTAATTGGCTCAAAGAACGAGGAATTGAGAGAATCA
CGCAGCCAGCAAAGACTATGATGCAACAGTTTTTGATATTCGAAAAGACGGTTTTGT
CAATATTTCAACATCCTACAAGCGATTCCAAGTTTTCAAGCTGGTTGGCATAAGAG
TGCATATGGGAACTGGTGGTATCAAGCGCCTGATTCTACAGGAGAGTATGCTGTCGG
TTGGAATGAAATCGAAGGTGAATGGTATTACTTTAACCAAACGGGTATCTTGTTACA
GAATCAATGGAAAAAATGGAACAATCATTGGTTCTATITGACAGACTCTGGTGCTTC
TGCTAAAAATTGGAAGAAAATCGCTGGAATCTGGTATTTATTTTAACAAAGAAACC
AGATGGAAATTGGTTGGATTCAAGATA)*AGAGCAGTGGTATTATTTGGATGTTGAT
GGTTCTATGAAGACAGGATGGCTTCAATATATGGGCAATGGTATTACTTTGCTCCA
TCAGGGGAAATGAAAATGGGCTGGGTAAAAGATAAAGAAACCTGGTACTATATGGA
TTCTACTGGTGTCATGAAGACAGGTGAGATGAAGTTGCTGGTCAACATTATTATCT
GGAAGATTCAGGAGCTATGAAGCAAGGCTGGCATAAAAAGGCAAATGATTGGTATT
TCTACAAGACAGACGGTTCACGAGCTGTGGGTTGGATCAAGGACAAGGATAAATGG
TACTTCTTGAAAGAAAATGGTCAATTACTTGTGAACGGTAAGACACCAGAAGGTTAT
ACTGTGGATTCAAGTGGTGCCTGGTTAGTGGATGTTTCGATCGAGAATCTGCTACA
ATTAAAACTACAAGTCATTCAGAAATAAAAGAATCCAAAGAAGTAGTGAAAAAGGA
TCTTGAAAATAAAGAAACGAGTCAACATGAAAGTGTTACAAATTTTTCAACTAGTCA
AGATTTGACATCCTCAACTTCACAAAGCTCTGAAACGAGTGTAAACAAATCGGAATC
AGAACAGTAG (SEQ. ID. NO. 191)
MKKKLTSLALVGAFLGLSWYGNVQAQESSGNKIHFINVQEGGSDAIILESNGHFAMVDT
GEDYDFPDGSDSRYPWREGIETSYKHVLTDRVFRRLKELGVQKIDFILVTHTHSDHIGN
VDELLSTYPVDRVYLKKYSDSRITNSERLWDNLYGYDKVLQTAAEKGVSVIQNITQGD
AHFQFGDMDIQLYNYENETDSSGELKKIWDDNSNSLISVVKVNGKKIYLGGDLDNVHG
AEDKYGPLIGKVDLMKFNHHHDTNKSNTKDFIKNLSPSLIVQTSDSLPWJGVDSRYVNW
LKERGILERINAASKDYDATVFDIRKDGFVNISTSYKPIPSFQAGWHKSAYGNWWYQAP
DSTGEYAVGWNEIEGEWYYFNQTGILLQNQWKKWNNHWFYLTDSGASAKNWKKIAGI
WYYFNKENQMEIGWIQDKEQWYYLDVDGSMKTGWLQYMGQWYYFAPSGEMKMGW
VKDKETWYYMDSTGVMKTGEIEVAGQHYYLEDSGAMKQGWHHKKANDWYFYKTDGS
RAVGWIKDKDKWYFLKENGQLLVNGKTPEGYTVDSSGAWLVDVSIEKSATIKTTSHSEI
KESKEVVKKDLENKETSQHESVTMYSTSQDLTSSTSQSSETSVNKSESEQZ

ID309

(SEQ. ID. NO. 204)
ATGGAAATTAATGTGAGTAAATTAAGAACAGATTTGCCTCAAGTCGGCGTGCAACC
ATATAGGCAAGTACACGCACACTCAACTGGGAATCCGCATTCAACCGTACAGAATG
AAGCGGATTATCACTGGCGGAAAGACCCAGAATTAGGTTTTTTCTCGCACATTGTTG
GGAACGGTTGCATCATGCAGGTAGGACCTGTTGATAATGGTGCCTGGGACGTTGGG
GGCGGTTGGAATGCTGAGACCTATGCAGCGGTTGAACTGATTGAAAGCCATTCAAC
CAAAGAAGAGTTCATGACGGACTACCGCCTTTATATCGAACTCTTACGCAATCTAGC
AGATGAAGCAGGTTTGCCGAAAACGCTTGATACAGGGAGTTTAGCTGGAATTAAAA
CGCACGAGTATTGCACGAATAACCAACCAAACAACCACTCAGACCACGTTGACCCT
TATCCATATCTTGCTAAATGGGGCATTAGCCGTGAGCAGTTTAAGCATGATATTGAG
AACGGCTTGACGATTGAAACAGGCTGGCAGAAGAATGACACTGGCTACTGGTACGT
ACATTCAGACGGCTCTTATCCAAAAGACAAGTTTGAGAAAATCAATGGCACTTGGTA
CTACTTTGACAGTTCAGGCTATATGCTTGCAGACCGCTGGAGGAAGCACACAGACG
GCAACTGGTACTGGTTCGACAACTCAGGCGAAATGGCTACAGGCTGGAAGAAATC
GCTGATAAGTGGTACTATTTCAACGAAGAAGGTGCCATGAAGACAGGCTGGGTCAA
GTACAAGGACACTTGGTACTACTTAGACGCTAAAGAAGGCGCCATGGTATCAAATG

TABLE 4-continued

CCTTTATCCAGTCAGCGGACGGAACAGGCTGGTACTACCTCAAACCAGACGGAACA
CTGGCAGACAAGCCAGAATTCACAGTAGAGCCAGATGGCTTGATTACAGTAAAATA
A (SEQ. ID. NO. 192)
MEINVSKLRTDLPQVGVQPYRQVHAHSTGNPHSTVQNEADYHWRKDPELGFFSHIVGN
GCIMQVGPVDNGAWDVGGGWNAETYAAVELIESHSTKEEFMTDYRLYIELLRNLADEA
GLPKTLDTGSLAGIKTHEYCTNNQPNNHSDHVDPYPYLAKWGISREQFKHDIENGLTIET
GWQKNDTGYWYVHSDGSYPKDKFEKINGTWYYFDSSGYMLADRWRKHTDGNWYWF
DNSGEMATGWKKIADKWYYFNEEGAMKTGWVKYKDTWYYLDAKEGAMVSNAFIQS
ADGTGWYYLKPDGTLADKPEFTVEPDGLITVKZ

ID310

(SEQ. ID. NO. 205)
ATGGGCACAACAGGATTTACAATAATTGACTTAATTATCTTGATTGTTTATTTACTTG
CGGTGTTGGTTGCAGGTATCTATTTCTCTAAAAAAGAGATGAAAGGAAAAGAGTTCT
TTAAAGGAGATGGTTCGGTTCTTCGGTATGTTACTTCGGTATCCATTTTTGCCACAAT
GCTCAGTCCGATTTCCTTCTTGGGACTCGCTGGTAGCTCTTATGCAGGTAGCTGGATT
TTATGGTTTGCTCAATTAGGGATGGTAGTAGCTATTCCACTGACAATTCGTTTTATCT
TACCTATCTTTGCACGGATAGACATCGATACGGCATATGATTACTTGGATAAACGTT
TTAATTCTAAAGCACTTCGTATTATTTCAGCACTCTTGTTTATTATTTATCAATTGGG
ACGTATGTCTATCATTATGTACCTCCCATCAGCTGGTTTATCAGTATTCAGAGGAATT
GACATCAATATTTTGATTATTTTGATGGGTGTAGTTGCAATTGTTTATTCTTATACTG
GTGGTCTAAAATCCGTATTATGGACAGACTTTATTCAAGGTGTGATTCTGATTAGTG
GTGTCGTTTAGCTTTATTTGTACTGATTGCTAATATTAAAGGTGGCTTGGTGCAGT
AGCAGAAACATTAGCAAACGGGAAATTCCTTGCTGCAAATGAAAAACTTTTCGATC
CTAACTTGCTTTCAAACTCCATCTTTTTAATTGTGATGGGTTCAGGCTTTACAATCTT
GTCTTCCTATGCTTCATCTCAAGATTTGGTTCAACGTTTTACTACAACACAAAATATT
AAGAAACTTAATAAGATGTGTTCACAAAGCCTGTTTTGTCACTTGCAACTGCAACA
GTCTTTTACTTGATTGGTACAGGCTTGTACGTATTCTATCAAGTACAAAATGCAGAT
AGTGCAGCTAGCAATATCCCTCAAGACCAAATCTTTATGTACTTTATTGCATACCAG
TACCAGTAGGTATCACAGGTTTGATCTTGGCAGCGATTTATGCAGCATCTCAATCA
ACTATTTCAACAGGTTTGAACTCTGRTGCAACTTCATGGACATTGGATATTCAAGAT
GTCATTTCTAAAAATATGTCAGACAATCGTCGTACGAAAATTGCACAATTCGTATCT
CTAGCAGTAGGTTTATTCTCAATTGGTGTTTCCATTGTCATGGCTCACTCAGATATTA
AATCTGCATACGAATGGTTCAATAGTTTCATGGGACTTGTACTTGGTCTACTTGGTG
GTGTATTTATTCTTGGATTTGTTTCTAAAAAAGCAAATAAACAAGGTGCTTATGCAG
CGCTGATTGTATCAACCATCGTCATGGTATTTATTAAATACTTCCTTCCTCCAACAGC
TGTTAGCTACTGGGCATATTCATTGATTTCAATCTCTGTATCAGTAGTTTCAGGTTAT
ATTGTATCTGTTCTTACTGGAAATAAAGTATCTGCACCTAAATACAACGATRCAT
GATATTACAGAAATTAAAGCGGATTCAAGTTGGGAAGTTCGTCACTAA (SEQ. ID. NO. 193)
MGTTGFTIIDLIILIVYLLAVLVAGIYFSKKEMKGKEFFKGDGSVPWYVTSVSIFATMLSPI
SFLGLAGSSYAGSWILWFAQLGMVVAIPLTIRFILPIFARIDIDTAYDYLDKRFNSKALRII
SALLFIIYQLGRMSIIMYLPSAGLSVLTGIDINLLIILMGVVAIVYSYTGGLKSVLWTDFIQG
VILISGVVLALFVLIANIKGGFGAVAETLANGKFLAANEKLFDPNLLSNSIFLIVMGSGFTI
LSSYASSQDLVQRFTTTQNIKKLN14LFTNGVLSLATAIVFYLIGTGLYVFYQVQNADSA
ASNIPQDQIFMYFIAYQLPVGITGLILAAIYAASQSTISTGLNSVATSWTLDIQDVISKNMS
DNRRTKIAQFVSLAVGLFSIGVSIVMAHSDIKSAYEWFNSFMGLVLGLLGGVFILGFVSK
KANKQGAYAALIVSTIVMVFIKYFLPPTAVSYWAYSLISISVSVVSGYIVSVLTGNKVSA
PKYTTIHDITEIKADSSWEVRHZ

ID311

(SEQ. ID. NO. 206)
ATGAAAATTAATAAAAAATATCTAGCAGGTTCAGTGGCAGTCCTTGCCCTAAGTGTT
TGTTCCTATGAGCTTGGTCGTCACCAAGCTGGTCAGGATAAGAAAGAGTCTAATCGA
GTTGCTTATATAGATGGTGATCAGGCTCGTCAAAAGGCAGAAAACTTGACACCAGA
TGAAGTCAGTAAGAGGGAGGGGATCAACGCCGAACAAATCCTCATCAAGATTACGG
ATCAAGGTTATGTGACCTCTCATGGAGAACCATTATCATTACTATAATGGCAAGCTCC
CTTATGATGCCATCATCAGTGAAGAGCTCCTCATGAAAGATCCGAATTATCAGTTGA
AGGATTCAGACATTGTCAATGAAATCAAGGGTGGTTATGTCATCAAGGTAGACGGA
AAATACTATGTTThCCTTAAGGATGCAGCTCATGCGGATAATATTCGGACAAAAGAA
GAGATTAAACGTCAGAAGCAGGAACGCAGTCATAATCACGGGTCAGGAGCTAACGA
TCATGCAGTAGCTGCAGCCAGAGCCCAAGGACGCTATACAACGGATGATGGGTATA
TCTTCAATGCATCTGATATCATTGAGGACACGGGTGATGCTTATATCGTTCCTCACG
GCGACCATTACCATTACATTCCTAAGAATGAGTTATCAGCTAGCGAGTTAGCTGCTG
CAGAAGCCTATTGGAATGGGAAGCAGGGATCTCGTCCTTCTTCAAGTTCTAGTTATA
ATGCAAATCCAGCTCAACCAAGATTGTCAGAGAACCACAATCTGACTGTCACTCAA
ACTTATCATCAAATCAAGGGGAAACATTCAAGCCTTTTACGTGAATHGTATGCT
AAACCCTTATCAGAACGCCCATTGGAATCTGATGGCCTTATTTTCGACCCAGCGCAA
ATCACAAGTCGAACCCCCAGAGGTGTAGCTGTCCCTCATGGTAACCATTACCACTTT
ATCCCTTATGAACAAATCTCTGAATTGGAAAAACGAATTGCTCGTATTATTCCCCTTC
GTTATCGTTCAAACCATTGGGTACCAGATTCAAGACCAGAACAACCAAGTCCACAAT
CGACTCCGGAACCTAGTCCAAGTCCGCAACCTGCACCAAATCCTCAACCAGCTCCAA
GCAATCCAATTGATGAGAAATTGGTCAAAGAAGCTGTTCGAAAAGTAGGCGATGGT
TATGTCTTTGAGGAGAATGGAGTTTCTCGTTATATCCCAGCCAAGGATCTTTCAGCA

TABLE 4-continued

```
GAAACAGCAGCAGGCATTGATAGCAAACTGGCCAAGCAGGAAAGTTTATCTCATAA
GCTAGGAGCTAAGAAAACTGACCTCCCATCTAGTGATCGAGAATTTTACAATAAGG
CTTATGACTTACTAGCAAGAATTCACCAAGATTTACTTGATAATAAAGGTCGACAAG
TGATTTTGAGGCTTTGGATAACCTGTTGGAACGACTCAAGGATGTCCCAAGTGATA
AAGTCAAGTTAGTGGATGATATTCTTGCCTTCTTAGCTCCGATTCGTCATCCAGAAC
GTTTAGGAAAACCAAATGCGCAAATTACCTACACTGATGATGAGATTCAAGTAGCC
AAGTTGGCAGGCAAGTACACAACAGAAGACGGTTATATCTTTGATCCTCGTGATATA
ACCAGTGATGAGGGGGATGCCTATGTAACTCCACATATGACCCATAGCCACTGGATT
AAAAAAGATAGTTTGTCTGAAGCTGAGAGAGCGGCAGCCCAGGCTTATGCTAAAGA
GAAAGGTTTGACCCCTCCTTCGACAGACCATCAGGATTCAGGAAATACTGAGGCAA
AAGGAGCAGAAGCTATCTACAACCGCGTGAAAGCAGCTAAGAAGGTGCCACTTGAT
CGTATGCCTTACAATCTTCAATATACTGTAGAAGTCAAAAACGGTAGTTTAATCATA
CCTCATTATGACCATTACCATAACATCAAATTTGAGTGGTTTGACGAAGGCCTTTAT
GAGGCACCTAAGGGGTATACTCTTGAGGATCTTTTGGCGACTGTCAAGTACTATGTC
GAACATCCAAACGAACGTCCGCATTCAGATAATGGTTTTGGTAACGCTAGCGACCAT
GTTCAAAGAAACAAAAATGGTCAAGCTGATACCAATCAAACGGAAAAACCAAGCG
AGGAGAAACCTCAGACAGAAAACCTGAGGAAGAAACCCCTCGAGAAGAGAAACC
GCAAAGCGAGAAACCAGAGTCTCCAAAACCAACAGAGGAACCAGAAGAATCACCA
GAGGAATCAGAAGAACCTCAGGTCGAGACTGAAAAGGTTGAAGAAAAACTGAGAG
AGGCTGAAGATTACTTGGAAAAATCCAGGATCCAATTATCAAGTCCAATGCCAAA
GAGACTCTCACAGGATTAAAAAATAATTTACTATTTGGCACCCAGGACAACAATACT
ATTATGGCAGAAGCTGAAAAACTATTGGCTTTATTAAAGGAGAGTAAGTAA
```

(SEQ. ID. NO. 194)
```
MKINKKYLAGSVAVLALSVCSYELGRHQAGQDKKESNRVAYIDGDQAGQKAENLTPD
EVSKREGINAEQIVIKITDQGYVTSHGDHYHYYNGKVPYDAIISEELLMKDPNYQLKDSD
IVNEIKGGYVIKVDGKYYVYLKDAAHADNIRTKEEIKRQKQERSHNHGSGANDHAVAA
ARAQGRYTTDDGYIFNASDIIEDTGDAYIVPHGDHYHYIPKNELSASELAAAEAYWNGK
QGSRPSSSSSYNANPAQPRLSENWNTTVTPTYHQNQGENISSLLRELYAKPLSERJVESD
GLIFDPAQITSRTARGVAVPHGNHYHFIPYEQMSELEKRIARIIPLRYRSNHWVPDSRPEQ
PSPQSTPEPSPSPQPAP4PQPAPSNPIDEKLVKEAVRKVGDGYVFEENGVSRYIPAKDLSA
ETAAGIDSKLAKQESLSHKLGAKKTDLPSSDREFYNKAYDLLARIHQDLLDNKGRQVDF
EALDNLLERLKDVPSDKVKLVDDILAFLAPLRHPERLGKPNAQITYTDDEIQVAKLAGKY
TTEDGYIFDPRDITSDEGDAYVTPHMTHSHWIKKDSLSEAERAAAQAYAKEKGLTPPST
DHQDSGNTEAKGAEAIYNRNKAAKKVPLDRMPYNLQYTVEVKNGSLIIPHYDHYHNIK
FEWFDEGLYEAPKGYTLEDLLATVKYYVEHPNERPHSDNGFGNASDHVQRNKNGQAD
TNQTEKPSEEKPQTEKPEEETPREEKPQSEKPESPKPTEEPEESPEESEEPQVETEKVEEKL
REAEDLLGKIQDPIIKSNAKETLTGLKNNLLFGTQDNNTIMAEAEKLLALLKESKZ
```

ID312

(SEQ. ID. NO. 307)
```
ATGGAGGGATGGTTAGAGTGCATTATTGCCTGTATTTGGCGATTACAAGCTATCT
AAACTTACTACGCCTATTCTTCAACAGCAAGTAAACAAATGGGCTGACAAGGCAAA
TAAAGGCGAAAAGGGGCATTTGCTAACTACTCTTTGCTCCATAACATGAATAAGCG
TATTTTGAAATATGGCGTAGCTATCCAGGTAATACAATACAACCCAGCTAATGATGT
CATCGTTCCACGCAAACAGCAAAAGAAAAGGCTGCTGTCAAATACTTAGACAACA
AAGAATTAAAACAGTTTCTTGATTATTTAGATGCTCTGGATCAATCAAATTATGAGA
ACTTATTTGATGTTGTTCTGTATAAGACTTTATTGGCCACTGGTTGCCGTATTAGTGA
GGCTCTGGCTCTTGAATGGTCTGATATTGACCTAGAAAGCGGTGTTATCAGCATCAA
TAAGACACTAAACCGCTATCAGGAAATAAACTCACCTAAATCAAGCGCTGGTTATC
GTGATATACCAATAGACAAAGCCACATTACTTTTTACTGAAACAATACAAAAACCGTC
AACAAATTCAGTCTTGGAAATTAGGCCGATCTGAAACAGTTGTATTCTCGTATTTA
CGGAGAAATATGCTTATGCTTGTAACTTACGCAAACGCCTAAATAAGCATTTTGATG
CTGCTGGAGTAACTAACGTATCATTTCATGGTTTCCGCCATACACATACTACTATGAT
GCTCTATGCTCAGGTTAGCCCGAAAGATGTTCAGTATAGATTAGGCCACTCTAATTT
AATGATCACTGAAAATACTTACTGGCATACTAACCAAGAGAATGCAAAAAAAGCCG
TCTCAAATTATGAAACAGCTATCAACAATTTATAA
```

(SEQ. ID. NO. 195)
```
MEGLVRVHLLPVFGDYKLSKTTPILQQQVNKWADKANKGEKGAFANYSLLHNMNKR
ILKYGVAIQVIQYNPANDVIVPRKQQKEKAAVKYLDNKELKQFLDYLDALDQSNYQNL
FDVVLYKTLLATGCRISEALALEWSDIDLESGVISINKTLNRYQEISPKSSAGYRDIPIDK
ATLLLLKQYKNRQQIQSWKLGRSETVVFSVFTEKYAYACNLRKRLNKHFDAAGVTNVS
FHGFRHTHTTMMLYAQVSPKDVQRLGHSNLMITENTYWHTNQENAKKAVSNYETAI
NNLZ
```

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07648708B2). An electronic copy of the "Sequence Listing" will also be available from the USPTO upon request and payment of the fee set forth in 37 CFR 1.19(b)(3).

What is claimed is:

1. An isolated *Streptococcus pneumoniae* polypeptide comprising the amino acid sequence of SEQ ID NO: 155; or a polypeptide comprising the amino acid sequence having at least 90% sequence identity with SEQ ID NO: 155.

2. The polypeptide of claim 1, wherein said polypeptide comprises the amino acid sequence having at least 95% identity with SEQ ID NO: 155.

3. The polypeptide of claim 1, wherein said polypeptide comprises the amino acid sequence of SEQ ID NO: 155.

4. An immunogenic and/or antigenic composition comprising the polypeptide of claim 1 and one or more excipients, diluents, or adjuvants.

5. The composition of claim 4, wherein said composition is an antigenic composition.

6. The composition of claim 4, wherein said composition is an immunogenic composition.

7. A fusion protein comprising (a) the amino acid sequence of SEQ ID NO: 155; or
  (b) a polypeptide comprising amino acid sequence having at least 90% sequence identity with SEQ ID NO: 155.

* * * * *